United States Patent
Malone et al.

(10) Patent No.: US 11,447,527 B2
(45) Date of Patent: *Sep. 20, 2022

(54) ENDOGENOUS GAG-BASED CAPSIDS AND USES THEREOF

(71) Applicant: VNV NEWCO INC., New York, NY (US)

(72) Inventors: Colin Malone, Brooklyn, NY (US); Ian Peikon, Bethpage, NY (US); Zachary Gilbert, Brooklyn, NY (US); Andrey Pisarev, Long Beach Township, NJ (US); Adam Fraites, Long Beach Township, NJ (US); Jessica Crisp, Phoenix, AZ (US)

(73) Assignee: VNV NEWCO INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/382,092

(22) Filed: Jul. 21, 2021

(65) Prior Publication Data

US 2021/0347829 A1 Nov. 11, 2021

Related U.S. Application Data

(63) Continuation of application No. 17/277,119, filed as application No. PCT/US2019/051786 on Sep. 18, 2019.

(60) Provisional application No. 62/733,015, filed on Sep. 18, 2018.

(51) Int. Cl.
| | | |
|---|---|---|
| *C07K 14/005* | (2006.01) | |
| *A61K 38/00* | (2006.01) | |
| *C07K 14/435* | (2006.01) | |
| *C07K 16/00* | (2006.01) | |
| *C12N 9/22* | (2006.01) | |
| *C12N 15/11* | (2006.01) | |
| *C12N 15/90* | (2006.01) | |
| *A61K 48/00* | (2006.01) | |
| *C07K 14/46* | (2006.01) | |
| *C12N 15/87* | (2006.01) | |

(52) U.S. Cl.
CPC ............ *C07K 14/005* (2013.01); *A61K 38/00* (2013.01); *A61K 48/0008* (2013.01); *C07K 14/435* (2013.01); *C07K 14/46* (2013.01); *C07K 16/00* (2013.01); *C12N 9/22* (2013.01); *C12N 15/11* (2013.01); *C12N 15/87* (2013.01); *C12N 15/907* (2013.01); *C12N 2310/20* (2017.05)

(58) Field of Classification Search
CPC .... C07K 14/005; C07K 14/435; C07K 16/00; A61K 38/00

See application file for complete search history.

(56) References Cited

U.S. PATENT DOCUMENTS

| | | |
|---|---|---|
| 4,510,245 A | 4/1985 | Cousens et al. |
| 4,737,323 A | 4/1988 | Martin et al. |
| 4,837,028 A | 6/1989 | Allen |
| 4,897,355 A | 1/1990 | Eppstein et al. |
| 4,968,615 A | 11/1990 | Koszinowski et al. |
| 5,000,960 A | 3/1991 | Wallach |
| 5,168,062 A | 12/1992 | Stinski |
| 5,260,065 A | 11/1993 | Mathur |
| 5,543,158 A | 8/1996 | Gref et al. |
| 5,855,913 A | 1/1999 | Hanes et al. |
| 5,869,326 A | 2/1999 | Hofmann |
| 5,985,309 A | 11/1999 | Edwards et al. |
| 6,007,845 A | 12/1999 | Domb |
| 6,479,626 B1 | 11/2002 | Kim et al. |
| 6,534,261 B1 | 3/2003 | Cox, III et al. |
| 6,607,882 B1 | 8/2003 | Cox, III et al. |
| 6,746,838 B1 | 6/2004 | Choo et al. |
| 6,794,136 B1 | 9/2004 | Eisenberg et al. |
| 6,824,978 B1 | 11/2004 | Cox, III et al. |
| 6,866,997 B1 | 3/2005 | Choo et al. |
| 6,903,185 B2 | 6/2005 | Kim et al. |
| 6,919,438 B1 | 7/2005 | Alliel et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,220,719 B2 | 5/2007 | Case et al. |
| 7,241,573 B2 | 7/2007 | Choo et al. |
| 7,241,574 B2 | 7/2007 | Choo et al. |
| 7,442,550 B1 | 10/2008 | Mallet et al. |
| 7,534,439 B2 | 5/2009 | Alliel et al. |
| 7,585,849 B2 | 9/2009 | Liu et al. |

(Continued)

FOREIGN PATENT DOCUMENTS

| | | |
|---|---|---|
| CA | 2331923 C | 2/2014 |
| CA | 2383877 C | 4/2014 |

(Continued)

OTHER PUBLICATIONS

Pastuzyn et al. "The Neuronal Gene Arc Encodes a Repurposed Retrotransposon Gag Protein that Mediates Intercellular RNA Transfer" Cell 172:275-288. (Year: 2018).*

(Continued)

*Primary Examiner* — Sudhakar Katakam
*Assistant Examiner* — Zachary J Miknis
(74) *Attorney, Agent, or Firm* — Wilson Sonsini Goodrich & Rosati

(57) ABSTRACT

Disclosed herein, in certain embodiments, are recombinant Arc and endogenous Gag polypeptides, and methods of using recombinant Arc and endogenous Gag polypeptides.

25 Claims, 8 Drawing Sheets

Specification includes a Sequence Listing.

(56) References Cited

U.S. PATENT DOCUMENTS

| | | |
|---|---|---|
| 7,595,376 B2 | 9/2009 | Kim et al. |
| 7,776,321 B2 | 8/2010 | Cascalho et al. |
| 8,021,867 B2 | 9/2011 | Smith et al. |
| 8,084,213 B2 | 12/2011 | Sepp et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,318,173 B2 | 11/2012 | August et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,518,694 B2 | 8/2013 | Hardy et al. |
| 8,597,657 B2 | 12/2013 | Renard et al. |
| 8,697,359 B1 | 4/2014 | Zhang |
| 8,709,843 B2 | 4/2014 | Shakuda |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,254,311 B2 | 2/2016 | Bancel et al. |
| 9,481,905 B2 | 11/2016 | Chen et al. |
| 9,555,091 B2 | 1/2017 | Kim et al. |
| 9,827,332 B2 | 11/2017 | Bancel et al. |
| 11,129,892 B1 * | 9/2021 | Gilbert ............. A61K 39/145 |
| 2004/0171156 A1 | 9/2004 | Hartley et al. |
| 2011/0027239 A1 | 2/2011 | Paek |
| 2011/0265198 A1 | 10/2011 | Gregory et al. |
| 2011/0293703 A1 | 12/2011 | Mahon et al. |
| 2012/0017290 A1 | 1/2012 | Cui et al. |
| 2012/0251560 A1 | 10/2012 | Dahlman et al. |
| 2013/0236946 A1 | 9/2013 | Gouble |
| 2013/0302401 A1 | 11/2013 | Ma et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0308304 A1 | 10/2014 | Manoharan |
| 2014/0310830 A1 | 10/2014 | Zhang et al. |
| 2014/0328759 A1 | 11/2014 | Cullis |
| 2014/0348900 A1 | 11/2014 | Zhu |
| 2015/0184139 A1 | 7/2015 | Zhang et al. |
| 2017/0087087 A1 | 3/2017 | Leonard et al. |
| 2019/0240351 A1 | 8/2019 | Bancel et al. |
| 2019/0300902 A1 | 10/2019 | Galy |
| 2020/0330586 A1 | 10/2020 | Holst et al. |
| 2020/0347100 A1 | 11/2020 | Zhang |
| 2021/0047375 A1 | 2/2021 | Lu et al. |
| 2021/0189432 A1 | 6/2021 | Shepherd et al. |
| 2021/0261957 A1 | 8/2021 | Petris et al. |

FOREIGN PATENT DOCUMENTS

| | | |
|---|---|---|
| CN | 101952436 B | 3/2013 |
| CN | 109563139 A | 4/2019 |
| EP | 1090122 B1 | 7/2008 |
| EP | 2241626 A2 | 10/2010 |
| EP | 2385058 B1 | 11/2013 |
| EP | 2764103 A2 | 8/2014 |
| EP | 2771468 A1 | 9/2014 |
| EP | 2784162 A1 | 10/2014 |
| EP | 2241626 B1 | 1/2016 |
| EP | 3445774 A1 | 2/2019 |
| EP | 3452101 A2 | 3/2019 |
| JP | 4283475 B2 | 6/2009 |
| JP | 4824731 B2 | 11/2011 |
| JP | 5309159 B2 | 10/2013 |
| JP | 2019514369 A | 6/2019 |
| KR | 101164602 B1 | 7/2012 |
| KR | 20180135034 A | 12/2018 |
| WO | WO-9212237 A1 | 7/1992 |
| WO | WO-9749450 A1 | 12/1997 |
| WO | WO-9852609 A1 | 11/1998 |
| WO | WO-2004087748 A1 | 10/2004 |
| WO | WO-2009042727 A1 | 4/2009 |
| WO | WO-2011028929 A2 | 3/2011 |
| WO | WO-2012135025 A2 | 10/2012 |
| WO | WO-2013151663 A1 | 10/2013 |
| WO | WO-2013151664 A1 | 10/2013 |
| WO | WO-2013158141 A1 | 10/2013 |
| WO | WO-2014018423 A2 | 1/2014 |
| WO | WO-2014093595 A1 | 6/2014 |
| WO | WO-2014093622 A2 | 6/2014 |
| WO | WO-2014093635 A1 | 6/2014 |
| WO | WO-2014093655 A2 | 6/2014 |
| WO | WO-2014093661 A2 | 6/2014 |
| WO | WO-2014093694 A1 | 6/2014 |
| WO | WO-2014093701 A1 | 6/2014 |
| WO | WO-2014093709 A1 | 6/2014 |
| WO | WO-2014093712 A1 | 6/2014 |
| WO | WO-2014093718 A1 | 6/2014 |
| WO | WO-2014118272 A1 | 8/2014 |
| WO | WO-2014204723 A1 | 12/2014 |
| WO | WO-2014204724 A1 | 12/2014 |
| WO | WO-2014204725 A1 | 12/2014 |
| WO | WO-2014204726 A1 | 12/2014 |
| WO | WO-2014204727 A1 | 12/2014 |
| WO | WO-2014204728 A1 | 12/2014 |
| WO | WO-2014204729 A1 | 12/2014 |
| WO | WO-2015058052 A1 | 4/2015 |
| WO | WO-2015070083 A1 | 5/2015 |
| WO | WO-2015089351 A1 | 6/2015 |
| WO | WO-2015089354 A1 | 6/2015 |
| WO | WO-2015089364 A1 | 6/2015 |
| WO | WO-2015089419 A2 | 6/2015 |
| WO | WO-2015089427 A1 | 6/2015 |
| WO | WO-2015089462 A1 | 6/2015 |
| WO | WO-2015089465 A1 | 6/2015 |
| WO | WO-2015089473 A1 | 6/2015 |
| WO | WO-2015089486 A2 | 6/2015 |
| WO | WO-2016049258 A2 | 3/2016 |
| WO | WO-2016094867 A1 | 6/2016 |
| WO | WO-2016094872 A1 | 6/2016 |
| WO | WO-2016094874 A1 | 6/2016 |
| WO | WO-2016106236 A1 | 6/2016 |
| WO | WO-2016106244 A1 | 6/2016 |
| WO | WO-2016149426 A1 | 9/2016 |
| WO | WO-2016161516 A1 | 10/2016 |
| WO | WO-2017068077 A1 | 4/2017 |
| WO | WO-2017182607 A1 | 10/2017 |
| WO | WO-2017191274 A2 | 11/2017 |
| WO | WO-2018209113 A1 | 11/2018 |
| WO | WO-2018213708 A1 | 11/2018 |
| WO | WO-2018213726 A1 | 11/2018 |
| WO | WO-2018234576 A1 | 12/2018 |
| WO | WO-2019005884 A1 | 1/2019 |
| WO | WO-2019005886 A1 | 1/2019 |
| WO | WO-2019018423 A1 | 1/2019 |
| WO | WO-2019060746 A1 | 3/2019 |
| WO | WO-2019067225 A1 | 4/2019 |

(56) References Cited

FOREIGN PATENT DOCUMENTS

| WO | WO-2019071048 A1 | 4/2019 |
|---|---|---|
| WO | WO-2019077149 A1 | 4/2019 |
| WO | WO-2019077150 A1 | 4/2019 |
| WO | WO-2019118497 A1 | 6/2019 |
| WO | WO-2019126709 A1 | 6/2019 |
| WO | WO-2019126762 A2 | 6/2019 |
| WO | WO-2020043908 A1 | 3/2020 |
| WO | WO-2020061229 A2 | 3/2020 |
| WO | WO-2020131862 A1 | 6/2020 |
| WO | WO-2020252455 A1 | 12/2020 |
| WO | WO-2021055855 A1 | 3/2021 |
| WO | WO-2021236513 A1 | 11/2021 |

OTHER PUBLICATIONS

Segel et al. "Mammalian retrovirus-like protein PEG10 packages its own mRNA and can be psuedotyped for mRNA delivery" Science 373:882-889. (Year: 2021).*
Alvarez-Erviti et al. Delivery of siRNA to the mouse brain by systemic injection of targeted exosomes. Nature Biotechnol. 29:341-345 (2011).
Ashley et al. Retrovirus-like Gag protein Arc1 binds RNA and traffics across synaptic boutons. Cell 172:262-274 (2018).
Balvay et al. Translational control of retroviruses. Nat rev Microbiol 5(2):128-49 (2007).
Becker et al. Extracellular vesicles in cancer: cell-to-cell mediators of metastasis. Cancer Cell 30:836-848 (2016).
Besser et al. Clinical Responses in a Phase II Study Using Adoptive Transfer of Short-term Cultured Tumor Infiltration Lymphocytes in Metastatic Melanoma Patients. Clinical Cancer Research 16(9):2646-2655 (2010).
Bramham et al. The Arc of synaptic memory. Exp. Brain Res. 200:125-140 (2010).
Brigham et al. Expression of a prokaryotic gene in cultured lung endothelial cells after lipofection with a plasmid vector. Am. J. Resp. Cell. Mol. Biol. 1:95-100 (1989).
Brown. Propellant-Driven Aerosols of Proteins. Aerosol Science and Technology 24(1):45-56 (1994).
Budnik et al. Extracellular vesicles round off communication in the nervous system. Nat. Rev. Neurosci. 17:160-172 (2016).
Campbell et al. In vitro assembly properties of human immunodeficiency virus type 1 Gag protein lacking the p6 domain. J. Virol. 73:2270-2279 (1999).
Campillos et al. Computational characterization of multiple Gag-like human proteins. Trends Genet. 22(11):585-9 (2006).
Carlson et al. Reconstitution of selective HIV-1 RNA packaging in vitro by membrane-bound Gag assemblies. eLife 5:e14663 (2016).
Chowdhury et al. Arc/Arg3.1 interacts with the endocytic machinery to regulate AMPA receptor trafficking. Neuron 52:445-459 (2006).
Chuong et al. Regulatory activities of transposable elements: from conflicts to benefits. Nat. Rev. Genet. 18:71-8 (2017).
Comas-Garcia et al. On the selective packaging of genomic RNA by HIV-1. Viruses 8(9):246 (2016).
Co-pending U.S. Appl. No. 17/382,102, inventors Malone; Colin et al., filed Jul. 21, 2021.
Cornelis et al. Retro-viral envelope gene captures and syncytin exaptation for placentation in marsupials. PNAS USA 112:E487-E496 (2015).
Daberkow et al. Arc mRNA induction in striatal efferent neurons associated with response learning. Eur. J. Neurosci. 26:228-241 (2007).
Day et al. Arc: Building a bridge from viruses to memory. Biochem. J. 469(1):p. el-e3 (2015).
De Solis et al. Is Arc mRNA unique: a search for mRNAs that localize to the distal dendrites of dentate gyrus granule cells following neural activity. Front. Mol. Neurosci. 10:314 (2017).

Delchambre et al., The Gag Precursor of Simian Immunodeficiency Virus Assembles Into Virus-Like Particles. The EMBO Journal 8(9):2653-26660 (1989).
Dudley et al. Cancer Regression and Autoimmunity in Patients After Clonal Repopulation with Antitumor Lvmohocytes. Science 298:850-854 (2002).
Dudley et al. Adoptive Cell Transfer Therapy Following Non-Myeloablative but Lymphodepleting Chemotherapy for the Treatment of Patients With Refractory Metastatic Melanoma. J Clin Oncol. 23(10):2346-2357 (2005).
Fauré et al. Exosomes are released by cultured cortical neurones. Mol. Cell. Neurosci. 31:642-648 (2006).
Feigner et al. Lipofection: A Highly Efficient, Lipid-Mediated DNA-Transfection Procedure. PNAS USA 84(21): 7413-7417 (1987).
Feschotte et al. Endogenous viruses: insights into viral evolution and impact on host biology. Nat. Rev. Genet. 13:283-296 (2012).
Freed. HIV-1 assembly, release and maturation. Nat. Rev. Microbiol. 13:484-496 (2015).
Fromer et al. De novo mutations in schizophrenia implicate synaptic networks. Nature 506:179-184 (2014).
Ganser et al. Assembly and analysis of conical models for the HIV-1 core. Science 283:80-83 (1999).
Gibson et al. Enzymatic assembly of DNA molecules up to several hundred kilobases. Nat Methods. 6(5):343-5 (2009).
Greer et al. The Angelman syndrome protein Ube3A regulates synapse development by ubiquitinating arc. Cell 140:704-716 (2010).
Gsheysen et al, Assembly and Release of Hiv-1 Precursor Pr55Gag Virus-Like Particles from Recombinant 3aculovirus-Infected Insect Cells. Cell 59(1):103-112 (1989).
Guzowski et al. Environment-specific expression of the immediate-early gene Arc in hippo-campal neuronal ensembles. Nat. Neurosci. 2:1120-1124 (1999).
Guzowski et al. Inhibition of activity-dependent arc protein expression in the rat hippocampus impairs the maintenance of long-term potentiation and the consolidation of long-term memory. J. Neurosci. 20:3993-4001 (2000).
Hamann et al. Foamy virus protein-nucleic acid interactions during particle morphogenesis. Viruses 8(9):243 (2016).
Hansen et al. Ty3 GAG3 and POL3 genes encode the components of intracellular particles. J. Virol. 66:1414-1424 (1992).
Heraud-Farlow et al. The multifunctional Staufen proteins: conserved roles from neurogenesis to synaptic plasticity. Trends Neurosci. 37:470-479 (2014).
Irie et al. Cognitive Function Related to the Sirh11/Zcchc16 Gene Acquired from an LTR Retro-transposon in Eutherians. PLoS Genet. 11:e1005521 (2015).
Johnson et al, Gene Therapy with Human and Mouse T-Cell Receptors Mediates Cancer Regression and Targets gormal Tissues Expressing Cognate Antigen. Blood 114(3):535-546 (2009).
Kalos et al. T cells with chimeric antigen receptors have potent antitumor effects and can establish memory in patients with advanced leukemia. Sci Transl Med 3(95):95ra73 (2011).
Kaneko-Ishino et al. The role of genes domesticated from LTR retrotransposons and retroviruses in mammals. Front. Microbiol. 3:262 (2012).
Korkut et al. Trans-synaptic transmission of vesicular Wnt signals through Evi/Wntless. Cell 139:393-404 (2009).
Kraft et al. Visual experience sculpts whole-cortex spontaneous infraslow activity patterns through an Arc-dependent mechanism. PNAS USA 114:E9952-E9961 (2017).
Kutluay et al. Global changes in the RNA binding specificity of HIV-1 gag regulate virion genesis. Cell 159:1096-1109 (2014).
Lachenal et al. Release of exosomes from differentiated neurons and its regulation by synaptic glutamatergic activity. Mol. Cell. Neurosci. 46:409-418 (2011).
Lefebvre et al. Comparative transcriptomic analysis of human and *Drosophila* extracellular vesicles. Sci. Rep. 6:27680 (2016).
Lyu et al. Delivering Cas9/sgRNA ribonucleoprotein (RNP) by lentiviral capsid-based bionanoparticles for efficient 'hit-and-run' genome editing. Nucleic Acids Res 1:1-13 (2019).
Macia et al. Dynasore, a cell-permeable inhibitor of dynamin. Dev. Cell 10:839-850 (2006).

(56) References Cited

OTHER PUBLICATIONS

Mailler et al. The life-cycle of the HIV-1 Gag-RNA complex. Viruses 8(9):248 (2016).
Malik et al. Poised for contagion: evolutionary origins of the infectious abilities of invertebrate retroviruses. Genome Res. 10:1307-1318 (2000).
Managò et al. Genetic disruption of Arc/Arg3.1 in mice causes alterations in dopamine and neurobehavioral phenotypes related to schizophrenia. Cell Rep. 16:2116-2128 (2016).
Maruyama et al. Targetability of Novel Immunoliposomes Modified with Amphipathic Poly(Ethylene Glycol) S Sonjugated at their Distal Terminals to Monoclonal Antibodies. Biochimica et Biophysica Acta (BBA)—Biomembranes 1234(1):74-80 (1995).
Mattei et al. Retrovirus maturation-an extraordinary structural transformation. Curr. Opin. Virol. 18:27-35 (2016).
McCurry et al. Loss of Arc renders the visual cortex impervious to the effects of sensory experience or deprivation. Nat. Neurosci. 13:450-457 (2010).
Mikuni et al. Arc/Arg3.1 is a postsynaptic mediator of activity-dependent synapse elimination in the developing cerebellum. Neuron 78:1024-1035 (2013).
Mokany et al. MNAzymes, a versatile new class of nucleic acid enzymes that can function as biosensors and molecular switches. J Am Chem Soc 132(2):1051-1059 (2010).
Montagna et al. VSV-G-Enveloped Vesicles for Traceless Delivery of CRISPR-Cas9. Mol Ther Nucleic Acids. 12:453-462 (2018).
Morgan et al. Cancer regression in patients after transfer of genetically engineered lymphocytes. Science 314(5796):126-129 (2006).
Mouland et al. The double-stranded RNA-binding protein Staufen is incorporated in human immunodeficiency virus type 1: evidence for a role in genomic RNA encapsidation. J. Virol. 74:5441-5451(2000).
Myrum et al. Arc is a flexible modular protein capable of reversible self-oligomerization. Biochem. J. 468(1):145-158 (2015).
Naville et al. Not so bad after all: retroviruses and long terminal repeat retrotransposons as a source of new genes invertebrates. Clin Microbiol Infect 22(4):312-323 (2016).
NCBI, GenBank accession No. NP_001269464.1, 'paraneoplastic antigen Ma3 isoform 2 [*Homo sapiens*]' (Jun. 30, 2018).
NCBI, GenBank accession No. XP_018887452.1, 'activity-regulated cytoskeleton-associated protein [Gorilla gorilla gorilla]' (Nov. 4, 2016).
NCBI, GenBank accession No. XP_020755692.1, 'activity-regulated cytoskeleton-associated protein [Odocoileus virginianus texanus]' (Apr. 28, 2017).
Nielsen et al. The Capsid Domain of Arc Changes Its Oligomerization Propensity through Direct Interaction with the NMDA Receptor. Structure 27(7):1071 (2019).
Nolte-'T Hoen et al. Extracellular vesicles and viruses: Are they close relatives? PNAS USA 113:9155-9161 (2016).
Okuno et al. Inverse synaptic tagging of inactive synapses via dynamic interaction of Arc/Arg3.1 with CaMKIIβ. Cell 149:886-898 (2012).
Park et al. Elongation factor 2 and fragile X mental retardation protein control the dynamic translation of Arc/Arg3.1 essential for mGluR-LTD. Neuron 59:70-83 (2008).
Pastuzyn et al. Activity-dependent Arc expression and homeostatic synaptic plasticity are altered in neurons from a mouse model of Angelman syndrome. Front. Mol. Neurosci. 10:234 (2017).
Pastuzyn et al. The Neuronal Gene Arc Encodes a Repurposed Retrotransposon Gag Protein that Mediates Intercellular RNA Transfer. Cell 172:275-288 (2018).
PCT/US2018/032105 International Search Report and Written Opinion dated Aug. 1, 2018.
PCT/US2019/051786 International Search Report and Written Opinion dated Mar. 20, 2020.
PCT/US2020/051637 International Search Report and Written Opinion dated Feb. 3, 2021.
Piazza et al. Immunotherapy of Respiratory Syncytial Virus Infection in Cotton Rats (*Sigmodon fulviventer*) Using gG in a Small-Particle Aerosol. The Journal of Infectious Diseases 166(6):1422-4 (1992).
Pinkstaff et al. Internal initiation of translation of five dendritically localized neuronal mRNAs. PNAS USA 98:2770-2775 (2001).
Plath et al. Arc/Arg3.1 is essential for the consolidation of synaptic plasticity and memories. Neuron 52:437-444 (2006).
Purcell et al. A poly-genic burden of rare disruptive mutations in schizophrenia. Nature 506:185-190 (2014).
Purdy et al. Critical role of conserved hydrophobic residues within the major homology region in mature retroviral capsid assembly. J. Virol. 82:5951-5961 (2008).
Rajendran et al. Alzheimer's disease β-amyloid peptides are released in association with exosomes. PNAS USA 103:11172-11177 (2006).
Raposo et al. Extracellular vesicles: exosomes, microvesicles, and friends. J. Cell Biol. 200:373-383 (2013).
Shepherd et al. Arc/Arg3.1 mediates homeostatic synaptic scaling of AMPA receptors. Neuron 52:475-484 (2006).
Shepherd et al. New views of Arc, a master regulator of synaptic plasticity. Nat. Neurosci. 14:279-284 (2011).
Smit. Interspersed repeats and other mementos of transposable elements in mammalian genomes. Curr. Opin. Genet. Dev. 9:657-663 (1999).
Spuch et al. Liposomes for Targeted Delivery of Active Agents against Neurodegenerative Diseases (Alzheimer's Disease and Parkinson's Disease). Journal of Drug Delivery 2011 (469679): 2011:469679 (2011).
Steward et al. Synaptic activation causes the mRNA for the IEG Arc to localize selectively near activated postsynaptic sites on dendrites. Neuron 21:741-751 (1998).
Taylor et al. A comparative analysis of the foamy and ortho virus capsid structures reveals an ancient domain duplication. BMC Struct. Biol. 17(1):3 (2017).
Tkach et al. Communication by extracellular vesicles: where we are and where we need to go. Cell 164:1226-1232 (2016).
Tonjes et al. Characterization of Human Endogenous Retrovirus Type K Virus-like Particles Generated from Recombinant Baculoviruses. Virology 233(2):280-291 (1997).
Tsai. Penetration of nonenveloped viruses into the cytoplasm. Annu. Rev. Cell Dev. Biol. 23:23-43 (2007).
Ufer et al. Arc/Arg3.1 governs inflammatory dendritic cell migration from the skin and thereby controls T cell activation. Sci. Immunol. 1:eaaf8665 (2016).
Valadi et al. Exosome-mediated transfer of mRNAs and microRNAs is a novel mechanism of genetic exchange between cells. Nat. Cell Biol. 9:654-659 (2007).
Vlach et al. Structural and molecular determinants of HIV-1 Gag binding to the plasma membrane. Front Microbiol 6:232 (2015).
Wahlgren et al. Plasma Exosomes can Deliver Exogenous Short Interfering RNA to Monocytes and Lymphocytes. Nucleic Acids Res 40(17):e130 (2012).
Wang et al. In vivo two-photon imaging reveals a role of arc in enhancing orientation specificity in visual cortex. Cell 126:-389-402 (2006).
Waung et al. Rapid translation of Arc/Arg3.1 selectively mediates mGluR-dependent LTD through persistent increases in AMPAR endocytosis rate. Neuron 59:84-97 (2008).
Wu et al. Arc/Arg3.1 regulates an endosomal pathway essential for activity-dependent b-amyloid generation. Cell 147:615-628 (2011).
Zappulli et al. Extracellular vesicles and intercellular communication within the nervous system. J. Clin. Invest. 126:1198-1207 (2016).
Zhang et al. Structural Basis of Arc Binding to Synaptic Proteins: Implications for Cognitive Diseases. Neuron 86(2):490-500 (2015).
Zhou et al. Novel reference genes for quantifying transcriptional responses of *Escherichia coli* to protein overexpression by quantitative PCR. BMC Mol. Biol. 12:18 (2011).
Abudayeh et al. C2c2 is a single-component programmable RNA-guided RNA-targeting CRISPR effector. Science 353(6299):aaf5573 (2016).

(56) References Cited

OTHER PUBLICATIONS

Akinc et al. Targeted Delivery of TNAi Therapeutics With Endogenous and Exogenous Ligand-Based Mechanisms. Mol Ther 18(7):1357-1364 (2010).
Alhasan et al.: Exosome encased spherical nucleic acid gold nanoparticle conjugates as potent microRNA regulation agents. Small. 10(1): 186-192 (2014).
Allerson et al. Fully 2'-modified oligonucleotide duplexes with improved in vitro potency and stability compared to unmodified small interfering RNA. J Med Chem. 48:901-904 (2005).
Altinoglu et al. Intracellular delivery of the PTEN protein using cationic lipidoids for cancer therapy. Biomater Sci. 4(12):1773-80 (2016).
Altschul et al. Basic local alignment search tool. J Mol Biol 215(3):403-410 (1990).
An et al. Envelope gene of the human endogenous retrovirus HERV-W encodes a functional retrovirus envelope. J. Virol. 75:3488-3489 (2001).
Antony et al. The human endogenous retrovirus envelope glycoprotein, Syncytin-1, regulates neuroinflammation and its receptor expression in multiple sclerosis: a role for endoplasmic reticulum chaperones in astrocytes. J Immunology 179(2):1210-1224 (2007).
Anzalone, et al. Search-and-replace genome editing without double-strand breaks or donor DNA. Nature 576, 149-157 (2019).
Balachandran et al. Vesicular stomatitis virus (VSV) therapy of tumors. IUBMB Life 50:135-8 (2000).
Baldrick. Pharmaceutical Excipient Development: The Need for Preclinical Guidance. Regul Toxicol Pharmacology 32(2):210-218 (2000).
Bartlett et al. Impact of tumor-specific targeting on the biodistribution and efficacy of siRNA nanoparticles measured by multimodality in vivo imaging. PNAS USA 104(39):15549-15554 (2007).
Basha et al. Influence of cationic lipid composition on gene silencing properties of lipid nanoparticle formulations of siRNA in antigen-presenting cells. Molecular Therapy 19(12):2186-200 (2011).
Benit et al. Identification, phylogeny, and evolution of retroviral elements based on their envelope genes. J. Virol. 75:11709-11719 (2001).
Boch et al. Breaking the Code of DNA Binding Specificity of TAL-Type III Effectors. Science 326:1509-1512 (Dec. 11, 2009).
Boshart et al. A very strong enhancer is located upstream of an immediate early gene of human cytomegalovirus. Cell. 41(2):521-30 (1985).
Bramsen et al. Development of Therapeutic-Grade Small Interfering RNAs by Chemical Engineering. Front Genet. 3:154 (2012).
Brandt et al. A family of neofunctionalized Ty3/gypsy retrotransposon genes in mammalian genomes. Cytogenet Genome Res 110(1-4):307-17 (2005).
Brandt et al. Transposable elements as a source of genetic innovation: expression and evolution of a family of retrotransposon-derived neogenes in mammals. Gene 345:101-111 (2005).
Canver et al.: BCL11A enhancer dissection by Cas9-mediated in situ saturating mutagenesis. Nature. 527(7577): 192-197 (2015).
Carr et al. Genome engineering. Nat Biotechnol. 27(12):1151-62 (2009).
Cermak et al., Efficient design and assembly of custom TALEN and other TAL effector-based constructs for DNA targeting. Nucleic Acids Research 39(12): e82 (2011).
Chen et al. Dynamic Imaging of Genomic Loci in Living Human Cells by an Optimized CRISPR/Cas System. Cell. 155(7):1479-1491 (2013).
Chen et al. Genome-wide CRISPR screen in a mouse model of tumor growth and metastasis. Cell. 160(6):1246-60 (2015).
Choi et al. Mechanism for the endocytosis of spherical nucleic acid nanoparticle conjugates. PNAS USA 110(19): 7625-7630 (2013).
Chung et al. Polycistronic RNA polymerase II expression vectors for RNA interference based on BIC/miR-155. Nucleic Acids Res 34(7):e53 (2006).
Coelho et al. Safety and efficacy of RN Ai therapy for transthyretin amyloidosis. New Engl J Med. 369(9):819-829 (2013).
Cong et al. Multiplex genome engineering using CRISPR/Cas systems. Science 339:819-823 (2013).
Co-pending U.S. Appl. No. 17/277,119, inventors Malone; Colin et al., filed Mar. 17, 2021.
Co-pending U.S. Appl. No. 17/473,209, inventors Malone; Colin et al., filed Sep. 13, 2021.
Co-pending U.S. Appl. No. 17/497,174, inventors Malone; Colin et al., filed Oct. 8, 2021.
Cox et al. RNA editing with CRISPR-Cas13. Science 358:1019-1027 (2017).
Craven et al. Dynamic interactions of the Gag polyprotein. Morphogenesis and maturation of retroviruses. pp. 65-94 (1996).
Cutler et al.: Polyvalent nucleic acid nanostructures. J Am Chem Soc. 133(24): 9254-9257 (2011).
Cutler et al. Spherical nucleic acids. J Am Chem Soc. 134(3):1376-1391 (2012).
Dahlman et al. In vivo endothelial siRNA delivery using polymeric nanoparticleswith low molecular weight. Nat Nanotechnol, 9(8):648-655 (2014).
Delamarre et al. A Novel Human T-leukemia Virus Type 1 Cell-To-Cell Transmission Assay Permits Definition of SU Glycoprotein Amino Acids Important for Infectivity. J. Virol. 71(1):259-266 (1997).
Dellinger et al. Streamlined process for the chemical synthesis of RNA using 2'-O-thionocarbamate-protected nucleoside phosphoramidites in the solid phase. J Am Chem Soc 133(30):11540-11556 (Jun. 20, 2011).
Deng et al. CASFISH: CRISPR/Cas9-mediated in situ labeling of genomic loci in fixed cells. PNAS USA 112:11870-11875 (2015).
Dickson et al. Protein biosynthesis and assembly. RNA tumor viruses (Weiss, N. Teich, H. Varmus, and J. Coffin, Eds. Cold Spring Harbor Laboratory, Cold Spring Harbor, N.Y. 1:513-648 (1984).
Doench et al. Rational design of highly active sgRNAs for CRISPR-Cas9-mediated gene inactivation. Nat Biotechnol 32:1262-1267 (2014).
Doyon et al. Enhancing zinc-finger-nuclease activity with improved obligate heterodimeric architectures. Nat Methods. 8(1):74-9 (2011).
File History for U.S. Appl. No. 16/876,731, filed Oct. 8, 2021 entitled Vaccine Compositions Comprising Endogenous Gag Polypeptides (downloaded Dec. 7, 2021).
File History for U.S. Appl. No. 17/277,119, filed Mar. 17, 2021 entitled Arc-Based Capsids and Uses Thereof (downloaded Dec. 7, 2021).
File History for U.S. Appl. No. 17/382,102, filed Jul. 21, 2021 entitled Arc-Based Capsids and Uses Thereof (downloaded Dec. 7, 2021).
File History for U.S. Appl. No. 17/473,209, filed Sep. 13, 2021 entitled Arc-Based Capsids and Uses Thereof (downloaded Dec. 7, 2021).
File History for U.S. Appl. No. 17/497,174, filed Oct. 8, 2021 entitled Arc-Based Capsids and Uses Thereof (downloaded Dec. 7, 2021).
Gao et al. Antibody-targeted immunoliposomes for cancer treatment. Mini. Rev. Med. Chem. 13(14):2026-2035 (2013).
Gao et al.: Engineered Cpf1 variants with altered PAM specificities. Nat Biotechnol 35(8): 789-792 (2017).
Gaudeli et al. Programmable base editing of A•T to G•C in genomic DNA without DNA cleavage. Nature 551:464-471 (2017).
Gross et al.: In vitro assembly properties of purified bacterially expressed capsid proteins of human immunodeficiency virus. Eur J Biochem. 249(2):592-600 (1997).
Haffar et al. Human immunodeficiency virus-like, non-replication, Gag-Env particles assemble in a recombinant vaccinia virus expression system. J. Virol. 64:2653-59 (1990).
Hendel et al. Chemically modified guide RN as enhance CRISPR-Cas genomeediting in human primary cells. Nat. Biotechnol. 33:985-989 (2015).
Hicke et al. Escort aptamers: a delivery service for diagnosis and therapy. J Clin Invest 106:923-928 (2000).
Howard, et al. Intracerebral drug delivery in rats with lesion-induced memory deficits. J Neurosurg. Jul. 1989;71(1):105-12.
Hsu et al. Development and applications of CRISPR-Cas9 for genome engineering. Cell 157(6):1262-78 (2014).

(56) References Cited

OTHER PUBLICATIONS

Hsu et al. DNA targeting specificity of RNA-guided Cas9 nucleases. Nat Biotechnol 31(9):827-832 (2013).
Hugo. Retrotransposon Gag like (RLT). Gene Nomenclature Committee. Available at https://www.genenames.org/data/genegroup/#!/group/1409 (Accessed Dec. 3, 2021).
Hunter. Macromolecular interactions in the assembly of HIV and other retroviruses. Seminars in Virology 5:71-83 (1994).
Inoue et al. An inducible translocation strategy to rapidly activate and inhibit small GTPase signaling pathways. Nat Methods 2(6):415-418 (2005).
Jensen et al. Spherical nucleic acid nanoparticle conjugates as an RNAi-based therapy for glioblastoma. Sci Transl Med. 5(209):209ra152 (2013).
Jiang, et al. RNA-guided editing of bacterial genomes using CRISPR-Cas systems. Nat Biotechnol. Mar. 2013;31(3):233-9. doi: 10.1038/nbt.2508. Epub Jan. 29, 2013.
Karlin, et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87:2264-2268 (1990).
Keefe et al. Aptamers as therapeutics. Nat. Rev. Drug Discov. 9:537-550 (2010).
Kim et al. Chimeric restriction endonuclease. PNAS USA. 91(3):883-7 (1994).
Kim et al. Highly efficient RNA-guided genome editing in human cells via delivery of purified Cas9 ribonucleoproteins. Genome Res. 24(6):1012-9 (2014).
Kim et al., Hybrid restriction enzymes: Zinc finger fusions to Fok I cleavage domain. Proc Natl Acad Sci 93: 1156-1160 (1996).
Kleinstiver et al. Engineered CRISPR-Cas9 nucleases with altered PAM specificities. Nature 523(7561):481-485 (2015).
Komor, et al. Programmable editing of a target base in genomic DNA without double-stranded DNA cleavage. Nature 533, 420-424 (2016).
Konermann et al.: Genome-scale transcriptional activation by an engineered CRISPR-Cas9 complex. Nature 517(7536):583-588 (2015).
Konermann et al.: Optical control of mammalian endogenous transcription and epigenetic states. Nature. 500(7463): 472-476 (2013).
Koonin et al., Origins and evolution of CRISPR-Cas systems. Phil Trans R. Soc. B 374(1772) 6 pages (2019).
Krausslich et al. Intracellular transport of retroviral capsid components. Morphogenesis and Maturation of Retroviruses pp. 25-64 (1996).
Lavillette et al. The envelope glycoprotein of human endogenous retrovirus type W uses a divergent family of amino acid transporters/cell surface receptors. J. Virol. 76:6442-6452 (2002).
Lee et al. Synthetically modified guide RNA and donor DNA are a versatile platform for CRISPR-Cas9 engineering. eLife. 6:e25312 (2017).
Levy et al. Cytosine and adenine base editing of the brain, liver, retina, heart and skeletal muscle of mice via adeno-associated viruses. Nat Biomed Eng 4(1):97-110 (2020).
Levy-Nissenbaum et al. Nanotechnology and aptamers: applications in drug delivery. Trends Biotechnol 26.8:442-449 (2008).
Li, et al. Base editing with a Cpf1-cytidine deaminase fusion. Nat. Biotechnol. 36:324-327 (2018).
Li et al. Cell culture processes for monoclonal antibody production. Mabs. 2(5):466-477 (2010).
Li et al., Engineering CRISPR-Cpf1 crRNAs and mRNAs to maximize genome editing efficiency. Nat Biomed Eng. 1(5):0066 (2017).
Liang et al. Engineering the ABA Plant Stress Pathway for Regulation of Induced Proximity. Sci Signal 4(164):rs2 (2011).
Lim et al. Altering the RNA binding specificity of a translational repressor. J Biol Chem 269(12):9006-9010 (1994).
Liu et al. Engineering cell signaling using tunable CRISPR-Cpf1-based transcription factors. Nat Commun 8:2095 (2017).

Madisen et al. Expression of the human immunodeficiency virus gag gene in insect cells. Virology 158:248-250 (1987).
Makarova et al. Classification and nomenclature of CRISPR-Cas systems: where from here?. The CRISPR Journal 1(5):325-336 (2018).
Makarova et al. Evolutionary classification of CRISPR-Cas systems: a burst of class 2 and derived variants. Nat Rev Microbiol. 18(2): 67-83 (2020).
Manjappa et al. Antibody derivatization and conjugation strategies: application in preparation of stealth immunoliposome to target chemotherapeutics to tumor, J. Control. Release 150(1):2-22 (2011).
Matsuda et al. Controlled expression of transgenes introduced by in vivo electroporation. PNAS 104(3):1027-2032 (2007).
Mirkin, C.: Interview: An interview with Chad Mirkin: nanomedicine expert. Interviewed by Hannah Stanwix. Nanomedicine (Lond). 7(5): 635-638 (2012).
Miyamoto et al. Rapid and orthogonal logic gating with a gibberellin-induced dimerization system. Nat Chem Biol 8(5):465-70 (2012).
Molavi et al. Anti-CD30 antibody conjugated liposomal doxorubicin with significantly improved therapeutic efficacy against anaplastic large cell lymphoma, Biomaterials 34(34):8718-25 (2013).
Morgan, R. A., et al., (2006), Cancer Regression in Patients After Transfer of Genetically Engineered Lymphocytes, Science 314:126-129.
Moscou, et al. A simple cipher governs DNA recognition by TAL effectors. Science. Dec. 11, 2009;326(5959):1501.
Nair et al. Multivalent N-acetylgalactosamine-conjugated siRNA localizes in hepatocytes and elicits robust RNAi-mediated gene silencing. J Am Chem Soc. 136(49):16958-16961 (2014).
Nakamura, et al., Codon usage tabulated from international DNA sequence databases: status for the year 2000. Nucleic Acids Res. 28(1):292 (2000).
Nishida et al., Targeted nucelotide editing using hybrid prokaryotic and vertebrate adaptive immune systems. Science 353(6305):aaf8729 (2016).
Nishimasu et al. Crystal Structure of Cas9 in Complex with Guide RNA and Target DNA. Cell 156(5):935-949 (2014).
Nishimasu et al. Crystal Structure of *Staphylococcus aureus* Cas9. Cell 162:1113-1126 (2015).
Nowak et al. Guide RNA engineering for versatile Cas9 functionality. Nucleic Acids Res. 44(20):9555-9564 (2016).
O'Hare et al. Transformation of mouse fibroblasts to methotrexate resistance by a recombinant plasmid expressing a prokaryotic dihydrofolate reductase. PNAS USA 78(3):1527-31 (1981).
Ostergaard et al. Efficient Synthesis and Biological Evaluation of 5'-GalNAc Conjugated Antisense Oligonucleotides. Bioconjugate Chem., 26(8):1451-1455 (2015).
Paige et al. RNA mimics of green fluorescent protein. Science 333(6042):642-6 (2011).
Paix et al. High Efficiency, Homology-Directed Genome Editing in Caenorhabditis elegans Using CRISPR-Cas9 Ribonucleoprotein Complexes. Genetics 201(1):47-54 (Sep. 2015).
Pang et al. PNMA family: Protein interaction network and cell signalling pathways implicated in cancer and apoptosis. Cell Signal 45:54-62 (2018).
Pardridge. Preparation of Trojan Horse Liposomes (THLs) for Gene Transfer across the Blood-Brain Barrier. Cold Spring Harb Protoc 2010(4):pdb.prot5407 (2010).
Parnas et al. A Genome-wide CRISPR Screen in Primary Immune Cells to Dissect Regulatory Networks. Cell 162:675-686 (Jul. 30, 2015).
PCT/US2021/032757 International Search Report and Written Opinion dated Sep. 14, 2021.
Peters et al. Recruitment of CRISPR-Cas systems by Tn7-like transposons. PNAS USA 114(35):E7358-E7366 (2017).
Platt, et al. CRISPR-Cas9 knockin mice for genome editing and cancer modeling. Cell 159(2):440-455 (2014).
Poulter et al. A retrotransposon family from the pufferfish (fugu) Fugu rubripesl. Gene 215:241-249 (1998).
Qiu et al. Mutation detection using Surveyor nuclease. Biotechniques 36:702-707 (2004).
Ramanan et al. CRISPR/Cas9 cleavage of viral DNA efficiently suppresses hepatitis B virus. Sci Rep 5:10833 (2015).

(56) References Cited

OTHER PUBLICATIONS

Ran et al. Double nicking by RNA-guided CRISPR Cas9 for enhanced genome editing specificity. Cell 154:1380-1389 (2013).
Ran et al. Genome engineering using the CRISPR-Cas9 system. Nature Protocols 8:2281-2308 (2013).
Ran et al. In vivo genome editing using *Staphylococcus aureus* Cas9. Nature. 520(7546):186-191 (2015).
Rees et al. Base editing: precision chemistry on the genome and transcriptome of living cells. Nat. Rev. Genet. 19(12):770-788 (2018).
Rosenberg et al. Early Assembly Step of a Retroviral Envelope Glycoprotein: Analysis Using a Dominant Negative Assay. J. Cell Biol. 145:57-68 (1999).
Smith et al. Human immunodeficiency virus type 1 Pr55gag and Pr160gag-pol expressed from a simian virus 40 late-replacement vector are efficiently processed and assembled into virus-like particles, J. Virol. 64:2743-50 (1990).
Sofou et al. Antibody-targeted liposomes in cancer therapy and imaging, Expert Opin. Drug Deliv. 5(2):189-204 (2008).
Sommerfelt et al. Importance of the p12 protein in Mason-Pfizer monkey virus assembly and infectivity. J. Virol. 66:7005-11 (1992).
Sonoke et al. Galactose-modified cationic liposomes as a liver-targeting delivery system for small interfering RNA. Biol Pharm Bull. 34(8):1338-42 (2011).
Strecker et al. RNA-guided DNA insertion with CRISPR-associated transposases. Science 365:48-53 (2019).
Sun et al. Cocoon-like self-degradable DNA nanoclew for anticancer drug delivery. J Am. Chem. Soc. 136:14722-14725 (2014).
Sun et al. Self-assembled DNA nanoclews for the efficient delivery of CRISPR-Cas9 for genome editing. Angew. Chem. Int. Ed.54(41):12029-12033 (2015).
Surace et al. Lipoplexes targeting the CD44 hyaluronic acid receptor for efficient transfection of breast cancer cells. J. Mol Pharm 6(4):1062-73 (2009).
Suzuki et al. In vivo genome editing via CRISPR/Cas9 mediated homology-independent targeted integration. Nature 540(7631):144-149 (2016).
Swiech et al. In vivo interrogation of gene function in the mammalian brain using CRISPR-Cas9. Nat Biotechnol 33:102-106 (2015).
Tabernero et al. First-in-Human Trial of an RNA Interference Therapeutic Targeting VEGF and KSP in Cancer Patients with Liver Involvement. Cancer Discovery 3(4):363-470 (Apr. 2013).
Takebe et al. SR alpha promoter: an efficient and versatile mammalian cDNA expression system composed of the simian virus 40 early promoter and the R-U5 segment of human T-cell leukemia virus type 1 long terminal repeat. Mol. Cell. Biol. 8(1):466-472 (1988).
Takeda et al. Synthetic and nature-derived lipid nanoparticles for neural regeneration. Neural Regen Res. 10(5):689-90 (May 2015).
Tato et al. A mutant of Rous sarcoma virus with a thermolabile defect in the virus envelope. Virology 88:71-81 (1978).
Topuzoğullari et al. An insight into the epitope-based peptide vaccine design strategy and studies against COVID-19. Turk J. Biol 44(3):215-227 (2020).
Torchilin. Antibody-modified liposomes for cancer chemotherapy. Expert Opin. Drug Deliv. 5(9):1003-1025 (2008).
Tristem. Identification and characterization of novel human endogenous retrovirus families by phylogenetic screening of the human genome mapping project database. J. Virol. 74:3715-3730 (2000).
Tsai et al., Dimeric CRISPR RNA-guided FokI nucleases for highly specific genome editing Nat. Biotechnol., 32(6):569-576 (2014).
Tuerk. Systematic evolution of ligands by exponential enrichment: RNA ligands to bacteriophage T4 DNA polymerase. Science 249:505-510 (1990).
U.S. Appl. No. 16/876,731 Office Action dated Apr. 5, 2021.
U.S. Appl. No. 16/876,731 Office Action dated Jan. 12, 2021.
U.S. Appl. No. 16/876,731 Office Action dated Nov. 17, 2020.
Vaux et al. Spike—nucleocapsid interaction in Semliki Forest virus reconstructed using network antibodies. Nature 336:36-42 (1988).
Wang et al. Combinatorially designed lipid-like nanoparticles for intracellular delivery of cytotoxic protein for cancer therapy. Agnew Chem Int Ed Engl., 53(11):2893-8 (2014).
Wang et al. Efficient delivery of genome-editing proteins using bioreducible lipid nanoparticles. PNAS USA 113:2868-2873 (2016).
Wang et al. Enhanced intracellular siRNA delivery using bioreducible lipid-like nanoparticles. Adv. Healthc Mater. 3(9):1398-403 (2014).
Wang et al. Genetic screens in human cells using CRISPR-Cas9 system. Science 343:80-84 (2014).
Wang et al. Hyaluronic Acid Modification of RNase A and its Intracellular Delivery Using Lipid-like Nanoparticles. J Control Release 263:39-45 (2017).
Wang et al. Integrating Protein Engineering and Bioorthogonal Click Conjugation for Extracellular Vesicle Modulation and Intracellular Delivery. PloS One 10(11):e0141860 (2015).
Wang et al. One-step generation of mice carrying mutations in multiple genes by CRISPR/Cas-mediated genome engineering. Cell 153:910-918 (2013).
Wang. Lyophilization and development of solid protein pharmaceuticals. Int. J. Pharm., 203(1-2):1-60 (2000).
Weintraub, K.: Biomedicine: The new gold standard. Nature. 495(7440):S14-S16 (2013).
Wills et al. Creation and expression of myristylated forms of Rous sarcoma virus Gag protein in mammalian cells. J. Virol. 63:4331-43 (1989).
Wu et al. Genome-wide binding of the CRISPR endonuclease Cas9 in mammalian cells. Nat Biotechnol. 32(7):670-676 (2014).
Xu et al. Sequence determinants of improved CRISPR sgRNA design. Genome Res 25:1147-1157 (Aug. 2015).
Yan et al. Cas13d Is a Compact RNA-Targeting Type VI CRISPR Effector Positively Modulated by a WYL-Domain-Containing Accessory Protein. Molecular Cell 70(2):327-339 (2018).
Yoshida et al. SARS-CoV-2-induced humoral immunity through B cell epitope analysis and neutralizing activity in COVID-19 infected individuals in Japan. bioRxiv (2020).
Young et al. Hollow spherical nucleic acids for intracellular gene regulation based upon biocompatible silica shells. Nano Lett. 12(7):3867-3871 (2012).
Zetsche et al. A split-Cas9 architecture for inducible genome editing and transcription modulation. Nat Biotechnol 33:139-142 (2015).
Zetsche et al. Cpf1 is a single RNA-guided endonuclease of a class 2 CRISPR-Cas system. Cell 163:759-771 (2015).
Zhang et al.: A Strategy for increasing drug solubility and efficacy through covalent attachment to polyvalent DNA-nanoparticle conjugates. ACS Nano. 5(9): 6962-6970 (2011).
Zhang et al. Antibody-linked spherical nucleic acids for cellular targeting. J. Am. Chem. Soc. 134:16488-1691 (2012).
Zheng et al. Topical delivery of siRNA-based spherical nucleic acid nanoparticle conjugates for gene regulation. PNAS USA 109(30):11975-11980 (2012).
Zhou et al. Aptamer-targeted cell-specific RNA interference. Silence 1(1):4 (2010).
Zuker et al. Optimal computer folding of large RNA sequences using thermodynamics and auxiliary information. Nucleic Acids Res. 9:133-148 (1981).
Hao et al.: Nucleic acid-gold nanoparticle conjugates as mimics of microRNA. Small. 7(22): 3158-3162 (2011).
U.S. Appl. No. 17/382,102 Office Action dated Feb. 22, 2022.
U.S. Appl. No. 17/497,174 Restriction Requirement dated Apr. 4, 2022.
Rueckert. Chapter 32: Picornaviruses and Their Replication. Virology. B. N. Fields et al. (eds.) Raven Press, New York, pp. 705-738 (1985).
Saudek et al. A preliminary trial of the programmable implantable medication system for insulin delivery. N. Engl. J. Med. 321:574 (1989).
Scaringe. Advanced 5'-Silyl-2'-Orthoester Approach to RNA Oligonucleotide Synthesis. Methods Enzymology. 317:3-18 (2000).
Scaringe et al. Novel RNA synthesis method using 5'-0-silyl-2'-0-orthoester protecting groups. J Am Chem Soc 120:11820-11821 (1998).

(56) References Cited

OTHER PUBLICATIONS

Schiffelers et al. Cancer siRNA therapy by tumor selective delivery with ligand-targeted sterically stabilized nanoparticle. Nucleic Acids Res 32(19):e149 (2004).
Shalem et al. Genome-scale CRISPR-Cas9 knockout screening in human cells. Science 343(6166):84-87 (2014).
Shalem, et al. High-throughput functional genomics using CRISPR-Cas9. Nature Reviews Genetics16.5 (2015): 299.
Shmakov et al. Discovery and Functional Characterization of Diverse Class 2 CRISPR-Cas Systems. Mol Cell 60(3):385-397 (2015).
Slaymaker et al. Rationally engineered Cas9 nucleases with improved specificity. Science 351(6268):84-88 (Jan. 1, 2016).
Smith et al. Human immunodeficiency virus type 1 Pr55gag and Pr160gag-pol expressed from a simian virus 40 late-replacement vector are efficiently processed and assembled into virus-like particles, J. Virol. 64:2743-50 (1990).
Abed et al. The Gag protein PEG10 binds to RNA and regulates trophoblast stem cell lineage specification. PLoS One 14(4):e0214110 (2019).
Lizatovic et al. A Protein-Based Encapsulation System with Calcium-Controlled Cargo Loading and Detachment. Angew Chem Int Ed Engl 57(35):11334-11338 (2018).
Volff et al. Cellular Genes Derived from Gypsy/Ty3 Retrotransposons in Mammalian Genomes. An N Y Acad Sci 1178(1):233-243 (2009).
Woycechowsky. Protein capsids as molecular containers: Cargo Loading and controlled release. J Nanomater Mol Nanotechnol 6:5 (2017).

* cited by examiner

Engineered Arc

Reengineering Arc to carry specific RNA payload

Reengineering Arc to remove off-function effects

Delivering Cre-Loaded Capsids

SEQUENCE LISTING

<160> NUMBER OF SEQ ID NOS: 85

<210> SEQ ID NO 1
<211> LENGTH: 396
<212> TYPE: PRT
<213> ORGANISM: Homo sapiens

<400> SEQUENCE: 1

Gly Glu Leu Asp His Arg Thr Ser Gly Gly Leu His Ala Tyr Pro Gly
1               5                   10                  15

Pro Arg Gly Gly Gln Val Ala Lys Pro Asn Val Ile Leu Gln Ile Gly
            20                  25                  30

Lys Cys Arg Ala Glu Met Leu Glu His Val Arg Arg Thr His Arg His
        35                  40                  45

Leu Leu Ala Glu Val Ser Lys Gln Val Glu Arg Glu Leu Lys Gly Leu

His Arg Ser Val Gly Lys Leu Glu Ser Asn Leu Asp Gly Tyr Val Pro
65                  70                  75                  80

Thr Ser Asp Ser Gln Arg Trp Lys Lys Ser Ile Lys Ala Cys Leu Cys
            85                  90                  95

Arg Cys Gln Glu Thr Ile Ala Asn Leu Glu Arg Trp Val Lys Arg Glu
                100                 105                 110

Met His Val Trp Arg Glu Val Phe Tyr Arg Leu Glu Arg Trp Ala Asp
            115                 120                 125

Arg Leu Glu Ser Thr Gly Gly Lys Tyr Pro Val Gly Ser Glu Ser Ala
        130                 135                 140

Arg His Thr Val Ser Val Gly Val Gly Gly Pro Glu Ser Tyr Cys His
145                 150                 155                 160

Glu Ala Asp Gly Tyr Asp Tyr Thr Val Ser Pro Tyr Ala Ile Thr Pro
                165                 170                 175

Pro Pro Ala Ala Gly Glu Leu Pro Gly Gln Glu Pro Ala Glu Ala Gln
            180                 185                 190

Gln Tyr Gln Pro Trp Val Pro Gly Glu Asp Gly Gln Pro Ser Pro Gly
        195                 200                 205

Val Asp Thr Gln Ile Phe Glu Asp Pro Arg Glu Phe Leu Ser His Leu
210                 215                 220

Glu Glu Tyr Leu Arg Gln Val Gly Gly Ser Glu Glu Tyr Trp Leu Ser
225                 230                 235                 240

Gln Ile Gln Asn His Met Asn Gly Pro Ala Lys Lys Trp Trp Glu Phe
                245                 250                 255

Lys Gln Gly Ser Val Lys Asn Trp Val Glu Phe Lys Lys Glu Phe Leu
            260                 265                 270

Gln Tyr Ser Glu Gly Thr Leu Ser Arg Glu Ala Ile Gln Arg Glu Leu
        275                 280                 285

Asp Leu Pro Gln Lys Gln Gly Glu Pro Leu Asp Gln Phe Leu Trp Arg
290                 295                 300

Lys Arg Asp Leu Tyr Gln Thr Leu Tyr Val Asp Ala Asp Glu Glu Glu
305                 310                 315                 320

Ile Ile Gln Tyr Val Val Gly Thr Leu Gln Pro Lys Leu Lys Arg Phe
                325                 330                 335

Leu Arg His Pro Leu Pro Lys Thr Leu Glu Gln Leu Ile Gln Arg Gly
            340                 345                 350

Met Glu Val Gln Asp Asp Leu Glu Gln Ala Ala Glu Pro Ala Gly Pro
        355                 360                 365

His Leu Pro Val Glu Asp Glu Ala Glu Thr Leu Thr Pro Ala Pro Asn
370                 375                 380

Ser Glu Ser Val Ala Ser Asp Arg Thr Gln Pro Glu
385                 390                 395

<210> SEQ ID NO 2
<211> LENGTH: 396
<212> TYPE: PRT
<213> ORGANISM: Orcinus orca

<400> SEQUENCE: 2

Gly Glu Leu Asp Gln Arg Thr Thr Gly Gly Leu His Ala Tyr Pro Ala
1               5                   10                  15

Pro Arg Gly Gly Pro Val Ala Lys Pro Asn Val Ile Leu Gln Ile Gly
            20                  25                  30

-continued

```
Lys Cys Arg Ala Glu Met Leu Glu His Val Arg Arg Thr His Arg His
         35                  40                  45

Leu Leu Thr Glu Val Ser Lys Gln Val Glu Arg Glu Leu Lys Gly Leu
 50                  55                  60

His Arg Ser Val Gly Lys Leu Glu Ser Asn Leu Asp Gly Tyr Val Pro
 65                  70                  75                  80

Thr Gly Asp Ser Gln Arg Trp Arg Lys Ser Ile Lys Ala Cys Leu Cys
                 85                  90                  95

Arg Cys Gln Glu Thr Ile Ala Asn Leu Glu Arg Trp Val Lys Arg Glu
            100                 105                 110

Met His Val Trp Arg Glu Val Phe Tyr Arg Leu Glu Arg Trp Ala Asp
        115                 120                 125

Arg Leu Glu Ser Met Gly Gly Lys Tyr Pro Val Gly Ser Asn Pro Ser
    130                 135                 140

Arg His Thr Thr Ser Val Gly Val Gly Gly Pro Glu Ser Tyr Gly His
145                 150                 155                 160

Glu Ala Asp Thr Tyr Asp Tyr Thr Val Ser Pro Tyr Ala Ile Thr Pro
                165                 170                 175

Pro Pro Ala Ala Gly Glu Leu Pro Gly Gln Glu Ala Val Glu Ala Gln
            180                 185                 190

Gln Tyr Pro Pro Trp Gly Leu Gly Glu Asp Gly Gln Pro Ser Pro Gly
        195                 200                 205

Val Asp Thr Gln Ile Phe Glu Asp Pro Arg Glu Phe Leu Ser His Leu
    210                 215                 220

Glu Glu Tyr Leu Arg Gln Val Gly Gly Ser Glu Glu Tyr Trp Leu Ser
225                 230                 235                 240

Gln Ile Gln Asn His Met Asn Gly Pro Ala Lys Lys Trp Trp Glu Tyr
                245                 250                 255

Lys Gln Gly Ser Val Lys Asn Trp Val Glu Phe Lys Lys Glu Phe Leu
            260                 265                 270

Gln Tyr Ser Glu Gly Ala Leu Ser Arg Glu Ala Val Gln Arg Glu Leu
        275                 280                 285

Asp Leu Pro Gln Lys Gln Gly Glu Pro Leu Asp Gln Phe Leu Trp Arg
    290                 295                 300

Lys Arg Asp Leu Tyr Gln Thr Leu Tyr Val Asp Ala Asp Glu Glu Glu
305                 310                 315                 320

Ile Ile Gln Tyr Val Val Gly Thr Leu Gln Pro Lys Leu Lys Arg Phe
                325                 330                 335

Leu Arg Pro Pro Leu Pro Lys Thr Leu Glu Gln Leu Ile Gln Lys Gly
            340                 345                 350

Met Glu Val Glu Asp Gly Leu Glu Gln Val Ala Glu Pro Ala Ser Pro
        355                 360                 365

His Leu Pro Thr Glu Glu Ser Glu Ala Leu Thr Pro Ala Leu Thr
    370                 375                 380

Ser Glu Ser Val Ala Ser Asp Arg Thr Gln Pro Glu
385                 390                 395
```

<210> SEQ ID NO 3
<211> LENGTH: 390
<212> TYPE: PRT
<213> ORGANISM: Odocoileus virginianus texanus

<400> SEQUENCE: 3

```
Gly Glu Leu Asp His Arg Thr Thr Gly Gly Leu His Ala Tyr Pro Ala
 1               5                  10                  15
```

Pro Arg Gly Gly Pro Ala Ala Lys Pro Asn Val Ile Leu Gln Ile Gly
            20                  25                  30

Lys Cys Arg Ala Glu Met Leu Glu His Val Arg Arg Thr His Arg His
        35                  40                  45

Leu Leu Ala Glu Val Ser Lys Gln Val Glu Arg Glu Leu Lys Gly Leu
    50                  55                  60

His Arg Ser Val Gly Lys Leu Glu Ser Asn Leu Asp Gly Tyr Val Pro
65                  70                  75                  80

Thr Gly Asp Ser Gln Arg Trp Lys Lys Ser Ile Lys Ala Cys Leu Ser
                85                  90                  95

Arg Cys Gln Glu Thr Ile Ala Asn Leu Glu Arg Trp Val Lys Arg Glu
            100                 105                 110

Met His Val Trp Arg Glu Val Phe Tyr Arg Leu Glu Arg Trp Ala Asp
        115                 120                 125

Arg Leu Glu Ser Gly Gly Lys Tyr Pro Val Gly Ser Asp Pro Ala
    130                 135                 140

Arg His Thr Val Ser Val Gly Val Gly Pro Glu Ser Tyr Cys Gln
145                 150                 155                 160

Asp Ala Asp Asn Tyr Asp Tyr Thr Val Ser Pro Tyr Ala Ile Thr Pro
                165                 170                 175

Pro Pro Ala Ala Gly Gln Leu Pro Gly Gln Glu Glu Val Glu Ala Gln
            180                 185                 190

Gln Tyr Pro Pro Trp Ala Pro Gly Glu Asp Gly Gln Leu Ser Pro Gly
        195                 200                 205

Val Asp Thr Gln Val Phe Glu Asp Pro Arg Glu Phe Leu Arg His Leu
    210                 215                 220

Glu Asp Tyr Leu Arg Gln Val Gly Gly Ser Glu Glu Tyr Trp Leu Ser
225                 230                 235                 240

Gln Ile Gln Asn His Met Asn Gly Pro Ala Lys Lys Trp Trp Glu Tyr
                245                 250                 255

Lys Gln Gly Ser Val Lys Asn Trp Val Glu Phe Lys Lys Glu Phe Leu
            260                 265                 270

Gln Tyr Ser Glu Gly Thr Leu Ser Arg Glu Ala Ile Gln Arg Glu Leu
        275                 280                 285

Asp Leu Pro Gln Lys Gln Gly Glu Pro Leu Asp Gln Phe Leu Trp Arg
    290                 295                 300

Lys Arg Asp Leu Tyr Gln Thr Leu Tyr Val Asp Ala Glu Glu Glu
305                 310                 315                 320

Ile Ile Gln Tyr Val Val Gly Thr Leu Gln Pro Lys Leu Lys Arg Phe
                325                 330                 335

Leu Arg Pro Pro Leu Pro Lys Thr Leu Glu Gln Leu Ile Gln Lys Gly
            340                 345                 350

Met Glu Val Gln Asp Gly Leu Glu Gln Ala Ala Glu Pro Ala Ala Glu
        355                 360                 365

Glu Ala Glu Ala Leu Thr Pro Ala Leu Thr Asn Glu Ser Val Ala Ser
    370                 375                 380

Asp Arg Thr Gln Pro Glu
385                 390

<210> SEQ ID NO 4
<211> LENGTH: 401
<212> TYPE: PRT
<213> ORGANISM: Ornithorhynchus anatinus

<400> SEQUENCE: 4

```
Gly Glu Leu Asp Arg Leu Asn Pro Ser Ser Gly Leu His Pro Ser Ser
1               5                   10                  15
Gly Leu His Pro Tyr Pro Gly Leu Arg Gly Gly Ala Thr Ala Lys Pro
            20                  25                  30
Asn Val Ile Leu Gln Ile Gly Lys Cys Arg Ala Glu Met Leu Glu His
        35                  40                  45
Val Arg Lys Thr His Arg His Leu Leu Thr Glu Val Ser Arg Gln Val
    50                  55                  60
Glu Arg Glu Leu Lys Gly Leu His Lys Ser Val Gly Lys Leu Glu Ser
65                  70                  75                  80
Asn Leu Asp Gly Tyr Val Pro Ser Ser Asp Ser Gln Arg Trp Lys Lys
                85                  90                  95
Ser Ile Lys Ala Cys Leu Ser Arg Cys Gln Glu Thr Ile Ala His Leu
            100                 105                 110
Glu Arg Trp Val Lys Arg Glu Met Asn Val Trp Arg Glu Val Phe Tyr
        115                 120                 125
Arg Leu Glu Arg Trp Ala Asp Arg Leu Glu Ala Met Gly Gly Lys Tyr
    130                 135                 140
Pro Ala Gly Glu Gln Ala Arg Arg Thr Val Ser Val Gly Val Gly Gly
145                 150                 155                 160
Pro Glu Thr Cys Cys Pro Gly Asp Glu Ser Tyr Asp Cys Pro Ile Ser
                165                 170                 175
Pro Tyr Ala Val Pro Pro Ser Thr Gly Glu Ser Pro Glu Ser Leu Asp
            180                 185                 190
Gln Gly Asp Gln His Tyr Gln Gln Trp Phe Ala Leu Pro Glu Glu Ser
        195                 200                 205
Pro Val Ser Pro Gly Val Asp Thr Gln Ile Phe Glu Asp Pro Arg Glu
    210                 215                 220
Phe Leu Arg His Leu Glu Lys Tyr Leu Lys Gln Val Gly Gly Thr Glu
225                 230                 235                 240
Glu Asp Trp Leu Ser Gln Ile Gln Asn His Met Asn Gly Pro Ala Lys
                245                 250                 255
Lys Trp Trp Glu Tyr Lys Gln Gly Ser Val Lys Asn Trp Leu Glu Phe
            260                 265                 270
Lys Lys Glu Phe Leu Gln Tyr Ser Glu Gly Thr Leu Thr Arg Asp Ala
        275                 280                 285
Leu Lys Arg Glu Leu Asp Leu Pro Gln Lys Gln Gly Glu Pro Leu Asp
    290                 295                 300
Gln Phe Leu Trp Arg Lys Arg Asp Leu Tyr Gln Thr Leu Tyr Val Asp
305                 310                 315                 320
Ala Asp Glu Glu Glu Ile Ile Gln Tyr Val Val Gly Thr Leu Gln Pro
                325                 330                 335
Lys Leu Lys Arg Phe Leu His His Pro Leu Pro Lys Thr Leu Glu Gln
            340                 345                 350
Leu Ile Gln Arg Gly Gln Glu Val Gln Asn Gly Leu Glu Pro Thr Asp
        355                 360                 365
Asp Pro Ala Gly Gln Arg Thr Gln Ser Glu Asp Asn Asp Glu Ser Leu
    370                 375                 380
Thr Pro Ala Val Thr Asn Glu Ser Thr Ala Ser Glu Gly Thr Leu Pro
385                 390                 395                 400
Glu
```

```
<210> SEQ ID NO 5
<211> LENGTH: 404
<212> TYPE: PRT
<213> ORGANISM: Anser cygnoides domesticus

<400> SEQUENCE: 5

Gly Gln Leu Asp Asn Val Thr Asn Ala Gly Ile His Ser Phe Gln Gly
1               5                   10                  15

His Arg Gly Val Ala Asn Lys Pro Asn Val Ile Leu Gln Ile Gly Lys
            20                  25                  30

Cys Arg Ala Glu Met Leu Glu His Val Arg Arg Thr His Arg His Leu
        35                  40                  45

Leu Ser Glu Val Ser Lys Gln Val Glu Arg Glu Leu Lys Gly Leu Gln
    50                  55                  60

Lys Ser Val Gly Lys Leu Glu Asn Asn Leu Glu Asp His Val Pro Thr
65                  70                  75                  80

Asp Asn Gln Arg Trp Lys Lys Ser Ile Lys Ala Cys Leu Ala Arg Cys
                85                  90                  95

Gln Glu Thr Ile Ala His Leu Glu Arg Trp Val Lys Arg Glu Met Asn
            100                 105                 110

Val Trp Lys Glu Val Phe Phe Arg Leu Glu Lys Trp Ala Asp Arg Leu
        115                 120                 125

Glu Ser Met Gly Gly Lys Tyr Cys Pro Gly His Gly Lys Gln Thr
    130                 135                 140

Val Ser Val Gly Val Gly Gly Pro Glu Ile Arg Pro Ser Gly Glu
145                 150                 155                 160

Ile Tyr Asp Tyr Ala Leu Asp Met Ser Gln Met Tyr Ala Leu Thr Pro
                165                 170                 175

Pro Pro Gly Glu Met Pro Ser Ile Pro Gln Ala His Asp Ser Tyr Gln
            180                 185                 190

Trp Val Ser Val Ser Glu Asp Ala Pro Ala Ser Pro Val Glu Thr Gln
        195                 200                 205

Val Phe Glu Asp Pro Arg Glu Phe Leu Ser His Leu Glu Glu Tyr Leu
    210                 215                 220

Lys Gln Val Gly Gly Thr Glu Glu Tyr Trp Leu Ser Gln Ile Gln Asn
225                 230                 235                 240

His Met Asn Gly Pro Ala Lys Lys Trp Trp Glu Tyr Lys Gln Asp Ser
                245                 250                 255

Val Lys Asn Trp Val Glu Phe Lys Lys Glu Phe Leu Gln Tyr Ser Glu
            260                 265                 270

Gly Thr Leu Thr Arg Asp Ala Ile Lys Arg Glu Leu Asp Leu Pro Gln
        275                 280                 285

Lys Glu Gly Glu Pro Leu Asp Gln Phe Leu Trp Arg Lys Arg Asp Leu
    290                 295                 300

Tyr Gln Thr Leu Tyr Val Asp Ala Asp Glu Glu Ile Ile Gln Tyr
305                 310                 315                 320

Val Val Gly Thr Leu Gln Pro Lys Leu Lys Arg Phe Leu Ser Tyr Pro
                325                 330                 335

Leu Pro Lys Thr Leu Glu Gln Leu Ile Gln Arg Gly Lys Glu Val Gln
            340                 345                 350

Gly Asn Met Asp His Ser Asp Glu Pro Ser Pro Gln Arg Thr Pro Glu
        355                 360                 365

Ile Gln Ser Gly Asp Ser Val Glu Ser Met Pro Pro Ser Thr Thr Ala
    370                 375                 380
```

Ser Pro Val Pro Ser Asn Gly Thr Gln Pro Glu Pro Ser Pro Pro
385                 390                 395                 400

Ala Thr Val Ile

<210> SEQ ID NO 6
<211> LENGTH: 395
<212> TYPE: PRT
<213> ORGANISM: Pelecanus crispus

<400> SEQUENCE: 6

Gly Gln Leu Asp Asn Val Thr Asn Ala Gly Ile His Ser Phe Gln Gly
1               5                   10                  15

His Arg Gly Val Ala Asn Lys Pro Asn Val Ile Leu Gln Ile Gly Lys
            20                  25                  30

Cys Arg Ala Glu Met Leu Glu His Val Arg Arg Thr His Arg His Leu
        35                  40                  45

Leu Ser Glu Val Ser Lys Gln Val Glu Arg Glu Leu Lys Gly Leu Gln
    50                  55                  60

Lys Ser Val Gly Lys Leu Glu Asn Asn Leu Glu Asp His Val Pro Thr
65                  70                  75                  80

Asp Asn Gln Arg Trp Lys Lys Ser Ile Lys Ala Cys Leu Ala Arg Cys
                85                  90                  95

Gln Glu Thr Ile Ala His Leu Glu Arg Trp Val Lys Arg Glu Met Asn
            100                 105                 110

Val Trp Lys Glu Val Phe Phe Arg Leu Glu Lys Trp Ala Asp Arg Leu
        115                 120                 125

Glu Ser Met Gly Gly Lys Tyr Cys Pro Gly Glu His Gly Lys Gln Thr
    130                 135                 140

Val Ser Val Gly Val Gly Gly Pro Glu Ile Arg Pro Ser Glu Gly Glu
145                 150                 155                 160

Ile Tyr Asp Tyr Ala Leu Asp Met Ser Gln Met Tyr Ala Leu Thr Pro
                165                 170                 175

Pro Pro Gly Glu Val Pro Ser Ile Pro Gln Ala His Asp Ser Tyr Gln
            180                 185                 190

Trp Val Ser Val Ser Glu Asp Ala Pro Ala Ser Pro Val Glu Thr Gln
        195                 200                 205

Val Phe Glu Asp Pro Arg Glu Phe Leu Ser His Leu Glu Glu Tyr Leu
    210                 215                 220

Lys Gln Val Gly Gly Thr Glu Glu Tyr Trp Leu Ser Gln Ile Gln Asn
225                 230                 235                 240

His Met Asn Gly Pro Ala Lys Lys Trp Trp Glu Tyr Lys Gln Asp Ser
                245                 250                 255

Val Lys Asn Trp Val Glu Phe Lys Lys Glu Phe Leu Gln Tyr Ser Glu
            260                 265                 270

Gly Thr Leu Thr Arg Asp Ala Ile Lys Arg Glu Leu Asp Leu Pro Gln
        275                 280                 285

Lys Glu Gly Glu Pro Leu Asp Gln Phe Leu Trp Arg Lys Arg Asp Leu
    290                 295                 300

Tyr Gln Thr Leu Tyr Val Asp Ala Asp Glu Glu Ile Ile Gln Tyr
305                 310                 315                 320

Val Val Gly Thr Leu Gln Pro Lys Leu Lys Arg Phe Leu Ser Tyr Pro
                325                 330                 335

Leu Pro Lys Thr Leu Glu Gln Leu Ile Gln Arg Gly Lys Glu Val Gln
            340                 345                 350

Gly Asn Met Asp His Ser Glu Glu Pro Ser Pro Gln Arg Thr Pro Glu
            355                 360                 365

Ile Gln Ser Gly Asp Ser Val Asp Ser Val Pro Pro Ser Thr Thr Ala
370                 375                 380

Ser Pro Val Pro Ser Asn Gly Thr Gln Pro Glu
385                 390                 395

<210> SEQ ID NO 7
<211> LENGTH: 395
<212> TYPE: PRT
<213> ORGANISM: Haliaeetus albicilla

<400> SEQUENCE: 7

Gly Gln Leu Asp Asn Val Thr Asn Ala Gly Ile His Ser Phe Gln Gly
1               5                   10                  15

His Arg Gly Val Ala Asn Lys Pro Asn Val Ile Leu Gln Ile Gly Lys
            20                  25                  30

Cys Arg Ala Glu Met Leu Glu His Val Arg Arg Thr His Arg His Leu
        35                  40                  45

Leu Ser Glu Val Ser Lys Gln Val Glu Arg Glu Leu Lys Gly Leu Gln
50                  55                  60

Lys Ser Val Gly Lys Leu Glu Asn Asn Leu Glu Asp His Val Pro Thr
65                  70                  75                  80

Asp Asn Gln Arg Trp Lys Lys Ser Ile Lys Ala Cys Leu Ala Arg Cys
                85                  90                  95

Gln Glu Thr Ile Ala His Leu Glu Arg Trp Val Lys Arg Glu Met Asn
            100                 105                 110

Val Trp Lys Glu Val Phe Phe Arg Leu Glu Lys Trp Ala Asp Arg Leu
        115                 120                 125

Glu Ser Met Gly Gly Lys Tyr Cys Pro Gly Asp His Gly Lys Gln Thr
130                 135                 140

Val Ser Val Gly Val Gly Gly Pro Glu Ile Arg Pro Ser Glu Gly Glu
145                 150                 155                 160

Ile Tyr Asp Tyr Ala Leu Asp Met Ser Gln Met Tyr Ala Leu Thr Pro
                165                 170                 175

Pro Pro Gly Glu Val Pro Ser Ile Pro Gln Ala His Asp Ser Tyr Gln
            180                 185                 190

Trp Val Ser Thr Ser Glu Asp Ala Pro Ala Ser Pro Val Glu Thr Gln
        195                 200                 205

Val Phe Glu Asp Pro Arg Glu Phe Leu Ser His Leu Glu Glu Tyr Leu
210                 215                 220

Lys Gln Val Gly Gly Thr Glu Glu Tyr Trp Leu Ser Gln Ile Gln Asn
225                 230                 235                 240

His Met Asn Gly Pro Ala Lys Lys Trp Trp Glu Tyr Lys Gln Asp Ser
                245                 250                 255

Val Lys Asn Trp Val Glu Phe Lys Lys Glu Phe Leu Gln Tyr Ser Glu
            260                 265                 270

Gly Thr Leu Thr Arg Asp Ala Ile Lys Arg Glu Leu Asp Leu Pro Gln
        275                 280                 285

Lys Glu Gly Glu Pro Leu Asp Gln Phe Leu Trp Arg Lys Arg Asp Leu
290                 295                 300

Tyr Gln Thr Leu Tyr Val Asp Ala Asp Glu Glu Ile Ile Gln Tyr
305                 310                 315                 320

Val Val Gly Thr Leu Gln Pro Lys Leu Lys Arg Phe Leu Ser Tyr Pro

```
                    325                 330                 335
Leu Pro Lys Thr Leu Glu Gln Leu Ile Gln Arg Gly Lys Glu Val Gln
                340                 345                 350

Gly Asn Met Asp His Ser Glu Glu Pro Ser Pro Gln Arg Thr Pro Glu
            355                 360                 365

Ile Gln Ser Gly Asp Ser Val Asp Ser Val Pro Pro Ser Thr Thr Ala
        370                 375                 380

Ser Pro Val Pro Ser Asn Gly Thr Gln Pro Glu
385                 390                 395

<210> SEQ ID NO 8
<211> LENGTH: 465
<212> TYPE: PRT
<213> ORGANISM: Ophiophagus hannah

<400> SEQUENCE: 8

Gly Ser Trp Gly Leu Gln Arg His Val Ala Asp Glu Arg Arg Gly Leu
1               5                   10                  15

Ala Thr Pro Thr Tyr Gly Ala Val Cys Ser Ile Arg Glu Lys Lys Ala
            20                  25                  30

Ser Gln Leu Ser Gly Gln Ser Cys Leu Glu Lys Glu Leu Leu Gly Trp
        35                  40                  45

Lys Cys Thr Glu Ala Ile Val Glu Met Met Gln Val Asp Asn Phe Asn
50                  55                  60

His Gly Asn Leu His Ser Cys Gln Gly His Arg Gly Met Ala Asn His
65                  70                  75                  80

Lys Pro Asn Val Ile Leu Gln Ile Gly Lys Cys Arg Ala Glu Met Leu
                85                  90                  95

Asp His Val Arg Arg Thr His Arg His Leu Leu Thr Glu Val Ser Lys
            100                 105                 110

Gln Val Glu Arg Glu Leu Lys Ser Leu Gln Lys Ser Val Gly Lys Leu
        115                 120                 125

Glu Asn Asn Leu Glu Asp His Val Pro Ser Ala Ala Glu Asn Gln Arg
130                 135                 140

Trp Lys Lys Ser Ile Lys Ala Cys Leu Ala Arg Cys Gln Glu Thr Ile
145                 150                 155                 160

Ala His Leu Glu Arg Trp Val Lys Arg Glu Ile Asn Val Trp Lys Glu
                165                 170                 175

Val Phe Phe Arg Leu Glu Lys Trp Ala Asp Arg Leu Glu Ser Gly Gly
            180                 185                 190

Gly Lys Tyr Gly Pro Gly Asp Gln Ser Arg Gln Thr Val Ser Val Gly
        195                 200                 205

Val Gly Ala Pro Glu Ile Gln Pro Arg Lys Glu Ile Tyr Asp Tyr
210                 215                 220

Ala Leu Asp Met Ser Gln Met Tyr Ala Leu Thr Pro Pro Met Gly
225                 230                 235                 240

Glu Asp Pro Asn Val Pro Gln Ser His Asp Ser Tyr Gln Trp Ile Thr
                245                 250                 255

Ile Ser Asp Asp Ser Pro Pro Ser Pro Val Glu Thr Gln Ile Phe Glu
            260                 265                 270

Asp Pro Arg Glu Phe Leu Thr His Leu Glu Asp Tyr Leu Lys Gln Val
        275                 280                 285

Gly Gly Thr Glu Glu Tyr Trp Leu Ser Gln Ile Gln Asn His Met Asn
290                 295                 300
```

```
Gly Pro Ala Lys Lys Trp Glu Tyr Lys Gln Asp Ser Val Lys Asn
305                 310                 315                 320

Trp Leu Glu Phe Lys Lys Glu Phe Leu Gln Tyr Ser Glu Gly Thr Leu
                325                 330                 335

Thr Arg Asp Ala Ile Lys Gln Glu Leu Asp Leu Pro Gln Lys Asp Gly
                340                 345                 350

Glu Pro Leu Asp Gln Phe Leu Trp Arg Lys Arg Asp Leu Tyr Gln Thr
            355                 360                 365

Leu Tyr Ile Asp Ala Glu Glu Glu Val Ile Gln Tyr Val Val Gly
370                 375                 380

Thr Leu Gln Pro Lys Leu Lys Arg Phe Leu Ser His Pro Tyr Pro Lys
385                 390                 395                 400

Thr Leu Glu Gln Leu Ile Gln Arg Gly Lys Glu Val Glu Gly Asn Leu
                405                 410                 415

Asp Asn Ser Glu Glu Pro Ser Pro Gln Arg Ser Pro Lys His Gln Leu
            420                 425                 430

Gly Gly Ser Val Glu Ser Leu Pro Pro Ser Ser Thr Ala Ser Pro Val
            435                 440                 445

Ala Ser Asp Glu Thr His Pro Asp Val Ser Ala Pro Val Thr Val
450                 455                 460

Ile
465

<210> SEQ ID NO 9
<211> LENGTH: 451
<212> TYPE: PRT
<213> ORGANISM: Austrofundulus limnaeus

<400> SEQUENCE: 9

Gly Asp Gly Glu Thr Gln Ala Glu Asn Pro Ser Thr Ser Leu Asn Asn
1               5                   10                  15

Thr Asp Glu Asp Ile Leu Glu Gln Leu Lys Lys Ile Val Met Asp Gln
                20                  25                  30

Gln His Leu Tyr Gln Lys Glu Leu Lys Ala Ser Phe Glu Gln Leu Ser
            35                  40                  45

Arg Lys Met Phe Ser Gln Met Glu Gln Met Asn Ser Lys Gln Thr Asp
50                  55                  60

Leu Leu Leu Glu His Gln Lys Gln Thr Val Lys His Val Asp Lys Arg
65                  70                  75                  80

Val Glu Tyr Leu Arg Ala Gln Phe Asp Ala Ser Leu Gly Trp Arg Leu
                85                  90                  95

Lys Glu Gln His Ala Asp Ile Thr Thr Lys Ile Ile Pro Glu Ile Ile
            100                 105                 110

Gln Thr Val Lys Glu Asp Ile Ser Leu Cys Leu Ser Thr Leu Cys Ser
            115                 120                 125

Ile Ala Glu Asp Ile Gln Thr Ser Arg Ala Thr Thr Val Thr Gly His
            130                 135                 140

Ala Ala Val Gln Thr His Pro Val Asp Leu Leu Gly Glu His His Leu
145                 150                 155                 160

Gly Thr Thr Gly His Pro Arg Leu Gln Ser Thr Arg Val Gly Lys Pro
                165                 170                 175

Asp Asp Val Pro Glu Ser Pro Val Ser Leu Phe Met Gln Gly Glu Ala
            180                 185                 190

Arg Ser Arg Ile Val Gly Lys Ser Pro Ile Lys Leu Gln Phe Pro Thr
            195                 200                 205
```

Phe Gly Lys Ala Asn Asp Ser Ser Asp Pro Leu Gln Tyr Leu Glu Arg
    210                 215                 220

Cys Glu Asp Phe Leu Ala Leu Asn Pro Leu Thr Asp Glu Glu Leu Met
225                 230                 235                 240

Ala Thr Leu Arg Asn Val Leu His Gly Thr Ser Arg Asp Trp Trp Asp
            245                 250                 255

Val Ala Arg His Lys Ile Gln Thr Trp Arg Glu Phe Asn Lys His Phe
        260                 265                 270

Arg Ala Ala Phe Leu Ser Glu Asp Tyr Glu Asp Glu Leu Ala Glu Arg
    275                 280                 285

Val Arg Asn Arg Ile Gln Lys Glu Asp Glu Ser Ile Arg Asp Phe Ala
290                 295                 300

Tyr Met Tyr Gln Ser Leu Cys Lys Arg Trp Asn Pro Ala Ile Cys Glu
305                 310                 315                 320

Gly Asp Val Val Lys Leu Ile Leu Lys Asn Ile Asn Pro Gln Leu Pro
            325                 330                 335

Ser Gln Leu Arg Ser Arg Val Thr Thr Val Asp Glu Leu Val Arg Leu
        340                 345                 350

Gly Gln Gln Leu Glu Lys Asp Arg Gln Asn Gln Leu Gln Tyr Glu Leu
    355                 360                 365

Arg Lys Ser Ser Gly Lys Ile Ile Gln Lys Ser Ser Ser Cys Glu Thr
370                 375                 380

Ser Ala Leu Pro Asn Thr Lys Ser Thr Pro Asn Gln Gln Asn Pro Ala
385                 390                 395                 400

Thr Ser Asn Arg Pro Pro Gln Val Tyr Cys Trp Arg Cys Lys Gly His
            405                 410                 415

His Ala Pro Ala Ser Cys Pro Gln Trp Lys Ala Asp Lys His Arg Ala
        420                 425                 430

Gln Pro Ser Arg Ser Ser Gly Pro Gln Thr Leu Thr Asn Leu Gln Ala
    435                 440                 445

Gln Asp Ile
    450

<210> SEQ ID NO 10
<211> LENGTH: 396
<212> TYPE: PRT
<213> ORGANISM: Physeter catodon

<400> SEQUENCE: 10

Gly Glu Leu Asp Gln Arg Ala Ala Gly Gly Leu Arg Ala Tyr Pro Ala
1               5                   10                  15

Pro Arg Gly Gly Pro Val Ala Lys Pro Ser Val Ile Leu Gln Ile Gly
            20                  25                  30

Lys Cys Arg Ala Glu Met Leu Glu His Val Arg Arg Thr His Arg His
        35                  40                  45

Leu Leu Thr Glu Val Ser Lys Gln Val Glu Arg Glu Leu Lys Gly Leu
    50                  55                  60

His Arg Ser Val Gly Lys Leu Glu Gly Asn Leu Asp Gly Tyr Val Pro
65                  70                  75                  80

Thr Gly Asp Ser Gln Arg Trp Lys Lys Ser Ile Lys Ala Cys Leu Cys
                85                  90                  95

Arg Cys Gln Glu Thr Ile Ala Asn Leu Glu Arg Trp Val Lys Arg Glu
            100                 105                 110

Met His Val Trp Arg Glu Val Phe Tyr Arg Leu Glu Arg Trp Ala Asp

```
                115                 120                 125
Arg Leu Glu Ser Met Gly Gly Lys Tyr Pro Val Gly Thr Asn Pro Ser
            130                 135                 140

Arg His Thr Val Ser Val Gly Val Gly Gly Pro Gly Tyr Ser His
145                 150                 155                 160

Glu Ala Asp Thr Tyr Asp Tyr Thr Val Ser Pro Tyr Ala Ile Thr Pro
                165                 170                 175

Pro Pro Ala Ala Gly Glu Leu Pro Gly Gln Glu Ala Val Glu Ala Gln
            180                 185                 190

Gln Tyr Pro Pro Trp Gly Leu Gly Glu Asp Gly Gln Pro Gly Pro Gly
                195                 200                 205

Val Asp Thr Gln Ile Phe Glu Asp Pro Arg Glu Phe Leu Ser His Leu
            210                 215                 220

Glu Glu Tyr Leu Arg Gln Val Gly Gly Ser Glu Glu Tyr Trp Leu Ser
225                 230                 235                 240

Gln Ile Gln Asn His Met Asn Gly Pro Ala Lys Lys Trp Trp Glu Phe
                245                 250                 255

Lys Gln Gly Ser Val Lys Asn Trp Val Glu Phe Lys Lys Glu Phe Leu
            260                 265                 270

Gln Tyr Ser Glu Gly Thr Leu Ser Arg Glu Ala Ile Gln Arg Glu Leu
                275                 280                 285

Asp Leu Pro Gln Lys Gln Gly Glu Pro Leu Asp Gln Phe Leu Trp Arg
            290                 295                 300

Lys Arg Asp Leu Tyr Gln Thr Leu Tyr Val Asp Ala Glu Glu Glu
305                 310                 315                 320

Ile Ile Gln Tyr Val Val Gly Thr Leu Gln Pro Lys Leu Lys Arg Phe
                325                 330                 335

Leu Arg Pro Pro Leu Pro Lys Thr Leu Glu Gln Leu Ile Gln Lys Gly
            340                 345                 350

Met Glu Val Gln Asp Gly Leu Glu Gln Ala Ala Glu Pro Ala Ser Pro
                355                 360                 365

Arg Leu Pro Pro Glu Glu Glu Ser Glu Ala Leu Thr Pro Ala Leu Thr
            370                 375                 380

Ser Glu Ser Val Ala Ser Asp Arg Thr Gln Pro Glu
385                 390                 395

<210> SEQ ID NO 11
<211> LENGTH: 404
<212> TYPE: PRT
<213> ORGANISM: Meleagris gallopavo

<400> SEQUENCE: 11

Gly Gln Leu Asp Asn Val Thr Asn Ala Gly Ile His Ser Phe Gln Gly
1               5                   10                  15

His Arg Gly Val Ala Asn Lys Pro Asn Val Ile Leu Gln Ile Gly Lys
            20                  25                  30

Cys Arg Ala Glu Met Leu Glu His Val Arg Arg Thr His Arg His Leu
        35                  40                  45

Leu Ser Glu Val Ser Lys Gln Val Glu Arg Glu Leu Lys Gly Leu Gln
    50                  55                  60

Lys Ser Val Gly Lys Leu Glu Asn Asn Leu Glu Asp His Val Pro Thr
65                  70                  75                  80

Asp Asn Gln Arg Trp Lys Lys Ser Ile Lys Ala Cys Leu Ala Arg Cys
                85                  90                  95
```

Gln Glu Thr Ile Ala His Leu Glu Arg Trp Val Lys Arg Glu Met Asn
                100                 105                 110

Val Trp Lys Glu Val Phe Phe Arg Leu Glu Lys Trp Ala Asp Arg Leu
            115                 120                 125

Glu Ser Met Gly Gly Lys Tyr Cys Pro Gly Glu His Gly Lys Gln Thr
        130                 135                 140

Val Ser Val Gly Val Gly Pro Glu Ile Arg Pro Ser Glu Gly Glu
145                 150                 155                 160

Ile Tyr Asp Tyr Ala Leu Asp Met Ser Gln Met Tyr Ala Leu Thr Pro
                165                 170                 175

Gly Pro Gly Glu Val Pro Ser Ile Pro Gln Ala His Asp Ser Tyr Gln
            180                 185                 190

Trp Val Ser Val Ser Glu Asp Ala Pro Ala Ser Pro Val Glu Thr Gln
        195                 200                 205

Ile Phe Glu Asp Pro His Glu Phe Leu Ser His Leu Glu Glu Tyr Leu
210                 215                 220

Lys Gln Val Gly Gly Thr Glu Glu Tyr Trp Leu Ser Gln Ile Gln Asn
225                 230                 235                 240

His Met Asn Gly Pro Ala Lys Lys Trp Trp Glu Tyr Lys Gln Asp Ser
                245                 250                 255

Val Lys Asn Trp Val Glu Phe Lys Lys Glu Phe Leu Gln Tyr Ser Glu
            260                 265                 270

Gly Thr Leu Thr Arg Asp Ala Ile Lys Arg Glu Leu Asp Leu Pro Gln
        275                 280                 285

Lys Glu Gly Glu Pro Leu Asp Gln Phe Leu Trp Arg Lys Arg Asp Leu
    290                 295                 300

Tyr Gln Thr Leu Tyr Val Asp Ala Asp Glu Glu Ile Ile Gln Tyr
305                 310                 315                 320

Val Val Gly Thr Leu Gln Pro Lys Leu Lys Arg Phe Leu Ser Tyr Pro
                325                 330                 335

Leu Pro Lys Thr Leu Glu Gln Leu Ile Gln Arg Gly Lys Glu Val Gln
            340                 345                 350

Gly Asn Met Asp His Ser Glu Glu Pro Ser Pro Gln Arg Thr Pro Glu
        355                 360                 365

Ile Gln Ser Gly Asp Ser Val Glu Ser Met Pro Pro Ser Thr Thr Ala
    370                 375                 380

Ser Pro Val Pro Ser Asn Gly Thr Gln Pro Glu Pro Pro Ser Pro Pro
385                 390                 395                 400

Ala Thr Val Ile

<210> SEQ ID NO 12
<211> LENGTH: 409
<212> TYPE: PRT
<213> ORGANISM: Pogona vitticeps

<400> SEQUENCE: 12

Gly Gln Leu Glu Asn Ile Asn Gln Gly Ser Leu His Ala Phe Gln Gly
1               5                   10                  15

His Arg Gly Val Val His Asn Asn Lys Pro Asn Val Ile Leu Gln Ile
            20                  25                  30

Gly Lys Cys Arg Ala Glu Met Leu Glu His Val Arg Arg Thr His Arg
        35                  40                  45

His Leu Leu Thr Glu Val Ser Lys Gln Val Glu Arg Glu Leu Lys Gly
    50                  55                  60

Leu Gln Lys Ser Val Gly Lys Leu Glu Asn Asn Leu Glu Asp His Val
65                  70                  75                  80

Pro Ser Ala Ala Glu Asn Gln Arg Trp Lys Lys Ser Ile Lys Ala Cys
                85                  90                  95

Leu Ala Arg Cys Gln Glu Thr Ile Ala Asn Leu Glu Arg Trp Val Lys
            100                 105                 110

Arg Glu Met Asn Val Trp Lys Glu Val Phe Phe Arg Leu Glu Arg Trp
        115                 120                 125

Ala Asp Arg Leu Glu Ser Gly Gly Lys Tyr Cys His Ala Asp Gln
    130                 135                 140

Gly Arg Gln Thr Val Ser Val Gly Val Gly Pro Glu Val Arg Pro
145                 150                 155                 160

Ser Glu Gly Glu Ile Tyr Asp Tyr Ala Leu Asp Met Ser Gln Met Tyr
                165                 170                 175

Ala Leu Thr Pro Pro Met Gly Asp Val Pro Val Ile Pro Gln Pro
            180                 185                 190

His Asp Ser Tyr Gln Trp Val Thr Asp Pro Glu Glu Ala Pro Pro Ser
        195                 200                 205

Pro Val Glu Thr Gln Ile Phe Glu Asp Pro Arg Glu Phe Leu Thr His
    210                 215                 220

Leu Glu Asp Tyr Leu Lys Gln Val Gly Gly Thr Glu Glu Tyr Trp Leu
225                 230                 235                 240

Ser Gln Ile Gln Asn His Met Asn Gly Pro Ala Lys Lys Trp Trp Glu
                245                 250                 255

Tyr Lys Gln Asp Ser Val Lys Asn Trp Leu Glu Phe Lys Lys Glu Phe
            260                 265                 270

Leu Gln Tyr Ser Glu Gly Thr Leu Thr Arg Asp Ala Ile Lys Gln Glu
        275                 280                 285

Leu Asp Leu Pro Gln Lys Glu Gly Glu Pro Leu Asp Gln Phe Leu Trp
    290                 295                 300

Arg Lys Arg Asp Leu Tyr Gln Thr Leu Tyr Val Glu Ala Glu Glu Glu
305                 310                 315                 320

Glu Val Ile Gln Tyr Val Val Gly Thr Leu Gln Pro Lys Leu Lys Arg
                325                 330                 335

Phe Leu Ser His Pro Tyr Pro Lys Thr Leu Glu Gln Leu Ile Gln Arg
            340                 345                 350

Gly Lys Glu Val Glu Gly Asn Leu Asp Asn Ser Glu Glu Pro Ser Pro
        355                 360                 365

Gln Arg Thr Pro Glu His Gln Leu Gly Asp Ser Val Glu Ser Leu Pro
    370                 375                 380

Pro Ser Thr Thr Ala Ser Pro Ala Gly Ser Asp Lys Thr Gln Pro Glu
385                 390                 395                 400

Ile Ser Leu Pro Pro Thr Thr Val Ile
                405

<210> SEQ ID NO 13
<211> LENGTH: 404
<212> TYPE: PRT
<213> ORGANISM: Alligator sinensis

<400> SEQUENCE: 13

Gly Gln Leu Asp Ser Val Thr Asn Ala Gly Val His Thr Tyr Gln Gly
1               5                   10                  15

His Arg Ser Val Ala Asn Lys Pro Asn Val Ile Leu Gln Ile Gly Lys
            20                  25                  30

Cys Arg Thr Glu Met Leu Glu His Val Arg Arg Thr His Arg His Leu
            35                  40                  45

Leu Thr Glu Val Ser Lys Gln Val Glu Arg Glu Leu Lys Gly Leu Gln
 50                  55                  60

Lys Ser Val Gly Lys Leu Glu Asn Asn Leu Glu Asp His Val Pro Thr
 65                  70                  75                  80

Asp Asn Gln Arg Trp Lys Lys Ser Ile Lys Ala Cys Leu Ala Arg Cys
                85                  90                  95

Gln Glu Thr Ile Ala His Leu Glu Arg Trp Val Lys Arg Glu Met Asn
            100                 105                 110

Val Trp Lys Glu Val Phe Phe Arg Leu Glu Arg Trp Ala Asp Arg Leu
            115                 120                 125

Glu Ser Met Gly Gly Lys Tyr Cys Pro Thr Asp Ser Ala Arg Gln Thr
            130                 135                 140

Val Ser Val Gly Val Gly Gly Pro Glu Ile Arg Pro Ser Glu Gly Glu
145                 150                 155                 160

Ile Tyr Asp Tyr Ala Leu Asp Met Ser Gln Met Tyr Ala Leu Thr Pro
                165                 170                 175

Ser Pro Gly Glu Leu Pro Ser Val Pro Gln Pro His Asp Ser Tyr Gln
            180                 185                 190

Trp Val Thr Ser Pro Glu Asp Ala Pro Ala Ser Pro Val Glu Thr Gln
            195                 200                 205

Val Phe Glu Asp Pro Arg Glu Phe Leu Cys His Leu Glu Glu Tyr Leu
            210                 215                 220

Lys Gln Val Gly Gly Thr Glu Glu Tyr Trp Leu Ser Gln Ile Gln Asn
225                 230                 235                 240

His Met Asn Gly Pro Ala Lys Lys Trp Trp Glu Tyr Lys Gln Asp Thr
                245                 250                 255

Val Lys Asn Trp Val Glu Phe Lys Lys Glu Phe Leu Gln Tyr Ser Glu
            260                 265                 270

Gly Thr Leu Thr Arg Asp Ala Ile Lys Arg Glu Leu Asp Leu Pro Gln
            275                 280                 285

Lys Asp Gly Glu Pro Leu Asp Gln Phe Leu Trp Arg Lys Arg Asp Leu
            290                 295                 300

Tyr Gln Thr Leu Tyr Ile Asp Ala Asp Glu Glu Gln Ile Ile Gln Tyr
305                 310                 315                 320

Val Val Gly Thr Leu Gln Pro Lys Leu Lys Arg Phe Leu Ser Tyr Pro
                325                 330                 335

Leu Pro Lys Thr Leu Glu Gln Leu Ile Gln Lys Gly Lys Glu Val Gln
            340                 345                 350

Gly Ser Leu Asp His Ser Glu Glu Pro Ser Pro Gln Arg Ala Ser Glu
            355                 360                 365

Ala Arg Thr Gly Asp Ser Val Glu Thr Leu Pro Pro Ser Thr Thr Thr
            370                 375                 380

Ser Pro Asn Thr Ser Ser Gly Thr Gln Pro Glu Ala Pro Ser Pro Pro
385                 390                 395                 400

Ala Thr Val Ile

<210> SEQ ID NO 14
<211> LENGTH: 404
<212> TYPE: PRT
<213> ORGANISM: Alligator mississippiensis

<400> SEQUENCE: 14

```
Gly Gln Leu Asp Ser Val Thr Asn Ala Gly Val His Thr Tyr Gln Gly
1               5                   10                  15

His Arg Gly Val Ala Asn Lys Pro Asn Val Ile Leu Gln Ile Gly Lys
                20                  25                  30

Cys Arg Thr Glu Met Leu Glu His Val Arg Arg Thr His Arg His Leu
            35                  40                  45

Leu Thr Glu Val Ser Lys Gln Val Glu Arg Glu Leu Lys Gly Leu Gln
        50                  55                  60

Lys Ser Val Gly Lys Leu Glu Asn Asn Leu Glu Asp His Val Pro Thr
65                  70                  75                  80

Asp Asn Gln Arg Trp Lys Lys Ser Ile Lys Ala Cys Leu Ala Arg Cys
                85                  90                  95

Gln Glu Thr Ile Ala His Leu Glu Arg Trp Val Lys Arg Glu Met Asn
            100                 105                 110

Val Trp Lys Glu Val Phe Phe Arg Leu Glu Arg Trp Ala Asp Arg Leu
        115                 120                 125

Glu Ser Met Gly Gly Lys Tyr Cys Pro Thr Asp Ser Ala Arg Gln Thr
        130                 135                 140

Val Ser Val Gly Val Gly Gly Pro Glu Ile Arg Pro Ser Glu Gly Glu
145                 150                 155                 160

Ile Tyr Asp Tyr Ala Leu Asp Met Ser Gln Met Tyr Ala Leu Thr Pro
                165                 170                 175

Ser Pro Gly Glu Leu Pro Ser Ile Pro Gln Pro His Asp Ser Tyr Gln
            180                 185                 190

Trp Val Thr Ser Pro Glu Asp Ala Pro Ala Ser Pro Val Glu Thr Gln
            195                 200                 205

Val Phe Glu Asp Pro Arg Glu Phe Leu Cys His Leu Glu Glu Tyr Leu
        210                 215                 220

Lys Gln Val Gly Gly Thr Glu Glu Tyr Trp Leu Ser Gln Ile Gln Asn
225                 230                 235                 240

His Met Asn Gly Pro Ala Lys Lys Trp Trp Glu Tyr Lys Gln Asp Thr
                245                 250                 255

Val Lys Asn Trp Val Glu Phe Lys Lys Glu Phe Leu Gln Tyr Ser Glu
            260                 265                 270

Gly Thr Leu Thr Arg Asp Ala Ile Lys Arg Glu Leu Asp Leu Pro Gln
        275                 280                 285

Lys Asp Gly Glu Pro Leu Asp Gln Phe Leu Trp Arg Lys Arg Asp Leu
290                 295                 300

Tyr Gln Thr Leu Tyr Ile Asp Ala Asp Glu Glu Ile Ile Gln Tyr
305                 310                 315                 320

Val Val Gly Thr Leu Gln Pro Lys Leu Lys Arg Phe Leu Ser Tyr Pro
            325                 330                 335

Leu Pro Lys Thr Leu Glu Gln Leu Ile Gln Lys Gly Lys Glu Val Gln
            340                 345                 350

Gly Ser Leu Asp His Ser Glu Pro Ser Pro Gln Arg Ala Ser Glu
                355                 360                 365

Ala Arg Thr Gly Asp Ser Val Glu Ser Leu Pro Ser Thr Thr Thr
            370                 375                 380

Ser Pro Asn Ala Ser Ser Gly Thr Gln Pro Glu Ala Pro Ser Pro Pro
385                 390                 395                 400

Ala Thr Val Ile
```

```
<210> SEQ ID NO 15
<211> LENGTH: 408
<212> TYPE: PRT
<213> ORGANISM: Gekko japonicus

<400> SEQUENCE: 15

Gly Gln Leu Glu Asn Val Asn His Gly Asn Leu His Ser Phe Gln Gly
1               5                   10                  15

His Arg Gly Gly Val Ala Asn Lys Pro Asn Val Ile Leu Gln Ile Gly
            20                  25                  30

Lys Cys Arg Ala Glu Met Leu Asp His Val Arg Arg Thr His Arg His
        35                  40                  45

Leu Leu Thr Glu Val Ser Lys Gln Val Glu Arg Glu Leu Lys Gly Leu
    50                  55                  60

Gln Lys Ser Val Gly Lys Leu Glu Asn Asn Leu Glu Asp His Val Pro
65                  70                  75                  80

Ser Ala Val Glu Asn Gln Arg Trp Lys Lys Ser Ile Lys Ala Cys Leu
                85                  90                  95

Ser Arg Cys Gln Glu Thr Ile Ala His Leu Glu Arg Trp Val Lys Arg
            100                 105                 110

Glu Met Asn Val Trp Lys Glu Val Phe Phe Arg Leu Glu Arg Trp Ala
        115                 120                 125

Asp Arg Leu Glu Ser Gly Gly Lys Tyr Cys His Gly Asp Asn His
    130                 135                 140

Arg Gln Thr Val Ser Val Gly Val Gly Gly Pro Glu Val Arg Pro Ser
145                 150                 155                 160

Glu Gly Glu Ile Tyr Asp Tyr Ala Leu Asp Met Ser Gln Met Tyr Ala
                165                 170                 175

Leu Thr Pro Pro Ser Pro Gly Asp Val Pro Val Ser Gln Pro His
            180                 185                 190

Asp Ser Tyr Gln Trp Val Thr Val Pro Glu Asp Thr Pro Pro Ser Pro
        195                 200                 205

Val Glu Thr Gln Ile Phe Glu Asp Pro Arg Glu Phe Leu Thr His Leu
    210                 215                 220

Glu Asp Tyr Leu Lys Gln Val Gly Gly Thr Glu Glu Tyr Trp Leu Ser
225                 230                 235                 240

Gln Ile Gln Asn His Met Asn Gly Pro Ala Lys Lys Trp Trp Glu Tyr
                245                 250                 255

Lys Gln Asp Ser Val Lys Asn Trp Leu Glu Phe Lys Lys Glu Phe Leu
            260                 265                 270

Gln Tyr Ser Glu Gly Thr Leu Thr Arg Asp Ala Ile Lys Glu Glu Leu
        275                 280                 285

Asp Leu Pro Gln Lys Asp Gly Glu Pro Leu Asp Gln Phe Leu Trp Arg
    290                 295                 300

Lys Arg Asp Leu Tyr Gln Thr Leu Tyr Val Glu Ala Asp Glu Glu
305                 310                 315                 320

Val Ile Gln Tyr Val Gly Thr Leu Gln Pro Lys Leu Lys Arg Phe
                325                 330                 335

Leu Ser His Pro Tyr Pro Lys Thr Leu Glu Gln Leu Ile Gln Arg Gly
            340                 345                 350

Lys Glu Val Glu Gly Asn Leu Asp Asn Ser Glu Glu Pro Thr Pro Gln
        355                 360                 365

Arg Thr Pro Glu His Gln Leu Cys Gly Ser Val Glu Ser Leu Pro Pro
    370                 375                 380
```

```
Ser Ser Thr Val Ser Pro Val Ala Ser Asp Gly Thr Gln Pro Glu Thr
385                 390                 395                 400

Ser Pro Leu Pro Ala Thr Val Ile
                405

<210> SEQ ID NO 16
<211> LENGTH: 455
<212> TYPE: PRT
<213> ORGANISM: Homo sapiens

<400> SEQUENCE: 16

Gly Pro Leu Thr Leu Leu Gln Asp Trp Cys Arg Gly Glu His Leu Asn
1               5                   10                  15

Thr Arg Arg Cys Met Leu Ile Leu Gly Ile Pro Glu Asp Cys Gly Glu
                20                  25                  30

Asp Glu Phe Glu Glu Thr Leu Gln Glu Ala Cys Arg His Leu Gly Arg
            35                  40                  45

Tyr Arg Val Ile Gly Arg Met Phe Arg Arg Glu Glu Asn Ala Gln Ala
50                  55                  60

Ile Leu Leu Glu Leu Ala Gln Asp Ile Asp Tyr Ala Leu Leu Pro Arg
65                  70                  75                  80

Glu Ile Pro Gly Lys Gly Pro Trp Glu Val Ile Val Lys Pro Arg
                85                  90                  95

Asn Ser Asp Gly Glu Phe Leu Asn Arg Leu Asn Arg Phe Leu Glu Glu
                100                 105                 110

Glu Arg Arg Thr Val Ser Asp Met Asn Arg Val Leu Gly Ser Asp Thr
            115                 120                 125

Asn Cys Ser Ala Pro Arg Val Thr Ile Ser Pro Glu Phe Trp Thr Trp
130                 135                 140

Ala Gln Thr Leu Gly Ala Ala Val Gln Pro Leu Leu Glu Gln Met Leu
145                 150                 155                 160

Tyr Arg Glu Leu Arg Val Phe Ser Gly Asn Thr Ile Ser Ile Pro Gly
                165                 170                 175

Ala Leu Ala Phe Asp Ala Trp Leu Glu His Thr Thr Glu Met Leu Gln
            180                 185                 190

Met Trp Gln Val Pro Glu Gly Glu Lys Arg Arg Arg Leu Met Glu Cys
        195                 200                 205

Leu Arg Gly Pro Ala Leu Gln Val Val Ser Gly Leu Arg Ala Ser Asn
210                 215                 220

Ala Ser Ile Thr Val Glu Glu Cys Leu Ala Ala Leu Gln Gln Val Phe
225                 230                 235                 240

Gly Pro Val Glu Ser His Lys Ile Ala Gln Val Lys Leu Cys Lys Ala
                245                 250                 255

Tyr Gln Glu Ala Gly Glu Lys Val Ser Ser Phe Val Leu Arg Leu Glu
            260                 265                 270

Pro Leu Leu Gln Arg Ala Val Glu Asn Asn Val Ser Arg Arg Asn
        275                 280                 285

Val Asn Gln Thr Arg Leu Lys Arg Val Leu Ser Gly Ala Thr Leu Pro
290                 295                 300

Asp Lys Leu Arg Asp Lys Leu Leu Met Lys Gln Arg Lys Pro
305                 310                 315                 320

Pro Gly Phe Leu Ala Leu Val Lys Leu Arg Glu Glu Glu Trp
                325                 330                 335

Glu Ala Thr Leu Gly Pro Asp Arg Glu Ser Leu Glu Gly Leu Glu Val
            340                 345                 350
```

```
Ala Pro Arg Pro Pro Ala Arg Ile Thr Gly Val Gly Ala Val Pro Leu
            355                 360                 365

Pro Ala Ser Gly Asn Ser Phe Asp Ala Arg Pro Ser Gln Gly Tyr Arg
    370                 375                 380

Arg Arg Arg Gly Arg Gly Gln His Arg Arg Gly Gly Val Ala Arg Ala
385                 390                 395                 400

Gly Ser Arg Gly Ser Arg Lys Arg Lys Arg His Thr Phe Cys Tyr Ser
                405                 410                 415

Cys Gly Glu Asp Gly His Ile Arg Val Gln Cys Ile Asn Pro Ser Asn
            420                 425                 430

Leu Leu Leu Ala Lys Glu Thr Lys Glu Ile Leu Glu Gly Gly Glu Arg
            435                 440                 445

Glu Ala Gln Thr Asn Ser Arg
    450                 455

<210> SEQ ID NO 17
<211> LENGTH: 448
<212> TYPE: PRT
<213> ORGANISM: Homo sapiens

<400> SEQUENCE: 17

Gly Ala Leu Thr Leu Leu Glu Asp Trp Cys Lys Gly Met Asp Met Asp
1               5                   10                  15

Pro Arg Lys Ala Leu Leu Ile Val Gly Ile Pro Met Glu Cys Ser Glu
            20                  25                  30

Val Glu Ile Gln Asp Thr Val Lys Ala Gly Leu Gln Pro Leu Cys Ala
        35                  40                  45

Tyr Arg Val Leu Gly Arg Met Phe Arg Arg Glu Asp Asn Ala Lys Ala
    50                  55                  60

Val Phe Ile Glu Leu Ala Asp Thr Val Asn Tyr Thr Thr Leu Pro Ser
65                  70                  75                  80

His Ile Pro Gly Lys Gly Gly Ser Trp Glu Val Val Lys Pro Arg
                85                  90                  95

Asn Pro Asp Asp Glu Phe Leu Ser Arg Leu Asn Tyr Phe Leu Lys Asp
            100                 105                 110

Glu Gly Arg Ser Met Thr Asp Val Ala Arg Ala Leu Gly Cys Cys Ser
        115                 120                 125

Leu Pro Ala Glu Ser Leu Asp Ala Glu Val Met Pro Gln Val Arg Ser
    130                 135                 140

Pro Pro Leu Glu Pro Pro Lys Glu Ser Met Trp Tyr Arg Lys Leu Lys
145                 150                 155                 160

Val Phe Ser Gly Thr Ala Ser Pro Ser Pro Gly Glu Glu Thr Phe Glu
                165                 170                 175

Asp Trp Leu Glu Gln Val Thr Glu Ile Met Pro Ile Trp Gln Val Ser
            180                 185                 190

Glu Val Glu Lys Arg Arg Arg Leu Leu Glu Ser Leu Arg Gly Pro Ala
        195                 200                 205

Leu Ser Ile Met Arg Val Leu Gln Ala Asn Asn Asp Ser Ile Thr Val
    210                 215                 220

Glu Gln Cys Leu Asp Ala Leu Lys Gln Ile Phe Gly Asp Lys Glu Asp
225                 230                 235                 240

Phe Arg Ala Ser Gln Phe Arg Phe Leu Gln Thr Ser Pro Lys Ile Gly
                245                 250                 255

Glu Lys Val Ser Thr Phe Leu Leu Arg Leu Glu Pro Leu Leu Gln Lys
```

```
            260                 265                 270
Ala Val His Lys Ser Pro Leu Ser Val Arg Ser Thr Asp Met Ile Arg
            275                 280                 285

Leu Lys His Leu Leu Ala Arg Val Ala Met Thr Pro Ala Leu Arg Gly
            290                 295                 300

Lys Leu Glu Leu Leu Asp Gln Arg Gly Cys Pro Pro Asn Phe Leu Glu
305                 310                 315                 320

Leu Met Lys Leu Ile Arg Asp Glu Glu Trp Glu Asn Thr Glu Ala
            325                 330                 335

Val Met Lys Asn Lys Glu Lys Pro Ser Gly Arg Gly Arg Gly Ala Ser
            340                 345                 350

Gly Arg Gln Ala Arg Ala Glu Ala Ser Val Ser Ala Pro Gln Ala Thr
            355                 360                 365

Val Gln Ala Arg Ser Phe Ser Asp Ser Ser Pro Gln Thr Ile Gln Gly
            370                 375                 380

Gly Leu Pro Pro Leu Val Lys Arg Arg Leu Leu Gly Ser Glu Ser
385                 390                 395                 400

Thr Arg Gly Glu Asp His Gly Gln Ala Thr Tyr Pro Lys Ala Glu Asn
            405                 410                 415

Gln Thr Pro Gly Arg Glu Gly Pro Gln Ala Ala Gly Glu Glu Leu Gly
            420                 425                 430

Asn Glu Ala Gly Ala Gly Ala Met Ser His Pro Lys Pro Trp Glu Thr
            435                 440                 445

<210> SEQ ID NO 18
<211> LENGTH: 399
<212> TYPE: PRT
<213> ORGANISM: Homo sapiens

<400> SEQUENCE: 18

Gly Ala Val Thr Met Leu Gln Asp Trp Cys Arg Trp Met Gly Val Asn
1               5                   10                  15

Ala Arg Arg Gly Leu Leu Ile Leu Gly Ile Pro Glu Asp Cys Asp Asp
                20                  25                  30

Ala Glu Phe Gln Glu Ser Leu Glu Ala Ala Leu Arg Pro Met Gly His
            35                  40                  45

Phe Thr Val Leu Gly Lys Ala Phe Arg Glu Glu Asp Asn Ala Thr Ala
        50                  55                  60

Ala Leu Val Glu Leu Asp Arg Glu Val Asn Tyr Ala Leu Val Pro Arg
65                  70                  75                  80

Glu Ile Pro Gly Thr Gly Gly Pro Trp Asn Val Val Phe Val Pro Arg
                85                  90                  95

Cys Ser Gly Glu Glu Phe Leu Gly Leu Gly Arg Val Phe His Phe Pro
            100                 105                 110

Glu Gln Glu Gly Gln Met Val Glu Ser Val Ala Gly Ala Leu Gly Val
        115                 120                 125

Gly Leu Arg Arg Val Cys Trp Leu Arg Ser Ile Gly Gln Ala Val Gln
        130                 135                 140

Pro Trp Val Glu Ala Val Arg Cys Gln Ser Leu Gly Val Phe Ser Gly
145                 150                 155                 160

Arg Asp Gln Pro Ala Pro Gly Glu Glu Ser Phe Glu Val Trp Leu Asp
                165                 170                 175

His Thr Thr Glu Met Leu His Val Trp Gln Gly Val Ser Glu Arg Glu
            180                 185                 190
```

```
Arg Arg Arg Arg Leu Leu Glu Gly Leu Arg Gly Thr Ala Leu Gln Leu
            195                 200                 205

Val His Ala Leu Leu Ala Glu Asn Pro Ala Arg Thr Ala Gln Asp Cys
    210                 215                 220

Leu Ala Ala Leu Ala Gln Val Phe Gly Asp Asn Glu Ser Gln Ala Thr
225                 230                 235                 240

Ile Arg Val Lys Cys Leu Thr Ala Gln Gln Ser Gly Glu Arg Leu
                245                 250                 255

Ser Ala Phe Val Leu Arg Leu Glu Val Leu Gln Lys Ala Met Glu
            260                 265                 270

Lys Glu Ala Leu Ala Arg Ala Ser Ala Asp Arg Val Arg Leu Arg Gln
    275                 280                 285

Met Leu Thr Arg Ala His Leu Thr Glu Pro Leu Asp Glu Ala Leu Arg
    290                 295                 300

Lys Leu Arg Met Ala Gly Arg Ser Pro Ser Phe Leu Glu Met Leu Gly
305                 310                 315                 320

Leu Val Arg Glu Ser Glu Ala Trp Glu Ala Ser Leu Ala Arg Ser Val
                325                 330                 335

Arg Ala Gln Thr Gln Glu Gly Ala Gly Ala Arg Ala Gly Ala Gln Ala
            340                 345                 350

Val Ala Arg Ala Ser Thr Lys Val Glu Ala Val Pro Gly Gly Pro Gly
    355                 360                 365

Arg Glu Pro Glu Gly Leu Leu Gln Ala Gly Gly Gln Glu Ala Glu Glu
    370                 375                 380

Leu Leu Gln Glu Gly Leu Lys Pro Val Leu Glu Glu Cys Asp Asn
385                 390                 395

<210> SEQ ID NO 19
<211> LENGTH: 399
<212> TYPE: PRT
<213> ORGANISM: Homo sapiens

<400> SEQUENCE: 19

Gly Ala Val Thr Met Leu Gln Asp Trp Cys Arg Trp Met Gly Val Asn
1               5                   10                  15

Ala Arg Arg Gly Leu Leu Ile Leu Gly Ile Pro Glu Asp Cys Asp Asp
            20                  25                  30

Ala Glu Phe Gln Glu Ser Leu Glu Ala Ala Leu Arg Pro Met Gly His
            35                  40                  45

Phe Thr Val Leu Gly Lys Val Phe Arg Glu Glu Asp Asn Ala Thr Ala
    50                  55                  60

Ala Leu Val Glu Leu Asp Arg Glu Val Asn Tyr Ala Leu Val Pro Arg
65                  70                  75                  80

Glu Ile Pro Gly Thr Gly Gly Pro Trp Asn Val Phe Val Pro Arg
            85                  90                  95

Cys Ser Gly Glu Glu Phe Leu Gly Leu Gly Arg Val Phe His Phe Pro
                100                 105                 110

Glu Gln Glu Gly Gln Met Val Glu Ser Val Ala Gly Ala Leu Gly Val
            115                 120                 125

Gly Leu Arg Arg Val Cys Trp Leu Arg Ser Ile Gly Gln Ala Val Gln
130                 135                 140

Pro Trp Val Glu Ala Val Arg Tyr Gln Ser Leu Gly Val Phe Ser Gly
145                 150                 155                 160

Arg Asp Gln Pro Ala Pro Gly Glu Glu Ser Phe Glu Val Trp Leu Asp
            165                 170                 175
```

```
His Thr Thr Glu Met Leu His Val Trp Gln Gly Val Ser Glu Arg Glu
            180                 185                 190

Arg Arg Arg Arg Leu Leu Glu Gly Leu Arg Gly Thr Ala Leu Gln Leu
        195                 200                 205

Val His Ala Leu Leu Ala Glu Asn Pro Ala Arg Thr Ala Gln Asp Cys
    210                 215                 220

Leu Ala Ala Leu Ala Gln Val Phe Gly Asp Asn Glu Ser Gln Ala Thr
225                 230                 235                 240

Ile Arg Val Lys Cys Leu Thr Ala Gln Gln Gln Ser Gly Glu Arg Leu
                245                 250                 255

Ser Ala Phe Val Leu Arg Leu Glu Val Leu Leu Gln Lys Ala Met Glu
            260                 265                 270

Lys Glu Ala Leu Ala Arg Ala Ser Ala Asp Arg Val Arg Leu Arg Gln
        275                 280                 285

Met Leu Thr Arg Ala His Leu Thr Glu Pro Leu Asp Glu Ala Leu Arg
    290                 295                 300

Lys Leu Arg Met Ala Gly Arg Ser Pro Ser Phe Leu Glu Met Leu Gly
305                 310                 315                 320

Leu Val Arg Glu Ser Glu Ala Trp Glu Ala Ser Leu Ala Arg Ser Val
                325                 330                 335

Arg Ala Gln Thr Gln Glu Gly Ala Gly Ala Arg Ala Gly Ala Gln Ala
            340                 345                 350

Val Ala Arg Ala Ser Thr Lys Val Glu Ala Val Pro Gly Gly Pro Gly
        355                 360                 365

Arg Glu Pro Glu Gly Leu Arg Gln Ala Gly Gly Gln Glu Ala Glu Glu
    370                 375                 380

Leu Leu Gln Glu Gly Leu Lys Pro Val Leu Glu Glu Cys Asp Asn
385                 390                 395

<210> SEQ ID NO 20
<211> LENGTH: 475
<212> TYPE: PRT
<213> ORGANISM: Homo sapiens

<400> SEQUENCE: 20

Gly Val Glu Asp Leu Ala Ala Ser Tyr Ile Val Leu Lys Leu Glu Asn
1               5                   10                  15

Glu Ile Arg Gln Ala Gln Val Gln Trp Leu Met Glu Asn Ala Ala
            20                  25                  30

Leu Gln Ala Gln Ile Pro Glu Leu Gln Lys Ser Gln Ala Ala Lys Glu
        35                  40                  45

Tyr Asp Leu Leu Arg Lys Ser Ser Glu Ala Lys Glu Pro Gln Lys Leu
    50                  55                  60

Pro Glu His Met Asn Pro Pro Ala Ala Trp Glu Ala Gln Lys Thr Pro
65                  70                  75                  80

Glu Phe Lys Glu Pro Gln Lys Pro Pro Glu Pro Gln Asp Leu Leu Pro
                85                  90                  95

Trp Glu Pro Pro Ala Ala Trp Glu Leu Gln Glu Ala Pro Ala Ala Pro
            100                 105                 110

Glu Ser Leu Ala Pro Pro Ala Thr Arg Glu Ser Gln Lys Pro Pro Met
        115                 120                 125

Ala His Glu Ile Pro Thr Val Leu Glu Gly Gln Gly Pro Ala Asn Thr
    130                 135                 140

Gln Asp Ala Thr Ile Ala Gln Glu Pro Lys Asn Ser Glu Pro Gln Asp
```

```
                145                 150                 155                 160
        Pro Pro Asn Ile Glu Lys Pro Gln Glu Ala Pro Glu Tyr Gln Glu Thr
                        165                 170                 175

Ala Ala Gln Leu Glu Phe Leu Glu Leu Pro Pro Gln Glu Pro Leu
                    180                 185                 190

Glu Pro Ser Asn Ala Gln Glu Phe Leu Glu Leu Ser Ala Ala Gln Glu
                        195                 200                 205

Ser Leu Glu Gly Leu Ile Val Val Glu Thr Ser Ala Ala Ser Glu Phe
                    210                 215                 220

Pro Gln Ala Pro Ile Gly Leu Glu Ala Thr Asp Phe Pro Leu Gln Tyr
        225                 230                 235                 240

Thr Leu Thr Phe Ser Gly Asp Ser Gln Lys Leu Pro Glu Phe Leu Val
                        245                 250                 255

Gln Leu Tyr Ser Tyr Met Arg Val Arg Gly His Leu Tyr Pro Thr Glu
                    260                 265                 270

Ala Ala Leu Val Ser Phe Val Gly Asn Cys Phe Ser Gly Arg Ala Gly
                        275                 280                 285

Trp Trp Phe Gln Leu Leu Leu Asp Ile Gln Ser Pro Leu Leu Glu Gln
                    290                 295                 300

Cys Glu Ser Phe Ile Pro Val Leu Gln Asp Thr Phe Asp Asn Pro Glu
        305                 310                 315                 320

Asn Met Lys Asp Ala Asn Gln Cys Ile His Gln Leu Cys Gln Gly Glu
                        325                 330                 335

Gly His Val Ala Thr His Phe His Leu Ile Ala Gln Glu Leu Asn Trp
                    340                 345                 350

Asp Glu Ser Thr Leu Trp Ile Gln Phe Gln Glu Gly Leu Ala Ser Ser
                        355                 360                 365

Ile Gln Asp Glu Leu Ser His Thr Ser Pro Ala Thr Asn Leu Ser Asp
                    370                 375                 380

Leu Ile Thr Gln Cys Ile Ser Leu Glu Glu Lys Pro Asp Pro Asn Pro
        385                 390                 395                 400

Leu Gly Lys Ser Ser Ala Glu Gly Asp Gly Pro Glu Ser Pro Pro
                        405                 410                 415

Ala Glu Asn Gln Pro Met Gln Ala Ala Ile Asn Cys Pro His Ile Ser
                        420                 425                 430

Glu Ala Glu Trp Val Arg Trp His Lys Gly Arg Leu Cys Leu Tyr Cys
                    435                 440                 445

Gly Tyr Pro Gly His Phe Ala Arg Asp Cys Pro Val Lys Pro His Gln
                    450                 455                 460

Ala Leu Gln Ala Gly Asn Ile Gln Ala Cys Gln
        465                 470                 475

<210> SEQ ID NO 21
<211> LENGTH: 239
<212> TYPE: PRT
<213> ORGANISM: Homo sapiens

<400> SEQUENCE: 21

Gly Val Gln Pro Gln Thr Ser Lys Ala Glu Ser Pro Ala Leu Ala Ala
        1               5                   10                  15

Ser Pro Asn Ala Gln Met Asp Asp Val Ile Asp Thr Leu Thr Ser Leu
                        20                  25                  30

Arg Leu Thr Asn Ser Ala Leu Arg Arg Glu Ala Ser Thr Leu Arg Ala
                    35                  40                  45
```

```
Glu Lys Ala Asn Leu Thr Asn Met Leu Glu Ser Val Met Ala Glu Leu
    50                  55                  60

Thr Leu Leu Arg Thr Arg Ala Arg Ile Pro Gly Ala Leu Gln Ile Thr
65                  70                  75                  80

Pro Pro Ile Ser Ser Ile Thr Ser Asn Gly Thr Arg Pro Met Thr Thr
                85                  90                  95

Pro Pro Thr Ser Leu Pro Glu Pro Phe Ser Gly Asp Pro Gly Arg Leu
            100                 105                 110

Ala Gly Phe Leu Met Gln Met Asp Arg Phe Met Ile Phe Gln Ala Ser
                115                 120                 125

Arg Phe Pro Gly Glu Ala Glu Arg Val Ala Phe Leu Val Ser Arg Leu
            130                 135                 140

Thr Gly Glu Ala Glu Lys Trp Ala Ile Pro His Met Gln Pro Asp Ser
145                 150                 155                 160

Pro Leu Arg Asn Asn Tyr Gln Gly Phe Leu Ala Glu Leu Arg Arg Thr
                165                 170                 175

Tyr Lys Ser Pro Leu Arg His Ala Arg Arg Ala Gln Ile Arg Lys Thr
                180                 185                 190

Ser Ala Ser Asn Arg Ala Val Arg Glu Arg Gln Met Leu Cys Arg Gln
                195                 200                 205

Leu Ala Ser Ala Gly Thr Gly Pro Cys Pro Val His Pro Ala Ser Asn
            210                 215                 220

Gly Thr Ser Pro Ala Pro Ala Leu Pro Ala Arg Ala Arg Asn Leu
225                 230                 235

<210> SEQ ID NO 22
<211> LENGTH: 113
<212> TYPE: PRT
<213> ORGANISM: Homo sapiens

<400> SEQUENCE: 22

Gly Asp Gly Arg Val Gln Leu Met Lys Ala Leu Leu Ala Gly Pro Leu
1               5                   10                  15

Arg Pro Ala Ala Arg Arg Trp Arg Asn Pro Ile Pro Phe Pro Glu Thr
            20                  25                  30

Phe Asp Gly Asp Thr Asp Arg Leu Pro Glu Phe Ile Val Gln Thr Ser
            35                  40                  45

Ser Tyr Met Phe Val Asp Glu Asn Thr Phe Ser Asn Asp Ala Leu Lys
    50                  55                  60

Val Thr Phe Leu Ile Thr Arg Leu Thr Gly Pro Ala Leu Gln Trp Val
65                  70                  75                  80

Ile Pro Tyr Ile Arg Lys Glu Ser Pro Leu Leu Asn Asp Tyr Arg Gly
                85                  90                  95

Phe Leu Ala Glu Met Lys Arg Val Phe Gly Trp Glu Glu Asp Glu Asp
            100                 105                 110

Phe

<210> SEQ ID NO 23
<211> LENGTH: 113
<212> TYPE: PRT
<213> ORGANISM: Homo sapiens

<400> SEQUENCE: 23

Gly Glu Gly Arg Val Gln Leu Met Lys Ala Leu Leu Ala Arg Pro Leu
1               5                   10                  15

Arg Pro Ala Ala Arg Arg Trp Arg Asn Pro Ile Pro Phe Pro Glu Thr
```

```
                  20                  25                  30

Phe Asp Gly Asp Thr Asp Arg Leu Pro Glu Phe Ile Val Gln Thr Ser
                35                  40                  45

Ser Tyr Met Phe Val Asp Glu Asn Thr Phe Ser Asn Asp Ala Leu Lys
         50                  55                  60

Val Thr Phe Leu Ile Thr Arg Leu Thr Gly Pro Ala Leu Gln Trp Val
 65                  70                  75                  80

Ile Pro Tyr Ile Lys Lys Glu Ser Pro Leu Leu Ser Asp Tyr Arg Gly
                85                  90                  95

Phe Leu Ala Glu Met Lys Arg Val Phe Gly Trp Glu Glu Asp Glu Asp
                100                 105                 110

Phe

<210> SEQ ID NO 24
<211> LENGTH: 364
<212> TYPE: PRT
<213> ORGANISM: Homo sapiens

<400> SEQUENCE: 24

Gly Pro Arg Gly Arg Cys Arg Gln Gln Gly Pro Arg Ile Pro Ile Trp
 1               5                  10                  15

Ala Ala Ala Asn Tyr Ala Asn Ala His Pro Trp Gln Gln Met Asp Lys
                20                  25                  30

Ala Ser Pro Gly Val Ala Tyr Thr Pro Leu Val Asp Pro Trp Ile Glu
                35                  40                  45

Arg Pro Cys Cys Gly Asp Thr Val Cys Val Arg Thr Thr Met Glu Gln
         50                  55                  60

Lys Ser Thr Ala Ser Gly Thr Cys Gly Lys Pro Ala Glu Arg Gly
 65                  70                  75                  80

Pro Leu Ala Gly His Met Pro Ser Ser Arg Pro His Arg Val Asp Phe
                85                  90                  95

Cys Trp Val Pro Gly Ser Asp Pro Gly Thr Phe Asp Gly Ser Pro Trp
                100                 105                 110

Leu Leu Asp Arg Phe Leu Ala Gln Leu Gly Asp Tyr Met Ser Phe His
                115                 120                 125

Phe Glu His Tyr Gln Asp Asn Ile Ser Arg Val Cys Glu Ile Leu Arg
                130                 135                 140

Arg Leu Thr Gly Arg Ala Gln Ala Trp Ala Ala Pro Tyr Leu Asp Gly
145                 150                 155                 160

Asp Leu Pro Leu Pro Asp Asp Tyr Glu Leu Phe Cys Gln Asp Leu Lys
                165                 170                 175

Glu Val Val Gln Asp Pro Asn Ser Phe Ala Glu Tyr His Ala Val Val
                180                 185                 190

Thr Cys Pro Leu Pro Leu Ala Ser Ser Gln Leu Pro Val Ala Pro Gln
                195                 200                 205

Leu Pro Val Val Arg Gln Tyr Leu Ala Arg Phe Leu Glu Gly Leu Ala
                210                 215                 220

Leu Asp Met Gly Thr Ala Pro Arg Ser Leu Pro Ala Ala Met Ala Thr
225                 230                 235                 240

Pro Ala Val Ser Gly Ser Asn Ser Val Ser Arg Ser Ala Leu Phe Glu
                245                 250                 255

Gln Gln Leu Thr Lys Glu Ser Thr Pro Gly Pro Lys Glu Pro Pro Val
                260                 265                 270

Leu Pro Ser Ser Thr Cys Ser Ser Lys Pro Gly Pro Val Glu Pro Ala
```

-continued

```
            275                 280                 285

Ser Ser Gln Pro Glu Glu Ala Ala Pro Thr Pro Val Pro Arg Leu Ser
    290                 295                 300

Glu Ser Ala Asn Pro Pro Ala Gln Arg Pro Asp Pro Ala His Pro Gly
305                 310                 315                 320

Gly Pro Lys Pro Gln Lys Thr Glu Glu Val Leu Glu Thr Gly
                    325                 330                 335

Asp Gln Glu Val Ser Leu Gly Thr Pro Gln Glu Val Glu Ala Pro
            340                 345                 350

Glu Thr Pro Gly Glu Pro Pro Leu Ser Pro Gly Phe
                355                 360

<210> SEQ ID NO 25
<211> LENGTH: 146
<212> TYPE: PRT
<213> ORGANISM: Homo sapiens

<400> SEQUENCE: 25

Gly Val Asp Glu Leu Val Leu Leu His Ala Leu Leu Met Arg His
1               5                   10                  15

Arg Ala Leu Ser Ile Glu Asn Ser Gln Leu Met Glu Gln Leu Arg Leu
                20                  25                  30

Leu Val Cys Glu Arg Ala Ser Leu Leu Arg Gln Val Arg Pro Pro Ser
            35                  40                  45

Cys Pro Val Pro Phe Pro Glu Thr Phe Asn Gly Glu Ser Ser Arg Leu
        50                  55                  60

Pro Glu Phe Ile Val Gln Thr Ala Ser Tyr Met Leu Val Asn Glu Asn
65                  70                  75                  80

Arg Phe Cys Asn Asp Ala Met Lys Val Ala Phe Leu Ile Ser Leu Leu
                85                  90                  95

Thr Gly Glu Ala Glu Glu Trp Val Val Pro Tyr Ile Glu Met Asp Ser
            100                 105                 110

Pro Ile Leu Gly Asp Tyr Arg Ala Phe Leu Asp Glu Met Lys Gln Cys
        115                 120                 125

Phe Gly Trp Asp Asp Asp Asp Asp Asp Glu Glu Glu Glu Asp
    130                 135                 140

Asp Tyr
145

<210> SEQ ID NO 26
<211> LENGTH: 549
<212> TYPE: PRT
<213> ORGANISM: Homo sapiens

<400> SEQUENCE: 26

Gly Pro Val Asp Leu Gly Gln Ala Leu Gly Leu Leu Pro Ser Leu Ala
1               5                   10                  15

Lys Ala Glu Asp Ser Gln Phe Ser Glu Ser Asp Ala Ala Leu Gln Glu
                20                  25                  30

Glu Leu Ser Ser Pro Glu Thr Ala Arg Gln Leu Phe Arg Gln Phe Arg
            35                  40                  45

Tyr Gln Val Met Ser Gly Pro His Glu Thr Leu Lys Gln Leu Arg Lys
        50                  55                  60

Leu Cys Phe Gln Trp Leu Gln Pro Glu Val His Thr Lys Glu Gln Ile
65                  70                  75                  80

Leu Glu Ile Leu Met Leu Glu Gln Phe Leu Thr Ile Leu Pro Gly Glu
```

-continued

```
                85                  90                  95
Ile Gln Met Trp Val Arg Lys Gln Cys Pro Gly Ser Gly Glu Glu Ala
            100                 105                 110
Val Thr Leu Val Glu Ser Leu Lys Gly Asp Pro Gln Arg Leu Trp Gln
            115                 120                 125
Trp Ile Ser Ile Gln Val Leu Gly Gln Asp Ile Leu Ser Glu Lys Met
        130                 135                 140
Glu Ser Pro Ser Cys Gln Val Gly Glu Val Glu Pro His Leu Glu Val
145                 150                 155                 160
Val Pro Gln Glu Leu Gly Leu Glu Asn Ser Ser Ser Gly Pro Gly Glu
                165                 170                 175
Leu Leu Ser His Ile Val Lys Glu Glu Ser Asp Thr Glu Ala Glu Leu
            180                 185                 190
Ala Leu Ala Ala Ser Gln Pro Ala Arg Leu Glu Glu Arg Leu Ile Arg
            195                 200                 205
Asp Gln Asp Leu Gly Ala Ser Leu Leu Pro Ala Ala Pro Gln Glu Gln
        210                 215                 220
Trp Arg Gln Leu Asp Ser Thr Gln Lys Glu Gln Tyr Trp Asp Leu Met
225                 230                 235                 240
Leu Glu Thr Tyr Gly Lys Met Val Ser Gly Ala Gly Ile Ser His Pro
                245                 250                 255
Lys Ser Asp Leu Thr Asn Ser Ile Glu Phe Gly Glu Glu Leu Ala Gly
            260                 265                 270
Ile Tyr Leu His Val Asn Glu Lys Ile Pro Arg Pro Thr Cys Ile Gly
            275                 280                 285
Asp Arg Gln Glu Asn Asp Lys Glu Asn Leu Asn Leu Glu Asn His Arg
        290                 295                 300
Asp Gln Glu Leu Leu His Ala Ser Cys Gln Ala Ser Gly Glu Val Pro
305                 310                 315                 320
Ser Gln Ala Ser Leu Arg Gly Phe Phe Thr Glu Asp Glu Pro Gly Cys
                325                 330                 335
Phe Gly Glu Gly Glu Asn Leu Pro Glu Ala Leu Gln Asn Ile Gln Asp
            340                 345                 350
Glu Gly Thr Gly Glu Gln Leu Ser Pro Gln Glu Arg Ile Ser Glu Lys
            355                 360                 365
Gln Leu Gly Gln His Leu Pro Asn Pro His Ser Gly Glu Met Ser Thr
        370                 375                 380
Met Trp Leu Glu Glu Lys Arg Glu Thr Ser Gln Lys Gly Gln Pro Arg
385                 390                 395                 400
Ala Pro Met Ala Gln Lys Leu Pro Thr Cys Arg Glu Cys Gly Lys Thr
                405                 410                 415
Phe Tyr Arg Asn Ser Gln Leu Ile Phe His Gln Arg Thr His Thr Gly
            420                 425                 430
Glu Thr Tyr Phe Gln Cys Thr Ile Cys Lys Lys Ala Phe Leu Arg Ser
            435                 440                 445
Ser Asp Phe Val Lys His Gln Arg Thr His Thr Gly Glu Lys Pro Cys
        450                 455                 460
Lys Cys Asp Tyr Cys Gly Lys Gly Phe Ser Asp Phe Ser Gly Leu Arg
465                 470                 475                 480
His His Glu Lys Ile His Thr Gly Glu Lys Pro Tyr Lys Cys Pro Ile
                485                 490                 495
Cys Glu Lys Ser Phe Ile Gln Arg Ser Asn Phe Asn Arg His Gln Arg
            500                 505                 510
```

Val His Thr Gly Glu Lys Pro Tyr Lys Cys Ser His Cys Gly Lys Ser
         515                 520                 525

Phe Ser Trp Ser Ser Leu Asp Lys His Gln Arg Ser His Leu Gly
         530                 535                 540

Lys Lys Pro Phe Gln
545

<210> SEQ ID NO 27
<211> LENGTH: 351
<212> TYPE: PRT
<213> ORGANISM: Homo sapiens

<400> SEQUENCE: 27

Gly Thr Leu Arg Leu Leu Glu Asp Trp Cys Arg Gly Met Asp Met Asn
1               5                   10                  15

Pro Arg Lys Ala Leu Leu Ile Ala Gly Ile Ser Gln Ser Cys Ser Val
            20                  25                  30

Ala Glu Ile Glu Glu Ala Leu Gln Ala Gly Leu Ala Pro Leu Gly Glu
        35                  40                  45

Tyr Arg Leu Leu Gly Arg Met Phe Arg Arg Asp Glu Asn Arg Lys Val
    50                  55                  60

Ala Leu Val Gly Leu Thr Ala Glu Thr Ser His Ala Leu Val Pro Lys
65                  70                  75                  80

Glu Ile Pro Gly Lys Gly Gly Ile Trp Arg Val Ile Phe Lys Pro Pro
                85                  90                  95

Asp Pro Asp Asn Thr Phe Leu Ser Arg Leu Asn Glu Phe Leu Ala Gly
            100                 105                 110

Glu Gly Met Thr Val Gly Glu Leu Ser Arg Ala Leu Gly His Glu Asn
        115                 120                 125

Gly Ser Leu Asp Pro Glu Gln Gly Met Ile Pro Glu Met Trp Ala Pro
    130                 135                 140

Met Leu Ala Gln Ala Leu Glu Ala Leu Gln Pro Ala Leu Gln Cys Leu
145                 150                 155                 160

Lys Tyr Lys Lys Leu Arg Val Phe Ser Gly Arg Glu Ser Pro Glu Pro
                165                 170                 175

Gly Glu Glu Glu Phe Gly Arg Trp Met Phe His Thr Thr Gln Met Ile
            180                 185                 190

Lys Ala Trp Gln Val Pro Asp Val Glu Lys Arg Arg Arg Leu Leu Glu
        195                 200                 205

Ser Leu Arg Gly Pro Ala Leu Asp Val Ile Arg Val Leu Lys Ile Asn
    210                 215                 220

Asn Pro Leu Ile Thr Val Asp Glu Cys Leu Gln Ala Leu Glu Glu Val
225                 230                 235                 240

Phe Gly Val Thr Asp Asn Pro Arg Glu Leu Gln Val Lys Tyr Leu Thr
                245                 250                 255

Thr Tyr His Lys Asp Glu Glu Lys Leu Ser Ala Tyr Val Leu Arg Leu
            260                 265                 270

Glu Pro Leu Leu Gln Lys Leu Val Gln Arg Gly Ala Ile Glu Arg Asp
        275                 280                 285

Ala Val Asn Gln Ala Arg Leu Asp Gln Val Ile Ala Gly Ala Val His
    290                 295                 300

Lys Thr Ile Arg Arg Glu Leu Asn Leu Pro Glu Asp Gly Pro Ala Pro
305                 310                 315                 320

Gly Phe Leu Gln Leu Leu Val Leu Ile Lys Asp Tyr Glu Ala Ala Glu

```
                        325                 330                 335
Glu Glu Glu Ala Leu Leu Gln Ala Ile Leu Glu Gly Asn Phe Thr
                340                 345                 350

<210> SEQ ID NO 28
<211> LENGTH: 708
<212> TYPE: PRT
<213> ORGANISM: Homo sapiens

<400> SEQUENCE: 28

Gly Thr Glu Arg Arg Arg Asp Glu Leu Ser Glu Glu Ile Asn Asn Leu
1               5                   10                  15

Arg Glu Lys Val Met Lys Gln Ser Glu Glu Asn Asn Asn Leu Gln Ser
                20                  25                  30

Gln Val Gln Lys Leu Thr Glu Glu Asn Thr Thr Leu Arg Glu Gln Val
        35                  40                  45

Glu Pro Thr Pro Glu Asp Glu Asp Asp Ile Glu Leu Arg Gly Ala
    50                  55                  60

Ala Ala Ala Ala Ala Pro Pro Pro Ile Glu Glu Cys Pro Glu
65                  70                  75                  80

Asp Leu Pro Glu Lys Phe Asp Gly Asn Pro Asp Met Leu Ala Pro Phe
                85                  90                  95

Met Ala Gln Cys Gln Ile Phe Met Glu Lys Ser Thr Arg Asp Phe Ser
            100                 105                 110

Val Asp Arg Val Arg Val Cys Phe Val Thr Ser Met Met Thr Gly Arg
        115                 120                 125

Ala Ala Arg Trp Ala Ser Ala Lys Leu Glu Arg Ser His Tyr Leu Met
    130                 135                 140

His Asn Tyr Pro Ala Phe Met Met Glu Met Lys His Val Phe Glu Asp
145                 150                 155                 160

Pro Gln Arg Arg Glu Val Ala Lys Arg Lys Ile Arg Arg Leu Arg Gln
                165                 170                 175

Gly Met Gly Ser Val Ile Asp Tyr Ser Asn Ala Phe Gln Met Ile Ala
            180                 185                 190

Gln Asp Leu Asp Trp Asn Glu Pro Ala Leu Ile Asp Gln Tyr His Glu
        195                 200                 205

Gly Leu Ser Asp His Ile Gln Glu Leu Ser His Leu Glu Val Ala
    210                 215                 220

Lys Ser Leu Ser Ala Leu Ile Gly Gln Cys Ile His Ile Glu Arg Arg
225                 230                 235                 240

Leu Ala Arg Ala Ala Ala Arg Lys Pro Arg Ser Pro Pro Arg Ala
                245                 250                 255

Leu Val Leu Pro His Ile Ala Ser His His Gln Val Asp Pro Thr Glu
            260                 265                 270

Pro Val Gly Gly Ala Arg Met Arg Leu Thr Gln Glu Glu Lys Glu Arg
        275                 280                 285

Arg Arg Lys Leu Asn Leu Cys Leu Tyr Cys Gly Thr Gly Gly His Tyr
    290                 295                 300

Ala Asp Asn Cys Pro Ala Lys Ala Ser Lys Ser Pro Ala Gly Lys
305                 310                 315                 320

Leu Pro Gly Pro Ala Val Glu Gly Pro Ser Ala Thr Gly Pro Glu Ile
                325                 330                 335

Ile Arg Ser Pro Gln Asp Asp Ala Ser Ser Pro His Leu Gln Val Met
            340                 345                 350
```

```
Leu Gln Ile His Leu Pro Gly Arg His Thr Leu Phe Val Arg Ala Met
            355                 360                 365
Ile Asp Ser Gly Ala Ser Gly Asn Phe Ile Asp His Glu Tyr Val Ala
370                 375                 380
Gln Asn Gly Ile Pro Leu Arg Ile Lys Asp Trp Pro Ile Leu Val Glu
385                 390                 395                 400
Ala Ile Asp Gly Arg Pro Ile Ala Ser Gly Pro Val Val His Glu Thr
                405                 410                 415
His Asp Leu Ile Val Asp Leu Gly Asp His Arg Glu Val Leu Ser Phe
                420                 425                 430
Asp Val Thr Gln Ser Pro Phe Phe Pro Val Val Leu Gly Val Arg Trp
            435                 440                 445
Leu Ser Thr His Asp Pro Asn Ile Thr Trp Ser Thr Arg Ser Ile Val
            450                 455                 460
Phe Asp Ser Glu Tyr Cys Arg Tyr His Cys Arg Met Tyr Ser Pro Ile
465                 470                 475                 480
Pro Pro Ser Leu Pro Pro Ala Pro Gln Pro Leu Tyr Tyr Pro
                485                 490                 495
Val Asp Gly Tyr Arg Val Tyr Gln Pro Val Arg Tyr Tyr Val Gln
                500                 505                 510
Asn Val Tyr Thr Pro Val Asp Glu His Val Tyr Pro Asp His Arg Leu
                515                 520                 525
Val Asp Pro His Ile Glu Met Ile Pro Gly Ala His Ser Ile Pro Ser
            530                 535                 540
Gly His Val Tyr Ser Leu Ser Glu Pro Glu Met Ala Ala Leu Arg Asp
545                 550                 555                 560
Phe Val Ala Arg Asn Val Lys Asp Gly Leu Ile Thr Pro Thr Ile Ala
                565                 570                 575
Pro Asn Gly Ala Gln Val Leu Gln Val Lys Arg Gly Trp Lys Leu Gln
            580                 585                 590
Val Ser Tyr Asp Cys Arg Ala Pro Asn Asn Phe Thr Ile Gln Asn Gln
            595                 600                 605
Tyr Pro Arg Leu Ser Ile Pro Asn Leu Glu Asp Gln Ala His Leu Ala
610                 615                 620
Thr Tyr Thr Glu Phe Val Pro Gln Ile Pro Gly Tyr Gln Thr Tyr Pro
625                 630                 635                 640
Thr Tyr Ala Ala Tyr Pro Thr Tyr Pro Val Gly Phe Ala Trp Tyr Pro
                645                 650                 655
Val Gly Arg Asp Gly Gln Gly Arg Ser Leu Tyr Val Pro Val Met Ile
                660                 665                 670
Thr Trp Asn Pro His Trp Tyr Arg Gln Pro Val Pro Gln Tyr Pro
            675                 680                 685
Pro Pro Gln Pro Pro Pro Pro Pro Pro Pro Pro Pro Pro Ser
            690                 695                 700
Tyr Ser Thr Leu
705

<210> SEQ ID NO 29
<211> LENGTH: 1188
<212> TYPE: DNA
<213> ORGANISM: Homo sapiens

<400> SEQUENCE: 29 gggagctgg accaccggac cagcggcggg ctccacgcct accccgggcc gcggggcggg      60
```

| | |
|---|---|
| caggtggcca agcccaacgt gatcctgcag atcgggaagt gccgggccga gatgctggag | 120 |
| cacgtgcggc ggacgcaccg gcacctgctg gccgaggtgt ccaagcaggt ggagcgcgag | 180 |
| ctgaagggc tgcaccggtc ggtcgggaag ctggagagca acctggacgg ctacgtgccc | 240 |
| acgagcgact cgcagcgctg gaagaagtcc atcaaggcct gcctgtgccg ctgccaggag | 300 |
| accatcgcca acctggagcg ctgggtcaag cgcgagatgc acgtgtggcg cgaggtgttc | 360 |
| taccgcctgg agcgctgggc cgaccgcctg gagtccacgg gcggcaagta cccggtgggc | 420 |
| agcgagtcag cccgccacac cgtttccgtg ggcgtggggg gtcccgagag ctactgccac | 480 |
| gaggcagacg gctacgacta caccgtcagc ccctacgcca tcaccccgcc cccagccgct | 540 |
| ggcgagctgc ccgggcagga gcccgccgag gcccagcagt accagccgtg ggtccccggc | 600 |
| gaggacgggc agcccagccc cggcgtggac acgcagatct tcgaggaccc tcgagagttc | 660 |
| ctgagccacc tagaggagta cttgcggcag gtgggcggct ctgaggagta ctggctgtcc | 720 |
| cagatccaga atcacatgaa cgggccggcc aagaagtggt gggagttcaa gcagggctcc | 780 |
| gtgaagaact gggtggagtt caagaaggag ttcctgcagt acagcgaggg cacgctgtcc | 840 |
| cgagaggcca tccagcgcga gctggacctg ccgcagaagc agggcgagcc gctggaccag | 900 |
| ttcctgtggc gcaagcggga cctgtaccag acgctctacg tggacgcgga cgaggaggag | 960 |
| atcatccagt acgtggtggg caccctgcag cccaagctca gcgttcct gcgccacccc | 1020 |
| ctgcccaaga ccctggagca gctcatccag aggggcatgg aggtgcagga tgacctggag | 1080 |
| caggcggccg agccggccgg cccccacctc ccggtggagg atgaggcgga gaccctcacg | 1140 |
| cccgcccca acagcgagtc cgtggccagt gaccggaccc agcccgag | 1188 |

<210> SEQ ID NO 30
<211> LENGTH: 1188
<212> TYPE: DNA
<213> ORGANISM: Orcinus orca

<400> SEQUENCE: 30

| | |
|---|---|
| ggggaattgg atcaacgtac taccggtggc cttcacgcat accctgcacc acgcggggc | 60 |
| cctgtcgcga agccaaatgt catcctgcag attgggaagt gccgggctga gatgctggag | 120 |
| cacgtccgtc ggacgcatcg tcatcttctt actgaggtgt caaaacaggt ggagcgtgaa | 180 |
| ctcaaaggct tgcaccgcag cgttgggaaa cttgaaagca acttagatgg ctatgtgccg | 240 |
| actgcgaca gccagcgttg gcgtaagtcc atcaaagcat gtttgtgtcg ttgccaggaa | 300 |
| acgattgcaa acctggagcg ttgggtcaaa cgggagatgc atgtctggcg tgaagtattt | 360 |
| tatcgtttag agcgttgggc cgatcgttta gagagcatgg gtggtaagta ccctgtgggg | 420 |
| agcaacccctt ctcggcatac gacgtcagtc ggtgttggcg ggccgagtc ctacggtcat | 480 |
| gaagcggaca cctacgacta taccgtaagc ccttatgcta ttaccccacc acctgcggcc | 540 |
| ggcgaattac ctggccagga agccgttgag gctcaacaat ccctccttg ggggctgggc | 600 |
| gaggatggtc aacctagccc aggggtagac acgcaaatct ttgaggaccc acgggagttt | 660 |
| ctttcccacc tggaagaata cctgcgtcag gttggtggga gcgaagaata ctggctgtca | 720 |
| caaattcaaa accatatgaa tggtcctgca aaaaatggt gggaatataa acagggttcc | 780 |
| gtgaaaaact gggttgagtt taaaaggag tttcttcaat attccgaggg cgccctcagt | 840 |
| cgggaggcgg tccaacgcga gttggacttg ccacagaaac aggggaacc actcgatcaa | 900 |
| ttcctttggc ggaaacgtga cctttaccag acattgtacg tggatgcaga tgaggaagaa | 960 |
| attatccaat atgttgtggg gaccctgcag ccgaaactga acgtttcct tcgcccgccg | 1020 |

```
ctgcctaaaa cgttggaaca acttattcag aaaggtatgg aggtcgagga tggcttagaa    1080
caagtcgcag agccggcctc gccacacttg cctacagagg aggaatcgga ggcgctgacc    1140
ccagcactta catcagagtc agtggcatca gaccggacac aaccagag                 1188
```

<210> SEQ ID NO 31
<211> LENGTH: 1170
<212> TYPE: DNA
<213> ORGANISM: Odocoileus virginianus texanus

<400> SEQUENCE: 31

```
ggggagttag atcaccgtac aacgggggggg ttgcacgcat accctgctcc acgtggcggg     60
ccggcagcta agccaaacgt aatcctgcag attgggaagt gccgggcaga gatgttggag    120
cacgtccggc ggacccaccg gcacctcctg gctgaagtgt ctaaacaagt agaacgggaa    180
ctcaaaggtc ttcatcgtag cgtcgggaaa ttggaatcga atttggacgg gtatgttcct    240
acaggcgact cacagcggtg gaaaaagagc atcaaggcct gcctgagtcg ctgccaggag    300
acgattgcta acctcgaacg ctgggttaag cgggagatgc acgtttggcg cgaagtcttc    360
taccggctgg agcgttgggc tgatcggctc gaatctggtg ggggtaagta tccagttggg    420
tccgaccctg ctcgccacac agtctcagtt ggcgtaggtg ggccggagtc gtattgccaa    480
gatgcggaca actatgatta tacagttttcc ccatacgcga tcacaccacc gccggcagca    540
gggcagctgc caggtcagga agaggttgag gcccagcagt atccaccatg gccccaggg     600 gaagacggcc agctttctcc tggggtggac actcaagttt ttgaagatcc gcgtgaattt    660
ctgcggcatt tagaagatta tctccgccag gtcgggggt  ctgaagagta ttggttaagc    720
caaattcaaa accatatgaa cggcccggcc aagaagtggt gggagtacaa gcaagggtct    780
gtgaaaaatt gggtggagtt taagaaagaa ttcttgcaat attctgaggg cactctttcg    840
cgtgaagcca tccaacgcga actcgactta ccgcagaaac aagggggaacc tctcgaccaa    900 tttctgtggc gcaaacgcga cctgtaccag actctttacg tcgatgctga ggaggaagaa    960
attattcaat acgtagttgg cacactgcag cctaagctta aacggttttt acgtccacca   1020
ttgccgaaga cgcttgaaca actcatccag aagggtatgg aggttcaaga tggtctggaa   1080
caggcagcgg aaccagcggc ggaggaggca gaagccctga cacctgcgtt aactaacgag   1140
tctgtcgcga gcgaccgcac ccagccggaa                                    1170
```

<210> SEQ ID NO 32
<211> LENGTH: 1203
<212> TYPE: DNA
<213> ORGANISM: Ornithorhynchus anatinus

<400> SEQUENCE: 32

```
ggggaattag accgcctgaa cccaagctca ggcctgcatc catcctctgg tttgcatcca     60
tacccaggtc tccggggcgg ggcaaccgcg aagcctaatg tcattttgca aattggcaaa    120
tgccgtgcgg aaatgcttga acacgtccgc aaaactcacc gtcatctcct cacagaagta    180
tcgcgccaag tagaacgcga gctcaaaggc cttcacaaaa gtgttggcaa gttggaatca    240
aatcttgatg ggtacgtacc gtcaagcgac tcccaacgct ggaagaaaag cattaaggcg    300
tgcttatccc gttgccaaga gacgattgcg catttagaac gctgggttaa acgtgaaatg    360
aatgtatggc gtgaggtgtt ctaccgtttg gaacgttggg cggaccgtct ggaggctatg    420
ggcggtaagt atcctgccgg tgagcaggcc cggcgtacag tttcagtggg cgttgggggc    480
```

```
cctgagacat gttgtccagg ggatgaaagt tatgattgtc cgatttctcc gtatgcagtt      540
ccaccttcca ccggcgagtc tccggaatcc ttagaccaag gggatcagca ctatcagcag      600
tggtttgccc tcccggagga gtccctgtt agccctgggg ttgatacca gatctttgaa        660 gatcctcgcg agtttttacg tcatctggag aagtacctga acaagtcgg cgggacagag       720 gaagactggc tttctcaaat ccagaatcac atgaatgggc cggcgaagaa gtggtgggag      780
tacaagcaag ggagtgttaa gaattggctt gaatttaaga aggaattttt acagtattcg      840
gagggcacac tgacgcggga cgcgttgaaa cgtgaactgg atctcccaca gaaacaaggc      900
gaaccacttg atcaattttt atggcggaag cgcgacttat atcagacact ctacgttgac      960
gccgatgaag aggaaatcat tcagtacgtc gtgggcactc ttcagccgaa attaaaacgc     1020
tttctccatc acccactccc taagacgctt gagcagctta tccaacgggg ccaagaagtt     1080
cagaatggtc tggagcctac cgacgatcct gcaggccaac gcactcaatc ggaggacaac     1140
gacgaaagcc ttaccctgc cgtcaccaat gagagtactg caagcgaggg caccctgcca      1200
gag                                                                   1203

<210> SEQ ID NO 33
<211> LENGTH: 1212
<212> TYPE: DNA
<213> ORGANISM: Anser cygnoides domesticus

<400> SEQUENCE: 33
gggcagcttg ataacgttac aaacgcgggc atccactcct tccaggggca tcgtggcgta       60
gcgaataagc caaatgtcat tctgcaaatt ggtaaatgtc gtgcggaaat gctggagcac      120
gttcgccgca cccaccgcca tttattatct gaagtatcta agcaggtaga acgtgagctg      180
aaagggctgc aaaagtccgt gggcaagctc gagaataact tggaggatca tgtccctaca      240
gataaccaac gctggaagaa gtccattaaa gcgtgcttgg ctcgttgtca agagactatc      300
gcgcatttag agcgttgggt gaaacgcgaa atgaacgtct ggaaggaggt gttttccgg      360 ctggaaaagt gggcagaccg gctggagtca atgggtggca agtactgccc gggcgaacac      420
gggaaacaaa ccgtcagtgt aggcgtgggg ggtcctgaaa tccggccttc ggaggggaa       480 atttatgatt atgctctgga tatgagccag atgtatgcac tcaccccacc tccaggcgaa      540
atgccatcaa tccacaagc ccatgacagc tatcagtggg ttagtgtctc agaagatgcc       600
ccggcgagcc ctgtcgaaac ccaggtattt gaggaccctc gggaattcct gtctcacctg      660
gaggaatacc tgaagcaggt aggcggcacg gaggagtatt ggttgtccca gatccagaat     720
cacatgaatg gtccggcaaa aaaatggtgg aatataaac aggactccgt taaaaactgg       780
gttgagttta aaaggaatt cttgcaatac tctgaaggta cttaactcg ggatgctatt        840 aagcgtgaac tcgacttgcc gcaaaaggaa ggtgaacctc ttgaccaatt cctttggcgg      900
aagcgggacc tctatcagac actttacgtg gacgcggatg aggaggagat cattcagtat      960
gtggtcggta ccctgcagcc gaagctcaag cgtttcctga gctatcctct cccaaagact     1020
ttagaacagc tcatccagcg cggtaaagaa gtgcaggta acatggatca ctccgatgag      1080
ccttcgccgc agcgtacacc tgaaattcaa tcaggtgact ccgtagaatc tatgccacct     1140
tcaacaacgg catctccggt tccatctaat ggtacccaac ctgagccgcc gagcccgcca     1200
gccaccgtta tc                                                         1212

<210> SEQ ID NO 34
<211> LENGTH: 1185
```

<212> TYPE: DNA
<213> ORGANISM: Pelecanus crispus

<400> SEQUENCE: 34

| | | | | | |
|---|---|---|---|---|---|
| gggcaacttg | acaacgtaac | aaacgctggg | attcactcct | ttcagggcca | ccgcggtgtc | 60 |
| gccaacaagc | caaacgtaat | cttgcaaatt | ggcaaatgcc | gtgcggagat | gttggaacac | 120 |
| gttcgtcgta | cacatcgtca | cttgctgtcg | gaagtctcta | aacaagtaga | acgtgaactt | 180 |
| aaagggcttc | aaaagtcagt | cggcaaattg | gaaaacaacc | ttgaagacca | tgtaccaacc | 240 |
| gacaatcagc | gttggaaaaa | gtctatcaaa | gcttgcctgg | cccgttgtca | agagacgatt | 300 |
| gctcacctgg | agcggtgggt | aaagcgcgag | atgaatgtgt | ggaaagaggt | cttcttccgc | 360 |
| ttggaaaaat | gggccgaccg | tttggagtcc | atgggcggta | atattgtcc | gggtgaacat | 420 |
| ggtaagcaaa | cagtctctgt | gggcgttggt | gggccggaga | ttcggccttc | tgaaggcgag | 480 |
| atttacgatt | atgcgctcga | catgtcccag | atgtatgcgc | ttacaccacc | accgggcgag | 540 |
| gtaccaagca | ttcctcaagc | gcatgacagt | tatcagtggg | ttagcgtatc | cgaagacgct | 600 |
| cctgcctcgc | cggtagagac | ccaggttttt | gaagatcctc | gtgaattttt | aagccacttg | 660 |
| gaggagtatt | tgaagcaggt | aggggggaca | gaggaatatt | ggctgtctca | gatccagaac | 720 |
| cacatgaatg | cccggctaa | aaagtggtgg | gaatacaaac | aagattcggt | aaagaattgg | 780 |
| gtagaattta | aaaaggagtt | tttacagtac | tcagagggga | ctctcacgcg | tgatgcgatc | 840 |
| aaacgcgagt | tggatcttcc | tcaaaaagag | ggggagccac | tcgatcagtt | cctctggcgc | 900 |
| aagcgggatc | tctaccaaac | actctacgta | gacgcagacg | aagaagagat | catccagtac | 960 |
| gtggtgggta | cgctccagcc | gaaactcaaa | cgtttcctca | gctacccact | tcctaagact | 1020 |
| ctggaacaac | tgattcagcg | gggcaaagag | gtccagggta | acatggacca | ttcagaggaa | 1080 |
| cctagtccgc | aacgtacacc | tgagatccaa | tctggggatt | ctgtcgattc | ggttccacct | 1140 |
| tctacaacag | cgtctccggt | gccgtcaaat | gggacccaac | cagag | | 1185 |

<210> SEQ ID NO 35
<211> LENGTH: 1185
<212> TYPE: DNA
<213> ORGANISM: Haliaeetus albicilla

<400> SEQUENCE: 35

| | | | | | |
|---|---|---|---|---|---|
| gggcagcttg | ataatgtaac | caatgcaggt | atccactctt | tccagggtca | ccgcggtgtg | 60 |
| gcaaacaagc | caaatgttat | tctgcaaatt | ggtaagtgtc | gcgctgagat | gttagaacac | 120 |
| gtccggcgca | cgcatcggca | tctcctgtca | gaggtttcaa | agcaggtaga | gcgtgaatta | 180 |
| aagggcctcc | agaagtccgt | aggtaaactc | gaaaataatc | ttgaagacca | cgttcctacc | 240 |
| gataatcaac | ggtggaaaaa | gtcaatcaag | gcgtgcttag | cacggtgtca | ggaaacgatc | 300 |
| gcgcacctcg | aacgttgggt | gaagcgcgaa | atgaatgtct | ggaaagaagt | gttcttccgg | 360 |
| cttgagaagt | gggctgatcg | gctcgaatcc | atgggtggca | atattgtcc | aggtgatcat | 420 |
| ggcaagcaaa | cggtctccgt | cggtgttggt | ggtccggaaa | tccggccgag | cgagggtgaa | 480 |
| atctatgact | acgctcttga | tatgtcccag | atgtatgcac | tcactcctcc | gccgggtgag | 540 |
| gtcccgtcga | tcccgcaggc | gcatgactca | taccaatggg | tgtcgactag | cgaagacgca | 600 |
| ccagcctccc | ctgttgaaac | tcaagtattc | gaggacccgc | gtgagttcct | gagccattta | 660 |
| gaggagtacc | ttaagcaggt | tggtggtacc | gaggaatact | ggttgagcca | gattcagaat | 720 |
| cacatgaacg | ggccggctaa | gaatggtgg | gaatacaagc | aggattcagt | caagaattgg | 780 |

```
gtcgaattta agaaggagtt tttgcagtac agtgagggga cgctcacacg cgacgctatc    840
aaacgggagc tggacctgcc acaaaaggag ggtgaaccgc ttgatcagtt tctttggcgc    900
aagcgtgatc tgtatcaaac cctgtatgtg gacgctgacg aagaagagat cattcagtac    960
gtggttggga ctctgcaacc aaagctgaag cgttttcttt cttatcctct ccctaagaca   1020
ctggaacagt taatccaacg tggcaaggag gtccagggta atatggacca ctctgaggaa   1080
ccgagcccgc aacgtactcc tgaaattcag agcggggata gtgtcgactc agttcctcca   1140
agtacgaccg catccccggt cccaagtaac ggtacccaac cagag                   1185
```

<210> SEQ ID NO 36
<211> LENGTH: 1395
<212> TYPE: DNA
<213> ORGANISM: Ophiophagus hannah

<400> SEQUENCE: 36

```
gggtcttggg gcttgcaacg tcacgtggct gatgaacgtc gtggcctcgc tacgcctacc     60 tacgcgcgg tttgttccat tcgggagaaa aaagcctccc aactgagcgg ccagagctgt    120
ttggagaaag agttgcttgg ttggaaatgt acggaggcaa tcgtggaaat gatgcaagtc    180
gataacttta accacggtaa cttacatagc tgccaaggcc atcgggggat ggcaaatcac    240
aaaccgaacg taatccttca aatcgggaaa tgtcgcgcag aaatgttaga ccacgtgcgt    300
cgcacccacc gccatctctt gacggaggtt tcgaagcagg tagaacgcga attgaagtct    360
ctccaaaagt cggttggcaa gctcgagaat aatctggaag accacgtgcc atcggcagcg    420
gagaaccaac gttggaagaa atcaattaaa gcctgcctgg cccggtgcca agaaacaatt    480
gctcacctcg aacgctgggt taaacgcgaa atcaacgtct ggaaagaagt attctttcgt    540
ctggagaagt gggcggaccg ccttgagtcg ggtggggggca agtatgggcc tggtgaccaa    600
agtcgtcaaa ctgtaagtgt cggtgttggg gccccagaaa tccaaccgcg gaaagaagaa    660
atctatgact acgctctcga catgtcgcag atgtatgcct aacaccacc gccgatgggt    720 gaagacccaa acgtacctca atcccacgat agctaccagt ggattaccat ctcagacgat    780
tcacctccgt cgccagtgga aactcaaatt ttcgaggatc cacgcgaatt ccttacccat    840
ctcgaggatt atcttaagca gtgggcggg actgaagaat attggttgag tcagattcaa    900
aatcatatga acggtccggc caagaaatgg tgggagtaca acaagattc cgtgaaaaac    960 tggttggaat tcaagaagga attccttcaa tactctgagg gtactttgac acgtgacgca   1020
attaaacaag aacttgactt accgcagaag acggcgagc cattggatca atttctttgg   1080
cggaagcggg acctgtatca gacgctctat attgatgcag aggaggaaga agtaatccaa   1140
tacgttgttg gcacactcca accgaaatta aaacgtttcc tttcccaccc gtatccgaaa   1200
actttggaac agttaatcca acgtgggaaa gaggtggaag gcaacctcga taactctgag   1260
gagcctagcc cgcaacggag tccaaagcac caattgggtg gtagcgtcga gagcctccca   1320
ccttcgtcga ccgcaagtcc tgttgcgtca gacgagactc acccagacgt gagcgcacct   1380
ccggtaacgg tgatt                                                    1395
```

<210> SEQ ID NO 37
<211> LENGTH: 1353
<212> TYPE: DNA
<213> ORGANISM: Austrofundulus limnaeus

<400> SEQUENCE: 37

```
ggggacggcg agactcaagc tgagaatcca tctaccagct tgaacaacac tgacgaagat     60
```

```
atcttggaac agctcaagaa aattgtcatg gatcaacaac acctgtatca gaaagaatta      120
aaggcatctt ttgaacaact cagtcgcaaa atgttttccc agatggaaca aatgaatagc      180
aagcaaacgg atctgctttt agaacatcaa aaacagactg tcaaacatgt agacaagcgc      240
gtggagtatt tgcgggcgca attcgatgca tcgttaggct ggcggttgaa agagcaacac      300
gcggatatta cgaccaaaat cattcctgag atcatccaaa cggtgaagga agatattagc      360
ctgtgtcttt ctacgctctg cagtatcgct gaagatatcc agacatcacg ggctaccact      420
gtcacagggc atgctgccgt acaaacccat cctgtggatc ttttgggtga acaccattta      480
gggaccacgg ggcacccacg cttacagtcg acccgtgtag ggaaaccaga cgacgtacct      540
gagtcgccgg taagcctgtt tatgcaaggt gaggcgcgtt cccggatcgt tggcaagagt      600
ccgattaaac tgcaatttcc gacgttcggc aaagcaaacg attcttccga cccactccaa      660
tatctggagc ggtgtgagga ctttcttgct cttaacccctt taactgatga ggaacttatg      720
gctactttgc ggaatgtgtt acatggcacc tctcgggatt ggtgggatgt cgcacgtcat      780
aaaatccaaa cttggcgtga gtttaataaa cacttccggg cggctttcct cagcgaggat      840
tatgaagatg agttggctga gcgcgtccgt aaccgcatcc aaaaagaaga tgagtctatc      900
cgcgatttcg cttatatgta tcagtccttg tgcaagcggt ggaaccctgc tatctgcgaa      960
ggtgatgtag taaagctcat cctgaagaac atcaatccac aactgccgtc tcagttacgc     1020
tcccgggtca cgaccgtgga tgagcttgtt cgcttgggcc agcagcttga aaaagatcgt     1080
cagaatcagc tccaatatga gcttcggaag agttccggca aaattatcca aaaatctagt     1140
tcgtgcgaaa cttcagcgct cccgaacacg aagagtacac ctaatcaaca aaaccctgct     1200
accagtaacc gtcctccaca ggtgtattgc tggcggtgta agggtcacca tgcccctgcc     1260
tcttgtccgc aatggaaagc tgataagcac cgtgcgcaac cttcgcggag ttctgggcca     1320
caaactctga ctaatctcca agctcaagac atc                                  1353
```

<210> SEQ ID NO 38
<211> LENGTH: 1188
<212> TYPE: DNA
<213> ORGANISM: Physeter catodon

<400> SEQUENCE: 38

```
ggggaattgg atcaacgtgc ggcaggggggc ttgcgcgcgt acccggcgcc gcgtggtggt       60
ccagttgcca aaccgagcgt aattcttcag attggtaagt gccgcgctga gatgctggaa      120
cacgtccgcc gcacgcatcg ccatcttctg acggaggtaa gtaaacaagt ggagcgcgaa      180 ctcaagggt tacatcggtc tgtcggtaag ttggagggca atttagacgg ctatgtgcct      240
accggtgatt cccaacgctg gaaaaaaagt atcaaggcgt gtctctgccg gtgtcaggaa      300
acaattgcaa atctcgagcg ttgggtgaaa cgtgagatgc atgtttggcg tgaggtattc      360
tatcgtttgg aacggtgggc agaccgtttg gagtctatgg ggggcaagta tccggtgggc      420
actaacccgt cgcggcacac agtaagtgtc ggggtagggg gcccggaagg ctattctcat      480 gaagcgggata cttatgacta cacggtgtct ccgtatgcta tcacgccacc gcctgccgcg      540
ggtgagttgc ctggtcaaga ggctgtcgag gcacaacagt accctccatg gggtctgggg      600
gaggacgggc aaccaggtcc gggcgtggac acgcagattt ttgaggaccc tcgcgaattt      660
ttgagccact tagaggagta cctgcggcaa gtagggggga gtgaagagta ctggttatcg      720
caaattcaaa atcatatgaa tggccctgcg aagaaatggt gggagttcaa acaggggtca      780
```

```
gtcaagaatt gggtcgagtt taagaaagaa ttttttgcaat acagtgaggg tacgttgagt    840
cgcgaggcca tccaacgtga actggacctc cctcagaagc aggggagcc gttagatcaa      900 tttttatggc ggaaacgtga cttataccaa accctctacg ttgacgctga ggaagaagaa    960
attattcaat atgttgtcgg tacgctgcag ccaaagctga agcggttcct ccgtcctcca    1020
ctccctaaaa ccttagaaca attaatccaa aaaggcatgg aagttcagga cgggttagaa    1080
caagcggccg aaccggcctc tccgcgtctg ccgccggaag aggagagtga ggctcttacg    1140
cctgcgctca cgagcgaatc agtagcctcc gatcggacac agccagag               1188
```

```
<210> SEQ ID NO 39
<211> LENGTH: 1212
<212> TYPE: DNA
<213> ORGANISM: Meleagris gallopavo

<400> SEQUENCE: 39
gggcagcttg acaatgtgac gaacgcgggg attcacagct ttcaagggca ccgcggcgtc     60
gccaacaaac cgaatgtcat tctgcaaatc ggtaaatgtc gtgctgaaat gcttgagcac    120
gttcgtcgta cccatcgtca cttgctttct gaagtatcaa acaagtgga gcgggaactc    180 aaaggcctgc aaaagtcagt gggtaaattg agaataacc tcgaagacca tgtacctaca    240
gacaaccagc ggtggaaaaa atctatcaag gcatgcctcg ctcgttgcca ggagactatt    300
gcccatcttg agcggtgggt gaaacgtgaa atgaacgtat ggaaggaagt attttttcgc    360
ttagagaagt gggctgatcg tcttgaatcg atgggcggca agtactgtcc tggggaacac    420
ggcaaacaaa ctgtatctgt cggcgtgggg ggcccggaga tccggccatc ggaaggggaa    480
atttatgatt atgctctcga catgtcccaa atgtatgctc tcacaccagg gccaggggaa    540
gtaccgtcaa ttccgcaagc acacgacagc taccaatggg tatctgtgag cgaggacgcg    600
cctgcctctc cggttgagac gcaaatctttt gaggacccac atgaattttt gtctcatctt    660
gaagaatatc tcaaacaggt tggcggcaca gaagaatact ggttatctca gatccagaat    720
cacatgaacg gcccggctaa aaagtggtgg gagtataagc aagattccgt aaagaactgg    780
gtcgaattca gaaagagtt tcttcaatac tctgagggta ctctgacgcg cgatgcaatt    840
aagcgggagt tagaccttcc acaaaaagag ggggagcctc ttgaccagtt cctgtggcgt    900
aagcgcgacc tctatcagac actttacgtc gacgctgatg aagaagagat tattcaatat    960
gttgtgggta cccctgcagcc aaagcttaag cgtttcctta gctacccact tccgaaaact   1020
ctggagcagc tcattcaacg cggtaaggaa gtgcagggca acatggacca ctctgaagag   1080
cctagcccgc agcgcactcc tgaaatccaa tcaggtgaca gtgtggagtc aatgccgccg   1140
tcaaccaccg cttctccggt acctagcaac gggacgcaac cagagcctcc aagcccaccg   1200
gctacagtca tc                                                       1212
```

```
<210> SEQ ID NO 40
<211> LENGTH: 1227
<212> TYPE: DNA
<213> ORGANISM: Pogona vitticeps

<400> SEQUENCE: 40
gggcaacttg agaatattaa ccaaggttcc ctgcacgcgt ttcagggtca tcgcggcgtg     60
gtccataaca acaagcctaa cgttattctc cagatcggga agtgccgcgc cgaaatgctg    120
gagcatgtgc ggcgcaccca tcgccatttg ctcactgaag tatcaaaaca ggtggagcgt    180
gagttgaagg ggttgcagaa aagtgtaggc aaacttgaaa ataatttaga agaccacgta    240
```

```
ccaagtgcgg ctgagaacca acgctggaag aagtcgatta aagcctgctt agcgcgttgt      300
caggagacca ttgcgaactt ggaacgctgg gttaaacgtg agatgaatgt ttggaaggag      360 gtcttttttcc gcttagagcg ctgggcagat cgcctcgaat ccgggggtgg caagtactgc     420
catgcagacc agggtcgcca aactgtcagc gtaggtgttg gtggtcctga agtgcgtccg      480
tctgaaggtg aaatttacga ttacgcgttg gatatgagcc aaatgtacgc cttgactccg      540
ccgcctatgg gtgatgttcc agtaattcct cagccgcatg acagttatca gtgggtgaca      600
gatccggaag aagcgccacc aagtccggtt gagacacaaa ttttcgagga ccctcgggag      660
tttctgaccc atcttgagga ttatttaaaa caagtcggcg ggacagagga atattggctc      720
tcacagatcc aaaatcatat gaatgggcca gcgaaaaagt ggtgggaata taaacaggat      780
agtgtgaaga actggcttga gttcaaaaaa gaattcttgc agtactcaga aggcacgtta      840
acgcgggacg ctattaaaca ggaacttgac cttccacaaa aagaagggga accgctggat      900
caattcctct ggcgcaaacg cgatttgtac caaactctct acgtcgaggc agaagaagag      960
gaggtcatcc aatatgtagt tggcacactg caaccaaaac tgaagcggtt tctttctcat     1020
ccgtacccta aaaccctgga gcaactcatc cagcgcggga aggaagttga ggggaatttg     1080
gacaatagtg aagaaccgtc tccacagcgg accccagaac atcagctggg ggacagtgtg     1140
gaatctttgc cgcctagtac tacggcttcg cctgccggtt cggataaaac gcaacctgag     1200
attagcttac ctccaactac agtcatt                                         1227
```

<210> SEQ ID NO 41
<211> LENGTH: 1212
<212> TYPE: DNA
<213> ORGANISM: Alligator sinensis

<400> SEQUENCE: 41

```
gggcaattag attcggtaac caatgcgggc gtccacacct accagggcca tcggagcgtc       60
gccaataaac ctaacgtcat tcttcaaatc gggaaatgtc ggactgagat gctggagcat      120
gtccgtcgga ctcatcgcca cctgctcaca gaagtgtcaa agcaagtgga acgtgaactc      180
aagggcttac agaagagcgt gggcaaactg gaaaacaatc ttgaagacca tgtcccaact      240
gacaatcagc ggtggaagaa gtcaatcaag gcatgtctcg cgcgttgcca agagaccatt      300
gctcaccttg agcggtgggt gaaacgtgaa atgaacgtgt ggaaggaggt gttcttccgg      360
ttagaacgct gggccgaccg ccttgaatca atgggtggta aatactgccc gacggactct      420
gcacgtcaga cagttagcgt tggggtgggg ggcccggaaa ttcggcctag tgaaggcgaa      480
atctatgact acgcgctcga tatgagccaa atgtacgctc ttacgccgtc accgggcgaa      540
ttgccgtccg tccctcaacc gcatgattca taccagtggg tcactagtcc ggaagacgct      600
ccggcgtcac cagttgaaac gcaggtattc gaggatcctc gggagttctt gtgtcatttg      660
gaagagtacc tgaagcaggt tggcggtaca gaggaatatt ggctgagcca gattcagaat      720
catatgaatg gtcctgcaaa aaagtggtgg gaatataaac aagacacggt taagaattgg      780
gtggaattca agaaggagtt cttacaatac agtgagggta cacttacccg tgatgcgatt      840
aagcgggaat tagacctccc gcaaaaggac ggtgagcctc tggatcaatt tttatggcgt      900
aagcgtgacc tctatcagac attatacatt gatgccgatg aagaacagat cattcagtac      960
gtcgtgggga cattgcaacc taaactcaag cggttcttgt cctatccact tccaaaaact     1020
cttgaacaat taatccagaa agggaaggag gtgcagggtt cacttgacca cagcgaggag     1080
```

```
ccgagtcctc aacgtgcgag cgaggctcgg acgggcgata gtgtggaaac cttgccgcct   1140
tctaccacta catcaccaaa tacgtcatct ggtacacagc cagaggcacc atcgcctcca   1200
gcgacggtaa tc                                                       1212
```

<210> SEQ ID NO 42
<211> LENGTH: 1212
<212> TYPE: DNA
<213> ORGANISM: Alligator mississippiensis

<400> SEQUENCE: 42

```
gggcagttag acagtgtgac taacgccggg gtgcatacgt accagggca ccgcggggtc     60
gccaataagc caaatgtaat tctccagatt gggaagtgtc gtacagagat gttggaacat   120
gtccgtcgca ctcatcgcca cttgctcacc gaggtctcca acaagtaga acgcgaactc   180
aaggggctcc agaagagtgt tgggaagttg agaataacc tcgaagacca cgttccgaca   240
gataaccaac ggtggaaaaa gtctattaaa gcctgtctcg cccgttgtca agagacaatc   300
gcacacttgg aacgctgggt caaacgggag atgaatgtgt ggaaggaagt cttcttccgt   360
ctcgagcggt gggcggatcg tttagaaagt atgggcggta aatattgccc aactgactcg   420
gctcgtcaaa cggtgtcggt tggcgtaggc ggcccggaaa ttcgccctag cgagggtgag   480
atctatgact atgcacttga catgagtcag atgtatgcgt taactccgtc gccaggggag   540
cttccaagta ttccacagcc tcacgatagt tatcaatggg taacttctcc tgaagacgcc   600
ccagcatccc cagttgagac acaagtattc gaggaccctc gtgagtttct ctgtcacctc   660
gaggagtacc ttaaacaggt aggcgggacc gaagagtact ggttatcgca aatccaaaac   720
catatgaatg gtcctgccaa aaagtggtgg gagtataaac aagatactgt gaagaattgg   780
gtagagttca agaaagagtt cttacagtac tctgagggga cgttaactcg tgatgcgatc   840
aagcgcgaat ggatttacc tcagaaggac ggcgagccac tcgaccagtt cttatggcgc   900
aagcgtgact tgtatcaaac cctttatatc gatgctgacg aggaacaaat tatccagtac   960
gtagtcggta cgttgcaacc aaaacttaaa cgctttctga gctacccatt acctaaaacg  1020
ttggagcaac tgatccagaa aggtaaagag gtgcaaggga gcctggatca tagtgaagaa  1080
ccgagccctc agcgggcttc tgaagctcgg accggtgata gcgtcgaatc tttaccacct  1140
agtaccacaa ccagcccgaa tgcgtcatct ggtacccaac ctgaagcgcc ttccccacct  1200
gctacagtca tt                                                     1212
```

<210> SEQ ID NO 43
<211> LENGTH: 1224
<212> TYPE: DNA
<213> ORGANISM: Gekko japonicus

<400> SEQUENCE: 43

```
gggcagctcg agaatgtcaa ccatgggaac ctccattctt ttcaaggtca tcgcggcggc    60
gtcgccaaca agccaaacgt tatcttgcag atcggtaaat gtcgtgcaga gatgctggac   120
cacgtccggc ggacccaccg gcatttactg acagaggtat cgaaacaggt tgaacgtgag   180
ttgaagggt tacagaaatc agtagggaaa ttagaaaata acttagaaga ccatgtccct   240
tcagccgttg aaaaccagcg ttggaaaaaa tcgatcaagg cctgcctttc ccgctgccaa   300
gagaccattg cccaccttga gcgttgggtg aagcgcgaga tgaacgtatg gaaagaggtt   360
ttcttccgct tagagcggtg ggcagatcgg ttggaatctg ggggcgggaa atattgtcac   420
ggtgataatc atcgtcaaac agtatcagtc ggtgttggcg gccctgaggt acgtccatct   480
```

```
gaaggcgaaa tttacgatta cgctctcgac atgtcgcaaa tgtacgcttt aacaccgcct      540
agcccagggg atgtgcctgt agttagccag ccgcacgaca gctatcagtg ggttacggtt      600
ccggaggata cccctccatc cccggtggag acgcaaatct tcgaggaccc acgggagttc      660
ttgacccact tagaggatta cttaaagcaa gtgggggta cagaggaata ttggttatct       720
cagatccaga atcacatgaa cgggccagcc aagaagtggt gggagtataa gcaagactca      780
gtaaaaaatt ggctcgagtt taagaaggaa ttccttcagt attccgaggg gacacttacg      840
cgcgacgcta tcaaggaaga acttgacctc ccgcaaaagg acggggaacc tcttgatcag      900
ttcctgtggc gcaagcgcga cttgtaccag accctgtacg tggaggcgga tgaggaggag      960
gtgatccagt atgttgtggg gactttacaa cctaaattaa agcgttttct ctcacaccct     1020
tacccgaaaa cgttagagca acttatccaa cggggcaaag aggtggaagg gaacctcgac     1080
aattcagagg aaccaacacc tcagcgtact ccagaacacc aactgtgtgg ttctgtagaa     1140
tcgctgcctc cttcctctac cgtcagtcca gtggctagcg atggtactca acctgagact     1200
tcgccattgc cagcgactgt tatt                                           1224

<210> SEQ ID NO 44
<211> LENGTH: 1365
<212> TYPE: DNA
<213> ORGANISM: Homo sapiens

<400> SEQUENCE: 44
gggccattga cgttgttaca agactggtgt cgtggtgaac atttaaacac ccgccggtgc       60
atgttgatcc tcggtatccc agaagattgc ggcgaggatg agttcgaaga gacacttcag      120
gaggcgtgtc gccatttagg gcggtaccgc gtgatcggcc gcatgttccg tcgtgaggaa      180
aatgcccaag cgatcctctt ggaattggcg caggatattg actatgcctt actccctcgg      240
gaaatccctg ggaaaggcgg gccttgggag gtaattgtga agccgcgtaa ttccgacggc      300
gaattcttaa atcggcttaa tcgctttctt gaagaggagc gccgtacggt ctccgatatg      360
aaccgtgttt tgggctcgga tactaactgt tcagctcctc gtgtcaccat tagtcctgaa      420
ttctggactt gggcacagac gctgggcgca gctgtccaac cattgctcga acagatgctc      480
taccgggagt tacgggtctt cagtggcaat acgatttcca tcccaggtgc tctcgctttt      540
gacgcgtggc tggagcatac cacggaaatg cttcaaatgt ggcaggtgcc tgaaggggag      600
aaacggcggc gcttgatgga gtgtttgcgg gggccagccc tgcaagtcgt tagtgggtta      660
cgtgcatcga atgccagtat cactgtcgaa gagtgtcttg ctgcactgca gcaggtattc      720
ggtccagtgg aaagtcataa gattgcccaa gtaaagttat gcaaagctta ccaggaggct      780
ggggaaaaag taagcagctt cgttttgcgt ttggagccac tgcttcagcg tgctgtagaa      840
aacaacgtgg tcagtcgccg caatgtcaac caaacacgtc ttaagcgtgt tctgtcgggc      900
gccacccttc ctgacaagct gcgtgataaa ttgaagttaa tgaaacagcg ccgtaaaccg      960
ccgggtttct tggcgttggt taaactgtta cgtgaagagg aggagtggga ggccacctta     1020
gggccagacc gcgagtcatt ggagggtta gaagtggcac gcgcccgcc agcacggatt       1080 acgggtgttg gcgcagtacc tcttccggca tccgggaatt catttgatgc ccgtccttcg     1140
caagggtacc ggcgccgtcg gggtcgtggt cagcaccgtc ggggcggcgt tgctcgtgca     1200
ggctctcgtg gctctcgtaa gcggaaacgg cacaccttct gctattcctg tggtgaggat     1260
ggccatattc gtgtccaatg cattaaccct agcaatctcc tgttggctaa ggagaccaaa     1320
```

```
gagattttgg aagggggaga acgtgaagcg caaacgaatt cacgt              1365
```

<210> SEQ ID NO 45
<211> LENGTH: 1344
<212> TYPE: DNA
<213> ORGANISM: Homo sapiens

<400> SEQUENCE: 45

```
ggggctctta cgctcttaga agactggtgt aagggtatgg acatggaccc gcggaaggct    60
ctcctgattg taggtattcc gatggaatgc agtgagtgg aaatccagga tacagttaaa   120
gctggtcttc aacctctgtg cgcttatcgt gtactcggcc gtatgttccg gcggaggat   180
aatgcgaagg ctgttttcat tgagctggca gacaccgtga attacaccac gttaccgtct   240
cacattccgg gtaaagggg ttcctgggaa gtcgttgtta aacctcggaa ccctgacgac   300
gagttccttt ctcggcttaa ctacttcttg aaagatgagg gccgctcgat gacggatgtc   360
gcccgggcac tggggtgctg tagcttacct gcggaatcac tggacgcgga agtaatgcca   420
caggtccgct cccaccatt agaacctcca aaagagagta tgtggtaccg taagttaaaa   480
gtgtttagtg gtaccgcgtc gccttcgccg ggggaggaga catttgagga ctggttagag   540
caagtcaccg agatcatgcc tatctggcaa gtatctgaag ttgaaaagcg ccgtcggtta   600
ctggagtcac tccggggccc ggcactctca attatgcgcg tgttacaagc caataacgat   660
agcattaccg ttgaacagtg tttggatgca ttaaagcaga tctttggcga caggaagac   720
ttccgtgcct ctcaatttcg ttttcttcaa acgtcccta aaattgggga gaaggtgagt   780
acgttcctgc tgcgtttaga gccactcttg caaaaggccg ttcacaagag cccacttcg   840
gtacgtagta ctgatatgat tcggttaaag cacctgttgg cacgcgtagc catgacccg   900
gcactgcgtg gtaaactcga attactcgac caacgcgggt gcccacctaa ttttcttgag   960
ctgatgaagc tgatccggga tgaggaagag tgggagaata ctgaagctgt gatgaaaaat  1020
aaagagaaac cttcaggtcg tggccgcggt gcatcaggcc gtcaagctcg cgccgaggcc  1080
agtgtaagtg ctccgcaagc aacagtccaa gcacgtagct tctctgattc tagcccgcag  1140
acgattcagg ggggcttacc acctcttgtc aagcgtcggc gcctttggg ttcggagagc  1200
acacgtgggg aagaccacgg gcaagctact tatccgaaag cagagaatca gactccaggg  1260
cgtgagggcc cgcaggcggc tggggaggaa cttggtaatg aggccggggc cggcgcgatg  1320
tcccacccga aaccgtggga aacc                                       1344
```

<210> SEQ ID NO 46
<211> LENGTH: 1197
<212> TYPE: DNA
<213> ORGANISM: Homo sapiens

<400> SEQUENCE: 46

```
ggggctgtga caatgctcca ggactggtgc cgttggatgg gcgtgaacgc tcggcggggg    60
ctgttaatct taggtatccc tgaagactgt gacgatgcag agttccaaga gtcgttagaa   120
gctgcactcc gtcctatggg tcactttact gtactcggta aggccttccg cgaggaagac   180
aacgctaccg ctgcgctggt ggaattagat cgcgaggtta attacgcact tgttccacgc   240
gaaattccgg gcaccggcgg gccttggaac gtcgtgttcg ttcctcggtg ctccggcgag   300
gaattcctgg ggttaggccg cgtgttccac tttcctgaac aggagggcca aatggtagaa   360
tcggttgcgg gggcactggg ggtaggtctg cgccgcgtgt gttggttacg ctcgatcggg   420
caagctgtac aaccatgggt agaagctgtt cgctgccaaa gcttaggggt atttagtggt   480
```

-continued

```
cgtgatcaac ctgcacctgg tgaagaaagc ttcgaggtct ggttggatca tacgaccgag       540
atgttgcatg tgtggcaagg cgtgtcggaa cgggaacggc gccgtcgtct gctggaaggg       600
ctgcgtggca cagccttaca acttgtacat gccttactgg cagaaaatcc ggcacggaca       660
gcacaagatt gcttggctgc attagcccaa gttttggtg ataacgaaag ccaggcaacg       720
attcgtgtta aatgtttgac agcccaacag cagagtggcg aacgcctctc tgcgttcgtt       780
ctccgcttag aagtacttct gcaaaaggct atggagaagg aagcattggc gcgcgcgtca       840
gcggatcggg tgcgtcttcg tcagatgctg acacgcgcac atctcacaga gccgttggat       900
gaagccttac ggaaattgcg tatggcaggg cgttctccgt cttttttgga aatgctcggc       960
ttagtacgcg agtcagaggc ctgggaggca agtctggctc ggtccgtccg ggcgcaaacc      1020
caggagggtg caggggcccg gcggggggcc caagcagttg cgcgtgccag cactaaggtt      1080
gaagctgtac ctggtggccc tggccgggag ccagaaggtc tcctccaagc cggggggccaa      1140 gaagcggaag aacttctcca agagggctta aagccggttt tagaggaatg tgacaat         1197

<210> SEQ ID NO 47
<211> LENGTH: 1197
<212> TYPE: DNA
<213> ORGANISM: Homo sapiens

<400> SEQUENCE: 47
ggggcggtca ccatgttgca agactggtgt cggtggatgg gcgtgaatgc tcggcggggt        60
ttattgatct tgggtatccc agaagactgt gacgacgccg agtttcagga gtcgctcgag       120
gccgcccttc gtccaatggg gcattttacg gttctgggca aggtgttccg tgaagaggat       180
aacgctacag cagctcttgt ggagcttgac cgtgaggtga attatgcgtt agtacctcgc       240
gagattccag gtaccggtgg gccatggaac gtagtcttcg tcccacgttg ctcggggag       300 gaatttctgg ggcttgggcg cgtattccac tttccagaac aggaagggca gatggtcgaa       360
agcgtagcag gcgctcttgg cgttggtctc cggcgcgtgt gctggttacg ctccatcggc       420
caagcagtcc aaccatgggt tgaagccgta cgctatcaat cttaggtgt cttctcaggc       480 cgtgaccagc cggcgcctgg tgaggaatcc ttcgaagtct ggctcgatca tacaactgag       540
atgctgcatg tatggcaagg tgtctcagag cgggaacggc ggcggcggtt attgaggggg       600
ctccgtggga ctgcgctcca attagtacat gcgcttttgg ccgaaaatcc agcccgtact       660
gcccaagatt gtctggcagc actcgcccaa gtattcggcg acaacgaatc gcaggcaaca       720
atccgcgtaa agtgtcttac agcacagcag cagtcagggg aacgtcttag tgcgttcgtt       780
ctgcggctgg aagtgttact ccagaaagcc atggaaaagg aggcattggc tcgcgcgagc       840
gctgaccgtg tacgtctgcg gcaaatgctt actcgcgcac atctcaccga gcctctcgat       900
gaagcactgc ggaaactgcg catggcaggc cgcagcccgt cttttcctgga aatgttaggc       960 ttagtccggg agtccgaagc ctgggaggcc agtctggcac ggtcagtgcg ggcacaaacg      1020
caagagggtg caggggcacg gcgggtgca caagcagttg cacgtgcctc cactaaagtt      1080
gaggcagtgc cgggtgggcc aggccgtgaa ccggagggtt tgcgccaagc cggcgggcag      1140
gaagccgaag aattactcca agaaggttta aaaccggttt tggaggaatg cgataac          1197

<210> SEQ ID NO 48
<211> LENGTH: 1425
<212> TYPE: DNA
<213> ORGANISM: Homo sapiens
```

<400> SEQUENCE: 48

```
ggggtggaag atttggcggc atcttacatc gtattaaagc ttgagaacga atccggcag      60
gcgcaggtcc aatggttaat ggaggaaaac gccgccctgc aggcccagat ccctgaactt    120
caaaagtcgc aagccgcgaa ggagtatgat cttctgcgta aatcttcgga ggcgaaggag    180
ccgcaaaaac tgccagaaca tatgaatcca ccggccgctt gggaagcaca aaagactcca    240
gagtttaagg aaccacagaa acctcctgaa ccacaggatt tgcttccttg ggagccgcct    300
gctgcctggg agttgcaaga agcaccggct gcccctgagt cactggctcc gcctgcaacc    360
cgtgagtctc agaaaccacc tatggcgcat gaaatcccta ctgtattgga ggggcaaggg    420
cctgccaaca cacaagacgc tacgattgct caagaaccaa agaatagcga gccgcaagac    480
cctccaaata tcgagaaacc tcaggaagct ccggaatatc aagaaacagc ggcacagttg    540
gagttttag aacttcctcc acctcaggag ccactcgaac cgagcaatgc gcaagaattt     600
ctcgagttgt cggctgccca ggagtcctta gaaggcctca ttgtagttga aacgtccgcg    660
gcttcggagt tccacaggc tcctatcggg cttgaagcca ccgactttcc gctgcagtac     720
acgcttacct tctctggcga cagccagaag ttgccagaat ttttggtcca actctacagt    780
tatatgcggg tacgtgggca cttataccct accgaggcgg cgttagtgtc gtttgtaggc    840
aattgtttct cagggcgcgc gggctggtgg tttcagttgc ttttggatat ccagtcgcct    900
ctgttagaac agtgtgaaag ttttatcccg gttctccaag acacatttga caatccggaa    960
aacatgaagg acgcaaacca atgcatccac cagctttgtc agggcgaggg tcatgtggcc   1020
acacacttcc acctcattgc acaagagctt aattgggatg aaagcacgct gtggatccag   1080
ttccaggaag gcctggcctc atccatccag gatgaacttt cccatacatc gcctgctacc   1140
aacctgagtg atctgattac tcaatgcatc tcattagagg aaaagcctga cccaaacccg   1200
ttagggaagt cctcctcggc ggagggggat ggcccggaaa gtccgccagc agaaaaccaa   1260
cctatgcaag ctgcgatcaa ttgtcctcac atttccgaag cagagtgggt tcgttggcac   1320
aaaggccggc tttgtctcta ttgcggctat ccgggtcact tcgcacgtga ttgcccagtg   1380
aagccacacc aggcgttaca ggcagggaac attcaggctt gccaa                   1425
```

<210> SEQ ID NO 49
<211> LENGTH: 717
<212> TYPE: DNA
<213> ORGANISM: Homo sapiens

<400> SEQUENCE: 49

```
ggggtgcagc cgcagactag caaagctgaa tcgccggctc tcgctgcctc accgaacgca      60
caaatggatg acgttattga tacattaacc tccctgcgtc tgacgaattc ggctctgcgg    120
cgggaggcta gcactcttcg ggccgagaaa gcaaatttaa ctaatatgct cgagtcagtg    180
atggccgagt taacgctgtt acggacccgt gcgcggattc cgggggccct gcagattacg    240
ccaccaattt cgtctattac tagcaacggt actcgcccga tgacgactcc tccaactagt    300
ttacctgaac cgttttctgg cgatcctggc cggttagctg gtttccttat gcagatggac    360
cgttttatga tctttcaagc tagccggttt ccaggggagg cagagcgtgt tgcgttcctg    420
gtgtcgcgct taactggcga agcagaaaaa tgggccattc ctcacatgca accagactct    480
cctttgcgta caactatca aggcttctta gcagagttac ggcggaccta taagagcccg    540
ttgcgtcacg cccggcgggc gcaaatccgg aagacatcgg cctcgaaccg ggcagtccgt    600
gaacgccaaa tgctttgccg gcaacttgca tcagcaggta caggcccatg cccggtacac    660
```

```
cctgctagta acgggacttc cccggcaccg gcattaccag cacgggcgcg taactta      717
```

<210> SEQ ID NO 50
<211> LENGTH: 339
<212> TYPE: DNA
<213> ORGANISM: Homo sapiens

<400> SEQUENCE: 50

```
ggggacggtc gggtacagtt gatgaaggct ttattggctg gcccttacg tccggcggca    60
cgccgttggc ggaatcctat tccatttcca gagactttg atggggatac tgatcgcctc   120
ccggagttta tcgtccaaac ttcgtcctac atgttcgttg acgaaaatac tttctctaac   180
gacgctctga aagtgacatt tctcattacc cggctgacag gtccagcctt gcaatgggtc   240
attccgtaca ttcgtaaaga agcccgcctt cttaacgact atcggggttt cctggccgag   300
atgaagcggg tttttgggtg ggaagaggac gaggactttt                         339
```

<210> SEQ ID NO 51
<211> LENGTH: 339
<212> TYPE: DNA
<213> ORGANISM: Homo sapiens

<400> SEQUENCE: 51

```
ggggaaggtc gggtgcaact tatgaaagcg ttgcttgccc gcccgcttcg tccagcagca    60
cgtcgctggc ggaatccaat tcctttcccg gagactttg acggggacac cgatcggctc   120
ccagagttca ttgtgcagac gtcaagctat atgttcgtgg atgagaacac gttctctaac   180
gacgcgttga aagtgacttt cttaattacg cgtttgactg gcccggcttt acaatgggtg   240
attccataca ttaagaaaga gtcaccgctt ctcagtgatt atcgcggttt tttagccgag   300
atgaagcggg tcttcgggtg ggaagaagac gaagactttt                         339
```

<210> SEQ ID NO 52
<211> LENGTH: 1092
<212> TYPE: DNA
<213> ORGANISM: Homo sapiens

<400> SEQUENCE: 52

```
gggccgcgtg ggcgttgccg tcaacaaggt cctcggattc cgatttgggc agcggccaac    60
tatgccaacg cccaccgtg gcaacaaatg gataaggctt cgccaggcgt tgcttacaca   120
cctttggttg atccttggat tgagcggcct tgttgcggtg acacggtttg tgtgcgcacc   180
acaatggaac agaagagcac agcgtcaggc acttgtggtg gtaagcctgc tgagcgtggt   240
cctctcgcgg ggcatatgcc gagctcacgc ccacatcggg ttgatttctg ttgggttcct   300
ggtagcgacc caggcacatt cgacggcagt ccatggctct tagatcgctt tttggcgcaa   360
cttggtgatt acatgagttt tcactttgaa cactaccagg acaatatcag ccgtgtctgc   420
gagattcttc gtcggttaac gggccgcgct caggcatggg ctgctcctta cctgacgggg   480
gaccttccac tgccagacga ctacgaattg ttttgtcaag accttaagga ggtagtacag   540
gaccctaaca gtttcgccga gtatcacgcc gtggtgactt gtccactccc tcttgcttcg   600
tcccaacttc ctgtagctcc tcagcttccg gtggtacgcc aataccttgc gcgcttcttg   660
gagggccttg cttttggatat gggtacggcg cctcggtcac tcccggccgc tatggccaca   720
ccggcagtct ccggctcgaa ctccgtttct cgttctgcct tatttgaaca acaactcaca   780
aaggaatcca ctccaggccc gaaagagcca cctgttctcc ctagctcgac ttgctctagc   840
```

```
aaaccgggtc ctgtcgaacc agccagttca caacctgaag aggctgctcc taccccggtg      900
ccgcgtttgt cagagtcggc taacccaccg gctcagcgtc cagaccctgc tcaccctggt      960
ggtcctaaac cacaaaaaac cgaagaggaa gttttagaaa ctgaggggga ccaggaagtt     1020
agcctgggga cgccgcagga ggtcgtagaa gcgccggaaa caccaggtga accaccgctc     1080
agccctgggt tc                                                         1092

<210> SEQ ID NO 53
<211> LENGTH: 438
<212> TYPE: DNA
<213> ORGANISM: Homo sapiens

<400> SEQUENCE: 53
ggggttgatg aattggtgct cttgttgcac gcgctgttaa tgcgccatcg ggcgctttcc       60
attgaaaatt ctcagttgat ggagcaactt cgcttgttgg tctgcgaacg ggcgagcctt      120
cttcgtcagg tacgtccgcc gagctgtcca gtgccatttc ctgagacttt taacggggag      180
tcatcacggt tacctgagtt catcgtccaa accgcaagct atatgttagt taatgaaaat      240
cgcttttgca atgacgcaat gaaagtcgct tttttgatta gccttcttac tggtgaagca      300
gaagaatggg tcgtcccata cattgagatg gattcaccaa ttcttgggga ctaccgtgcg      360
ttcttggatg agatgaagca gtgttttggg tgggacgatg atgaagatga cgacgatgag      420
gaagaggagg atgactat                                                   438

<210> SEQ ID NO 54
<211> LENGTH: 1647
<212> TYPE: DNA
<213> ORGANISM: Homo sapiens

<400> SEQUENCE: 54
gggcctgtgg atttaggtca ggctttgggg ttgttgccat ccctcgctaa ggccgaagat       60
tcccaattta gcaaaagcga tgcagcttta caggaggaat tgtcttctcc ggaaaccgca      120
cggcaacttt ttcgtcaatt tcgctatcaa gtcatgtcgg ggcctcatga acactgaaa       180 cagttacgga agttatgttt tcagtggctg caacctgaag tccatacaaa ggaacaaatc      240
ctcgaaattc tgatgctgga acagttcttg accattctgc ctggtgaaat tcagatgtgg      300
gtccgcaagc agtgccctgg tagtggggag gaggcggtta cgttagtaga atccctgaaa      360
ggtgatccac aacggctctg caatggatc tccatccaag tcctgggtca ggatatcctg      420
tctgagaaaa tggagtcacc ttcttgccag gtgggcgaag tggagccaca cctggaagtt      480
gtacctcagg aactggggtt agagaattca tcttcagggc cggggggact tctttcgcac      540
atcgtgaaag aggagtctga cactgaagca gagttggcgt tagcggcatc ccagccagct      600
cgtttggaag aacggctgat tcgggatcag gaccttgggg cgtccctcct cccggcagca      660
ccgcaggagc aatggcgtca attagacagc actcaaaaag aacaatattg ggacctgatg      720
ctggagacct acggcaaaat ggtatccggc gcgggtatct cacacccgaa gtccgattta      780
acgaactcaa ttgagttcgg tgaagagttg gcaggtatt atttacatgt aaacgaaaag      840
attccgcggc ctacctgcat tggtgaccgc caagaaaacg acaaagaaaa ccttaatttg      900
gaaaaccatc gtgaccagga attattacat gccagctgcc aggcctcggg cgaagtgcca      960
tcccaggcat cgttacgtgg cttctttacc gaggacgaac ctggttgctt cggcgaaggg     1020
gagaaccttc ctgaggcact tcagaatatc caggatgagg ggactggcga acagctgagc     1080
ccgcaagaac gcattagtga aaaacagttg ggtcaacatt tgccaaatcc gcactcgggg     1140
```

| | |
|---|---|
| gagatgtcga cgatgtggct tgaagaaaaa cgggagacca gccagaaagg ccaaccacgt | 1200 |
| gcaccaatgg cgcagaaatt gccaacgtgc cgcgaatgtg gcaaaacgtt ttatcgcaat | 1260 |
| agtcaactta tctttcacca acgcacacac accggtgaga catattttca atgcaccatc | 1320 |
| tgcaaaaagg cgtttctccg gtcatctgat ttcgtgaaac atcagcggac tcatactggc | 1380 |
| gaaaaacctt gtaaatgtga ctattgtggc aagggcttta gtgattttag cgggcttcgg | 1440 |
| catcacgaga agatccatac cggcgagaag ccatacaagt gtccaatctg tgagaaatct | 1500 |
| ttcatccagc gcagtaattt taaccgccac caacgggttc acaccggtga aaagccttat | 1560 |
| aaatgctcgc attgtggcaa gagcttcagc tggagctcct cgctcgataa gcatcaacgt | 1620 |
| tcacatctgg ggaagaagcc gttccaa | 1647 |

<210> SEQ ID NO 55
<211> LENGTH: 1053
<212> TYPE: DNA
<213> ORGANISM: Homo sapiens

<400> SEQUENCE: 55

| | |
|---|---|
| gggactctcc gcttacttga ggattggtgt cggggggatgg acatgaaccc acgtaaggcc | 60 |
| cttcttatcg ccgggatttc ccagtcatgt tcagtcgccg agattgaaga ggcgctccaa | 120 |
| gccgggcttg ctccttaggg cgagtatcgt ctccttgggc ggatgtttcg ccgcgatgaa | 180 |
| aatcgcaaag tagcgttggt tggtctcaca gctgaaacta gccatgcgct tgtacctaaa | 240 |
| gaaattcctg gtaaaggcgg gatctggcgg gttatttta aaccaccgga cccgacaat | 300 |
| acgtttcttt ctcgtttgaa tgagttcctc gcgggcgagg ggatgacggt ggggggaactt | 360 |
| agtcgtgctc ttggtcacga aaatgggtca ttagaccctg aacagggtat gattccggaa | 420 |
| atgtgggcgc cgatgctggc acaggctctg gaggctctcc aaccggcttt acagtgcctt | 480 |
| aagtacaaga agctgcgcgt tttttcaggg cgcgagtctc cagagccggg tgaggaggaa | 540 |
| ttcggccgtt ggatgttcca taccacccag atgatcaaag cgtggcaggt gccggatgtc | 600 |
| gagaaacgcc gccggctgtt ggaatcactc cgcgggccgg cacttgacgt tattcgggtt | 660 |
| ctgaaaatta acaacccgtt aattacggta gatgaatgtt tgcaagcact tgaagaggtc | 720 |
| tttggggtga ctgacaatcc tcgggaattg caagtaaaat acttaacgac ctaccataag | 780 |
| gacgaggaga attatcagc ctacgtactg cggctgaac cgctgctgca gaagctcgtc | 840 |
| cagcggggg ctattgaacg ggacgctgtt aatcaggctc gcctggatca ggtaatcgct | 900 |
| ggggcggtac ataaaactat ccgccgtgag ctgaacctgc ctgaagacgg gccggcgcca | 960 |
| ggctttcttc aactcctcgt tttgattaag gattacgagg cagctgaaga ggaggaagca | 1020 |
| ttacttcagg ccattcttga agggaacttt act | 1053 |

<210> SEQ ID NO 56
<211> LENGTH: 2124
<212> TYPE: DNA
<213> ORGANISM: Homo sapiens

<400> SEQUENCE: 56

| | |
|---|---|
| gggacagaac ggcgtcgcga cgaattaagt gaagaaatta taatcttcg tgaaaaggtt | 60 |
| atgaaacaga gtgaggaaaa caacaatctt caatcccaag tccagaaact cactgaggag | 120 |
| aatactacac tccgtgagca agttgaacct acacctgaag atgaagatga cgacattgag | 180 |
| ttgcggggcg cagcagccgc agccgcgcct ccgccgccga tcgaggagga atgcccggag | 240 |

```
gatttaccgg aaaaatttga tggtaatccg gacatgttag cgccattcat ggcccagtgc      300
caaattttta tggaaaagtc tacgcgcgat tttagtgtag atcgcgtacg tgtatgtttt      360
gtgacgagca tgatgactgg tcgcgcagcc cgttgggcgt cagcgaaatt ggagcggtcg      420
cactacctga tgcataatta cccggcgttc atgatggaga tgaaacacgt gtttgaagac      480
ccgcagcggc gggaggtggc caaacgcaag atccggcggt tgcggcaggg catgggcagc      540
gtaattgatt atagtaatgc gtttcaaatg attgcgcagg atctggattg gaatgaacct      600
gctctcattg atcaatatca tgaagggctt agtgaccata ttcaagagga actctctcac      660
ctggaagtgg ctaaatctct ctccgccctt attggccaat gcattcatat tgagcgccgt      720
cttgcacgtg ctgctgccgc tcggaaaccg cgtagtccac cacgggcttt agtgctccca      780
catatcgcgt cacaccatca agtagatcct actgagccag tgggggggtgc acgcatgcgc      840 ttaacccaag aagaaaagga acgtcgtcgt aagctgaatt tatgcctgta ctgcggcact      900
ggtggccatt atgccgataa ctgtcctgcc aaagccagta agtcaagccc ggctgggaaa      960
cttccaggtc ctgccgtcga gggcccttct gctaccggcc cagagattat ccgctccccg     1020
caagacgatg cgtcgtcgcc tcatctccag gtaatgctcc aaatccacct ccctggccgg     1080
cacacactct ttgtccgggc gatgattgac tctgggcgt ctggtaattt tattgatcac      1140
gagtatgttg ctcaaaatgg tatccctctc cggatcaaag actggcctat tctggttgaa     1200
gccatcgatg gccgtccgat cgcgagcggt cctgtggttc atgaaacgca tgacctcatc     1260
gttgatctgg gtgaccaccg tgaagtatta tcctttgatg tgactcagtc accgtttttt     1320
ccagttgttt gggcgtccg ttggctttcg actcacgatc ctaacatcac gtggtcgaca      1380
cggtcgattg tcttcgattc ggaatattgt cgttatcatt gccgcatgta ttcaccaatt     1440
ccgccgtctc tcccgccgcc tgcgccgcaa cctcctctgt attacccggt ggacggttac     1500
cgtgtttacc agccagttcg ctactactac gtacaaaacg tgtacacgcc tgttgatgaa     1560
cacgtgtacc cagatcaccg cctggtcgac cctcatattg agatgatccc gggtgcgcac     1620
tcgatcccat cgggccatgt ttattccttg tctgagccag aaatggccgc cttacgggat     1680
tttgtggccc ggaatgtcaa agacggcctg attaccccga caattgcacc aaacggtgct     1740
caggtgttgc aggtgaagcg gggctggaag ttgcaagtca gctatgattg tcgtgcgcca     1800
aacaacttca ctattcagaa ccaatatcca cgtctcagca tccctaatct cgaggaccag     1860
gcacatcttg caacatatac tgaatttgta cctcagattc ctggctatca gacttatcct     1920
acgtatgctg cctacccaac ataccccggta ggtttcgcat ggtacccagt aggccgggac     1980
gggcagggcc gctctttata tgttcctgtc atgattacat ggaacccgca ttggtaccgc     2040
cagcctccgg tcccacagta cccacctcct caacctccac cacctccgcc gcctcctcca     2100 ccgccaccctt cttactcgac atta                                            2124
```

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atgcatcacc atcaccatca cggctcaggg tctggtagcg aaaatctgta cttccagggg      60

<210> SEQ ID NO 58

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Met His His His His His His Gly Ser Gly Ser Gly Ser Glu Asn Leu
1               5                   10                  15

Tyr Phe Gln Gly
            20

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 59

His His His His His His
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Ser Gly Ser Gly Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Asn Leu Tyr Phe Gln Gly
1               5

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aagctcattt cctggtatga caacga                                          26

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 63
agggtctctc tcttcctctt gtgct                                           25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gctcaacctg ggaactgcat ctgat                                           25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
taatcctgtt tgctccccac gcttt                                           25

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggcccctcag ctccagtgat tc                                              22

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cctgttgtca ctctcctggc tctga                                           25

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gccaagacat aagaaacctc gcct                                            24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtgaatcaac atcctccctc cgtc                                      24

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MISC_FEATURE
<222> LOCATION: (1)..(25)
<223> OTHER INFORMATION: This sequence may encompass 1-5 "Glu Ala Ala
      Ala Lys" repeating units

<400> SEQUENCE: 70

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MISC_FEATURE
<222> LOCATION: (1)..(25)
<223> OTHER INFORMATION: This sequence may encompass 1-5 "Glu Ala Ala
      Ala Arg" repeating units

<400> SEQUENCE: 71

Glu Ala Ala Ala Arg Glu Ala Ala Ala Arg Glu Ala Ala Ala Arg Glu
1               5                   10                  15

Ala Ala Ala Arg Glu Ala Ala Ala Arg
            20                  25

<210> SEQ ID NO 72
<211> LENGTH: 50
<212> TYPE: PRT
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 72

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 73
<211> LENGTH: 40
<212> TYPE: PRT

```
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 73

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 74

Lys Glu Ser Gly Ser Val Ser Ser Glu Gln Leu Ala Gln Phe Arg Ser
1               5                   10                  15

Leu Asp

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Gly Lys Ser Ser Gly Ser Gly Ser Glu Ser Lys Ser Thr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Ala Ala Asn Leu Val Arg Gly Gly
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Gly Arg Ile Gly Phe Leu Arg Thr Ala
1               5                   10
```

```
<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Gly Arg Ser Ala
1               5

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Phe Leu Gly
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Leu Ala Leu
1

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (3)..(3)
<223> OTHER INFORMATION: S-ethylcysteine

<400> SEQUENCE: 81

Pro Ile Cys Phe Phe
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (5)..(5)
```

```
<223> OTHER INFORMATION: Ser or Thr

<400> SEQUENCE: 82

Pro Arg Xaa Xaa Xaa
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Glu Val Asp
1

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Trp Glu His Asp Gly
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Pro Leu Ala Leu Trp Arg Ser
1               5
```

ENDOGENOUS GAG-BASED CAPSIDS AND USES THEREOF

CROSS REFERENCE

This application is a continuation of U.S. patent application Ser. No. 17/277,119, filed Mar. 17, 2021, which is a national phase entry of International Application No. PCT/US2019/051786, filed Sep. 18, 2019, which claims the benefit of U.S. Provisional Patent Application No. 62/733,015, filed Sep. 18, 2018, each of which is incorporated herein by reference in its entirety.

SEQUENCE LISTING STATEMENT

The instant application contains a Sequence Listing which has been submitted electronically in ASCII format and is hereby incorporated by reference in its entirety. Said ASCII copy, created on Jan. 15, 2020, is named 54838_702_301_SL.txt and is 148,316 bytes in size.

SUMMARY OF THE DISCLOSURE

Disclosed herein, in certain embodiments, are recombinant and engineered Arc polypeptides and recombinant and engineered endogenous Gag (endo-Gag) polypeptides. In some embodiments, also included are Arc-based capsids and endo-Gag based capsids, either loaded or empty, and methods of preparing the capsids. Additionally included are methods of delivery of the Arc-based capsids and endo-Gag-based capsids to a site of interest.

Disclosed herein, in certain embodiments, is a capsid comprising a recombinant Arc polypeptide or a recombinant endogenous Gag polypeptide and a therapeutic agent. In some embodiments, the therapeutic agent is a nucleic acid. In some embodiments, the nucleic acid is an RNA. In some embodiments, the recombinant Arc polypeptide is a human Arc polypeptide comprising an amino acid sequence that is SEQ ID NO: 1 or an amino acid sequence that is at least 90% identical to the SEQ ID NO: 1. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is a human endogenous Gag polypeptide. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a capsid comprising a recombinant Arc polypeptide or a recombinant endogenous Gag polypeptide, wherein the recombinant Arc polypeptide is not a rat Arc polypeptide or a human Arc polypeptide. In some embodiments, the capsid further comprises a cargo. In some embodiments, the cargo is a nucleic acid. In some embodiments, the cargo is an RNA. In some embodiments, the cargo is a therapeutic agent. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a vector comprising DNA encoding a recombinant Arc polypeptide or a recombinant endogenous Gag polypeptide. In some embodiments, the vector further encodes a therapeutic agent. In some embodiments, the therapeutic agent is a nucleic acid. In some embodiments, the nucleic acid is an RNA. In some embodiments, the recombinant Arc polypeptide is a human Arc polypeptide comprising an amino acid sequence that is SEQ ID NO: 1 or an amino acid sequence that is at least 90% identical to the SEQ ID NO: 1. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is a human endogenous Gag polypeptide. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a vector comprising DNA encoding a recombinant Arc polypeptide or a recombinant endogenous Gag polypeptide, wherein the recombinant Arc polypeptide is not a rat Arc polypeptide or a human Arc polypeptide. In some embodiments, the vector further encodes a cargo. In some embodiments, the cargo is a nucleic acid. In some embodiments, the cargo is an RNA. In some embodiments, the cargo is a therapeutic agent. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a method of delivering a cargo to a cell comprising administering to the cell a capsid comprising a recombinant Arc polypeptide or a recombinant endogenous Gag polypeptide and a therapeutic agent. In some embodiments, the therapeutic agent is a nucleic acid. In some embodiments, the nucleic acid is an RNA. In some embodiments, the recombinant Arc polypeptide is a human Arc polypeptide comprising an amino acid sequence that is SEQ ID NO: 1 or an amino acid sequence that is at least 90% identical to the SEQ ID NO: 1. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is a human endogenous Gag polypeptide. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28. In some embodiments, the cell is a eukaryotic cell. In some embodiments, the cell is a vertebrate cell. In some embodiments, the cell is a mammalian cell. In some embodiments, the cell is a human cell. In some embodiments, the cargo is a nucleic acid. In some embodiments, the cell expresses a gene encoded by the nucleic acid. In some embodiments, the cargo is a therapeutic agent.

Disclosed herein, in certain embodiments, is a method of delivering a cargo to a cell comprising administering to the cell a capsid comprising a recombinant Arc polypeptide or a recombinant endogenous Gag polypeptide, wherein the recombinant Arc polypeptide is not a rat Arc polypeptide or a human Arc polypeptide. In some embodiments, the capsid further comprises a cargo. In some embodiments, the cargo is a nucleic acid. In some embodiments, the cargo is an RNA. In some embodiments, the cargo is a therapeutic agent. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28. In some embodiments, the cell is a eukaryotic cell. In some embodiments, the cell is a vertebrate cell. In some embodiments, the cell is a mammalian cell. In some embodiments, the cell is a human cell. In some embodiments, the cargo is a nucleic acid. In some embodiments, the cell expresses a gene encoded by the nucleic acid. In some embodiments, the cargo is a therapeutic agent.

Disclosed herein, in certain embodiments, is a method of transfecting a nucleic acid into a cell comprising administering to the cell a capsid comprising a recombinant Arc polypeptide or a recombinant endogenous Gag polypeptide and a therapeutic agent. In some embodiments, the therapeutic agent is a nucleic acid. In some embodiments, the nucleic acid is an RNA. In some embodiments, the recombinant Arc polypeptide is a human Arc polypeptide comprising an amino acid sequence that is SEQ ID NO: 1 or an amino acid sequence that is at least 90% identical to the SEQ ID NO: 1. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is a human endogenous Gag polypeptide. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a method of transfecting a nucleic acid into a cell comprising administering to the cell a capsid comprising a recombinant Arc polypeptide or a recombinant endogenous Gag polypeptide, wherein the recombinant Arc polypeptide is not a rat Arc polypeptide or a human Arc polypeptide. In some embodiments, the capsid further comprises a cargo. In some embodiments, the cargo is a nucleic acid. In some embodiments, the cargo is an RNA. In some embodiments, the cargo is a therapeutic agent. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is an endogenous Gag polypeptide comprising: a) an amino acid sequence that is SEQ ID NO: 12 or an amino acid sequence that is at least 90% identical to the SEQ ID NO: 12; b) an amino acid sequence that is SEQ ID NO: 13 or an amino acid sequence that is at least 90% identical to the SEQ ID NO: 13; c) an amino acid sequence that is SEQ ID NO: 14 or an amino acid sequence that is at least 90% identical to the SEQ ID NO: 14; d) an amino acid sequence that is SEQ ID NO: 15 or an amino acid sequence that is at least 90% identical to the SEQ ID NO: 15; e) an amino acid sequence that is SEQ ID NO: 16 or an amino acid sequence that is at least 90% identical to the SEQ ID NO: 16; f) an amino acid sequence that is SEQ ID NO: 17 or an amino acid sequence that is at least 90% identical to the SEQ ID NO: 17; g) an amino acid sequence that is SEQ ID NO: 18 or an amino acid sequence that is at least 90% identical to the SEQ ID NO: 18; g) an amino acid sequence that is SEQ ID NO: 19 or an amino acid sequence that is at least 90% identical to the SEQ ID NO: 19; g) an amino acid sequence that is SEQ ID NO: 20 or an amino acid sequence that is at least 90% identical to the SEQ ID NO: 20; g) an amino acid sequence that is SEQ ID NO: 21 or an amino acid sequence that is at least 90% identical to the SEQ ID NO: 21; or h) an amino acid sequence that is SEQ ID NO: 22 or an amino acid sequence that is at least 90% identical to the SEQ ID NO: 22.

Disclosed herein, in certain embodiments, is an engineered Arc or endo-Gag polypeptide comprising a cargo binding domain and at least one capsid forming subunit from an Arc or endo-Gag polypeptide. In some embodiments, the cargo binding domain comprises a nucleic acid binding domain. In some embodiments, the cargo binding domain comprises a polypeptide that binds to a small molecule. In some embodiments, the cargo binding domain comprises a polypeptide that binds to a protein, a peptide, or an antibody or binding fragment thereof. In some embodiments, the cargo binding domain comprises a polypeptide that binds to a peptidomimetic or a nucleotidomimetic. In some embodiments, the at least one capsid forming subunit comprises a polypeptide that corresponds to the CA N-lobe and/or CA C-lobe of SEQ ID NO: 1. In some embodiments, the engineered Arc or endo-Gag polypeptide further comprises a second capsid forming subunit from a different species of an Arc or endo-Gag polypeptide. In some embodiments, the second capsid forming subunit comprises a polypeptide that corresponds to the N-lobe and/or C-lobe of SEQ ID NO: 1. In some embodiments, the at least one capsid forming subunit and the second capsid forming subunit are each independently selected from a species of Arc or endo-Gag selected from a mammal, a rodent, a bird, a reptile, a fish, an insect, a fungus, or a plant. In some embodiments, the at least one capsid forming subunit and the second capsid forming subunit are from two different species. In some embodiments, the cargo binding domain is fused either directly or via a linker to the C-terminus of the at least one capsid forming subunit. In some embodiments, the cargo binding domain is fused either directly or via a linker to the N-terminus of the at least one capsid forming subunit. In some embodiments, the second capsid forming subunit is fused either directly or via a linker to the C-terminus of the at least one capsid forming subunit. In some embodiments, the second capsid forming subunit is fused either directly or via a linker to the N-terminus of the at least one capsid forming subunit. In some embodiments, the cargo binding domain is fused either directly or via a linker to the N-terminus of the at least one capsid forming subunit and the second capsid forming subunit is fused either directly or via a linker to the C-terminus of the at least one capsid forming subunit. In some embodiments, the cargo binding domain is fused either directly or via a linker to the C-terminus of the at least one capsid forming subunit and the second capsid forming subunit is fused either directly or via a linker to the N-terminus of the at least one capsid forming subunit. In some embodiments, the engineered Arc or endo-Gag polypeptide further comprises a second polypeptide. In some embodiments, the second polypeptide is fused either directly or via a linker to the at least one capsid forming subunit. In some embodiments, the second polypeptide is fused either directly or via a linker to the cargo binding domain. In some embodiments, the second polypeptide is a protein or an antibody or its binding fragments thereof. In some embodiments, the protein is a human protein or a viral protein. In some embodiments, the protein is a human Gag-like protein. In some embodiments, the protein is a de novo engineered protein designed to bind to a target receptor of interest. In some embodiments, the second polypeptide guides the delivery of a capsid formed by the engineered Arc or endo-Gag polypeptide to a target site of interest.

Disclosed herein, in certain embodiments, is a truncated Arc or endo-Gag polypeptide wherein a portion that is not involved with capsid-formation, nucleic acid binding, or delivery is removed. In some embodiments, the portion comprises a matrix (MA) domain, a reverse transcriptase (RT) domain, a nucleotide binding domain, or a combination thereof, provided that the nucleotide binding domain is not a human Arc RNA binding domain. In some embodiments, the portion comprises a CA C-lobe domain. In some embodiments, the portion comprises an N-terminal deletion, a C-terminal deletion, or a combination thereof. In some embodiments, the N-terminal deletion comprises a deletion of up to 10 amino acids, 20 amino acids, 30 amino acids, or 50 amino acids. In some embodiments, the C-terminal deletion comprises a deletion of up to 10 amino acids, 20 amino acids, 30 amino acids, or 50 amino acids.

Disclosed herein, in certain embodiments, is an Arc or endo-Gag-based capsid comprising an engineered Arc or endo-Gag polypeptide which may be a truncated Arc or endo-Gag polypeptide and a cargo encapsulated by the capsid formed by the engineered Arc or endo-Gag polypeptide. In some embodiments, the cargo is a nucleic acid molecule. In some embodiments, the nucleic acid molecule is DNA, RNA, or a mixture of DNA and RNA. In some embodiments, the DNA and the RNA are each independently single-stranded, double-stranded, or a mixture of single and double stranded. In some embodiments, the cargo is a small molecule. In some embodiments, the cargo is a protein. In some embodiments, the cargo is a peptide. In some embodiments, the cargo is an antibody or binding fragments thereof. In some embodiments, the cargo is a peptidomimetic or a nucleotidomimetic. In some embodiments, the Arc or endo-Gag-based capsid comprises one or more additional capsid subunits from one or more species of Arc or endo-Gag proteins that are different than the engineered Arc or endo-Gag polypeptide. In some embodiments, the Arc-based or endo-Gag-based capsid comprises one or more additional capsid subunits from non-Arc proteins. In some embodiments, the one or more additional capsid subunits comprise Copia protein, ASPRV1 protein, a protein from the SCAN domain family, a protein encoded by the Paraneoplastic Ma antigen family (e.g. PNMA5, PNMA6, PNMA6A, and PNMA6B), a protein from the retrotransposon Gag-like family (e.g. RTL3, RTL6, RTL8A, RTL8B), or a combination thereof. In some embodiments, the one or more additional capsid subunits comprise BOP, LDOC1, MOAP1, PEG10, PNMA3, PNMA5, PNMA6A, PNMA6B, RTL3, RTL6, RTL8A, RTL8B, and ZNF18. In some embodiments, the capsid has a diameter of at least 1 nm, 2 nm, 3 nm, 4 nm, 5 nm, 10 nm, 15 nm, 20 nm, 25 nm, 30 nm, 50 nm, 80 nm, 100 nm, 120 nm, 150 nm, 200 nm, 250 nm, 300 nm, 500 nm, 600 nm, or more. In some embodiments, the capsid has a diameter of from about 1 nm to about 600 nm, from about 1 nm to about 500 nm, from about 1 nm to about 200 nm, from about 1 nm to about 100 nm, from about 1 nm to about 50 nm, or from about 1 nm to about 30 nm. In some embodiments, the capsid has a reduced off-target effect. In some embodiments, the capsid does not have an off-target effect. In some embodiments, the capsid is formed ex-vivo. In some embodiments, the capsid is formed in-vitro.

Disclosed herein, in certain embodiments, is a nucleic acid polymer encoding a recombinant or engineered Arc polypeptide or a recombinant or engineered endogenous Gag polypeptide described herein.

Disclosed herein, in certain embodiments, is a vector comprising a nucleic acid polymer encoding a recombinant or engineered Arc polypeptide or a recombinant or engineered endogenous Gag polypeptide described herein.

Disclosed herein, in certain embodiments, is a method of preparing a loaded Arc-based or endo-Gag-based capsid comprising: incubating a plurality of recombinant or engineered Arc polypeptides or a plurality of recombinant or engineered endo-Gag polypeptides with a cargo in a solution for a time sufficient to generate the loaded capsid. In some embodiments, the method further comprises mixing the solution comprising the plurality of engineered Arc or endo-Gag polypeptides with a plurality of non-Arc or non-endo-Gag capsid forming subunits prior to incubating with the cargo. In some embodiments, the plurality of non-Arc or non-endo-Gag capsid forming subunits are mixed with the plurality of recombinant or engineered Arc or endo-Gag polypeptides at a ratio of 1:1, 2:1, 3:1, 4:1, 5:1, 6:1, 7:1, 8:1, 9:1, or 10:1. In some embodiments, the plurality of non-Arc or non-endo-Gag capsid forming subunits are mixed with the plurality of engineered Arc or endo-Gag polypeptides at a ratio of 1:2, 1:3, 1:4, 1:5, 1:6, 1:7, 1:8, 1:9, or 1:10. In some embodiments, the method further comprises mixing the solution comprising the plurality of truncated Arc or endo-Gag polypeptides with a plurality of non-Arc or endo-Gag capsid forming subunits prior to incubating with the cargo. In some embodiments, the plurality of non-Arc or endo-Gag capsid forming subunits are mixed with the plurality of truncated Arc or endo-Gag polypeptides at a ratio of 1:1, 2:1, 3:1, 4:1, 5:1, 6:1, 7:1, 8:1, 9:1, or 10:1. In some embodiments, the plurality of non-Arc or non-endo-Gag capsid forming subunits are mixed with the plurality of truncated Arc or endo-Gag polypeptides at a ratio of 1:2, 1:3, 1:4, 1:5, 1:6, 1:7, 1:8, 1:9, or 1:10. In some embodiments, the plurality of engineered Arc or endo-Gag polypeptides is obtained from a bacterial cell system, an insect cell system, or a mammalian cell system. In some embodiments, the plurality of engineered Arc or endo-Gag polypeptides is obtained from a cell-free system. In some embodiments, the plurality of truncated Arc or endo-Gag polypeptides is obtained from a bacterial cell system, an insect cell system, or a mammalian cell system. In some embodiments, the plurality of truncated Arc or endo-Gag polypeptides is obtained from a cell-free system. In some embodiments, the loaded Arc-based or endo-Gag capsid is formulated for systemic administration. In some embodiments, the loaded Arc or endo-Gag-based capsid is formulated for local administration. In some embodiments, the loaded Arc or endo-Gag-based capsid is formulated for parenteral administration. In some embodiments, the loaded Arc or endo-Gag-based capsid is formulated for oral administration. In some embodiments, the loaded Arc or endo-Gag-based capsid is formulated for topical administration. In some embodiments, the loaded Arc or endo-Gag-based capsid is formulated for sublingual or aerosol administration.

Disclosed herein, in certain embodiments, is use of an engineered or recombinant Arc-based or endo-Gag-based capsid for delivery of a cargo to a site of interest, comprising contacting a cell at the site of interest with an Arc-based or endo-Gag-based capsid for a time sufficient to facilitate cellular uptake of the capsid. In some embodiments, the cell is a tumor cell. In some embodiments, the tumor cell is a solid tumor cell. In some embodiments, the solid tumor cell is a cell from a bladder cancer, breast cancer, brain cancer, colorectal cancer, kidney cancer, liver cancer, lung cancer, pancreatic cancer, prostate cancer, skin cancer, stomach cancer, or thyroid cancer. In some embodiments, the tumor cell is from a hematologic malignancy. In some embodiments, the hematologic malignancy is a B-cell malignancy, or a T-cell malignancy. In some embodiments, the hematologic malignancy is chronic lymphocytic leukemia (CLL), small lymphocytic lymphoma (SLL), diffuse large B cell lymphoma (DLBCL), follicular lymphoma, mantle cell lymphoma, Burkitt lymphoma, cutaneous T-cell lymphoma, or peripheral T cell lymphoma. In some embodiments, the cell is a somatic cell. In some embodiments, the cell is a stem cell or a progenitor cell. In some embodiments, the cell is a mesenchymal stem or progenitor cell. In some embodiments, the cell is a hematopoietic stem or progenitor cell. In some embodiments, the cell is a muscle cell, a skin cell, a blood cell, or an immune cell. In some embodiments, a target protein is overexpressed or is depleted in the cell. In some embodiments, a target gene in the cell has one or more mutations. In some embodiments, the cell comprises an impaired splicing mechanism. In some embodiments, the use is an in vivo use. In some embodiments, the Arc-based capsid is administered systemically to a subject. In some embodiments, the Arc-based or endo-Gag-based capsid is administered via local administration to a subject. In some embodiments, the Arc-based or endo-Gag-based capsid is administered parenterally to a subject. In some embodiments, the Arc-based capsid is administered orally to a subject. In some embodiments, the Arc-based or endo-Gag-based capsid is administered topically to a subject. In some embodiments, the Arc-based or endo-Gag-based capsid is administered via sublingual or aerosol administration to a subject. In some embodiments, the use is an in vitro or ex vivo use.

Disclosed herein, in certain embodiments, is a kit comprising an engineered Arc or endo-Gag polypeptide, a truncated Arc or endo-Gag polypeptide, a vector encoding a recombinant or engineered Arc or endo-Gag polypeptide, or an Arc-based or endo-Gag-based capsid.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

DETAILED DESCRIPTION OF THE DISCLOSURE

Figure 1:
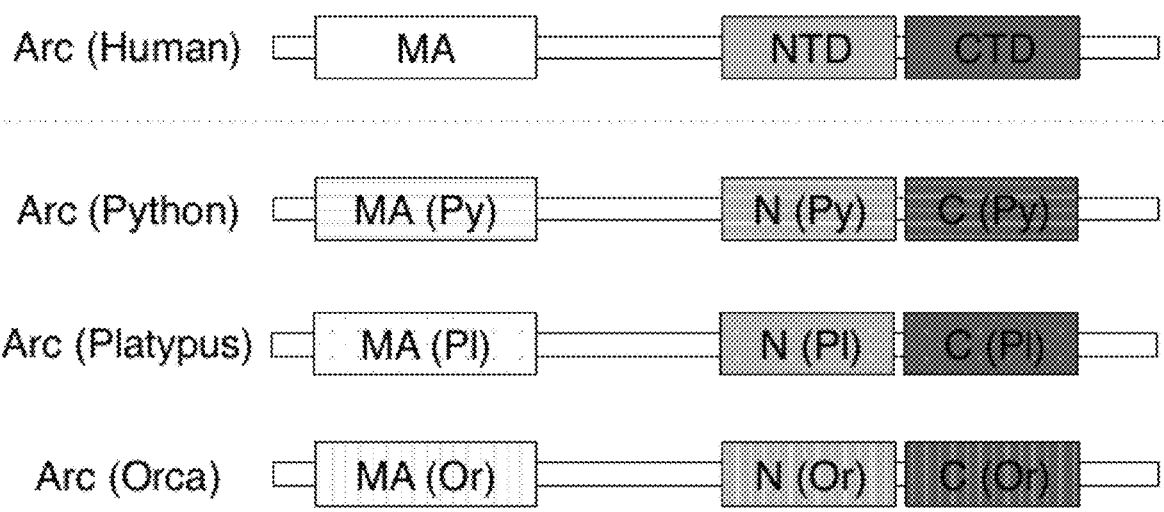
FIG. 1 is a representation of exemplary Arc polypeptides.

Administrating diagnostic or therapeutic agents to a site of interest with precision has presented an ongoing challenge. Available methods of delivering nucleic acids to cells have myriad limitations. For example, AAV viral vectors often used for gene therapy are immunogenic, have a limited payload capacity of <3 kb, suffer from poor bio-distribution, can only be administered by direct injection, and pose a risk of disrupting host genes by integration. Non-viral methods have different limitations. Liposomes are primarily delivered to the liver. Extracellular vesicles have a limited payload capacity of <1 kb, limited scalability, and purification difficulties. Thus, there is a recognized need for new methods of delivering therapeutic payloads.

Most molecules do not possess inherent affinity in the body. In other cases, the administered agents accumulate either in the liver and the kidney for clearance or in unintended tissue or cell types. Method for improving delivery includes coating the agent of choice with hydrophobic compounds or polymers. Such an approach increases the duration of said agent in circulation and augments hydrophobicity for cellular uptake. On the other hand, this approach does not actively direct cargo to the site of interest for delivery.

To specifically target sites where therapy is needed, therapeutic compounds are optionally fused to moieties such as ligands, antibodies, and aptamers that recognize and bind to receptors displayed on the surface of targeted cells. Upon reaching a cell of interest, the therapeutic compound is optionally further delivered to an intracellular target. For example, a therapeutic RNA can be translated to a protein if it comes into contact with a ribosome in the cytoplasm of the cell.

Arc (activity-regulated cytoskeleton-associated protein) regulates the endocytic trafficking of α-amino-3-hydroxy-5-methylisoxazole-4-propionic acid (AMPA) type glutamate receptors. Arc activities have been linked to synaptic strength and neuronal plasticity. Phenotypes of loss of Arc in experimental murine model included defective formation of long-term memory and reduced neuronal activity and plasticity.

Arc exhibits similar molecular properties to retroviral Gag proteins. The Arc gene may have originated from the Ty3/gypsy retrotransposon. An endogenous Gag (endo-Gag) protein is any protein endogenous to a eukaryotic organism, including Arc, that has predicted and annotated similarity to viral Gag proteins. Exemplary endo-Gag proteins are disclosed in Campillos M, Doerks T, Shah P K, and Bork P, Computational characterization of multiple Gag-like human proteins, Trends Genet. 2006 November; 22(11):585-9. An endo-Gag protein is optionally recombinantly expressed by any host cell, including a prokaryotic or eukaryotic cell, or a bacterial, yeast, insect, vertebrate, mammalian, or human cell. As described herein, in some embodiments an endo-Gag protein assembles into an endo-Gag capsid.

Disclosed herein, in certain embodiments, are Arc and endo-Gag polypeptides which assemble into a capsid for delivery of a cargo of interest. In some embodiments, also described herein are engineered Arc and endo-Gag polypeptides which assemble into a capsid for delivery of a cargo of interest. In additional embodiments, described herein are capsids, e.g., Arc-based or endo-Gag-based capsids, for delivery of a cargo of interest.

Arc Polypeptides and Endogenous Gag Polypeptides

In certain embodiments, disclosed herein is an Arc polypeptide. In certain embodiments, disclosed herein is an endo-Gag polypeptide. It should be understood that endo-Gag sequences are optional substitutes for Arc sequences to form any type of engineered Arc polypeptide described in this section.

In some instances, Arc is a non-human Arc polypeptide. In some instances, the Arc polypeptide comprises a full-length Arc polypeptide (e.g., a full-length non-human Arc polypeptide). In other instances, the Arc polypeptide comprises a fragment of non-human Arc, such as a truncated Arc polypeptide, that participates in the formation of a capsid. In additional instances, the Arc polypeptide comprises one or more domains of a non-human Arc polypeptide, in which at least one of the domains participates in the formation of a capsid. In further instances, the Arc polypeptide is a recombinant Arc polypeptide.

In some instances, endo-Gag is a non-human endo-Gag polypeptide. In some instances, the endo-Gag polypeptide comprises a full-length endo-Gag polypeptide (e.g., a full-length non-human endo-Gag polypeptide). In other instances, the endo-Gag polypeptide comprises a fragment of non-human endo-Gag, such as a truncated endo-Gag polypeptide, that participates in the formation of a capsid. In additional instances, the endo-Gag polypeptide comprises one or more domains of a non-human endo-Gag polypeptide, in which at least one of the domains participates in the formation of a capsid. In further instances, the endo-Gag polypeptide is a recombinant endo-Gag polypeptide.

In some embodiments, the Arc is a human Arc polypeptide with at least its RNA binding domain modified to bind to a cargo that is not native to the human Arc. In some instances, the Arc polypeptide comprises a full-length human Arc polypeptide with at least its RNA binding domain modified to bind to a cargo that is not native to the human Arc protein. In other instances, the Arc polypeptide comprises a human Arc fragment comprising modification(s) in at least its RNA binding domain. In additional instances, the Arc polypeptide comprises one or more domains of a human Arc polypeptide, in which at least one of the domains participates in the formation of a capsid and in which the RNA binding domain is modified to bind to a cargo that native human Arc protein does not bind to. In further instances, the Arc polypeptide is a recombinant human Arc polypeptide, with at least the RNA binding domain is modified to enable loading of a cargo that is not native to the human Arc protein.

In some embodiments, the Endo-Gag is a human Endo-Gag polypeptide with at least its RNA binding domain modified to bind to a cargo that is not native to the human endo-Gag. In some instances, the endo-Gag polypeptide comprises a full-length human endo-Gag polypeptide with at least its RNA binding domain modified to bind to a cargo that is not native to the human endo-Gag protein. In other instances, the endo-Gag polypeptide comprises a human endo-Gag fragment comprising modification(s) in at least its RNA binding domain to bind to a cargo that a native human endo-Gag protein does not bind to. In additional instances, the endo-Gag polypeptide comprises one or more domains of a human endo-Gag polypeptide, in which at least one of the domains participates in the formation of a capsid and in which the RNA binding domain is modified to bind to a cargo that is not native to the human endo-Gag protein. In further instances, the endo-Gag polypeptide is a recombinant human endo-Gag polypeptide, with at least the RNA binding domain is modified to enable loading of a cargo that is not native to the human endo-Gag protein.

In some instances, the Arc or endo-Gag polypeptide is an engineered Arc or endo-Gag polypeptide. As used herein, an engineered polypeptide is a recombinant polypeptide that is not identical in sequence to a full length, wild-type polypeptide. In some instances, the engineered Arc or endo-Gag polypeptide comprises a fragment of an Arc or endo-Gag polypeptide from a first species and at least an additional fragment from an Arc or endo-Gag polypeptide of a second species. In some cases, the first Arc or endo-Gag polypeptide is selected from a kingdom member of animalia, plantae, fungi, or protista. In some cases, the first species is selected from a mammal, a rodent, a bird, a reptile, a fish, a vertebrate, a eukaryote, an insect, a fungus, or a plant. In some cases, the second Arc polypeptide is selected from a kingdom member of animalia, plantae, fungi, or protista that is the same or different than the first Arc or endo-Gag polypeptide. In some cases, the second species is selected from a mammal, a rodent, a bird, a reptile, a fish, a vertebrate, a eukaryote, an insect, a fungus, or a plant that is different from the first species.

In some embodiments, an exemplary mammalian Arc or endo-Gag protein for expression as a recombinant or engineered Arc polypeptide is from the species *Homo sapiens*. Additional exemplary species of primate Arc or endo-Gag protein proteins for expression as a recombinant or engineered Arc polypeptide include: gorilla, *Pongo abehi, Pan paniscus, Macaca nemestrina, Chlorocebus sabaeus, Papio anubis, Rhinopithecus roxellana, Macaca fascicularis, Nomascus leucogenys, Callithrix jacchus, Aotus nancymaae, Cebus capucinus imitator, Saimiri boliviensis boliviensis, Otolemur garnettii, Macaca mulatta*, and *Macaca fascicularis*.

An exemplary species list of rodent Arc or endo-Gag proteins for expression as a recombinant or engineered Arc or endo-Gag polypeptide includes: *Fukomys damarensis, Microcebus murinus, Heterocephalus glaber, Propithecus coquereli, Marmota marmota marmota, Galeopterus variegatus, Cavia porcellus, Dipodomys ordii, Octodon degus, Castor canadensis Nannospalax galili, Carlito syrichta, Chinchilla lanigera, Mus musculus, Ictidomys tridecemlineatus, Rattus norvegicus, Microtus ochrogaster, Otolemur*

*garnettii, Meriones unguiculatus, Cricetulus griseus, Rattus norvegicus, Neotoma lepida, Jaculus jaculus, Mustela putorius furo, Mesocricetus auratus, Tupaia chinensis, Cricetulus griseus, Chrysochloris asiatica, Elephantulus edwardii, Erinaceus europaeus, Ochotona princeps, Sorex araneus, Monodelphis domestica, Echinops telfairi*, and *Condylura cristata*.

An exemplary species list of Arc or endo-Gag proteins for expression as a recombinant or engineered Arc or endo-Gag polypeptide includes: *Vulpes vulpes, Canis lupus* dingo, *Felis catus, Panthera pardus, Callorhinus ursinus, Odobenus rosmarus divergens, Equus asinus, Sus scrofa, Manis javanica, Ceratotherium simum simum, Leptonychotes weddellii, Enhydra lutris kenyoni, Lipotes vexillifer, Bos grunniens, Bubalus bubalis, Camelus dromedarius, Vicugna pacos, Orcinus orca, Neomonachus schauinslandi, Tursiops truncatus, Bos taurus, Capra hircus, Delphinapterus leucas, Ovis aries musimon, Balaenoptera acutorostrata scammoni, Neophocaena asiaeorientalis asiaeorientalis, Miniopterus natalensis, Pteropus alecto, Physeter catodon, Loxodonta africana, orycteropus afer afer, Bos mutus, Desmodus rotundus, Hipposideros armiger, Ailuropoda melanoleuca, Trichechus manatus latirostris, Rousettus latirostris, Rousettus aegyptiacus, Eptesicus fuscus, Rhinolophus sinicus, Cervus elaphus hippelaphus, Odocoileus virginianus texanus, Pantholops hodgsonii, Camelus bactrianus, Sarcophilus harrisii, Phascolarctos cinereus*, and *Ornithorhynchus anatinus*.

An exemplary species list of bird Arc or endo-Gag proteins for expression as a recombinant or engineered Arc or endo-Gag polypeptide includes: *Gallus gallus, Corvus cornix, cornix, Parus major, Corvus brachyrhynchos, Dromaius novaehollandiae*, and *Apteryx rowi*.

An exemplary species list of reptile Arc protein for expression as a recombinant or engineered Arc or endo-Gag polypeptide includes: *python bivittatus, Pogona vitticeps, Anolis carolinensis, Protobothrops mucrosquamatus, Alligator sinensis, Crocodylus porosus, Gavialis gangeticus, Alligator mississippiensis, Pelodiscus sinensis, Terrapene mexicana triunguis, Chrysemys picta belhi, Chelonia mydas, Nanorana parkeri, Xenopus tropicalis, Xenopus laevis*, and *Latimeria chalumnae,*

An exemplary species list of fish Arc protein for expression as a recombinant or engineered Arc or endo-Gag polypeptide includes: *Oncorhynchus mykiss, Acanthochromis polyacanthus, Oncorhynchus kisutch, Carassius auratus*, and *Austrofundulus limnaeus*.

An exemplary species list of insect Arc or endo-Gag proteins for expression as a recombinant or engineered Arc or endo-Gag polypeptide includes: *drosophila serrata, Drosophila bipectinata, Solenopsis invicta, Temnothorax curvispinosus, Drosophila melanogaster, Agrilus planipennis, Camponotus floridanus, Pogonomyrmex barbatus, Nilaparvata lugens, Bombyx mori, Tribolium castaneum*, and *Leptinotarsa decemlineata*.

An exemplary species list of plant Arc or endo-Gag proteins for expression as a recombinant or engineered Arc or endo-Gag polypeptide includes *Spinacia oleracea* and *Erythranthe guttata*.

An exemplary species list of fungi proteins for expression as a recombinant or engineered Arc or endo-Gag polypeptide includes: *Saccharomyces cerevisiae, Rhizopus delemar, Fusarium oxysporum, Cryptococcus neoformans, Rhizophagus irregularis, Fusarium fujikuroi, Candida albicans, Trichophyton rubrum, Pyrenophora tritici-repentis, Rhizopus microsporus, Rhizoctonia solani, Aspergillus flavus, Verticillium dahliae, Fusarium verticillioides, Aspergillus niger, Fusarium graminearum, Aspergillus fumigatus, Zymoseptoria tritici*, and *Trichoderma harzianum*.

An exemplary species list of protists Arc or endo-Gag proteins for expression as a recombinant or engineered Arc or endo-Gag polypeptide includes: *Entamoeba histolytica, Paulinella micropora, Guillardia theta, Oxyrrhis marina, Seminavis robusta, Euglena longa, Naegleria gruberi*, and *Trichomonas vaginalis*.

In some instances, Arc or endo-Gag comprises a capsid assembly/forming (CA) domain, a cargo binding domain (e.g., an RNA binding domain), and optionally a matrix (MA) domain, a reverse transcriptase (RT) domain, or a combination thereof. In some cases, the CA domain is further divided into an N-lobe domain and a C-lobe domain. In some cases, the cargo binding domain comprises an RNA binding domain, a DNA binding domain, a protein binding domain, a peptide binding domain, an antibody binding domain, a small molecule binding domain, or a peptidomimetic/nucleotidomimetic binding domain. Exemplary cargo binding domains include, but are not limited to, domains from GPCRs, antibodies or binding fragments thereof, lipoproteins, integrins, tyrosine kinases, DNA-binding proteins, RNA-binding proteins, nucleases, ligases, proteases, integrases, isomerases, phosphatases, GTPases, aromatases, esterases, adaptor proteins, G-proteins, GEFs, cytokines, interleukins, interleukin receptors, interferons, interferon receptors, caspases, transcription factors, neurotrophic factors and their receptors, growth factors and their receptors, signal recognition particle and receptor components, extracellular matrix proteins, integral components of membrane, ribosomal proteins, translation elongation factors, translation initiation factors, GPI-anchored proteins, tissue factors, dystrophin, utrophin, dystrobrevin, any fusions, combinations, subunits, derivatives, or domains thereof.

In some embodiments, one or more non-essential regions which are not involved in capsid formation or nucleic acid binding are removed from an Arc or endo-Gag protein to generate an Arc or endo-Gag polypeptide. In such instances, one or more non-essential regions, e.g., an N-terminal region (e.g., up to 10 amino acids, up to 20 amino acids, up to 30 amino acids, or up to 50 amino acids), a C-terminal region (e.g., up to 10 amino acids, up to 20 amino acids, up to 30 amino acids, or up to 50 amino acids), a RT domain, a MA domain, or a combination thereof, are deleted from an Arc or endo-Gag protein to generate an Arc or endo-Gag polypeptide. In some cases, only the essential regions involved in capsid assembly/forming and cargo binding remain in an Arc or endo-Gag polypeptide. In additional cases, only the essential region involved in capsid assembly/forming (e.g., the N-lobe and/or the C-lobe) remains in an Arc polypeptide.

In certain embodiments, the RT domain, the MA domain, and/or the endogenous RNA binding domain are replaced with other cargo binding domains: for example, replaced with a DNA binding domain, a protein binding domain, a peptide binding domain, an antibody binding domain, a small molecule binding domain, a peptidomimetic binding domain, or a nucleotidomimetic binding domain. In some embodiments, an Arc or endo-Gag polypeptide comprises truncations or modifications of domains involved in capsid forming, nucleic acid binding, or delivery.

In some embodiments, the Arc or endo-Gag polypeptide comprises a MA domain, a CA N-lobe, a CA C-lobe, a cargo binding domain, and a RT domain. In some instances, the Arc polypeptide comprises from N-terminus to C-terminus the following domains: the MA domain, the CA N-lobe, the CA C-lobe, the RT domain, and the cargo binding domain. In some instances, the Arc or endo-Gag polypeptide comprises from N-terminus to C-terminus the following domains: the MA domain, the RT domain, the cargo binding domain, the CA N-lobe, and the CA C-lobe. In some instances, the Arc or endo-Gag polypeptide comprises from N-terminus to C-terminus the following domains: the cargo binding domain, the MA domain, the RT domain, the CA N-lobe, and the CA C-lobe. In some instances, the domains are arranged in an order that does not impede capsid assembly and cargo binding. In some instances, each of the domains is either directly or indirectly fused to the respective two flanking domains.

In some embodiments, the Arc or endo-Gag polypeptide comprises a MA domain, a CA N-lobe, a CA C-lobe, and a cargo binding domain. In some instances, the Arc or endo-Gag polypeptide comprises from N-terminus to C-terminus the following domains: the MA domain, the CA N-lobe, the CA C-lobe, and the cargo binding domain. In some instances, the Arc polypeptide comprises from N-terminus to C-terminus the following domains: the MA domain, the cargo binding domain, the CA N-lobe, and the CA C-lobe. In some instances, the Arc or endo-Gag polypeptide comprises from N-terminus to C-terminus the following domains: the cargo binding domain, the MA domain, the CA N-lobe, and the CA C-lobe. In some instances, the domains are arranged in an order that does not impede capsid assembly and cargo binding. In some instances, each of the domains is either directly or indirectly fused to the respective two flanking domains.

In some embodiments, the Arc or endo-Gag polypeptide comprises a CA N-lobe, a CA C-lobe, and a cargo binding domain. In some instances, the Arc or endo-Gag polypeptide comprises from N-terminus to C-terminus the following domains: the CA N-lobe, the CA C-lobe, and the cargo binding domain. In some instances, the Arc or endo-Gag polypeptide comprises from N-terminus to C-terminus the following domains: the cargo binding domain, the CA N-lobe, and the CA C-lobe. In some instances, the domains are arranged in an order that does not impede capsid assembly and cargo binding. In some instances, each of the domains is either directly or indirectly fused to the respective two flanking domains.

In some embodiments, the Arc or endo-Gag polypeptide comprises a CA N-lobe and a cargo binding domain. In some instances, the Arc or endo-Gag polypeptide comprises from N-terminus to C-terminus the following domains: the CA N-lobe and the cargo binding domain. In some instances, the Arc or endo-Gag polypeptide comprises from N-terminus to C-terminus the following domains: the cargo binding domain and the CA N-lobe. In some instances, the domains are arranged in an order that does not impede capsid assembly and cargo binding. In some instances, the two domains are either directly or indirectly fused to each other.

In some embodiments, the Arc or endo-Gag polypeptide is engineered to comprise a cargo binding domain, a CA domain, a MA domain, or a RT domain from one or more additional species to generate an engineered Arc polypeptide. For example, the engineered Arc or endo-Gag polypeptide comprises a cargo binding domain, a CA domain, a MA domain, or a RT domain from a first species and a cargo binding domain, a CA domain, a MA domain, or a RT domain from a second species. In some cases, the first species is selected from a eukaryote, a vertebrate, a human, a mammal, a rodent, a bird, a reptile, a fish, an insect, a fungus, or a plant. In some cases, the second species is selected from a eukaryote, a vertebrate, a human, a mammal, a rodent, a bird, a reptile, a fish, an insect, a fungus, or a plant that is different from the first species.

In some instances, the engineered or endo-Gag Arc polypeptide comprises a cargo binding domain from a first species and a CA domain (e.g., a CA N-lobe and optionally a CA C-lobe) from a second species. The engineered Arc or endo-Gag polypeptide optionally comprises a MA domain and an RT domain from either the first species or the second species. In some cases, the first species is selected from a eukaryote, a vertebrate, a human, a mammal, a rodent, a bird, a reptile, a fish, an insect, a fungus, or a plant. In some cases, the second species is selected from a eukaryote, a vertebrate, a human, a mammal, a rodent, a bird, a reptile, a fish, an insect, a fungus, or a plant that is different from the first species.

In some instances, the engineered Arc or endo-Gag polypeptide comprises a cargo binding domain, a first CA domain, a second CA domain, and optionally a MA domain and/or a RT domain. In some cases, the cargo binding domain, the first CA domain, and optionally a MA domain and/or a RT domain are from a first species and the second CA domain is from a second species. In some cases, the first CA domain is from a first species and the cargo binding domain, the second CA domain, and optionally a MA domain and/or a RT domain are from a second species. In some instances, the domains are arranged in an order that does not impede capsid assembly and cargo binding. In some instances, each of the domains is either directly or indirectly fused to the respective two adjacent domains.

In some instances, the engineered Arc or endo-Gag polypeptide comprises a cargo binding domain, a first CA domain, and a second CA domain. In some cases, the cargo binding domain and the first CA domain are from a first species and the second CA domain is from a second species. In some cases, the first CA domain is from a first species and the cargo binding domain and the second CA domain are from a second species. In such cases, the engineered Arc or endo-Gag polypeptide comprises from the N-terminus to the C-terminus the following domains: a cargo binding domain, a first CA domain, and a second CA domain. In such cases, the engineered Arc or endo-Gag polypeptide comprises from the N-terminus to the C-terminus the following domains: a first CA domain, a cargo binding domain, and a second CA domain. In such cases, the engineered Arc or endo-Gag polypeptide comprises from the N-terminus to the C-terminus the following domains: a first CA domain, a second CA domain, and a cargo binding domain. In some instances, the domains are arranged in an order that does not impede capsid assembly and cargo binding. In some instances, each of the domains is either directly or indirectly fused to the respective two flanking domains.

In some instances, the engineered Arc or endo-Gag polypeptide further comprises a second polypeptide. In some instances, the second polypeptide is fused directly or indirectly via a linker to one or more of: a cargo binding domain, a first CA domain, a second CA domain, a MA domain if present, or a RT domain if present. In some cases, the second polypeptide is a protein (e.g., a human protein), an antibody or binding fragment thereof, a viral protein, a Gag-like protein (e.g., a human Gag-like protein), or a de novo engineered protein designed to bind to a target receptor of interest. In some instances, the antibody or binding fragment thereof comprises a humanized antibody or binding fragments thereof, a murine antibody or binding fragment thereof, a chimeric antibody or binding fragment thereof, a monoclonal antibody or binding fragment thereof, a multi-specific antibody or binding fragment thereof, a bispecific antibody or biding fragment thereof, a monovalent Fab', a divalent Fab$_2$, F(ab)'$_3$ fragments, a single-chain variable fragment (scFv), a bis-scFv, an (scFv)₂, a diabody, a minibody, a nanobody, a triabody, a tetrabody, a disulfide stabilized Fv protein (dsFv), a single-domain antibody (sdAb), an Ig NAR, a camelid antibody or binding fragment thereof, or a chemically modified derivative thereof. In some instances, the second polypeptide guides the delivery of a capsid formed by the engineered Arc polypeptide to a target site of interest.

In some embodiments, a nucleic acid sequence or amino acid sequence of the disclosure (for example, encoding an Arc polypeptide or endo-Gag polypeptide) has at least 70% homology, at least 71% homology, at least 72% homology, at least 73% homology, at least 74% homology, at least 75% homology, at least 76% homology, at least 77% homology, at least 78% homology, at least 79% homology, at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, at least 99% homology, at least 99.1% homology, at least 99.2% homology, at least 99.3% homology, at least 99.4% homology, at least 99.5% homology, at least 99.6% homology, at least 99.7% homology, at least 99.8% homology, at least 99.9% or at least 99.99% homology to an amino acid sequence provided herein. Various methods and software programs are used to determine the homology between two or sequences, such as NCBI BLAST, Clustal W, MAFFT, Clustal Omega, AlignMe, Praline, or another suitable method or algorithm.

In certain embodiments, the Arc polypeptide is a human polypeptide having the amino acid sequence of SEQ ID NO: 1 or a sequence having at least 90%, 91%, 92%, 93%, 94%, 95%, 96%, 97%, 98%, or 99% identity to SEQ ID NO: 1.

In certain embodiments, the Arc polypeptide is a killer whale polypeptide having the amino acid sequence of SEQ ID NO: 2 or a sequence having at least 90%, 91%, 92%, 93%, 94%, 95%, 96%, 97%, 98%, or 99% identity to SEQ ID NO: 2.

In certain embodiments, the Arc polypeptide is a white tailed deer polypeptide having the amino acid sequence of SEQ ID NO: 3 or a sequence having at least 90%, 91%, 92%, 93%, 94%, 95%, 96%, 97%, 98%, or 99% identity to SEQ ID NO: 3.

In certain embodiments, the Arc polypeptide is a platypus polypeptide having the amino acid sequence of SEQ ID NO: 4 or a sequence having at least 90%, 91%, 92%, 93%, 94%, 95%, 96%, 97%, 98%, or 99% identity to SEQ ID NO: 4.

In certain embodiments, the Arc polypeptide is a goose polypeptide having the amino acid sequence of SEQ ID NO: 5 or a sequence having at least 90%, 91%, 92%, 93%, 94%, 95%, 96%, 97%, 98%, or 99% identity to SEQ ID NO: 5.

In certain embodiments, the Arc polypeptide is a Dalmatian pelican polypeptide having the amino acid sequence of SEQ ID NO: 6 or a sequence having at least 90%, 91%, 92%, 93%, 94%, 95%, 96%, 97%, 98%, or 99% identity to SEQ ID NO: 6.

In certain embodiments, the Arc polypeptide is a white tailed eagle polypeptide having the amino acid sequence of SEQ ID NO: 7 or a sequence having at least 90%, 91%, 92%, 93%, 94%, 95%, 96%, 97%, 98%, or 99% identity to SEQ ID NO: 7.

In certain embodiments, the Arc polypeptide is a king cobra polypeptide having the amino acid sequence of SEQ ID NO: 8 or a sequence having at least 90%, 91%, 92%, 93%, 94%, 95%, 96%, 97%, 98%, or 99% identity to SEQ ID NO: 8.

In certain embodiments, the Arc polypeptide is a ray finned fish polypeptide having the amino acid sequence of SEQ ID NO: 9 or a sequence having at least 90%, 91%, 92%, 93%, 94%, 95%, 96%, 97%, 98%, or 99% identity to SEQ ID NO: 9.

In certain embodiments, the Arc polypeptide is a sperm whale polypeptide having the amino acid sequence of SEQ ID NO: 10 or a sequence having at least 90%, 91%, 92%, 93%, 94%, 95%, 96%, 97%, 98%, or 99% identity to SEQ ID NO: 10.

In certain embodiments, the Arc polypeptide is a turkey polypeptide having the amino acid sequence of SEQ ID NO: 11 or a sequence having at least 90%, 91%, 92%, 93%, 94%, 95%, 96%, 97%, 98%, or 99% identity to SEQ ID NO: 11.

In certain embodiments, the Arc polypeptide is a central bearded dragon polypeptide having the amino acid sequence of SEQ ID NO: 12 or a sequence having at least 90%, 91%, 92%, 93%, 94%, 95%, 96%, 97%, 98%, or 99% identity to SEQ ID NO: 12.

In certain embodiments, the Arc polypeptide is a Chinese alligator polypeptide having the amino acid sequence of SEQ ID NO: 13 or a sequence having at least 90%, 91%, 92%, 93%, 94%, 95%, 96%, 97%, 98%, or 99% identity to SEQ ID NO: 13.

In certain embodiments, the Arc polypeptide is an American alligator polypeptide having the amino acid sequence of SEQ ID NO: 14 or a sequence having at least 90%, 91%, 92%, 93%, 94%, 95%, 96%, 97%, 98%, or 99% identity to SEQ ID NO: 14.

In certain embodiments, the Arc polypeptide is a Japanese gekko polypeptide having the amino acid sequence of SEQ ID NO: 15 or a sequence having at least 90%, 91%, 92%, 93%, 94%, 95%, 96%, 97%, 98%, or 99% identity to SEQ ID NO: 15.

In certain embodiments, the endo-Gag polypeptide is a human PNMA3 polypeptide having the amino acid sequence of SEQ ID NO: 16 or a sequence having at least 90%, 91%, 92%, 93%, 94%, 95%, 96%, 97%, 98%, or 99% identity to SEQ ID NO: 16.

In certain embodiments, the endo-Gag polypeptide is a human PNMA5 polypeptide having the amino acid sequence of SEQ ID NO: 17 or a sequence having at least 90%, 91%, 92%, 93%, 94%, 95%, 96%, 97%, 98%, or 99% identity to SEQ ID NO: 17.

In certain embodiments, the endo-Gag polypeptide is a human PNMA6A polypeptide having the amino acid sequence of SEQ ID NO: 18 or a sequence having at least 90%, 91%, 92%, 93%, 94%, 95%, 96%, 97%, 98%, or 99% identity to SEQ ID NO: 18.

In certain embodiments, the endo-Gag polypeptide is a human PNMA6B polypeptide having the amino acid sequence of SEQ ID NO: 19 or a sequence having at least 90%, 91%, 92%, 93%, 94%, 95%, 96%, 97%, 98%, or 99% identity to SEQ ID NO: 19.

In certain embodiments, the endo-Gag polypeptide is a human RTL3 polypeptide having the amino acid sequence of SEQ ID NO: 20 or a sequence having at least 90%, 91%, 92%, 93%, 94%, 95%, 96%, 97%, 98%, or 99% identity to SEQ ID NO: 20.

In certain embodiments, the endo-Gag polypeptide is a human RTL6 polypeptide having the amino acid sequence of SEQ ID NO: 21 or a sequence having at least 90%, 91%, 92%, 93%, 94%, 95%, 96%, 97%, 98%, or 99% identity to SEQ ID NO: 21.

In certain embodiments, the endo-Gag polypeptide is a human RTL8A polypeptide having the amino acid sequence of SEQ ID NO: 22 or a sequence having at least 90%, 91%, 92%, 93%, 94%, 95%, 96%, 97%, 98%, or 99% identity to SEQ ID NO: 22.

In certain embodiments, the endo-Gag polypeptide is a human RTL8B polypeptide having the amino acid sequence of SEQ ID NO: 23 or a sequence having at least 90%, 91%, 92%, 93%, 94%, 95%, 96%, 97%, 98%, or 99% identity to SEQ ID NO: 23.

In certain embodiments, the endo-Gag polypeptide is a human BOP polypeptide having the amino acid sequence of SEQ ID NO: 24 or a sequence having at least 90%, 91%, 92%, 93%, 94%, 95%, 96%, 97%, 98%, or 99% identity to SEQ ID NO: 24.

In certain embodiments, the endo-Gag polypeptide is a human LDOC1 polypeptide having the amino acid sequence of SEQ ID NO: 25 or a sequence having at least 90%, 91%, 92%, 93%, 94%, 95%, 96%, 97%, 98%, or 99% identity to SEQ ID NO: 25.

In certain embodiments, the endo-Gag polypeptide is a human ZNF18 polypeptide having the amino acid sequence of SEQ ID NO: 26 or a sequence having at least 90%, 91%, 92%, 93%, 94%, 95%, 96%, 97%, 98%, or 99% identity to SEQ ID NO: 26.

In certain embodiments, the endo-Gag polypeptide is a human MOAP1 polypeptide having the amino acid sequence of SEQ ID NO: 27 or a sequence having at least 90%, 91%, 92%, 93%, 94%, 95%, 96%, 97%, 98%, or 99% identity to SEQ ID NO: 27.

In certain embodiments, the endo-Gag polypeptide is a human PEG10 polypeptide having the amino acid sequence of SEQ ID NO: 28 or a sequence having at least 90%, 91%, 92%, 93%, 94%, 95%, 96%, 97%, 98%, or 99% identity to SEQ ID NO: 28.

In some cases, the recombinant Arc or endo-Gag polypeptide is an Arc polypeptide illustrated in FIG. 1.

Figure 2:
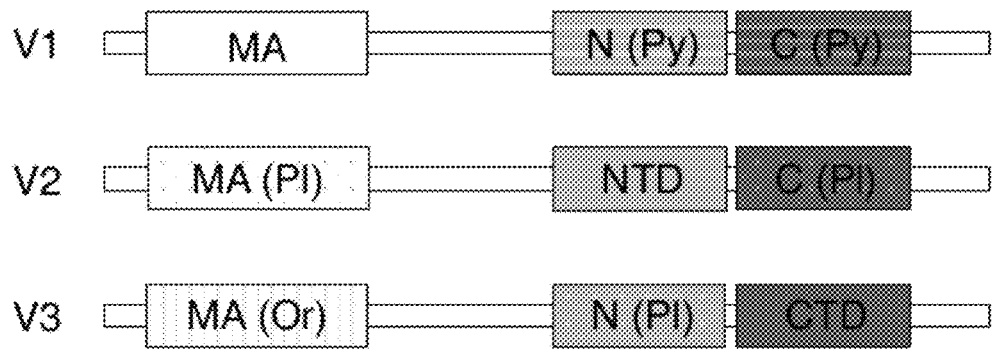
FIG. 2 is a representation of exemplary engineered Arc polypeptides.

In some cases, the engineered Arc or endo-Gag polypeptide is an engineered Arc polypeptide illustrated in FIG. 2.

Linkers

In certain embodiments, a polypeptide of the disclosure comprises a linker. In some embodiments, the linker is a peptide linker. In some instances, the linker is a rigid linker. In other instances, the linker is a flexible linker. In some cases, the linker is a non-cleavable linker. In other cases, the linker is a cleavable linker. In additional cases, the linker comprises a linear structure, or a non-linear structure (e.g., a cyclic structure).

In certain embodiments, non-cleavable linkers comprise short peptides of varying lengths. Exemplary non-cleavable linkers include (EAAAK)n (SEQ ID NO: 70), or (EAAAR)n (SEQ ID NO: 71), where n is from 1 to 5, and up to 30 residues of glutamic acid-proline or lysine-proline repeats. In some embodiments, the non-cleavable linker comprises (GGGGS)n (SEQ ID NO: 72) or (GGGS)n (SEQ ID NO: 73), wherein n is 1 to 10; KESGSVSSEQLAQFRSLD (SEQ ID NO: 74); or EGKSSGSGSESKST (SEQ ID NO: 75). In some embodiments, the non-cleavable linker comprises a poly-Gly/Ala polymer.

In certain embodiments, the linker is a cleavable linker, e.g., an extracellular cleavable linker or an intracellular cleavable linker. In some instances, the linker is designed for cleavage in the presence of particular conditions or in a particular environment (e.g., under physiological condition). For example, the design of a linker for cleavage by specific conditions, such as by a specific enzyme, allows the targeting of cellular uptake to a specific location.

In some embodiments, the linker is a pH-sensitive linker. In one instance, the linker is cleaved under basic pH conditions. In other instance, the linker is cleaved under acidic pH conditions.

In some embodiments, the linker is cleaved in vivo by endogenous enzymes (e.g., proteases) such as serine proteases including but not limited to thrombin, metalloproteases, furin, cathepsin B, necrotic enzymes (e.g., calpains), and the like. Exemplary cleavable linkers include, but are not limited to, GGAANLVRGG (SEQ ID NO: 76); SGRIGFLRTA (SEQ ID NO: 77); SGRSA (SEQ ID NO: 78); GFLG (SEQ ID NO: 79); ALAL (SEQ ID NO: 80); FK; PIC(Et)F-F (SEQ ID NO: 81), where C(Et) indicates S-ethylcysteine; PR(S/T)(L/I)(S/T) (SEQ ID NO: 82); DEVD (SEQ ID NO: 83); GWEHDG (SEQ ID NO: 84); RPLA-LWRS (SEQ ID NO: 85); or a combination thereof.

Capsids

In some embodiments, disclosed herein is a capsid. In some instances, the capsid comprises an Arc polypeptide and/or an endo-Gag polypeptide such as a Copia protein, ASPRV1 protein, a protein from the SCAN domain family, a protein encoded by the Paraneoplastic Ma antigen family, a protein or a combination of proteins chosen from the retrotransposon Gag-like family, or a combination thereof. Exemplary endo-Gag polypeptides are BOP, LDOC1, MOAP1, PEG10, PNMA3, PNMA5, PNMA6A, PNMA6B, RTL3, RTL6, RTL8A, RTL8B, and ZNF18. In some instances, the Arc polypeptide, the Copia protein, the ASPRV1 protein, the protein from the SCAN domain family, the protein encoded by the Paraneoplastic Ma antigen family, and the protein or a combination of proteins chosen from the retrotransposon Gag-like family are each independently a full-length polypeptide. In other instances, the Arc polypeptide, the Copia protein, the ASPRV1 protein, the protein from the SCAN domain family, the protein encoded by the Paraneoplastic Ma antigen family, and the protein or a combination of proteins chosen from the retrotransposon Gag-like family are each independently a functional fragment thereof, e.g., that is capable of forming a subunit of a capsid.

Arc-Based Capsids and Endo-Gag-Based Capsids

In some embodiments, the capsid comprises an Arc-based capsid. In some embodiments, the capsid comprises an endo-Gag-based capsid. In some instances, the Arc-based and/or endo-Gag capsid comprises a plurality of recombinant Arc polypeptides and/or endo-Gag polypeptides described above, a plurality of engineered Arc polypeptides and/or endo-Gag polypeptides described above, or a combination thereof. In some cases, the Arc-based capsid comprises a plurality of recombinant Arc polypeptides. In other cases, the Arc-based capsid comprises a plurality of engineered Arc polypeptides. In some cases, the endo-Gag-based capsid comprises a plurality of recombinant endo-Gag polypeptides. In other cases, the endo-Gag-based capsid comprises a plurality of engineered endo-Gag polypeptides.

In some embodiments, the Arc-based or endo-Gag-based capsid comprises a first plurality of Arc and/or endo-Gag polypeptides from a first species and a second plurality of Arc and/or endo-Gag polypeptides from at least a second species. In some cases, the first species is selected from a eukaryote, a vertebrate, a human, a mammal, a rodent, a bird, a reptile, a fish, an insect, a fungus, or a plant. In some cases, the second species is selected from a eukaryote, a vertebrate, a human, a mammal, a rodent, a bird, a reptile, a fish, an insect, a fungus, or a plant that is different from the first species.

In some instances, the ratio of the first plurality of Arc or endo-Gag polypeptides to the second plurality of Arc or endo-Gag polypeptides is 1:1, 2:1, 3:1, 4:1, 5:1, 6:1, 7:1, 8:1, 9:1, 10:1, 20:1, 50:1, or 100:1. In some cases, the ratio of the first plurality of Arc or endo-Gag polypeptides to the second plurality of Arc or endo-Gag polypeptides is 1:1. In some cases, the ratio of the first plurality of Arc or endo-Gag polypeptides to the second plurality of Arc or endo-Gag polypeptides is 2:1. In some cases, the ratio of the first plurality of Arc or endo-Gag polypeptides to the second plurality of Arc or endo-Gag polypeptides is 4:1. In some cases, the ratio of the first plurality of Arc or endo-Gag polypeptides to the second plurality of Arc or endo-Gag polypeptides is 5:1. In some cases, the ratio of the first plurality of Arc or endo-Gag polypeptides to the second plurality of Arc or endo-Gag polypeptides is 8:1. In some cases, the ratio of the first plurality of Arc or endo-Gag polypeptides to the second plurality of Arc polypeptides is 10:1. In some cases, the ratio of the first plurality of Arc or endo-Gag polypeptides to the second plurality of Arc or endo-Gag polypeptides is 20:1. In some cases, the ratio of the first plurality of Arc or endo-Gag polypeptides to the second plurality of Arc or endo-Gag polypeptides is 50:1. In some cases, the ratio of the first plurality of Arc or endo-Gag polypeptides to the second plurality of Arc or endo-Gag polypeptides is 100:1. In some instances, the ratio is the comparison in molar concentration. In some instances, the ratio is the comparison in the number of capsid forming subunits (e.g., each of the or engineered Arc polypeptide forms a capsid subunit).

In some instances, the ratio of the first plurality of Arc or endo-Gag polypeptides to the second plurality of Arc or endo-Gag polypeptides is 1:2, 1:3, 1:4, 1:5, 1:6, 1:7, 1:8, 1:9, 1:10, 1:20, or 1:50. In some cases, the ratio of the first plurality of Arc or endo-Gag polypeptides to the second plurality of Arc or endo-Gag polypeptides is 1:2. In some cases, the ratio of the first plurality of Arc or endo-Gag polypeptides to the second plurality of Arc or endo-Gag polypeptides is 1:5. In some cases, the ratio of the first plurality of Arc or endo-Gag polypeptides to the second plurality of Arc or endo-Gag polypeptides is 1:8. In some cases, the ratio of the first plurality of Arc or endo-Gag polypeptides to the second plurality of Arc or endo-Gag polypeptides is 1:10. In some cases, the ratio of the first plurality of Arc or endo-Gag polypeptides to the second plurality of Arc or endo-Gag polypeptides is 1:20. In some cases, the ratio of the first plurality of Arc or endo-Gag polypeptides to the second plurality of Arc or endo-Gag polypeptides is 1:50. In some instances, the ratio is the comparison in molar concentration. In some instances, the ratio is the comparison in the number of capsid forming subunits (e.g., each of the recombinant or engineered Arc or endo-Gag polypeptide forms a capsid subunit).

In some embodiments, the Arc-based capsid or endo-Gag-based capsid comprises a plurality of recombinant or engineered Arc polypeptides and a plurality of non-Arc proteins. Exemplary species of non-Arc proteins include but are not limited to, Copia, ASPRV1, a protein or a combination of proteins chosen from the SCAN domain family, a protein or a combination of proteins chosen from the Paraneoplastic Ma antigen family, and a protein or a combination of proteins chosen from the retrotransposon Gag-like family. Exemplary species of non-Arc proteins include BOP, LDOC1, MOAP1, PEG10, PNMA3, PNMA5, PNMA6A, PNMA6B, RTL3, RTL6, RTL8A, RTL8B, and ZNF18.

In some instances, the ratio of the plurality of recombinant or engineered Arc polypeptides to the plurality of non-Arc proteins is 1:1, 2:1, 3:1, 4:1, 5:1, 6:1, 7:1, 8:1, 9:1, 10:1, 20:1, 50:1, or 100:1. In some cases, the ratio of the plurality of recombinant or engineered Arc polypeptides to the plurality of non-Arc proteins is 1:1. In some cases, the ratio of the plurality of recombinant or engineered Arc polypeptides to the plurality of non-Arc proteins is 2:1. In some cases, the ratio of the plurality of recombinant or engineered Arc polypeptides to the plurality of non-Arc proteins is 4:1. In some cases, the ratio of the plurality of recombinant or engineered Arc polypeptides to the plurality of non-Arc proteins is 5:1. In some cases, the ratio of the plurality of recombinant or engineered Arc polypeptides to the plurality of non-Arc proteins is 8:1. In some cases, the ratio of the plurality of recombinant or engineered Arc polypeptides to the plurality of non-Arc proteins is 10:1. In some cases, the ratio of the plurality of recombinant or engineered Arc polypeptides to the plurality of non-Arc proteins is 20:1. In some cases, the ratio of the plurality of recombinant or engineered Arc polypeptides to the plurality of non-Arc proteins is 50:1. In some cases, the ratio of the plurality of recombinant or engineered Arc polypeptides to the plurality of non-Arc proteins is 100:1. In some instances, the ratio is the comparison in molar concentration. In some instances, the ratio is the comparison in the number of capsid forming subunits (e.g., each of the recombinant or engineered Arc polypeptide forms a capsid subunit).

In some instances, the ratio of the plurality of recombinant or engineered Arc polypeptides to the plurality of non-Arc proteins is 1:2, 1:3, 1:4, 1:5, 1:6, 1:7, 1:8, 1:9, 1:10, 1:20, or 1:50. In some cases, the ratio of the plurality of recombinant or engineered Arc polypeptides to the plurality of non-Arc proteins is 1:2. In some cases, the ratio of the plurality of recombinant or engineered Arc polypeptides to the plurality of non-Arc proteins is 1:5. In some cases, the ratio of the plurality of recombinant or engineered Arc polypeptides to the plurality of non-Arc proteins is 1:8. In some cases, the ratio of the plurality of recombinant or engineered Arc polypeptides to the plurality of non-Arc proteins is 1:10. In some cases, the ratio of the plurality of recombinant or engineered Arc polypeptides to the plurality of non-Arc proteins is 1:20. In some cases, the ratio of the plurality of recombinant or engineered Arc polypeptides to the plurality of non-Arc proteins is 1:50. In some instances, the ratio is the comparison in molar concentration. In some instances, the ratio is the comparison in the number of capsid forming subunits (e.g., each of the recombinant or engineered Arc polypeptide forms a capsid subunit).

In some embodiments, the capsid has a diameter of at least 1 nm, or more. In some instances, the capsid has a diameter of at least 2 nm, 3 nm, 4 nm, 5 nm, 10 nm, 15 nm, 20 nm, 25 nm, 30 nm, 40 nm, 50 nm, 60 nm, 70 nm, 80 nm, 90 nm, 100 nm, 150 nm, 200 nm, 300 nm, 400 nm, 500 nm, 600 nm, or more. In some instances, the capsid has a diameter of at least 5 nm, or more. In some cases, the capsid has a diameter of at least 10 nm, or more. In some instances, the capsid has a diameter of at least 20 nm, or more. In some cases, the capsid has a diameter of at least 30 nm, or more. In some cases, the capsid has a diameter of at least 40 nm, or more. In some cases, the capsid has a diameter of at least 50 nm, or more. In some cases, the capsid has a diameter of at least 80 nm, or more. In some cases, the capsid has a diameter of at least 100 nm, or more. In some cases, the capsid has a diameter of at least 200 nm, or more. In some cases, the capsid has a diameter of at least 300 nm, or more. In some cases, the capsid has a diameter of at least 400 nm, or more. In some cases, the capsid has a diameter of at least 500 nm, or more. In some cases, the capsid has a diameter of at least 600 nm, or more.

In some embodiments, the capsid has a diameter of at most 1 nm, or less. In some instances, the capsid has a diameter of at most 2 nm, 3 nm, 4 nm, 5 nm, 10 nm, 15 nm, 20 nm, 25 nm, 30 nm, 40 nm, 50 nm, 60 nm, 70 nm, 80 nm, 90 nm, 100 nm, 150 nm, 200 nm, 300 nm, 400 nm, 500 nm, 600 nm, or less. In some instances, the capsid has a diameter of at most 5 nm, or less. In some cases, the capsid has a diameter of at most 10 nm, or less. In some instances, the capsid has a diameter of at most 20 nm, or less. In some cases, the capsid has a diameter of at most 30 nm, or less. In some cases, the capsid has a diameter of at least 40 nm, or less. In some cases, the capsid has a diameter of at least 50 nm, or less. In some cases, the capsid has a diameter of at least 80 nm, or less. In some cases, the capsid has a diameter of at least 100 nm, or less. In some cases, the capsid has a diameter of at least 200 nm, or less. In some cases, the capsid has a diameter of at least 300 nm, or less. In some cases, the capsid has a diameter of at least 400 nm, or less. In some cases, the capsid has a diameter of at least 500 nm, or less. In some cases, the capsid has a diameter of at least 600 nm, or less.

In some embodiments, the capsid has a diameter of about 1 nm, 2 nm, 3 nm, 4 nm, 5 nm, 10 nm, 15 nm, 20 nm, 25 nm, 30 nm, 40 nm, 50 nm, 60 nm, 70 nm, 80 nm, 90 nm, 100 nm, 150 nm, 200 nm, 300 nm, 400 nm, 500 nm, or 600 nm. In some instances, the capsid has a diameter of about 5 nm. In some cases, the capsid has a diameter of about 10 nm. In some instances, the capsid has a diameter of about 20 nm. In some cases, the capsid has a diameter of about 30 nm. In some cases, the capsid has a diameter of about 40 nm. In some cases, the capsid has a diameter of about 50 nm. In some cases, the capsid has a diameter of about 80 nm. In some cases, the capsid has a diameter of about 100 nm. In some cases, the capsid has a diameter of about 200 nm. In some cases, the capsid has a diameter of about 300 nm. In some cases, the capsid has a diameter of about 400 nm. In some cases, the capsid has a diameter of about 500 nm. In some cases, the capsid has a diameter of about 600 nm.

In some embodiments, the capsid has a diameter of from about 1 nm to about 600 nm. In some instances, the capsid has a diameter of from about 2 nm to about 500 nm, from about 2 nm to about 400 nm, from about 2 nm to about 300 nm, from about 2 nm to about 200 nm, from about 2 nm to about 100 nm, from about 2 nm to about 50 nm, from about 2 nm to about 30 nm, from about 20 nm to about 400 nm, from about 20 nm to about 300 nm, from about 20 nm to about 200 nm, from about 20 nm to about 100 nm, from about 20 nm to about 50 nm, from about 20 nm to about 30 nm, from about 30 nm to about 500 nm, from about 30 nm to about 400 nm, from about 30 nm to about 300 nm, from about 30 nm to about 200 nm, from about 30 nm to about 100 nm, from about 30 nm to about 50 nm, from about 50 nm to about 300 nm, from about 50 nm to about 200 nm, from about 50 nm to about 100 nm, from about 2 nm to about 25 nm, from about 2 nm to about 20 nm, from about 2 nm to about 10 nm, from about 5 nm to about 25 nm, from about 5 nm to about 20 nm, from about 5 nm to about 10 nm, from about 10 nm to about 25 nm, or from about 10 nm to about 20 nm.

In some embodiments, the capsid has a reduced off-target effect. In some cases, the off-target effect is less than 10%, 5%, 4%, 3%, 2%, 1%, or 0.5%. In some cases, the off-target effect is no more than 10%, 5%, 4%, 3%, 2%, 1%, or 0.5%. In some cases, the capsid does not have an off-target effect.

In certain embodiments, the formation of Arc and/or endo-Gag-based capsids occurs either ex vivo or in vitro.

In some instances, the Arc and/or endo-Gag-based capsids is assembled in vivo.

In some instances, the Arc and/or endo-Gag-based capsids is stable at room temperature. In some cases, the Arc and/or endo-Gag-based capsids is empty. In other cases, the Arc and/or endo-Gag-based capsids is loaded (for example, loaded with a cargo and/or a therapeutic agent, e.g., a DNA or an RNA).

In some instances, the Arc and/or endo-Gag-based capsids is stable at a temperature from about 2° C. to about 37° C. In some instances, the Arc and/or endo-Gag-based capsids is stable at a temperature from about 2° C. to about 8° C., about 2° C. to about 4° C., about 20° C. to about 37° C., about 25° C. to about 37° C., about 20° C. to about 30° C., about 25° C. to about 30° C., or about 30° C. to about 37° C. In some cases, the Arc and/or endo-Gag-based capsid is empty. In other cases, the Arc and/or endo-Gag-based capsids is loaded (for example, loaded with a cargo and/or a therapeutic agent, e.g., a DNA or an RNA).

In some instances, the Arc and/or endo-Gag-based capsids is stable for at least about 1 day, 2 days, 4 days, 5 days, 7 days, 14 days, 28 days, 30 days, 60 days, 2 months, 3 months, 4 months, 5 months, 6 months, 12 months, 18 months, 24 months, 3 years, 5 years, or longer. In some case, the Arc and/or endo-Gag-based capsids has minimum degradation, e.g., less than 10%, 5%, 4%, 3%, 2%, 1%, 0.5% based on the total population of the Arc and/or endo-Gag-based capsids that is degraded. In some cases, the Arc and/or endo-Gag-based capsid is empty. In other cases, the Arc and/or endo-Gag-based capsids is loaded (for example, loaded with a therapeutic agent, e.g., a DNA or an RNA).

Additional Capsids

In some embodiments, the capsid comprises the Copia protein. In some instances, the Copia protein is from *Drosophila melanogaster* (UniProtKB—P04146), *Ceratitis capitate* (UniProtKB—W8BHY5), or *Drosophila simulans* (UniProtKB—Q08461).

In some embodiments, the capsid comprises the protein ASPRV1. The ASPRV1 protein is a structural protein that participates in the development and maintenance of the skin barrier. In some instances, the protein ASPRV1 is from *Homo sapiens* (UniProtKB—Q53RT3).

In some embodiments, the capsid comprises a protein from the SCAN domain family. SCAN domain is a superfamily of zinc finger transcription factors. SCAN domain is also known as leucine rich region (LeR) and functions as protein interaction domain that mediates self-association or selective association with other proteins.

In some embodiments, the capsid comprises a protein from the Paraneoplastic Ma antigen family. The Paraneoplastic Ma antigen family comprises about 14 members of neuro- and testis-specific proteins.

In some embodiments, the capsid comprises a protein encoded by a Retrotransposon Gag-like gene.

In some embodiments, the capsid comprises BOP, LDOC1, MOAP1, PEG10, PNMA3, PNMA5, PNMA6A, PNMA6B, RTL3, RTL6, RTL8A, RTL8B, and/or ZNF18.

Cargos

In some embodiments, a composition of the disclosure (for example, a capsid) comprises a cargo. In some embodiments, the cargo is a therapeutic agent. In some embodiments, the cargo is a nucleic acid molecule, a small molecule, a protein, a peptide, an antibody or binding fragment thereof, a peptidomimetic, or a nucleotidomimetic. In some instances, the cargo is a therapeutic cargo, comprising e.g., one or more drugs. In some instances, the cargo comprises a diagnostic tool, for profiling, e.g., one or more markers (such as markers associates with one or more disease phenotypes). In additional instances, the cargo comprises an imaging tool.

In some instances, the cargo is a nucleic acid molecule. Exemplary nucleic acid molecules include DNA, RNA, or a mixture of DNA and RNA. In some instances, the nucleic acid molecule is a DNA polymer. In some cases, the DNA is a single stranded DNA polymer. In other cases, the DNA is a double stranded DNA polymer. In additional cases, the DNA is a hybrid of single and double stranded DNA polymer.

In some embodiments, the nucleic acid molecule is a RNA polymer, e.g., a single stranded RNA polymer, a double stranded RNA polymer, or a hybrid of single and double stranded RNA polymers. In some instances, the RNA comprises and/or encodes an antisense oligoribonucleotide, a siRNA, an mRNA, a tRNA, an rRNA, a snRNA, a shRNA, microRNA, or a non-coding RNA.

In some embodiments, the nucleic acid molecule comprises a hybrid of DNA and RNA.

In some embodiments, the nucleic acid molecule is an antisense oligonucleotide, optionally comprising DNA, RNA, or a hybrid of DNA and RNA.

In some instances, the nucleic acid molecule comprises and/or encodes an mRNA molecule.

In some embodiments, the nucleic acid molecule comprises and/or encodes an RNAi molecule. In some cases, the RNAi molecule is a microRNA (miRNA) molecule. In other cases, the RNAi molecule is a siRNA molecule. The miRNA and/or siRNA are optionally double-stranded or as a hairpin, and further optionally encapsulated as precursor molecules.

In some embodiments, the nucleic acid molecule is for use in a nucleic acid-based therapy. In some instances, the nucleic acid molecule is for regulating gene expression (e.g., modulating mRNA translation or degradation), modulating RNA splicing, or RNA interference. In some cases, the nucleic acid molecule comprises and/or encodes an antisense oligonucleotide, microRNA molecule, siRNA molecule, mRNA molecule, for use in regulation of gene expression, modulating RNA splicing, or RNA interference.

In some instances, the nucleic acid molecule is for use in gene editing. Exemplary gene editing systems include, but are not limited to, CRISPR-Cas systems, zinc finger nuclease (ZFN) systems, and transcription activator-like effector nuclease (TALEN) systems. In some cases, the nucleic acid molecule comprises and/or encodes a component involved in the CRISPR-Cas systems, ZFN systems, or the TALEN systems.

In some cases, the nucleic acid molecule is for use in antigen production for therapeutic and/or prophylactic vaccine production. For example, the nucleic acid molecule encodes an antigen that is expressed and elicits a desirable immune response (e.g., a pro-inflammatory immune response, an anti-inflammatory immune response, an B cell response, an antibody response, a T cell response, a CD4+ T cell response, a CD8+ T cell response, a Th1 immune response, a Th2 immune response, a Th17 immune response, a Treg immune response, or a combination thereof).

In some cases, the nucleic acid molecule comprises a nucleic acid enzyme. Nucleic acid enzymes are RNA molecules (e.g., ribozymes) or DNA molecules (e.g., deoxyribozymes) that have catalytic activities. In some instances, the nucleic acid molecule is a ribozyme. In other instances, the nucleic acid molecule is a deoxyribozyme. In some cases, the nucleic acid molecule is a MNAzyme, which functions as a biosensor and/or a molecular switch (see, e.g., Mokany, et al., "MNAzymes, a versatile new class of nucleic acid enzymes that can function as biosensors and molecular switches," JACS 132(2): 1051-1059 (2010)).

In some instances, exemplary targets of the nucleic acid molecule include, but are not limited to, UL123 (human cytomegalovirus), APOB, AR (androgen receptor) gene, KRAS, PCSK9, CFTR, and SMN (e.g., SMN2).

In some embodiments, the nucleic acid molecule is at least 5 nucleotides or more in length. In some instances, the nucleic acid molecule is at least 6, 7, 8, 9, 10, 11, 12, 13, 14, 15, 16, 17, 18, 19, 20, 21, 22, 23, 24, 25, 26, 27, 28, 29, 30, 35, 40, 50, 60, 70, 80, 90, 100, 150, 200, 250, 300, 400, 500, 1000, 1500, 2000, 3000, 4000, 5000, 6000, 7000, 8000, 9000 nucleotides or more in length. In some instances, the nucleic acid molecule is at least 10 nucleotides or more in length. In some instances, the nucleic acid molecule is at least 12 nucleotides or more in length. In some instances, the nucleic acid molecule is at least 15 nucleotides or more in length. In some instances, the nucleic acid molecule is at least 18 nucleotides or more in length. In some instances, the nucleic acid molecule is at least 19 nucleotides or more in length. In some instances, the nucleic acid molecule is at least 20 nucleotides or more in length. In some instances, the nucleic acid molecule is at least 21 nucleotides or more in length. In some instances, the nucleic acid molecule is at least 22 nucleotides or more in length. In some instances, the nucleic acid molecule is at least 23 nucleotides or more in length. In some instances, the nucleic acid molecule is at least 24 nucleotides or more in length. In some instances, the nucleic acid molecule is at least 25 nucleotides or more in length. In some instances, the nucleic acid molecule is at least 26 nucleotides or more in length. In some instances, the nucleic acid molecule is at least 27 nucleotides or more in length. In some instances, the nucleic acid molecule is at least 28 nucleotides or more in length. In some instances, the nucleic acid molecule is at least 29 nucleotides or more in length. In some instances, the nucleic acid molecule is at least 30 nucleotides or more in length. In some instances, the nucleic acid molecule is at least 40 nucleotides or more in length. In some instances, the nucleic acid molecule is at least 50 nucleotides or more in length. In some instances, the nucleic acid molecule is at least 100 nucleotides or more in length. In some instances, the nucleic acid molecule is at least 200 nucleotides or more in length. In some instances, the nucleic acid molecule is at least 300 nucleotides or more in length. In some instances, the nucleic acid molecule is at least 500 nucleotides or more in length. In some instances, the nucleic acid molecule is at least 1000 nucleotides or more in length. In some instances, the nucleic acid molecule is at least 2000 nucleotides or more in length. In some instances, the nucleic acid molecule is at least 3000 nucleotides or more in length. In some instances, the nucleic acid molecule is at least 4000 nucleotides or more in length. In some instances, the nucleic acid molecule is at least 5000 nucleotides or more in length. In some instances, the nucleic acid molecule is at least 8000 nucleotides or more in length.

In some embodiments, the nucleic acid molecule is at most 12 nucleotides or less in length. In some instances, the nucleic acid molecule is at most 13, 14, 15, 16, 17, 18, 19, 20, 21, 22, 23, 24, 25, 26, 27, 28, 29, 30, 35, 40, 50, 60, 70, 80, 90, 100, 150, 200, 250, 300, 400, 500, 1000, 1500, 2000, 3000, 4000, 5000, 6000, 7000, 8000, 9000 nucleotides or less in length. In some instances, the nucleic acid molecule is at most 15 nucleotides or less in length. In some instances, the nucleic acid molecule is at most 18 nucleotides or less in length. In some instances, the nucleic acid molecule is at most 19 nucleotides or less in length. In some instances, the nucleic acid molecule is at most 20 nucleotides or less in length. In some instances, the nucleic acid molecule is at most 21 nucleotides or less in length. In some instances, the nucleic acid molecule is at most 22 nucleotides or less in length. In some instances, the nucleic acid molecule is at most 23 nucleotides or less in length. In some instances, the nucleic acid molecule is at most 24 nucleotides or less in length. In some instances, the nucleic acid molecule is at most 25 nucleotides or less in length. In some instances, the nucleic acid molecule is at most 26 nucleotides or less in length. In some instances, the nucleic acid molecule is at most 27 nucleotides or less in length. In some instances, the nucleic acid molecule is at most 28 nucleotides or less in length. In some instances, the nucleic acid molecule is at most 29 nucleotides or less in length. In some instances, the nucleic acid molecule is at most 30 nucleotides or less in length. In some instances, the nucleic acid molecule is at most 40 nucleotides or less in length. In some instances, the nucleic acid molecule is at most 50 nucleotides or less in length. In some instances, the nucleic acid molecule is at most 100 nucleotides or less in length. In some instances, the nucleic acid molecule is at most 200 nucleotides or less in length. In some instances, the nucleic acid molecule is at most 300 nucleotides or less in length. In some instances, the nucleic acid molecule is at most 500 nucleotides or less in length. In some instances, the nucleic acid molecule is at most 1000 nucleotides or less in length. In some instances, the nucleic acid molecule is at most 2000 nucleotides or less in length. In some instances, the nucleic acid molecule is at most 3000 nucleotides or less in length. In some instances, the nucleic acid molecule is at most 4000 nucleotides or less in length. In some instances, the nucleic acid molecule is at most 5000 nucleotides or less in length. In some instances, the nucleic acid molecule is at most 8000 nucleotides or less in length.

In some embodiments, the nucleic acid molecule is about 5 nucleotides in length. In some instances, the nucleic acid molecule is about 6, 7, 8, 9, 10, 11, 12, 13, 14, 15, 16, 17, 18, 19, 20, 21, 22, 23, 24, 25, 26, 27, 28, 29, 30, 35, 40, 50, 60, 70, 80, 90, 100, 150, 200, 250, 300, 400, 500, 1000, 1500, 2000, 3000, 4000, 5000, 6000, 7000, 8000, 9000 nucleotides in length. In some instances, the nucleic acid molecule is about 10 nucleotides in length. In some instances, the nucleic acid molecule is about 12 nucleotides in length. In some instances, the nucleic acid molecule is about 15 nucleotides in length. In some instances, the nucleic acid molecule is about 18 nucleotides in length. In some instances, the nucleic acid molecule is about 19 nucleotides in length. In some instances, the nucleic acid molecule is about 20 nucleotides in length. In some instances, the nucleic acid molecule is about 21 nucleotides in length. In some instances, the nucleic acid molecule is about 22 nucleotides in length. In some instances, the nucleic acid molecule is about 23 nucleotides in length. In some instances, the nucleic acid molecule is about 24 nucleotides in length. In some instances, the nucleic acid molecule is about 25 nucleotides in length. In some instances, the nucleic acid molecule is about 26 nucleotides in length. In some instances, the nucleic acid molecule is about 27 nucleotides in length. In some instances, the nucleic acid molecule is about 28 nucleotides in length. In some instances, the nucleic acid molecule is about 29 nucleotides in length. In some instances, the nucleic acid molecule is about 30 nucleotides in length. In some instances, the nucleic acid molecule is about 40 nucleotides in length. In some instances, the nucleic acid molecule is about 50 nucleotides in length. In some instances, the nucleic acid molecule is about 100 nucleotides in length. In some instances, the nucleic acid molecule is about 200 nucleotides in length. In some instances, the nucleic acid molecule is about 300 nucleotides in length. In some instances, the nucleic acid molecule is about 500 nucleotides in length. In some instances, the nucleic acid molecule is about 1000 nucleotides in length. In some instances, the nucleic acid molecule is about 2000 nucleotides in length. In some instances, the nucleic acid molecule is about 3000 nucleotides in length. In some instances, the nucleic acid molecule is about 4000 nucleotides in length. In some instances, the nucleic acid molecule is about 5000 nucleotides in length. In some instances, the nucleic acid molecule is about 8000 nucleotides in length.

In some embodiments, the nucleic acid molecule is from about 5 to about 10,000 nucleotides in length. In some instances, the nucleic acid molecule is from about 5 to about 9000 nucleotides in length, from about 5 to about 8000 nucleotides in length, from about 5 to about 7000 nucleotides in length, from about 5 to about 6000 nucleotides in length, from about 5 to about 5000 nucleotides in length, from about 5 to about 4000 nucleotides in length, from about 5 to about 3000 nucleotides in length, from about 5 to about 2000 nucleotides in length, from about 5 to about 1000 nucleotides in length, from about 5 to about 500 nucleotides in length, from about 5 to about 100 nucleotides in length, from about 5 to about 50 nucleotides in length, from about 5 to about 40 nucleotides in length, from about 5 to about 30 nucleotides in length, from about 5 to about 25 nucleotides in length, from about 5 to about 20 nucleotides in length, from about 10 to about 8000 nucleotides in length, from about 10 to about 7000 nucleotides in length, from about 10 to about 6000 nucleotides in length, from about 10 to about 5000 nucleotides in length, from about 10 to about 4000 nucleotides in length, from about 10 to about 3000 nucleotides in length, from about 10 to about 2000 nucleotides in length, from about 10 to about 1000 nucleotides in length, from about 10 to about 500 nucleotides in length, from about 10 to about 100 nucleotides in length, from about 10 to about 50 nucleotides in length, from about 10 to about 40 nucleotides in length, from about 10 to about 30 nucleotides in length, from about 10 to about 25 nucleotides in length, from about 10 to about 20 nucleotides in length, from about 18 to about 8000 nucleotides in length, from about 18 to about 7000 nucleotides in length, from about 18 to about 6000 nucleotides in length, from about 18 to about 5000 nucleotides in length, from about 18 to about 4000 nucleotides in length, from about 18 to about 3000 nucleotides in length, from about 18 to about 2000 nucleotides in length, from about 18 to about 1000 nucleotides in length, from about 18 to about 500 nucleotides in length, from about 18 to about 100 nucleotides in length, from about 18 to about 50 nucleotides in length, from about 18 to about 40 nucleotides in length, from about 18 to about 30 nucleotides in length, from about 18 to about 25 nucleotides in length, from about 12 to about 50 nucleotides in length, from about 20 to about 40 nucleotides in length, from about 20 to about 30 nucleotides in length, or from about 25 to about 30 nucleotides in length.

In some embodiments, the nucleic acid molecule comprises natural, synthetic, or artificial nucleotide analogues or bases. In some cases, the nucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some embodiments, a nucleotide analogue or artificial nucleotide base described above comprises a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, or disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety.

In some instances, the modification at the 2' hydroxyl group is a 2'-O-aminopropyl modification in which an extended amine group comprising a propyl linker binds the amine group to the 2' oxygen. In some instances, this modification neutralizes the phosphate-derived overall negative charge of the oligonucleotide molecule by introducing one positive charge from the amine group per sugar and thereby improves cellular uptake properties due to its zwitterionic properties.

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer.

In some embodiments, additional modifications at the 2' hydroxyl group include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA).

In some embodiments, a nucleotide analogue comprises a modified base such as, but not limited to, 5-propynyluridine, 5-propynylcytidine, 6-methyladenine, 6-methylguanine, N,N, -dimethyladenine, 2-propyladenine, 2propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides (such as 7-deaza-adenosine, 6-azouridine, 6-azocytidine, or 6-azothymidine), 5-methyl-2-thiouridine, other thio bases (such as 2-thiouridine, 4-thiouridine, and 2-thiocytidine), dihydrouridine, pseudouridine, queuosine, archaeosine, naphthyl and substituted naphthyl groups, any O- and N-alkylated purines and pyrimidines (such as N6-methyladenosine, 5-methylcarbonylmethyluridine, uridine 5-oxyacetic acid, pyridine-4-one, or pyridine-2-one), phenyl and modified phenyl groups such as aminophenol or 2,4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyi nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or are based on, mannoses, arabinoses, glucopyranoses, galactopyranoses, 4'-thioribose, and other sugars, heterocycles, or carbocycles. The term nucleotide also includes universal bases. By way of example, universal bases include but are not limited to 3-nitropyrrole, 5-nitroindole, or nebularine.

In some embodiments, a nucleotide analogue further comprises a morpholino, a peptide nucleic acid (PNA), a methylphosphonate nucleotide, a thiolphosphonate nucleotide, a 2'-fluoro N3-P5'-phosphoramidite, or a 1', 5'-anhydrohexitol nucleic acid (HNA). Morpholino or phosphorodiamidate morpholino oligo (PMO) comprises synthetic molecules whose structure mimics natural nucleic acid structure but deviates from the normal sugar and phosphate structures. In some instances, the five member ribose ring is substituted with a six member morpholino ring containing four carbons, one nitrogen, and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

In some embodiments, peptide nucleic acid (PNA) does not contain sugar ring or phosphate linkage and the bases are attached and appropriately spaced by oligoglycine-like molecules, therefore, eliminating a backbone charge.

In some embodiments, one or more modifications optionally occur at the internucleotide linkage. In some instances, modified internucleotide linkage includes, but is not limited to, phosphorothioates; phosphorodithioates; methylphosphonates; 5'-alkylenephosphonates; 5'-methylphosphonate; 3'-alkylene phosphonates; borontrifluoridates; borano phosphate esters and selenophosphates of 3'-5'linkage or 2'-5'linkage; phosphotriesters; thionoalkylphosphotriesters; hydrogen phosphonate linkages; alkyl phosphonates; alkylphosphonothioates; arylphosphonothioates; phosphoroselenoates; phosphorodiselenoates; phosphinates; phosphoramidates; 3'-alkylphosphoramidates; aminoalkylphosphoramidates; thionophosphoramidates; phosphoropiperazidates; phosphoroanilothioates; phosphoroanilidates; ketones; sulfones; sulfonamides; carbonates; carbamates; methylenehydrazos; methylenedimethylhydrazos; formacetals; thioformacetals; oximes; methyleneiminos; methylenemethyliminos; thioamidates; linkages with riboacetyl groups; aminoethyl glycine; silyl or siloxane linkages; alkyl or cycloalkyl linkages with or without heteroatoms of, for example, 1 to 10 carbons that are saturated or unsaturated and/or substituted and/or contain heteroatoms; linkages with morpholino structures, amides, or poly-amides wherein the bases are attached to the aza nitrogens of the backbone directly or indirectly; and combinations thereof.

In some embodiments, one or more modifications comprise a modified phosphate backbone in which the modification generates a neutral or uncharged backbone. In some instances, the phosphate backbone is modified by alkylation to generate an uncharged or neutral phosphate backbone. As used herein, alkylation includes methylation, ethylation, and propylation. In some cases, an alkyl group, as used herein in the context of alkylation, refers to a linear or branched saturated hydrocarbon group containing from 1 to 6 carbon atoms. In some instances, exemplary alkyl groups include, but are not limited to, methyl, ethyl, n-propyl, isopropyl, n-butyl, isobutyl, sec-butyl, tert-butyl, n-pentyl, isopentyl, neopentyl, hexyl, isohexyl, 1, 1-dimethylbutyl, 2,2-dimethylbutyl, 3,3-dimethylbutyl, and 2-ethylbutyl groups. In some cases, a modified phosphate is a phosphate group as described in U.S. Pat. No. 9,481,905.

In some embodiments, additional modified phosphate backbones comprise methylphosphonate, ethylphosphonate, methylthiophosphonate, or methoxyphosphonate. In some cases, the modified phosphate is methylphosphonate. In some cases, the modified phosphate is ethylphosphonate. In some cases, the modified phosphate is methylthiophosphonate. In some cases, the modified phosphate is methoxyphosphonate.

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3-terminus is optionally conjugated with an aninoalkyl group, e.g., a 3' C5-aninoalkyl dT. In an additional alternative, the 3'-terminus is optionally conjugated with an abasic site, e.g., with an apurinic or apyrimidinic site. In some instances, the 5'-terminus is conjugated with an aminoalkyl group, e.g., a 5'-O-alkylamino substituent. In some cases, the 5'-terminus is conjugated with an abasic site, e.g., with an apurinic or apyrimidinic site.

In some embodiments, exemplary nucleic acid cargos include, but are not limited to, Fomivirsen, Mipomersen, AZD5312 (AstraZeneca), Nusinersen, and SBO10 (Sterna Biologicals).

Small Molecules

In some embodiments, the cargo is a small molecule. In some instances, the small molecule is an inhibitor (e.g., a pan inhibitor or a selective inhibitor). In other instances, the small molecule is an activator. In additional cases, the small molecule is an agonist, antagonist, a partial agonist, a mixed agonist/antagonist, or a competitive antagonist.

In some embodiments, the small molecule is a drug that falls under the class of analgesics, antianxiety drugs, antiarrhythmics, antibacterials, antibiotics, anticoagulants and thrombolytics, anticonvulsants, antidepressants, antidiarrheals, antiemetics, antifungals, antihistamines, antihypertensives, anti-inflammatories, antineoplastics, antipsychotics, antipyretics, antivirals, barbiturates, beta-blockers, bronchodilators, cold cures, corticosteroids, cough suppressants, cytotoxics, decongestants, diuretics, expectorant, hormones, hypoglycemics, immunosuppressives, laxatives, muscle relaxants, sex hormones, sleeping drugs, or tranquilizers.

In some embodiments, the small molecule is an inhibitor, e.g., an inhibitor of a kinase pathway such as the Tyrosine kinase pathway or a Serine/Threonine kinase pathway. In some cases, the small molecule is a dual protein kinase inhibitor. In some cases, the small molecule is a lipid kinase inhibitor.

In some cases, the small molecule is a neuraminidase inhibitor.

In some cases, the small molecule is a carbonic anhydrase inhibitor.

In some embodiments, exemplary targets of the small molecule include, but are not limited to, vascular endothelial growth factor receptor 1 (VEGFR1), vascular endothelial growth factor receptor 2 (VEGFR2), vascular endothelial growth factor receptor 3 (VEGFR3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), cyclin-dependent kinase 4 (CDK4), cyclin-dependent kinase 6 (CDK6), a receptor tyrosine kinase, a phosphoinositide 3-kinase (PI3K) isoform (e.g., PI3Kδ, also known as p110δ), Janus kinase 1 (JAKI), Janus kinase 3 (JAK3), a receptor from the family of platelet-derived growth factor receptors (PDFG-R), and carbonic anhydrase (e.g., carbonic anhydrase I).

In some embodiments, the small molecule targets a viral protein, e.g., a viral envelope protein. In some embodiments, the small molecule decreases viral adsorption to a host cell. In some embodiments, the small molecule decreases viral entry into a host cell. In some embodiments, the small molecule decreases viral replication in a host or a host cell. In some embodiments, the small molecule decreases viral assembly.

In some embodiments, exemplary small molecule cargos include, but are not limited to, lenvatinib, palbociclib, regorafenib, idelalisib, tofacitinib, nintedanib, zanamivir, ethoxzolamide, and artemisinin.

Proteins

In some embodiments, the cargo is a protein. In some instances, the protein is a full-length protein. In other instances, the protein is a fragment, e.g., a functional fragment. In some cases, the protein is a naturally occurring protein. In additional cases, the protein is a de novo engineered protein. In further cases, the protein is a fusion protein. In further cases, the protein is a recombinant protein. Exemplary proteins include, but are not limited to, Fc fusion proteins, anticoagulants, blood factors, bone morphogenetic proteins, enzymes, growth factors, hormones, interferons, interleukins, and thrombolytics.

In some instances, the protein is for use in an enzyme replacement therapy.

In some cases, the protein is for use in antigen production for therapeutic and/or prophylactic vaccine production. For example, the protein comprises an antigen that elicits a desirable immune response (e.g., a pro-inflammatory immune response, an anti-inflammatory immune response, an B cell response, an antibody response, a T cell response, a CD4+ T cell response, a CD8+ T cell response, a Th1 immune response, a Th2 immune response, a Th17 immune response, a Treg immune response, or a combination thereof).

In some instances, exemplary protein cargos include, but are not limited to, romiplostim, liraglutide, a human growth hormone (rHGH), human insulin (BHI), follicle-stimulating hormone (FSH), Factor VIII, erythropoietin (EPO), granulocyte colony-stimulating factor (G-CSF), alpha-galactosidase A, alpha-L-iduronidase, N-acetylgalactosamine-4-sulfatase, domase alfa, tissue plasminogen activator (TPA), glucocerebrosidase, interferon-beta-1a, insulin-like growth factor 1 (IGF-1), or rasburicase.

Peptides

In some embodiments, the cargo is a peptide. In some instances, the peptide is a naturally occurring peptide. In other instances, the peptide is an artificial engineered peptide or a recombinant peptide. In some cases, the peptide targets a G-protein coupled receptor, an ion channel, a microbe, an anti-microbial target, a catalytic or other Ig-family of receptors, an intracellular target, a membrane-anchored target, or an extracellular target.

In some cases, the peptide comprises at least 2 amino acids. In some cases, the peptide comprises at least 3, 4, 5, 6, 7, 8, 9, 10, 15, 20, 25, 30, 35, 40, 45, 50, 60, 70, 80, 90, 100 amino acids. In some cases, the peptide comprises at least 10 amino acids. In some cases, the peptide comprises at least 15 amino acids. In some cases, the peptide comprises at least 20 amino acids. In some cases, the peptide comprises at least 30 amino acids. In some cases, the peptide comprises at least 40 amino acids. In some cases, the peptide comprises at least 50 amino acids. In some cases, the peptide comprises at least 60 amino acids. In some cases, the peptide comprises at least 70 amino acids. In some cases, the peptide comprises at least 80 amino acids. In some cases, the peptide comprises at least 90 amino acids. In some cases, the peptide comprises at least 100 amino acids.

In some cases, the peptide comprises at most 3 amino acids. In some cases, the peptide comprises at most 4, 5, 6, 7, 8, 9, 10, 15, 20, 25, 30, 35, 40, 45, 50, 60, 70, 80, 90, 100 amino acids. In some cases, the peptide comprises at most 10 amino acids. In some cases, the peptide comprises at most 15 amino acids. In some cases, the peptide comprises at most 20 amino acids. In some cases, the peptide comprises at most 30 amino acids. In some cases, the peptide comprises at most 40 amino acids. In some cases, the peptide comprises at most 50 amino acids. In some cases, the peptide comprises at most 60 amino acids. In some cases, the peptide comprises at most 70 amino acids. In some cases, the peptide comprises at most 80 amino acids. In some cases, the peptide comprises at most 90 amino acids. In some cases, the peptide comprises at most 100 amino acids.

In some cases, the peptide comprises from about 1 to about 10 kDa. In some cases, the peptide comprises from about 1 to about 9 kDa, about 1 to about 6 kDa, about 1 to about 5 kDa, about 1 to about 4 kDa, about 1 to about 3 kDa, about 2 to about 8 kDa, about 2 to about 6 kDa, about 2 to about 4 kDa, about 1.2 to about 2.8 kDa, about 1.5 to about 2.5 kDa, or about 1.5 to about 2 kDa.

In some embodiments, the peptide is a cyclic peptide. In some instances, the cyclic peptide is a macrocyclic peptide. In other instances, the cyclic peptide is a constrained peptide. The cyclic peptides are assembled with varied linkages, such as for example, head-to-tail, head-to-ide-chain, side-chain-to-tail, and side-chain-to-side-chain linkages. In some instances, a cyclic peptide (e.g., a macrocyclic or a constrained peptide) has a molecular weight from about 500 Dalton to about 2000 Dalton. In other instances, a cyclic peptide (e.g., a macrocyclic or a constrained peptide) ranges from about 10 amino acids to about 100 amino acids, from about 10 amino acids to about 70 amino acids, or from about 10 amino acids to about 50 amino acids.

In some cases, the peptide is for use in antigen production for therapeutic and/or prophylactic vaccine production. For example, the peptide comprises an antigen that elicits a desirable immune response (e.g., a pro-inflammatory immune response, an anti-inflammatory immune response, an B cell response, an antibody response, a T cell response, a CD4+ T cell response, a CD8+ T cell response, a Th1 immune response, a Th2 immune response, a Th17 immune response, a Treg immune response, or a combination thereof).

In some embodiments, the peptide comprises natural amino acids, unnatural amino acids, or a combination thereof. In some instances, an amino acid residue refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, α-amino acids, natural amino acids, non-natural amino acids, and amino acid analogs.

In some instances, α-amino acid refers to a molecule containing both an amino group and a carboxyl group bound to a carbon which is designated the α-carbon.

In some instances, β-amino acid refers to a molecule containing both an amino group and a carboxyl group in a β configuration.

In some embodiments, an amino acid analog is a racemic mixture. In some instances, the D isomer of the amino acid analog is used. In some cases, the L isomer of the amino acid analog is used. In some instances, the amino acid analog comprises chiral centers that are in the R or S configuration.

In some embodiments, exemplary peptide cargos include, but are not limited to, peginesatide, insulin, adrenocorticotropic hormone (ACTH), calcitonin, oxytocin, vasopressin, octreolide, and leuprorelin.

In some embodiments, exemplary peptide cargos include, but are not limited to, Televancin, Dalbavancin, Oritavancin, Anidulafungin, Lanreotide, Pasireotide, Romidepsin, Linaclotide, and Peginesatide.

Antibodies

In some embodiments, the cargo is an antibody or a binding fragment thereof. In some instances, the antibody or binding fragment thereof comprises a humanized antibody or binding fragment thereof, murine antibody or binding fragment thereof, chimeric antibody or binding fragment thereof, monoclonal antibody or binding fragment thereof, bispecific antibody or biding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, disulfide stabilized Fv protein (dsFv), single-domain antibody (sdAb), Ig NAR, camelid antibody or binding fragment thereof, or a chemically modified derivative thereof.

In some instances, the antibody or binding fragment thereof recognizes a cell surface protein. In some instances, the cell surface protein is an antigen expressed by a cancerous cell. In some instances, the cell surface protein is a neoepitope. In some instances, the cell surface protein comprises one or more mutations compared to a wild-type protein. Exemplary cancer antigens include, but are not limited to, alpha fetoprotein, ASLG659, B7-H3, BAFF-R, Brevican, CA125 (MUC16), CA15-3, CA19-9, carcinoembryonic antigen (CEA), CA242, CRIPTO (CR, CR1, CRGF, CRIPTO, TDGF1, teratocarcinoma-derived growth factor), CTLA-4, CXCR5, E16 (LAT1, SLC7A5), FcRH2 (IFGP4, IRTA4, SPAP1A (SH2 domain containing phosphatase anchor protein 1a), SPAPIB, SPAPIC), epidermal growth factor, ETBR, Fc receptor-like protein 1 (FCRH1), GEDA, HLA-DOB (Beta subunit of MHC class II molecule (Ia antigen), human chorionic gonadotropin, ICOS, IL-2 receptor, IL20Rα, Immunoglobulin superfamily receptor translocation associated 2 (IRTA2), L6, Lewis Y, Lewis X, MAGE-1, MAGE-2, MAGE-3, MAGE 4, MART1, mesothelin, MDP, MPF (SMR, MSLN), MCP1 (CCL2), macrophage inhibitory factor (MIF), MPG, MSG783, mucin, MUC1-KLH, Napi3b (SLC34A2), nectin-4, Neu oncogene product, NCA, placental alkaline phosphatase, prostate specific membrane antigen (PMSA), prostatic acid phosphatase, PSCA hlg, anti-transferrin receptor, p97, Purinergic receptor P2X ligand-gated ion channel 5 (P2X5), LY64 (Lymphocyte antigen 64 (RP105), gp100, P21, six transmembrane epithelial antigen of prostate (STEAP1), STEAP2, Sema 5b, tumor-associated glycoprotein 72 (TAG-72), TrpM4 (BR22450, FLJ20041, TRPM4, TRPM4B, transient receptor potential cation channel, subfamily M, member 4) and the like.

In some instances, the cell surface protein comprises clusters of differentiation (CD) cell surface markers. Exemplary CD cell surface markers include, but are not limited to, CD1, CD2, CD3, CD4, CD5, CD6, CD7, CD8, CD9, CD10, CD11a, CD11b, CD11c, CD11d, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L (L-selectin), CD62P, CD63, CD64, CD65, CD66a, CD66b, CD66c, CD66d, CD66e, CD71, CD79 (e.g., CD79a, CD79b), CD90, CD95 (Fas), CD103, CD104, CD125 (IL5RA), CD134 (OX40), CD137 (4-1BB), CD152 (CTLA-4), CD221, CD274, CD279 (PD-1), CD319 (SLAMF7), CD326 (EpCAM), and the like.

In some embodiments, exemplary antibodies or binding fragments thereof include, but are not limited to, zalutumumab (HuMax-EFGr, Genmab), abagovomab (Menarini), abituzumab (Merck), adecatumumab (MT201), alacizumab pegol, alemtuzumab (Campath®, MabCampath, or Campath-1H; Leukosite), AlloMune (BioTransplant), amatuximab (Morphotek, Inc.), anti-VEGF (Genetech), anatumomab mafenatox, apolizumab (huID10), ascrinvacumab (Pfizer Inc.), atezolizumab (MPDL3280A; Genentech/Roche), B43.13 (OvaRex, AltaRex Corporation), basiliximab (Simulect®, Novartis), belimumab (Benlysta®, GlaxoSmithKline), bevacizumab (Avastin®, Genentech), blinatumomab (Blincyto, AMG103; Amgen), BEC2 (ImGlone Systems Inc.), carlumab (Janssen Biotech), catumaxomab (Removab, Trion Pharma), CEAcide (Immunomedics), Cetuximab (Erbitux®, ImClone), citatuzumab bogatox (VB6-845), cixutumumab (IMC-A12, ImClone Systems Inc.), conatumumab (AMG 655, Amgen), dacetuzumab (SGN-40, huS2C6; Seattle Genetics, Inc.), daratumumab (Darzalex®, Janssen Biotech), detumomab, drozitumab (Genentech), durvalumab (MedImmune), dusigitumab (MedImmune), edrecolomab (MAbl7-1A, Panorex, Glaxo Wellcome), elotuzumab (Empliciti™, Bristol-Myers Squibb), emibetuzumab (Eli Lilly), enavatuzumab (Facet Biotech Corp.), enfortumab vedotin (Seattle Genetics, Inc.), enoblituzumab (MGA271, MacroGenics, Inc.), ensituxumab (Neogenix Oncology, Inc.), epratuzumab (LymphoCide, Immunomedics, Inc.), ertumaxomab (Rexomun®, Trion Pharma), etaracizumab (Abegrin, MedImmune), farletuzumab (MORAb-003, Morphotek, Inc), FBTA05 (Lymphomun, Trion Pharma), ficlatuzumab (AVEO Pharmaceuticals), figitumumab (CP-751871, Pfizer), flanvotumab (ImClone Systems), fresolimumab (GC1008, Aanofi-Aventis), futuximab, glaximab, ganitumab (Amgen), girentuximab (Rencarex®, Wilex AG), IMAB362 (Claudiximab, Ganymed Pharmaceuticals AG), imalumab (Baxalta), IMC-1C11 (ImClone Systems), IMC-C225 (Imclone Systems Inc.), imgatuzumab (Genentech/Roche), intetumumab (Centocor, Inc.), ipilimumab (Yervoy®, Bristol-Myers Squibb), iratumumab (Medarex, Inc.), isatuximab (SAR650984, Sanofi-Aventis), labetuzumab (CEA-CIDE, Immunomedics), lexatumumab (ETR2-ST01, Cambridge Antibody Technology), lintuzumab (SGN-33, Seattle Genetics), lucatumumab (Novartis), lumiliximab, mapatumumab (HGS-ETR1, Human Genome Sciences), matuzumab (EMD 72000, Merck), milatuzumab (hLL1, Immunomedics, Inc.), mitumomab (BEC-2, ImClone Systems), narnatumab (ImClone Systems), necitumumab (Portrazza™, Eli Lilly), nesvacumab (Regeneron Pharmaceuticals), nimotuzumab (h-R3, BIOMAb EGFR, TheraCIM, Theraloc, or CIMAher; Biotech Pharmaceutical Co.), nivolumab (Opdivo®, Bristol-Myers Squibb), obinutuzumab (Gazyva or Gazyvaro; Hoffmann-La Roche), ocaratuzumab (AME-133v, LY2469298; Mentrik Biotech, LLC), ofatumumab (Arzerra®, Genmab), onartuzumab (Genentech), Ontuxizumab (Morphotek, Inc.), oregovomab (OvaRex®, AltaRex Corp.), otlertuzumab (Emergent BioSolutions), panitumumab (ABX-EGF, Amgen), pankomab (Glycotope GMBH), parsatuzumab (Genentech), patritumab, pembrolizumab (Keytruda®, Merck), pemtumomab (Theragyn, Antisoma), pertuzumab (Perjeta, Genentech), pidilizumab (CT-011, Medivation), polatuzumab vedotin (Genentech/Roche), pritumumab, racotumomab (Vaxira®, Recombio), ramucirumab (Cyramza®, ImClone Systems Inc.), rituximab (Rituxan®, Genentech), robatumumab (Schering-Plough), Seribantumab (Sanofi/Merrimack Pharmaceuticals, Inc.), sibrotuzumab, siltuximab (Sylvant™, Janssen Biotech), Smart MI95 (Protein Design Labs, Inc.), Smart ID10 (Protein Design Labs, Inc.), tabalumab (LY2127399, Eli Lilly), taplitumomab paptox, tenatumomab, teprotumumab (Roche), tetulomab, TGN1412 (CD28-SuperMAB or TAB08), tigatuzumab (CD-1008, Daiichi Sankyo), tositumomab, trastuzumab (Herceptin®), tremelimumab (CP-672,206; Pfizer), tucotuzumab celmoleukin (EMD Pharmaceuticals), ublituximab, urelumab (BMS-663513, Bristol-Myers Squibb), volociximab (M200, Biogen Idec), and zatuximab.

In some instances, the antibody or binding fragments thereof is an antibody-drug conjugate (ADC). In some cases, the payload of the ADC comprises, for example, but is not limited to, an auristatin derivative, maytansine, a maytansinoid, a taxane, a calicheamicin, cemadotin, a duocarmycin, a pyrrolobenzodiazepine (PDB), or a tubulysin. In some instances, the payload comprises monomethyl auristatin E (MMAE) or monomethyl auristatin F (MMAF). In some instances, the payload comprises DM2 (mertansine) or DM4. In some instances, the payload comprises a pyrrolobenzodiazepine dimer.

Additional Cargos

In some embodiments, the cargo is a peptidomimetic. A peptidomimetic is a small protein-like polymer designed to mimic a peptide. In some instances, the peptidomimetic comprises D-peptides. In other instances, the peptidomimetic comprises L-peptides. Exemplary peptidomimetics include peptoids and β-peptides.

In some embodiments, the cargo is a nucleotidomimetic.

Vectors and Expression Systems

In certain embodiments, the Arc polypeptides, endo-Gag polypeptides, engineered Arc and engineered endo-Gag polypeptides described supra are encoded by plasmid vectors. In some embodiments, vectors include any suitable vectors derived from either a eukaryotic or prokaryotic sources. In some cases, vectors are obtained from bacteria (e.g. *E. coli*), insects, yeast (e.g. *Pichia pastoris*), algae, or mammalian sources.

Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBacl, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichi pastoris* vector, pGAPZA, B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors include p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Mammalian stable expression vector include pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells (ATCC® CCL-2™). Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., a yeast cell), an animal cell, or a plant cell. In some cases, a prokaryotic cell is a bacterial cell. Examples of bacterial cell include gram-positive bacteria or gram-negative bacteria. In some embodiments the gram-negative bacteria is anaerobic, rod-shaped, or both.

In some instances, gram-positive bacteria include Actinobacteria, Firmicutes or Tenericutes. In some cases, gram-negative bacteria include Aquificae, *Deinococcus-Thermus*, Fibrobacteres-Chlorobi Bacteroidetes (FCB group), Fusobacteria, Gemmatimonadetes, Nitrospirae, Planctomycetes-Verrucomicrobia Chlamydiae (PVC group), Proteobacteria, Spirochaetes or Synergistetes. In some embodiments, bacteria is Acidobacteria, Chloroflexi, Chrysiogenetes, Cyanobacteria, Deferribacteres, Dictyoglomi, Thermodesulfobacteria or Thermotogae. In some embodiments, a bacterial cell is *Escherichia coli*, *Clostridium botulinum*, or *Coli* bacilli.

Exemplary prokaryotic host cells include, but are not limited to, BL21, Mach1™, DH10B™, TOP10, DH5α, DH10Bac™, OmniMax™, MegaX™, DH12S™, INVI10, TOP10F', INVuF, TOP10/P3, ccdB Survival, PIR1, PIR2, Stbl2™, Stbl3™, or Stbl4™.

In some instances, animal cells include a cell from a vertebrate or from an invertebrate. In some cases, an animal cell includes a cell from a marine invertebrate, fish, insects, amphibian, reptile, mammal, or human. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. Schizosaccharomycetes (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces*, *SchizoSaccharomyces*, *Candida*, *Pichia*, *Hansenula*, *Kluyveromyces*, *ZygoSaccharomyces*, *Yarrowia*, *Trichosporon*, *Rhodosporidi*, *Aspergillus*, *Fusarium*, or *Trichoderma*. Exemplary yeast or filamentous fungi include, for example, the species: *Saccharomyces cerevisiae*, *SchizoSaccharomyces pombe*, *Candida utilis*, *Candida boidini*, *Candida albicans*, *Candida tropicalis*, *Candida stellatoidea*, *Candida glabrata*, *Candida krusei*, *Candida parapsilosis*, *Candida guilliermondii*, *Candida viswanathii*, *Candida lusitaniae*, *Rhodotorula mucilaginosa*, *Pichia metanolica*, *Pichia angusta*, *Pichia pastoris*, *Pichia anomala*, *Hansenula polymorpha*, *Kluyveromyces lactis*, *ZygoSaccharomyces rouxii*, *Yarrowia lipolytica*, *Trichosporon pullulans*, *Rhodosporidium toru-Aspergillus niger*, *Aspergillus nidulans*, *Aspergillus awamori*, *Aspergillus oryzae*, *Trichoderma reesei*, *Yarrowia lipolytica*, *Brettanomyces bruxellensis*, *Candida stellata*, *SchizoSaccharomyces pombe*, *Torulaspora delbrueckii*, *ZygoSaccharomyces baihi*, *Cryptococcus neoformans*, *Cryptococcus gattii*, or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVScl.

In some instances, additional animal cells include cells obtained from a mollusk, arthropod, annelid or sponge. In some cases, an additional animal cell is a mammalian cell, e.g., from a human, primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-Kl cells, Expi293F™ cells, Flp-In™ T-REx™ 293 cell line, Flp-In™-

293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cell line, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a primary cell. In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cell include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

Methods of Use

Disclosed herein, in certain embodiments, are methods of preparing a capsid which encapsulates a cargo. In some embodiments, the method comprises incubating a plurality of Arc or endo-Gag polypeptides, engineered Arc or endo-Gag polypeptides, and/or recombinant Arc or endo-Gag polypeptides with a cargo in a solution for a time sufficient to generate a loaded Arc-based capsid or endo-Gag-based capsid.

In some instances, the method comprises mixing a solution comprising a plurality of engineered and/or recombinant Arc polypeptides with a plurality of non-Arc capsid forming subunits prior to incubating with the cargo. In some cases, the plurality of non-Arc capsid forming subunits are mixed with the plurality of engineered and/or recombinant Arc polypeptides at a ratio of 1:1, 2:1, 3:1, 4:1, 5:1, 6:1, 7:1, 8:1, 9:1, or 10:1. In other cases, the plurality of non-Arc capsid forming subunits are mixed with the plurality of engineered and/or recombinant Arc polypeptides at a ratio of 1:2, 1:3, 1:4, 1:5, 1:6, 1:7, 1:8, 1:9, or 1:10.

In some cases, the time sufficient to generate a loaded Arc-based capsid or endo-Gag-based capsid is at least about 5 minutes, at least about 10 minutes, at least about 20 minutes, at least about 30 minutes, at least about 1 hour, at least about 2 hours, at least about 4 hours, at least about 6 hours, at least about 10 hours, at least about 12 hours, at least about 24 hours, or more.

In some cases, the Arc-based capsid or endo-Gag-based capsid is prepared at a temperature from about 2° C. to about 37° C. In some instances, the Arc-based capsid or endo-Gag-based capsid is prepared at a temperature from about 2° C. to about 8° C., about 2° C. to about 4° C., about 20° C. to about 37° C., about 25° C. to about 37° C., about 20° C. to about 30° C., about 25° C. to about 30° C., or about 30° C. to about 37° C.

In some cases, the Arc-based capsid or endo-Gag-based capsid is prepared at room temperature.

In some instances, the Arc-based capsid or endo-Gag-based capsid is further formulated for systemic administration.

In some instances, the Arc-based capsid or endo-Gag-based capsid is further formulated for local administration.

In some instances, the Arc-based capsid or endo-Gag-based capsid is further formulated for parenteral (e.g., intra-arterial, intra-articular, intradermal, intralesional, intramuscular, intraocular, intraosseous infusion, intraperitoneal, intrathecal, intravenous, intravitreal, or subcutaneous) administration.

In some instances, the Arc-based capsid or endo-Gag-based capsid is further formulated for topical administration.

In some instances, the Arc-based capsid or endo-Gag-based capsid is further formulated for oral administration.

In some instances, the Arc-based capsid or endo-Gag-based capsid is further formulated for sublingual administration.

In some instances, the Arc-based capsid or endo-Gag-based capsid is further formulated for aerosol administration.

In certain embodiments, also described herein is a use of an Arc-based capsid or endo-Gag-based capsid for delivery of a cargo to a site of interest. In some instances, the method comprises contacting a cell at the site of interest with an Arc-based capsid or endo-Gag-based capsid for a time sufficient to facilitate cellular uptake of the capsid.

In some cases, the cell is a muscle cell, a skin cell, a blood cell, or an immune cell (e.g., a T cell or a B cell).

In some instances, the cell is a tumor cell, e.g., a solid tumor cell or a cell from a hematologic malignancy. In some cases, the solid tumor cell is a cell from a bladder cancer, breast cancer, brain cancer, colorectal cancer, kidney cancer, liver cancer, lung cancer, pancreatic cancer, prostate cancer, skin cancer, stomach cancer, or thyroid cancer. In some cases, the cell from a hematologic malignancy is from a B-cell malignancy or a T-cell malignancy. In some cases, the cell is from a leukeuma, a lymphoma, a myeloma, chronic lymphocytic leukemia (CLL), small lymphocytic lymphoma (SLL), diffuse large B cell lymphoma (DLBCL), follicular lymphoma, mantle cell lymphoma, Burkitt lymphoma, cutaneous T-cell lymphoma, peripheral T cell lymphoma, multiple myeloma, plasmacytoma, acute lymphoblastic leukemia (ALL), acute myeloid leukemia (AML), or chronic myeloid leukemia (CML).

In some embodiments, the cell is a somatic cell. In some instances, the cell is a blood cell, a skin cell, a connective tissue cell, a bone cell, a muscle cell, or a cell from an organ.

In some embodiments, the cell is an epithelial cell, a connective tissue cell, a muscular cell, or a neuron.

In some instances, the cell is an endodermal cell, a mesodermal cell, or an ectodermal. In some instances, the endoderm comprises cells of the respiratory system, the intestine, the liver, the gallbladder, the pancreas, the islets of Langerhans, the thyroid, or the hindgut. In some cases, the mesoderm comprises osteochondroprogenitor cells, muscle cells, cells from the digestive system, renal stem cells, cells from the reproductive system, cells from the circulatory system (such as endothelial cells). Exemplary cells from the ectoderm comprise epithelial cells, cells of the anterior pituitary, cells of the peripheral nervous system, cells of the neuroendocrine system, cells of the eyes, cells of the central nervous system, cells of the ependymal, or cells of the pineal gland. In some cases, cells derived from the central and peripheral nervous system comprise neurons, Schwann cells, satellite glial cells, oligodendrocytes, or astrocytes. In some cases, neurons further comprise interneurons, pyramidal neurons, gabaergic neurons, dopaminergic neurons, serotoninergic neurons, glutamatergic neurons, motor neurons from the spinal cord, or inhibitory spinal neurons.

In some embodiments, the cell is a stem cell or a progenitor cell. In some cases, the cell is a mesenchymal stem or progenitor cell. In other cases, the cell is a hematopoietic stem or progenitor cell.

In some cases, a target protein is overexpressed or is depleted in the cell. In some cases, the target protein is overexpressed in the cell. In additional cases, the target protein is depleted in the cell.

In some cases, a target gene in the cell has one or more mutations.

In some cases, the cell comprises an impaired splicing mechanism.

In some instances, the Arc-based capsid is administered systemically to a subject in need thereof.

In other instances, the Arc-based capsid or endo-Gag-based capsid is administered locally to a subject in need thereof.

In some embodiments, the Arc-based capsid or endo-Gag-based capsid is administered parenterally, orally, topically, via sublingual, or by aerosol to a subject in need thereof. In some cases, the Arc-based capsid or endo-Gag-based capsid is administered parenterally to a subject in need thereof. In other cases, the Arc-based capsid or endo-Gag-based capsid is administered orally to a subject in need thereof. In additional cases, the Arc-based capsid or endo-Gag-based capsid is administered topically, via sublingual, or by aerosol to a subject in need thereof.

In some embodiments, a delivery component is combined with an Arc-based capsid or endo-Gag-based capsid for a targeted delivery to a site of interest. In some instances, the delivery component comprises a carrier, e.g., an extracellular vesicle such as a micelle, a liposome, or a microvesicle; or a viral envelope.

In some instances, the delivery component serves as a primary delivery vehicle for an Arc-based capsid or endo-Gag-based capsid which does not comprise its own delivery component (e.g., in which the second polypeptide is not present). In such cases, the delivery component directs the Arc-based capsid or endo-Gag-based capsid to a target site of interest and optionally facilitates intracellular uptake.

In other instances, the delivery component enhances target specificity and/or sensitivity of an Arc-based capsid's second polypeptide. In such cases, the delivery component enhances the specificity and/or affinity of the Arc-based capsid or endo-Gag-based capsid to the target site. In additional cases, the delivery components enhances the specificity and/or affinity by about 2-fold, 3-fold, 4-fold, 5-fold, 6-fold, 7-fold, 8-fold, 9-fold, 10-fold, 20-fold, 30-fold, 50-fold, 100-fold, 200-fold, 500-fold, or more. In further cases, the delivery components enhances the specificity and/or affinity by about 10%, 20%, 30%, 40%, 50%, 60%, 70%, 80%, 90%, 100%, 200%, 500%, or more. Further still, the delivery component optionally minimizes off-target effect by about 2-fold, 3-fold, 4-fold, 5-fold, 6-fold, 7-fold, 8-fold, 9-fold, 10-fold, 20-fold, 30-fold, 50-fold, 100-fold, 200-fold, 500-fold, or more. Further still, the delivery component optionally minimizes off-target effect by about 10%, 20%, 30%, 40%, 50%, 60%, 70%, 80%, 90%, 100%, 200%, 500%, or more.

In additional instances, the delivery component serves as a first vehicle that transports an Arc-based capsid to a general target region (e.g., a tumor microenvironment) and the Arc-based or endo-Gag-based capsid's second polypeptide serves as a second delivery molecule that drives the Arc-based capsid or endo-Gag-based capsid to the specific target site and optionally facilitates intracellular uptake. In such cases, the delivery component minimizes off-target effect by about 2-fold, 3-fold, 4-fold, 5-fold, 6-fold, 7-fold, 8-fold, 9-fold, 10-fold, 20-fold, 30-fold, 50-fold, 100-fold, 200-fold, 500-fold, or more. In such cases, the delivery component minimizes off-target effect by about 10%, 20%, 30%, 40%, 50%, 60%, 70%, 80%, 90%, 100%, 200%, 500%, or more.

In further instances, the delivery component serves as a first vehicle that transports an Arc-based capsid to a target site of interest and the Arc-based or endo-Gag-based capsid's second polypeptide serves as a second delivery molecule that facilitates intracellular uptake.

In some embodiments, the delivery component comprises an extracellular vesicle. In some instances, the extracellular vesicle comprises a microvesicle, a liposome, or a micelle. In some instances, the extracellular vesicle has a diameter of from about 10 nm to about 2000 nm, from about 10 nm to about 1000 nm, from about 10 nm to about 800 nm, from about 20 nm to about 600 nm, from about 30 nm to about 500 nm, from about 50 nm to about 200 nm, or from about 80 nm to about 100 nm.

In some embodiments, the delivery component comprises a microvesicle. Also known as circulating microvesicles or microparticles, microvesicles are membrane-bound vesicles that comprise phospholipids. In some instances, the microvesicle has a diameter of from about 50 nm to about 1000 nm, from about 100 nm to about 800 nm, from about 200 nm to about 500 nm, or from about 50 nm to about 400 nm.

In some instances, the microvesicle is originated from cell membrane inversion, exocytosis, shedding, blebbing, or budding. In some instances, the microvesicles are generated from differentiated cells. In other instances, the microvesicles are generated from undifferentiated cells, e.g., by blast cells, progenitor cells, or stem cells.

In some embodiments, the delivery component comprises a liposome. In some instances, the liposome comprises a plurality of lipopeptides, which are presented on the surface of the liposome, for targeted delivery to a site or region of interest. In some cases, the liposomes fuse with the target cell, whereby the contents of the liposome are then emptied into the target cell. In some cases, a liposome is endocytosed by cells that are phagocytic. Endocytosis is then followed by intralysosomal degradation of liposomal lipids and release of the encapsulated agents.

Exemplary liposomes suitable for incorporation include, and are not limited to, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). In some instances, a liposome comprises Amphipol (A8-35). Techniques for preparing liposomes are described in, for example, COLLOIDAL DRUG DELIVERY SYSTEMS, vol. 66 (J. Kreuter ed., Marcel Dekker, Inc. (1994)).

Depending on the method of preparation, liposomes are unilamellar or multilamellar, and vary in size with diameters ranging from about 20 nm to greater than about 1000 nm.

In some instances, liposomes provided herein also comprise carrier lipids. In some embodiments the carrier lipids are phospholipids. Carrier lipids capable of forming liposomes include, but are not limited to, dipalmitoylphosphatidylcholine (DPPC), phosphatidylcholine (PC; lecithin), phosphatidic acid (PA), phosphatidylglycerol (PG), phosphatidylethanolamine (PE), or phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE) and the like, or combinations thereof. In some embodiments, the liposomes further comprise a sterol (e.g., cholesterol) which modulates liposome formation. The carrier lipids are optionally any non-phosphate polar lipids.

In some embodiments, the delivery component comprises a micelle. In some instances, the micelle has a diameter from about 2 nm to about 250 nm, from about 20 nm to about 200 nm, from about 20 nm to about 100 nm, or from about 50 to about 100 nm.

In some instances, the micelle is a polymeric micelle, characterized by a core shell structure, in which the hydrophobic core is surrounded by a hydrophilic shell. In some cases, the hydrophilic shell further comprises a hydrophilic polymer or copolymer and a pH sensitive component.

Exemplary hydrophilic polymers or copolymers include, but are not limited to, poly(N-substituted acrylamides), poly(N-acryloyl pyrrolidine), poly(N-acryloyl piperidine), poly(N-acryl-L-amino acid amides), poly(ethyl oxazoline), methylcellulose, hydroxypropyl acrylate, hydroxyalkyl cellulose derivatives and poly(vinyl alcohol), poly(N-isopropylacrylamide), poly(N-vinyl-2-pyrrolidone), polyethyleneglycol derivatives, and combinations thereof.

The pH-sensitive moiety includes, but is not limited to, an alkylacrylic acid such as methacrylic acid, ethylacrylic acid, propyl acrylic acid and butyl acrylic acid, or an amino acid such as glutamic acid.

In some instances, the hydrophobic moiety constitutes the core of the micelle and includes, for example, a single alkyl chain, such as octadecyl acrylate or a double chain alkyl compound such as phosphatidylethanolamine or dioctadecylamine. In some cases, the hydrophobic moiety is optionally a water insoluble polymer such as a poly(lactic acid) or a poly(e-caprolactone).

Polymeric micelles exhibiting pH-sensitive properties are also contemplated and are formed, e.g., by using pH-sensitive polymers including, but not limited to, copolymers from methacrylic acid, methacrylic acid esters and acrylic acid esters, polyvinyl acetate phthalate, hydroxypropyl methyl cellulose phthalate, cellulose acetate phthalate, or cellulose acetate trimellitate.

In some embodiments, the delivery component comprises a viral envelope. Viral envelopes comprise glycoproteins, phospholipids, and additional proteins obtained from a host. In some instances, the viral envelope is permissive to a wide range of target cells. In other instances, the viral envelope is non-permissive and is specific to a target cell of interest. In some cases, the viral envelope comprises a cell-specific binding protein and optionally a fusogenic molecule that aids in the fusion of the cargo into a target cell. In some cases, the viral envelope comprises an endogenous viral envelope. In other cases, the viral envelope is a modified envelop, comprising one or more foreign proteins.

In some instances, the viral envelope is derived from a DNA virus. Exemplary enveloped DNA viruses include viruses from the family of Herpesviridae, Poxviridae, and Hepadnavirdae.

In other instances, the viral envelope is derived from an RNA virus. Exemplary enveloped RNA viruses include viruses from the family of Bunyaviridae, Coronaviridae, Filoviridae, Flaviviridae, Orthomyxoviridae, Paramyxoviridae, Rhabdoviridae, and Togaviridae.

In additional instances, the viral envelope is derived from a virus from the family of Retroviridae.

In some embodiments, the viral envelope is from an oncolytic virus, such as an oncolytic DNA virus from the family of Herpesviridae (for example, HSV1) or Poxviridae (for example, Vaccinia virus and myxoma virus); or an oncolytic RNA virus from the family of Rhabdoviridae (for example, VSV) or Paramyxoviridae (for example MV and NDV).

In some instances, the viral envelope further comprises a foreign or engineered protein that binds to an antigen or a cell surface molecule. Exemplary antigens and cell surface molecules for targeting include, but are not limited to, P-glycoprotein, Her2/Neu, erythropoietin (EPO), epidermal growth factor receptor (EGFR), vascular endothelial growth factor receptor (VEGF-R), cadherin, carcinoembryonic antigen (CEA), CD4. CD8, CD19. CD20, CD33, CD34, CD45, CD117 (c-kit), CD133, HLA-A. HLA-B, HLA-C, chemokine receptor 5 (CCRS), stem cell marker ABCG2 transporter, ovarian cancer antigen CA125, immunoglobulins, integrins, prostate specific antigen (PSA), prostate stem cell antigen (PSCA), dendritic cell-specific intercellular adhesion molecule 3-grabbing nonintegrin (DC-SIGN), thyroglobulin, granulocyte-macrophage colony stimulating factor (GM-CSF), myogenic differentiation promoting factor-1 (MyoD-1), Leu-7 (CD57), LeuM-1, cell proliferation-associated human nuclear antigen defined by the monoclonal antibody Ki-67 (Ki-67), viral envelope proteins, HIV gp120, or transferrin receptor.

In some embodiments, the Arc-based capsid or endo-Gag-based capsid is for in vitro use.

In some instances, the Arc-based capsid or endo-Gag-based capsid is for ex vivo use.

In some cases, the Arc-based capsid or endo-Gag-based capsid is for in vivo use.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

For example, the container(s) include a recombinant or engineered Arc or endo-Gag polypeptide described above. Such kits optionally include an identifying description or label or instructions relating to its use in the methods described herein. For example, a kit typically includes labels listing contents and/or instructions for use, and package inserts with instructions for use. A set of instructions will also typically be included.

Certain Terminologies

Unless defined otherwise, all technical and scientific terms used herein have the same meaning as is commonly understood. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the sequence of a CA N-lobe described herein corresponds to the human CA N-lobe. In some instances, the human CA N-lobe comprises residues 207-278 of SEQ ID NO: 1. In some instances, a CA N-lobe described herein comprises about 30%, 40%, 50%, 60%, 70%, 80%, 90%, 91%, 92%, 93%, 94%, 95%, 96%, 97% 98% or 99% sequence identity to residue 207-278 of SEQ ID NO: 1. In some cases, a CA N-lobe described herein shares a structural similarity with the human CA N-lobe. For example, a CA N-lobe described herein shares about 80%, 85%, 90%, 91%, 92%, 93%, 94%, 95%, 96%, 97% 98% or 99% structural similarity with the human CA N-lobe. In some cases, the CA N-lobe shares a high structural similarity (e.g., 80%, 90%, 91%, 92%, 93%, 94%, 95%, 96%, 97% 98% or 99% structural similarity) but does not share a high sequence identity (e.g., the sequence identity is lower than 80%, lower than 70%, lower than 60%, lower than 50%, lower than 40%, or lower than 30%). In some cases, the CA N-lobe comprises residues 207-278 of SEQ ID NO: 1.

As used herein, the sequence of a CA C-lobe described herein corresponds to the human CA C-lobe. In some instances, the human CA C-lobe comprises residues 278-370 of SEQ ID NO: 1. In some instances, a CA C-lobe described herein comprises about 30%, 40%, 50%, 60%, 70%, 80%, 90%, 91%, 92%, 93%, 94%, 95%, 96%, 97% 98% or 99% sequence identity to residue 278-370 of SEQ ID NO: 1. In some cases, a CA C-lobe described herein shares a structural similarity with the human CA C-lobe. For example, a CA C-lobe described herein shares about 80%, 85%, 90%, 91%, 92%, 93%, 94%, 95%, 96%, 97% 98% or 99% structural similarity with the human CA C-lobe. In some cases, the CA C-lobe shares a high structural similarity (e.g., 80%, 90%, 91%, 92%, 93%, 94%, 95%, 96%, 97% 98% or 99% structural similarity) but does not share a high sequence identity (e.g., the sequence identity is lower than 80%, lower than 70%, lower than 60%, lower than 50%, lower than 40%, or lower than 30%). In some cases, the CA C-lobe comprises residues 278-370 of SEQ ID NO: 1.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

EXAMPLES

These examples are provided for illustrative purposes only and not to limit the scope of the claims provided herein.

Figure 3A:
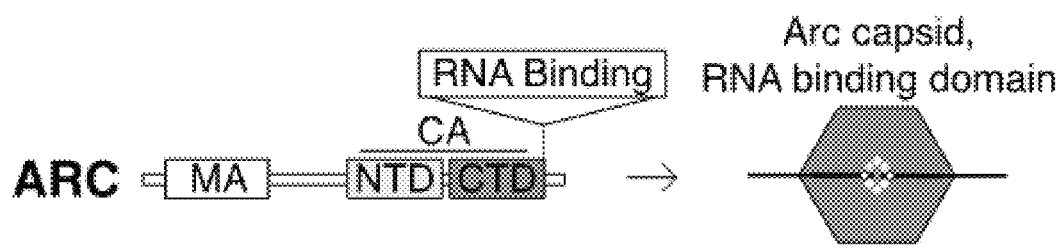
FIGS. 3A and 3B illustrate an exemplary method of engineering an Arc polypeptide to carry a specific cargo (FIG. 3A) (e.g., an RNA payload), or remove an off-function effect (FIG. 3B).
Figure 3B:
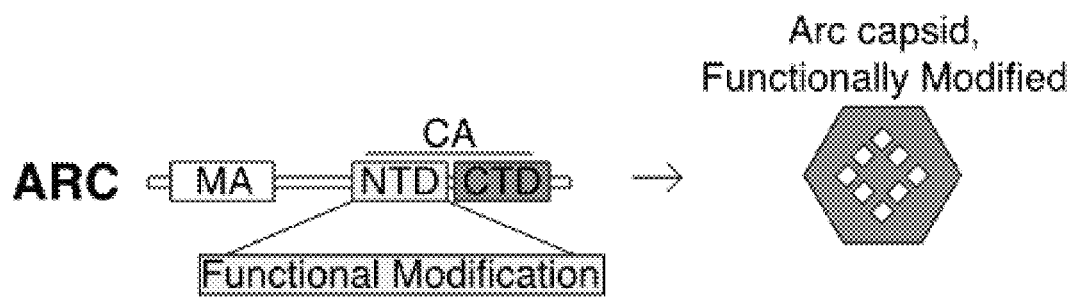

Example 1—Construction of DNA Vectors Encoding Recombinant Arc Proteins and Engineered Arc Proteins To construct recombinant DNA vectors for Arc expression, full length cDNA open reading frames, excluding the initial methionine, are inserted into a cloning vector and subsequently transferred into an expression vector according to standard methods. The same approach is used to construct recombinant DNA vectors for expressing endo-Gag proteins. Human Arc cDNA includes an annotated matrix domain (MA) and a capsid domain. The capsid domain has an N-terminal lobe (NTD) and a C-terminal lobe (CTD). FIG. 1 illustrates the structure of the Human Arc protein and the predicted structure of Arc from Python, Platypus, and Orca.

cDNAs encoding engineered Arc proteins are optionally generated by recombining Arc sequences from different species (FIG. 2), by inserting functional domains from other proteins into an Arc protein (FIG. 3A), by modifying the sequence of an Arc protein (FIG. 3B), and/or by any combination of the approaches exemplified in FIGS. 2-3. cDNAs encoding engineered endo-Gag proteins are likewise generated by recombining endo-Gag sequences from different species, by inserting functional domains from other proteins into an endo-Gag protein, by modifying the sequence of an endo-Gag protein, and/or by any combination of these approaches. Furthermore, an engineered endo-Gag protein optionally contains Arc sequences and an engineered Arc protein optionally contains endo-Gag sequences. Engineered Arc and endo-Gag protein monomers assemble into capsids.

cDNAs encoding the Arc and endo-Gag proteins of Table 1 were inserted into an expression vector derived from pET-41 a(+) (EMD Millipore (Novagen) Cat #70566). The entire cloning site of pET-41 a(+) was removed and replaced with the DNA having the nucleotide sequence of SEQ ID NO: 57, which encodes an alternative N-terminal tag having the amino acid sequence of SEQ ID NO: 58 and comprising a 6×His tag (SEQ ID NO: 59), a 6 amino acid spacer (SEQ ID NO: 60), and an AcTEV™ cleavage site (SEQ ID NO: 61). Arc and endo-Gag open reading frames without their starting methionine codon were inserted after the AcTEV™ cleavage site by Gibson assembly. Gibson D G, Young L, Chuang R Y, Venter J C, Hutchison C A 3rd, Smith H O (2009). "Enzymatic assembly of DNA molecules up to several hundred kilobases". Nature Methods. 6 (5): 343-345. After expression and AcTEV™ cleavage, the N-terminus of the resulting Arc or endo-Gag protein has a single residual Glycine from the AcTEV™ cleavage site.

SEQ ID NO: 57
ATGCATCACCATCACCATCACGGCTCAGGGTCTGGTAGCGAAAATCTGT
ACTTCCAGGGG

SEQ ID NO: 58
MHHHHHHGSGSGSENLYFQG

SEQ ID NO: 59
HHHHHH

SEQ ID NO: 60
GSGSGS

SEQ ID NO: 61
ENLYFQG

TABLE 1

Sequences of Arc and endo-Gag polypeptides and nucleotides.

| Gene | | Species | | SEQ ID NO: | |
|---|---|---|---|---|---|
| Name | Common name | Proper name | Sequence ID | Amino acid | DNA |
| Arc | Human | *Homo sapiens* | NP_056008.1 | 1 | 29 |
| Arc | Killer Whale | *Orcinus orca* | XP_004265337.1 | 2 | 30 |
| Arc | White Tailed Deer | *Odocoileus virginianus texanus* | XP_020755692.1 | 3 | 31 |
| Arc | Platypus | *Ornithorhynchus anatinus* | XP_001512750.1 | 4 | 32 |
| Arc | Goose | *Anser cygnoides domesticus* | XP_013046406.1 | 5 | 33 |
| Arc | Dalmation Pelican | *Pelecanus crispus* | KFQ60200.1 | 6 | 34 |
| Arc | White Tailed Eagle | *Haliaeetus albicilla* | KFQ04633.1 | 7 | 35 |
| Arc | King Cobra | *Ophiophagus hannah* | ETE60609.1 | 8 | 36 |
| Arc | Ray Finned Fish | *Austrofundulus limnaeus* | XP_013881732.1 | 9 | 37 |
| Arc | Sperm Whale | *Physeter catodon* | XP_007119193.2 | 10 | 38 |
| Arc | Turkey | *Meleagris gallopavo* | XP_010707654.1 | 11 | 39 |
| Arc | Central Bearded Dragon | *Pogona vitticeps* | XP_020633722.1 | 12 | 40 |
| Arc | Chinese Alligator | *Alligator sinensis* | XP_006027442.1 | 13 | 41 |
| Arc | American Alligator | *Alligator mississippiensis* | XP_019337372.1 | 14 | 42 |
| Arc | Japanese Gekko | *Gekko japonicus* | XP_015273745.1 | 15 | 43 |
| PNMA3 | Human | *Homo sapiens* | NP_001269464.1 | 16 | 44 |
| PNMA5 | Human | *Homo sapiens* | NP_001096620.1 | 17 | 45 |
| PNMA6A | Human | *Homo sapiens* | NP_116271.3 | 18 | 46 |
| PNMA6B | Human | *Homo sapiens* | SP_P0C5W0.1 | 19 | 47 |
| RTL3 | Human | *Homo sapiens* | NP_689907.1 | 20 | 48 |
| RTL6 | Human | *Homo sapiens* | NP_115663.2 | 21 | 49 |
| RTL8A | Human | *Homo sapiens* | NP_001071640.1 | 22 | 50 |
| RTL8B | Human | *Homo sapiens* | NP_001071641.1 | 23 | 51 |
| BOP | Human | *Homo sapiens* | NP_078903.3 | 24 | 52 |
| LDOC1 | Human | *Homo sapiens* | NP_036449.1 | 25 | 53 |
| ZNF18 | Human | *Homo sapiens* | NP_001290210.1 | 26 | 54 |
| MOAP1 | Human | *Homo sapiens* | AAG31786.1 | 27 | 55 |
| PEG10 | Human | *Homo sapiens* | NP_055883.2 | 28 | 56 |

Example 2—Expression and Purification of Arc and Endo-Gag Proteins

Figure 4A:
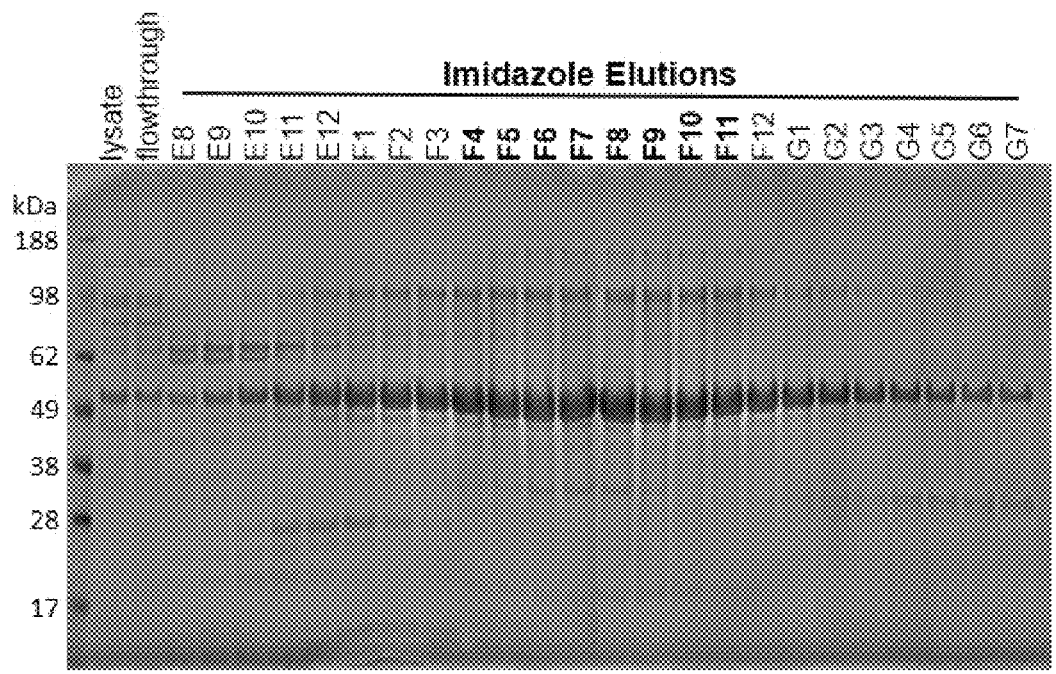
FIG. 4A shows the isolation of 6×His-tagged human Arc by elution from a HisTrap column with an imidazole gradient.

Expression vectors constructs comprising Arc and endo-Gag open reading frames were transformed into the Rosetta 2 (DE3)pLysS *E. coli* strain (Millipore Sigma, Cat #71403). Arc or endo-Gag expression was induced with 0.1 mM IPTG followed by a 16-hour incubation at 16° C. Cell pellets were lysed by sonication in 20 mM sodium phosphate pH 7.4, 0.1M NaCl, 40 mM imidazole, 1 mM DTT, and 10% glycerol. The lysate was treated with excess TURBO DNase (Thermo Fisher Scientific, Cat #AM2238), RNase Cocktail (Thermo Fisher Scientific, Cat #AM2286), and Benzonase Nuclease (Millipore Sigma, Cat #71205) to eliminate nucleic acids. NaCl was added to lysate in order to adjust the NaCl concentration to 0.5 M followed by centrifugation and filtration to remove cellular debris. 6×His-tagged recombinant protein was loaded onto a HisTrap HP column (GE Healthcare, Cat #17-5247-01), washed with buffer A (20 mM sodium phosphate pH 7.4, 0.5M NaCl, 40 mM imidazole, and 10% glycerol), and eluted with a linear gradient of buffer B (20 mM sodium phosphate pH 7.4, 0.5M NaCl, 500 mM imidazole, and 10% glycerol). Collection tubes were supplemented in advance with 10 µl of 0.5 M EDTA pH 8.0 per 1 ml eluate. The resulting Arc or endo-Gag protein is generally more than 95% pure as revealed by SDS-PAGE analysis, with a yield of up to 50 mg per 1 L of bacterial culture. FIG. 4A.

Figure 4B:
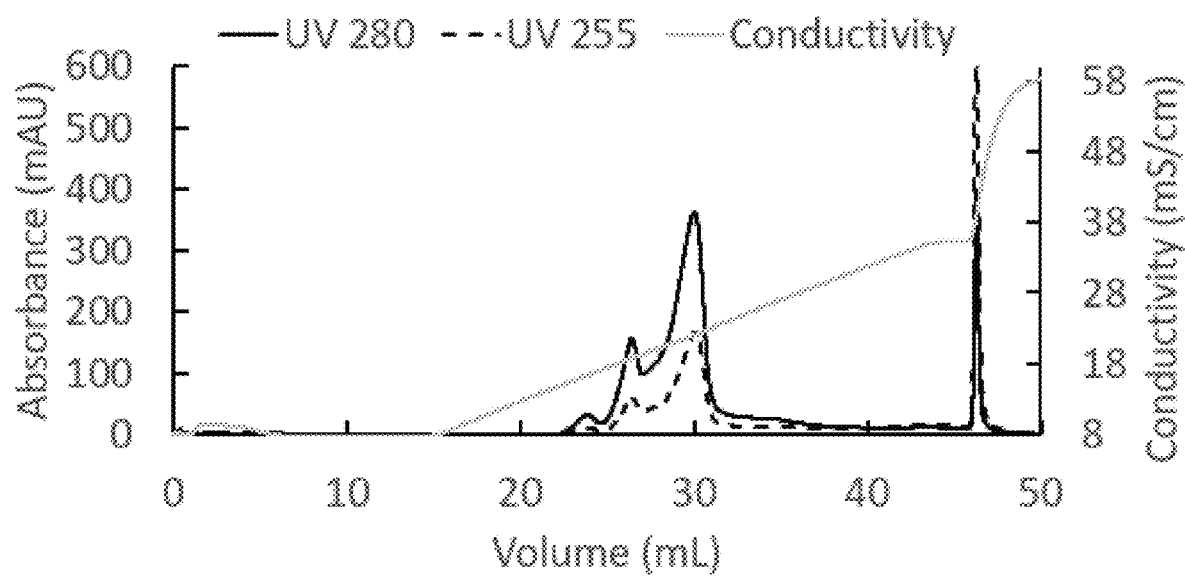
FIG. 4B shows the separation of 6×His-tagged human Arc from residual nucleic acids on a mono Q column eluted with a NaCl gradient.

Residual nucleic acid was removed by anion exchange chromatography on a mono Q 5/50 GL column (GE Healthcare, Cat #17516601). Before loading to the column, recombinant protein was buffer exchanged to buffer C (20 mM Tris-HCl pH 8.0, 100 mM NaCl, and 10% glycerol) using "Pierce Protein Concentrator PES, 10K MWCO, 5-20 ml" (Thermo Scientific, Cat #88528) according to the manufacturer's protocol. After loading, the mono Q resin was washed with 2 ml of buffer C. Arc and endo-Gag proteins were eluted using a linear gradient of buffer D (20 mM Tris-HCl pH 8.0, 500 mM NaCl, and 10% glycerol). RNA efficiently separated from Arc and eluted at 600 mM NaCl (FIG. 4B).

The N-terminal 6×His tag and spacer were removed from concentrating peak fractions of the mono Q purified Arc using a 10 kDa MWCO PES concentrator and then treating with 10% v/v of AcTEV™ Protease (Invitrogen™ #12575023). The cleavage efficiency is above 99% as revealed by SDS-PAGE assay. The protein is then diluted into HisTrap Buffer A and cleaned with HisTrap HP resin. The resulting purified Arc has an N-terminal Glycine residue and does not contain the initial methionine.

Example 3—Capsid Assembly

Cleaved Arc protein (1 mg/mL) was loaded into a 20 kDa MWCO dialysis cassette and dialyzed overnight in 1M sodium phosphate (pH 7.5) at room temperature. The following day, the solution was removed from the cassette, transferred to microcentrifuge tubes, and spun at max speed for 5 minutes in a tabletop centrifuge. The supernatant was transferred to a 100 kDa MWCO Regenerated Cellulose Amicon Ultrafiltration Centrifugal concentrator. The buffer was exchanged to PBS pH 7.5 and the volume was reduced 20-fold.

Figure 5:
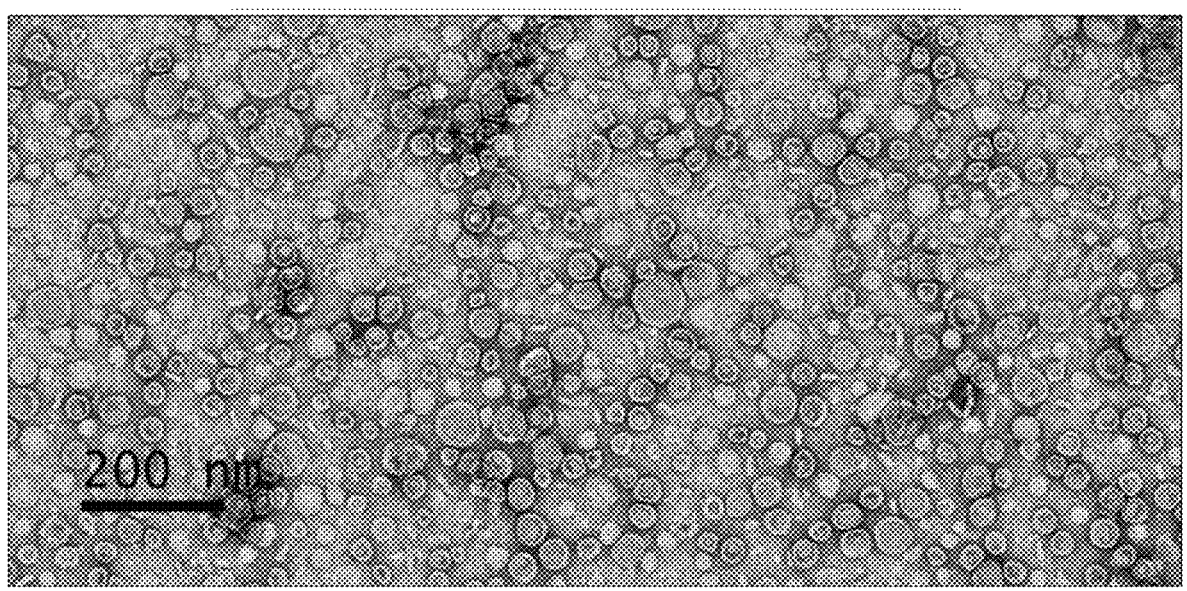
FIG. 5 shows a transmission electron microscope image of negatively stained human Arc capsids.
Figure 6:
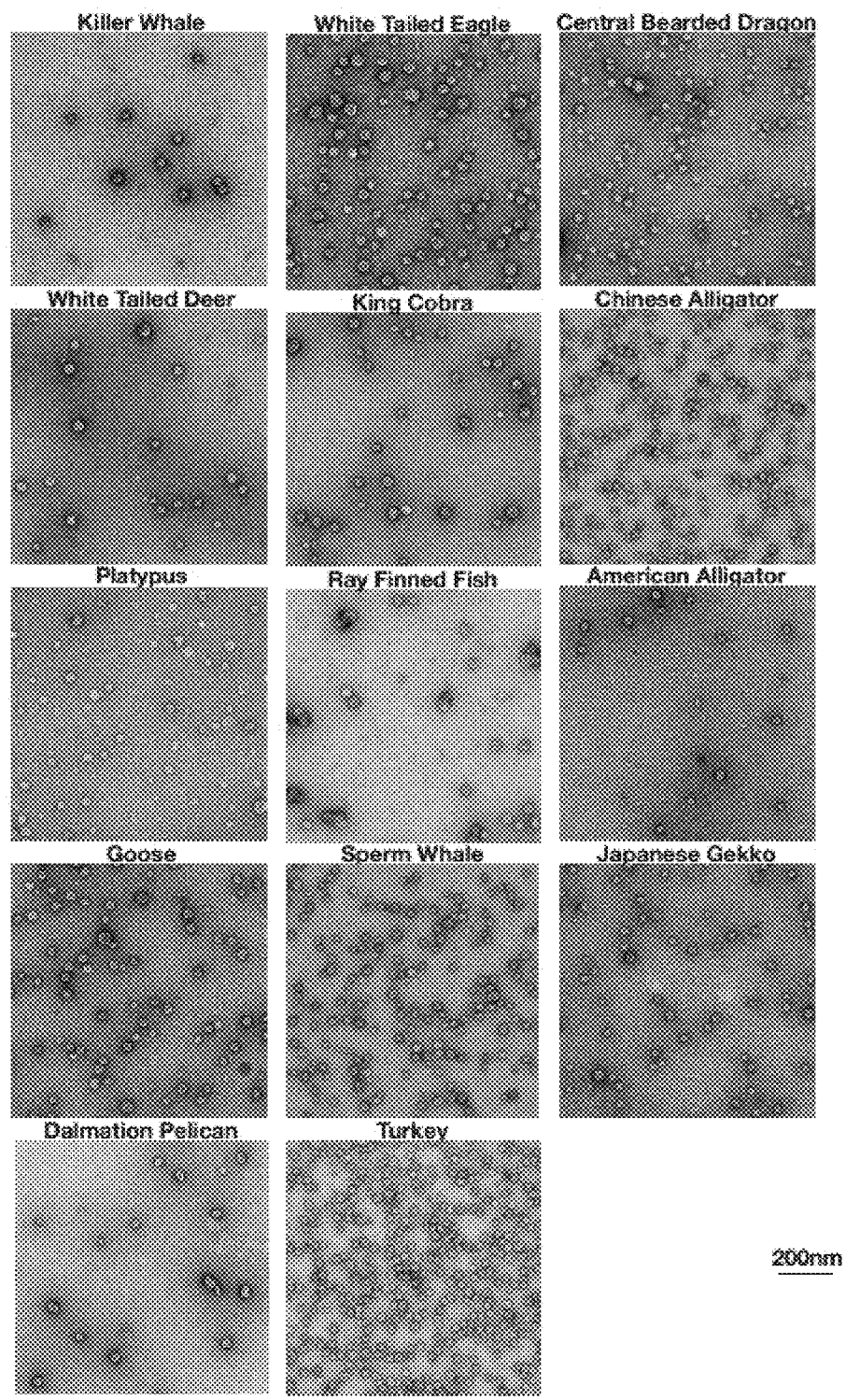
FIG. 6 shows transmission electron microscope images of negatively stained capsids formed from recombinantly expressed Arc orthologs.
Figure 7:
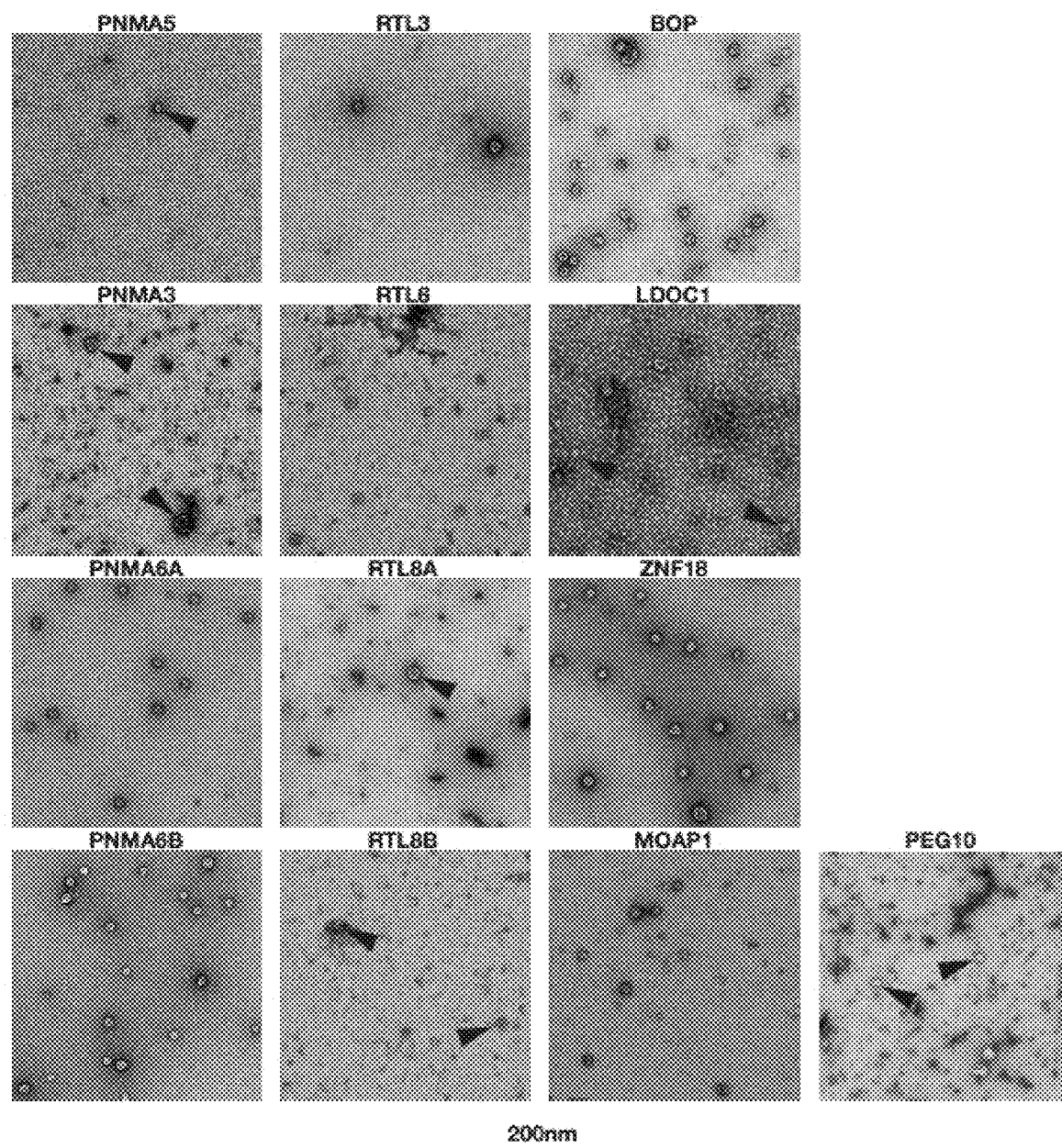
FIG. 7 shows transmission electron microscope images of negatively stained capsids formed from recombinantly expressed endo-Gag proteins.

Capsid assembly was assayed by transmission electron microscopy. EM grids (Carbon Support Film, Square Grid, 400 mesh, 5-6 nm, Copper, CF400-Cu-UL) were prepared by glow discharge. A 5 µL sample of purified Arc was applied to the grid for 20 seconds and then wicked away using filter paper. The grid was then washed with MilliQ $H_2O$, stained with 5 µL of 1% Uranyl Acetate in $H_2O$ for 30 seconds, and air dried for 1 minute. Images of Arc capsids were acquired using a FEI Talos L120C TEM equipped with a Gatan 4 k×4 k OneView camera. FIG. 5 shows concentrated human Arc capsids. FIG. 6 shows capsids formed from recombinantly expressed Arc orthologs from other vertebrate species. FIG. 7 shows capsids formed from recombinantly expressed endo-Gag genes from other vertebrate species.

Example 4—Selective Cellular Internalization of Arc Capsids

Capsids assembled from isolated recombinant human Arc protein (0.5 mg/ml) were fluorescently labeled by reacting with a 50-molar excess of NHS ester Alexa Fluor™ 594-NHS dye (Invitrogen™ #A20004) (dissolved in DMSO) in PBS (pH 8.5). Reactions were allowed to proceed for 2-hours in the dark. Alexa594-labeled capsids were then dialyzed with PBS (pH 7.5) overnight at room temperature in the dark with at least two buffer exchanges to remove any unlabeled dye.

Figure 8:
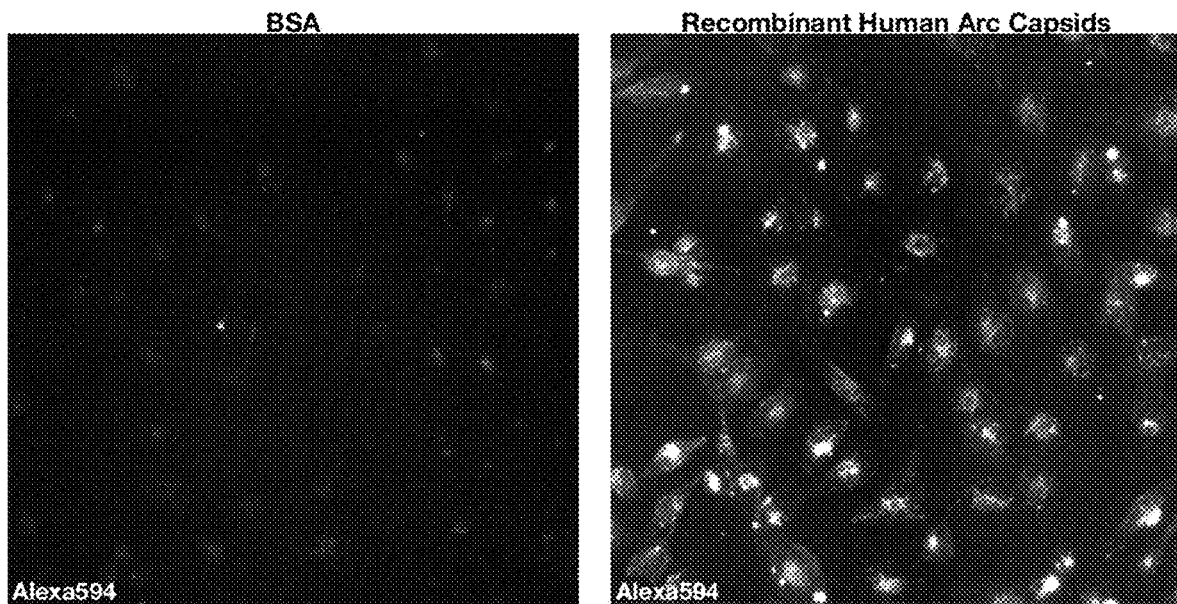
FIG. 8 shows selective internalization of Alexa594-labeled Arc capsids by HeLa cells.

HeLa cells (ATCC® CCL-2™) were seeded 24-hours prior to the experiment in 96-well plates at counts such that they reach ~80% confluency for treatment. Labeled-capsids were then spiked into complete tissue culture media to a final capsid concentration of 0.05 mg/ml. Treatments proceed for 4-hours at 37° C., and then cells are washed 3-times with imaging media (DMEM, no phenol red, with 10% FBS and 20 mM HEPES) containing 10 ug/ml Hoechst nuclear stain prior to imaging. Fluorescence microscopy revealed a punctate staining pattern, suggesting that the Arc capsids were internalized by the HeLa cells (FIG. 8). Little or no intracellular staining was observed after administration of Alexa Fluor™ 594-labeled bovine serum albumin (BSA) (final concentration of 0.05 mg/ml) or 45.6 µM Alexa Fluor™ 594 under identical conditions.

Example 5—Heterologous RNA Delivery by Arc Capsids

Figure 9:
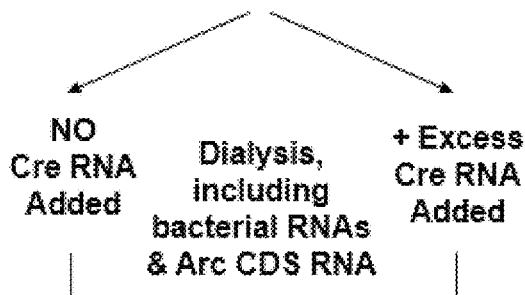
FIG. 9 shows the delivery of Cre RNA to HeLa cells by Arc capsids.
Figure 9:
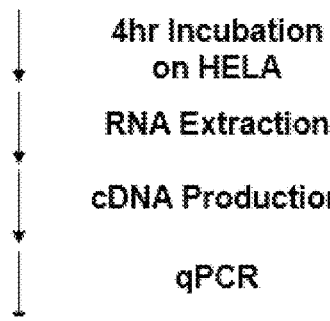
Figure 9:
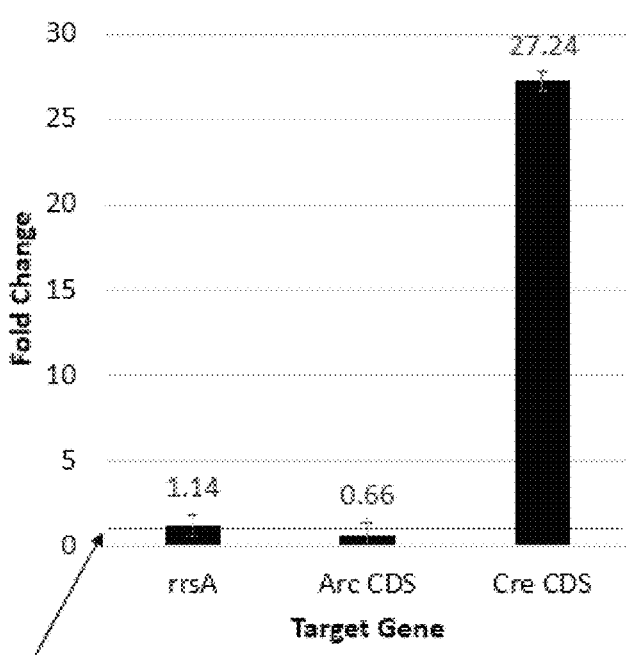

Human Arc capsids were loaded with Cre RNA by spiking in excess RNA during capsid formation (by dialysis into 1M sodium phosphate). Cre RNA-loaded capsids were administered to HeLa cells in biological triplicate at a final capsid concentration of 0.05 mg/ml for 4-hours at 37° C. The cells were then washed 3-times with ice-cold 1×PBS prior to RNA extraction (Invitrogen™ TRIzol™ Reagent #15596026). Purified cell-associated RNA was quantified by qPCR in technical triplicate, normalizing values to cellular GAPDH-levels, and comparing to *Escherichia coli* rrsA mRNA and Arc RNA that could have carried over from protein purification. Table 2 shows primers used for the PCR reaction. The amount of cell-associated Cre RNA detected was >27-fold higher when Arc capsid were loaded with Cre RNA compared to control capsids not loaded with Cre RNA (FIG. 9).

TABLE 2

Primers for qPCR quantification of RNA delivered by Arc capsids to HeLa cells

| Gene-Primer | Sequence | SEQ ID NO: |
|---|---|---|
| GAPDH-F | AAGCTCATTTCCTGGTATGACAACGA | 62 |
| GAPDH-R | AGGGTCTCTCTCTTCCTCTTGTGCT | 63 |
| rrsA-F | GCTCAACCTGGGAACTGCATCTGAT | 64 |
| rrsA-R | TAATCCTGTTTGCTCCCCACGCTTT | 65 |
| Arc CDS-F | GGCCCCTCAGCTCCAGTGATTC | 66 |
| Arc CDS-R | CCTGTTGTCACTCTCCTGGCTCTGA | 67 |
| Cre CDS-F | GCCAAGACATAAGAAACCTCGCCT | 68 |
| Cre CDS-R | GTGAATCAACATCCTCCCTCCGTC | 69 |

Figure 10:
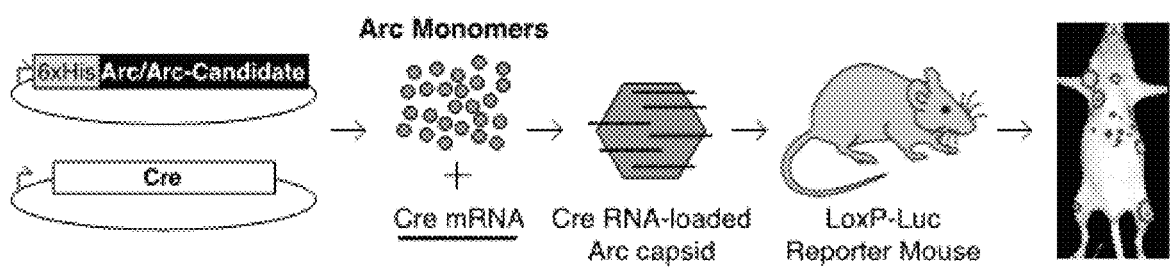
FIG. 10 illustrates methods for screening Arc and endo-Gag gene candidates for the ability to transmit a heterologous RNA payload.

FIG. 10 illustrates an alternative method of demonstrating the delivery of a heterologous RNA by an Arc or endo-Gag capsid. 6×His-tagged Arc or endo-Gag genes are expressed in a host cell. The resulting Arc monomers are mixed with translatable Cre mRNA under capsid forming conditions to form Cre mRNA loaded capsids. Cre-loaded capsids are then administered to LoxP-luciferase reporter mice. Upon successful delivery of Cre mRNA into mouse cells and subsequent translation of Cre recombinase protein, LoxP sites of the reporter are recombined, leading to luciferase expression, which is optionally detected by bioluminescence imaging upon administration of luciferin. This method is used to test the transmission potential of candidate Arc and endo-Gag genes. A positive luciferase signal indicates that the candidate Arc or endo-Gag gene encodes an Arc or endo-Gag protein capable of assembling into capsids that incorporate a heterologous cargo and deliver that cargo to a target cell.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 3

Arc and endo-Gag amino acid and nucleotide sequences

SEQ ID NO: 1
GELDHRTSGGLHAYPGPRGGQVAKPNVILQIGKCRAEMLEHVRRTHRHLLAEVSKQVERELKGLHRSVGKLESN
LDGYVPTSDSQRWKKSIKACLCRCQETIANLERWVKREMHVWREVFYRLERWADRLESTGGKYPVGSESARHT
VSVGVGGPESYCHEADGYDYTVSPYAITPPPAAGELPGQEPAEAQQYQPWVPGEDGQPSPGVDTQIFEDPREF
LSHLEEYLRQVGGSEEYWLSQIQNHMNGPAKKWWEFKQGSVKNWVEFKKEFLQYSEGTLSREAIQRELDLPQ
KQGEPLDQFLWRKRDLYQTLYVDADEEEIIQYVVGTLQPKLKRFLRHPLPKTLEQLIQRGMEVQDDLEQAAEPA
GPHLPVEDEAETLTPAPNSESVASDRTQPE

SEQ ID NO: 2
GELDQRTTGGLHAYPAPRGGPVAKPNVILQIGKCRAEMLEHVRRTHRHLLTEVSKQVERELKGLHRSVGKLESN
LDGYVPTGDSQRWRKSIKACLCRCQETIANLERWVKREMHVWREVFYRLERWADRLESMGGKYPVGSNPSR
HTTSVGVGGPESYGHEADTYDYTVSPYAITPPPAAGELPGQEAVEAQQYPPWGLGEDGQPSPGVDTQIFEDPR
EFLSHLEEYLRQVGGSEEYWLSQIQNHMNGPAKKWWEYKQGSVKNWVEFKKEFLQYSEGALSREAVQRELDL
PQKQGEPLDQFLWRKRDLYQTLYVDADEEEIIQYVVGTLQPKLKRFLRPPLPKTLEQLIQKGMEVEDGLEQVAEP
ASPHLPTEEESEALTPALTSESVASDRTQPE

SEQ ID NO: 3
GELDHRTTGGLHAYPAPRGGPAAKPNVILQIGKCRAEMLEHVRRTHRHLLAEVSKQVERELKGLHRSVGKLESN
LDGYVPTGDSQRWKKSIKACLSRCQETIANLERWVKREMHVWREVFYRLERWADRLESGGGKYPVGSDPARH
TVSVGVGGPESYCQDADNYDYTVSPYAITPPPAAGQLPGQEEVEAQQYPPWAPGEDGQLSPGVDTQVFEDPR
EFLRHLEDYLRQVGGSEEYWLSQIQNHMNGPAKKWWEYKQGSVKNWVEFKKEFLQYSEGTLSREAIQRELDL
PQKQGEPLDQFLWRKRDLYQTLYVDAEEEEIIQYVVGTLQPKLKRFLRPPLPKTLEQLIQKGMEVQDGLEQAAEP
AAEEAEALTPALTNESVASDRTQPE

SEQ ID NO: 4
GELDRLNPSSGLHPSSGLHPYPGLRGGATAKPNVILQIGKCRAEMLEHVRKTHRHLLTEVSRQVERELKGLHKSV
GKLESNLDGYVPSSDSQRWKKSIKACLSRCQETIAHLERWVKREMNVWREVFYRLERWADRLEAMGGKYPAG
EQARRTVSVGVGGPETCCPGDESYDCPISPYAVPPSTGESPESLDQGDQHYQQWFALPEESPVSPGVDTQIFED
PREFLRHLEKYLKQVGGTEEDWLSQIQNHMNGPAKKWWEYKQGSVKNWLEFKKEFLQYSEGTLTRDALKREL
DLPQKQGEPLDQFLWRKRDLYQTLYVDADEEEIIQYVVGTLQPKLKRFLHHPLPKTLEQLIQRGQEVQNGLEPTD
DPAGQRTQSEDNDESLTPAVTNESTASEGTLPE

SEQ ID NO: 5
GQLDNVTNAGIHSFQGHRGVANKPNVILQIGKCRAEMLEHVRRTHRHLLSEVSKQVERELKGLQKSVGKLENN
LEDHVPTDNQRWKKSIKACLARCQETIAHLERWVKREMNVWKEVFFRLEKWADRLESMGGKYCPGEHGKQT
VSVGVGGPEIRPSEGEIYDYALDMSQMYALTPPPGEMPSIPQAHDSYQWVSVSEDAPASPVETQVFEDPREFLS
HLEEYLKQVGGTEEYWLSQIQNHMNGPAKKWWEYKQDSVKNWVEFKKEFLQYSEGTLTRDAIKRELDLPQKE
GEPLDQFLWRKRDLYQTLYVDADEEEIIQYVVGTLQPKLKRFLSYPLPKTLEQLIQRGKEVQNMDHSDEPSPQR
TPEIQSGDSVESMPPSTTASPVPSNGTQPEPPSPPATVI

SEQ ID NO: 6
GQLDNVTNAGIHSFQGHRGVANKPNVILQIGKCRAEMLEHVRRTHRHLLSEVSKQVERELKGLQKSVGKLENN
LEDHVPTDNQRWKKSIKACLARCQETIAHLERWVKREMNVWKEVFFRLEKWADRLESMGGKYCPGEHGKQT
VSVGVGGPEIRPSEGEIYDYALDMSQMYALTPPPGEVPSIPQAHDSYQWVSVSEDAPASPVETQVFEDPREFLS
HLEEYLKQVGGTEEYWLSQIQNHMNGPAKKWWEYKQDSVKNWVEFKKEFLQYSEGTLTRDAIKRELDLPQKE
GEPLDQFLWRKRDLYQTLYVDADEEEIIQYVVGTLQPKLKRFLSYPLPKTLEQLIQRGKEVQNMDHSEEPSPQR
TPEIQSGDSVDSVPPSTTASPVPSNGTQPE

SEQ ID NO: 7
GQLDNVTNAGIHSFQGHRGVANKPNVILQIGKCRAEMLEHVRRTHRHLLSEVSKQVERELKGLQKSVGKLENN
LEDHVPTDNQRWKKSIKACLARCQETIAHLERWVKREMNVWKEVFFRLEKWADRLESMGGKYCPGDHGKQT
VSVGVGGPEIRPSEGEIYDYALDMSQMYALTPPPGEVPSIPQAHDSYQWVSVSEDAPASPVETQVFEDPREFLS
HLEEYLKQVGGTEEYWLSQIQNHMNGPAKKWWEYKQDSVKNWVEFKKEFLQYSEGTLTRDAIKRELDLPQKE
GEPLDQFLWRKRDLYQTLYVDADEEEIIQYVVGTLQPKLKRFLSYPLPKTLEQLIQRGKEVQNMDHSEEPSPQR
TPEIQSGDSVDSVPPSTTASPVPSNGTQPE

SEQ ID NO: 8
GSWGLQRHVADERRGLATPTYGAVCSIREKKASQLSGQSCLEKELLGWKCTEAIVEMMQVDNFNHGNLHSCQ
GHRGMANHKPNVILQIGKCRAEMLDHVRRTHRHLLTEVSKQVERELKSLQKSVGKLENNLEDHVPSAAENQR
WKKSIKACLARCQETIAHLERWVKREINVWKEVFFRLEKWADRLESGGGKYGPDGQSRQTVSVGVGGAPEIQPR
KEEIYDYALDMSQMYALTPPPMGEDPNVPQSHDSYQWITISDDSPPSPVETQIFEDPREFLTHLEDYLKQVGGT
EEYWLSQIQNHMNGPAKKWWEYKQDSVKNWLEFKKEFLQYSEGTLTRDAIKQELDLPQKDGEPLDQFLWRK
RDLYQTLYIDAEEEEVIQYVVGTLQPKLKRFLSHPYPKTLEQLIQRGKEVEGNLDNSEEPSPQRSPKHQLGGSVESL
PPSSTASPVASDETHPDVSAPPVTVI

SEQ ID NO: 9
GDGETQAENPSTSLNNTDEDILEQLKKIVMDQQHLYQKELKASFEQLSRKMFSQMEQMNSKQTDLLLEHQKQ
TVKHVDKRVEYLRAQFDASLGWRLKEQHADITTKIIPEIIQTVKEDISLCLSTLCSIAEDIQTSRATIVTGHAAVQTH
PVDLLGEHHLGTTGHPRLQSTRVGKPDDVPESPVSLFMQGEARSRIVGKSPIKLQFPTFGKANDSSDPLQYLERC
EDFLALNPLTDEELMATLRNVLHGTSRDWWDVARHKIQTWREFNKHFRAAFLSEDYEDELAERVRNRIQKEDE
SIRDFAYMYQSLCKRWNPAICEGDVVKLILKNINPQLPSQLRSRVTTVDELVRLGQQLEKDRQNQLQYELRKSSG
KIIQKSSSCETSALPNTKSTPNQQNPATSNRPPQVYCWRCKGHHAPASCPQWKADKHRAQPSRSSGPQTLTNL
QAQDI

SEQ ID NO: 10
GELDQRAAGGLRAYPAPRGGPVAKPSVILQIGKCRAEMLEHVRRTHRHLLTEVSKQVERELKGLHRSVGKLEGN
LDGYVPTGDSQRWKKSIKACLCRCQETIANLERWVKREMHVWREVFYRLERWADRLESMGGKYPVGTNPSR
HTVSVGVGGPEGYSHEADTYDYTVSPYAITPPPAAGELPGQEAVEAQQYPPWGLGEDGQPGPGVDTQIFEDP

TABLE 3-continued

Arc and endo-Gag amino acid and nucleotide sequences

REFLSHLEEYLRQVGGSEEYWLSQIQNHMNGPAKKWWEFKQGSVKNWVEFKKEFLQYSEGTLSREAIQRELDL
PQKQGEPLDQFLWRKRDLYQTLYVDAEEEEIIQYVVGTLQPKLKRFLRPPLPKTLEQLIQKGMEVQDGLEQAAEP
ASPRLPPEEESEALTPALTSESVASDRTQPE

SEQ ID NO: 11
GQLDNVTNAGIHSFQGHRGVANKPNVILQIGKCRAEMLEHVRRTHRHLLSEVSKQVERELKGLQKSVGKLENN
LEDHVPTDNQRWKKSIKACLARCQETIAHLERWVKREMNVWKEVFFRLEKWADRLESMGGKYCPGEHGKQT
VSVGVGGPEIRPSEGEIYDYALDMSQMYALTPGPGEVPSIPQAHDSYQWVSVSEDAPASPVETQIFEDPHEFLS
HLEEYLKQVGGTEEYWLSQIQNHMNGPAKKWWEYKQDSVKNWVEFKKEFLQYSEGTLTRDAIKRELDLPQKE
GEPLDQFLWRKRDLYQTLYVDADEEEIIQYVVGTLQPKLKRFLSYPLPKTLEQLIQRGKEVQGNMDHSEEPSPQR
TPEIQSGDSVESMPPSTTASPVPSNGTQPEPPSPPATVI

SEQ ID NO: 12
GQLENINQGSLHAFQGHRGVVHNNKPNVILQIGKCRAEMLEHVRRTHRHLLTEVSKQVERELKGLQKSVGKLE
NNLEDHVPSAAENQRWKKSIKACLARCQETIANLERWVKREMNVWKEVFFRLERWADRLESGGGKYCHADQ
GRQTVSVGVGGPEVRPSEGEIYDYALDMSQMYALTPPPMGDVPVIPQHDSYQWVTDPEEAPPSPVETQIFE
DPREFLTHLEDYLKQVGGTEEYWLSQIQNHMNGPAKKWWEYKQDSVKNWLEFKKEFLQYSEGTLTRDAIKQE
LDLPQKEGEPLDQFLWRKRDLYQTLYVEAEEEEVIQYVVGTLQPKLKRFLSHPYPKTLEQLIQRGKEVEGNLDNSE
EPSPQRTPEHQLGDSVESLPPSTTASPAGSDKTQPEISLPPTTVI

SEQ ID NO: 13
GQLDSVTNAGVHTYQGHRSVANKPNVILQIGKCRTEMLEHVRRTHRHLLTEVSKQVERELKGLQKSVGKLENN
LEDHVPTDNQRWKKSIKACLARCQETIAHLERWVKREMNVWKEVFFRLERWADRLESMGGKYCPTDSARQT
VSVGVGGPEIRPSEGEIYDYALDMSQMYALTPSPGELPSVPQHDSYQWVTSPEDAPASPVETQVFEDPREFLC
HLEEYLKQVGGTEEYWLSQIQNHMNGPAKKWWEYKQDTVKNWVEFKKEFLQYSEGTLTRDAIKRELDLPQKD
GEPLDQFLWRKRDLYQTLYIDADEEQIIQYVVGTLQPKLKRFLSYPLPKTLEQLIQKGKEVQGSLDHSEEPSPQRA
SEARTGDSVETLPPSTTTSPNTSSGTQPEAPSPPATVI

SEQ ID NO: 14
GQLDSVTNAGVHTYQGHRGVANKPNVILQIGKCRTEMLEHVRRTHRHLLTEVSKQVERELKGLQKSVGKLENN
LEDHVPTDNQRWKKSIKACLARCQETIAHLERWVKREMNVWKEVFFRLERWADRLESMGGKYCPTDSARQT
VSVGVGGPEIRPSEGEIYDYALDMSQMYALTPSPGELPSIPQHDSYQWVTSPEDAPASPVETQVFEDPREFLC
HLEEYLKQVGGTEEYWLSQIQNHMNGPAKKWWEYKQDTVKNWVEFKKEFLQYSEGTLTRDAIKRELDLPQKD
GEPLDQFLWRKRDLYQTLYIDADEEQIIQYVVGTLQPKLKRFLSYPLPKTLEQLIQKGKEVQGSLDHSEEPSPQRA
SEARTGDSVESLPPSTTTSPNASSGTQPEAPSPPATVI

SEQ ID NO: 15
GQLENVNHGNLHSFQGHRGGVANKPNVILQIGKCRAEMLDHVRRTHRHLLTEVSKQVERELKGLQKSVGKLE
NNLEDHVPSAVENQRWKKSIKACLSRCQETIAHLERWVKREMNVWKEVFFRLERWADRLESGGGKYCHGDN
HRQTVSVGVGGPEVRPSEGEIYDYALDMSQMYALTPPSPGDVPVVSQPHDSYQWVTVPEDTPPSPVETQIFED
PREFLTHLEDYLKQVGGTEEYWLSQIQNHMNGPAKKWWEYKQDSVKNWLEFKKEFLQYSEGTLTRDAIKEELD
LPQKDGEPLDQFLWRKRDLYQTLYVEADEEEVIQYVVGTLQPKLKRFLSHPYPKTLEQLIQRGKEVEGNLDNSEE
PTPQRTPEHQLCGSVESLPPSSTVSPVASDGTQPETSPLPATVI

SEQ ID NO: 16
GPLTLLQDWCRGEHLNTRRCMLILGIPEDCGEDEFEETLQEACRHLGYRVIGRMFRREENAQAILLELAQDIDY
ALLPREIPGKGGPWEVIVKPRNSDGEFLNRLNRFLEEERRTVSDMNRVLGSDTNCSAPRVTISPEFWTWAQTLG
AAVQPLLEQMLYRELRVFSGNTISIPGALAFDAWLEHTTEMLQMWQVPEGEKRRRLMECLRGPALQVVSGLR
ASNASITVEECLAALQQVFGPVESHKIAQVKLCKAYQEAGEKVSSFVLRLEPLLQRAVENNVVSRRNVNQTRLKR
VLSGATLPDKLRDKLKLMKQRRKPPGFLALVKLLREEEEWEATLGPDRESLEGLEVAPRPPARITGVGAVPLPAS
GNSFDARPSQGYRRRRGRGQHRRGGVARAGSRGSRKRKRHTFCYSCGEDGHIRVQCINPSNLLLAKETKEILEG
GEREAQTNSR

SEQ ID NO: 17
GALTLLEDWCKGMDMDPRKALLIVGIPMECSEVEIQDTVKAGLQPLCAYRVLGRMFRREDNAKAVFIELADTV
NYTTLPSHIPGKGGSWEVVVKPRNPDDEFLSRLNYFLKDEGRSMTDVARALGCCSLPAESLDAEVMPQVRSPPL
EPPKESMWYRKLKVFSGTASPSPGEETFEDWLEQVTEIMPIWQVSEVEKRRRLLESLRGPALSIMRVLQANNDS
ITVEQCLDALKQIFGDKEDFRASQFRRLQTSPKIGEKVSTFLLRLEPLLQKAVHKSPLSVRSTDMIRLKHLLARVAM
TPALRGKLELLDQRGCPPNFLELMKLIRDEEEWENTEAVMKNKEKPSGRGRGASGRQARAEASVSAPQATVQA
RSFSDSSPQTIQGGLPPLVKRRRLLGSESTRGEDHGQATYPKAENQTPGREGPQAAGEELGNEAGAGAMSHPK
PWET

SEQ ID NO: 18
GAVTMLQDWCRWMGVNARRGLLILGIPEDCDDAEFQESLEAALRPMGHFTVLGKAFREEDNATAALVELDRE
VNYALVPREIPGTGGPWNVVFVPRCSGEEFLGLGRVFHFPEQEGQMVESVAGALGVGLRRVCWLRSIGQAVQ
PWVEAVRCQSLGVFSGRDQPAPGEESFEVWLDHTTEMLHVWQGVSERERRRRLLEGLRGTALQLVHALLAEN
PARTAQDCLAALAQVFGDNESQATIRVKCLTAQQQSGERLSAFVLRLEVLLQKAMEKEALARASADRVRLRQM
LTRAHLTEPLDEALRKLRMAGRSPSFLEMLGLVRESEAWEASLARSVRAQTQEGAGARAGAQAVARASTKVEA
VPGGPGREPEGLLQAGGQEAEELLQEGLKPVLEECDN

SEQ ID NO: 19
GAVTMLQDWCRWMGVNARRGLLILGIPEDCDDAEFQESLEAALRPMGHFTVLGKVFREEDNATAALVELDRE
VNYALVPREIPGTGGPWNVVFVPRCSGEEFLGLGRVFHFPEQEGQMVESVAGALGVGLRRVCWLRSIGQAVQ
PWVEAVRYQSLGVFSGRDQPAPGEESFEVWLDHTTEMLHVWQGVSERERRRRLLEGLRGTALQLVHALLAEN
PARTAQDCLAALAQVFGDNESQATIRVKCLTAQQQSGERLSAFVLRLEVLLQKAMEKEALARASADRVRLRQM
LTRAHLTEPLDEALRKLRMAGRSPSFLEMLGLVRESEAWEASLARSVRAQTQEGAGARAGAQAVARASTKVEA
VPGGPGREPEGLRQAGGQEAEELLQEGLKPVLEECDN

TABLE 3-continued

Arc and endo-Gag amino acid and nucleotide sequences

SEQ ID NO: 20
GVEDLAASYIVLKLENEIRQAQVQWLMEENAALQAQIPELQKSQAAKEYDLLRKSSEAKEPQKLPEHMNPPAA
WEAQKTPEFKEPQKPPEPQDLLPWEPPAAWELQEAPAAPESLAPPATRESQKPPMAHEIPTVLEGQGPANTQ
DATIAQEPKNSEPQDPPNIEKPQEAPEYQETAAQLEFLELPPPQEPLEPSNAQEFLELSAAQESLEGLIVVETSAAS
EFPQAPIGLEATDFPLQYTLTFSGDSQKLPEFLVQLYSYMRVRGHLYPTEAALVSFVGNCFSGRAGWWFQLLLDI
QSPLLEQCESFIPVLQDTFDNPENMKDANQCIHQLCQGEGHVATHFHLIAQELNWDESTLWIQFQEGLASSIQ
DELSHTSPATNLSDLITQCISLEEKPDPNPLGKSSSAEGDGPESPPAENQPMQAAINCPHISEAEWVRWHKGRL
CLYCGYPGHFARDCPVKPHQALQAGNIQACQ

SEQ ID NO: 21
GVQPQTSKAESPALAASPNAQMDDVIDTLTSLRLTNSALRREASTLRAEKANLTNMLESVMAELTLLRTRARIPG
ALQITPPISSITSNGTRPMTTPPTSLPEPFSGDPGRLAGFLMQMDRFMIFQASRFPGEAERVAFLVSRLTGEAEK
WAIPHMQPDSPLRNNYQGFLAELRRTYKSPLRHARRAQIRKTSASNRAVREROMLCRQLASAGTGPCPVHPAS
NGTSPAPALPARARNL

SEQ ID NO: 22
GDGRVQLMKALLAGPLRPAARRWRNPIPFPETFDGDTDRLPEFIVQTSSYMFVDENTFSNDALKVTFLITRLTGP
ALQWVIPYIRKESPLLNDYRGFLAEMKRVFGWEEDEDF

SEQ ID NO: 23
GEGRVQLMKALLARPLRPAARRWRNPIPFPETFDGDTDRLPEFIVQTSSYMFVDENTFSNDALKVTFLITRLTGP
ALQWVIPYIKKESPLLSDYRGFLAEMKRVFGWEEDEDF

SEQ ID NO: 24
GPRGRCRQQGPRIPIWAAANYANAHPWQQMDKASPGVAYTPLVDPWIERPCCGDTVCVRTTMEQKSTASG
TCGGKPAERGPLAGHMPSSRPHRVDFCWVPGSDPGTFDGSPWLLDRFLAQLGDYMSFHFEHYQDNISRVCEI
LRRLTGRAQAWAAPYLDGDLPLPDDYELFCQDLKEVVQDPNSFAEYHAVVICPLPLASSQLPVAPQLPVVRQYL
ARFLEGLALDMGTAPRSLPAAMATPAVSGSNSVSRSALFEQQLTKESTPGPKEPPVLPSSTCSSKPGPVEPASSQ
PEEAAPTPVPRLSESANPPAQRPDPAHPGGPKPQKTEEEVLETEGDQEVSLGTPQEVVEAPETPGEPPLSPGF

SEQ ID NO: 25
GVDELVLLLHALLMRHRALSIENSQLMEQLRLLVCERASLLRQVRPPSCPVPFPETFNGESSRLPEFIVQTASYML
VNENRFCNDAMKVAFLISLLTGEAEEWVVPYIEMDSPILGDYRAFLDEMKQCFGWDDDEDDDEEEEDDY

SEQ ID NO: 26
GPVDLGQALGLLPSLAKAEDSQFSESDAALQEELSSPETARQLFRQFRYQVMSGPHETLKQLRKLCFQWLQPEV
HTKEQILEILMLEQFLTILPGEIQMWVRKQCPGSGEEAVTLVESLKGDPQRLWQWISIQVLGQDILSEKMESPSC
QVGEVEPHLEVVPQELGLENSSSGPGELLSHIVKEESDTEAELALAASQPARLEERLIRDQDLGASLLPAAPQEQ
WRQLDSTQKEQYWDLMLETYGKMVSGAGISHPKSDLTNSIEFGEELAGIYLHVNEKIPRPTCIGDRQENDKENL
NLENHRDQELLHASCQASGEVPSQASLRGFFTEDEPGCFGEGENLPEALQNIQDEGTGEQLSPQERISEKQLGQ
HLPNPHSGEMSTMWLEEKRETSQKGQPRAPMAQKLPTCRECGKTFYRNSQLIFHQRTHTGETYFQCTICKKAF
LRSSDFVKHQRTHTGEKPCKCDYCGKGFSDFSGLRHHEKIHTGEKPYKCPICEKSFIQRSNFNRHQRVHTGEKPY
KCSHCGKSFSWSSSLDKHQRSHLGKKPFQ

SEQ ID NO: 27
GTLRLLEDWCRGMDMNPRKALLIAGISQSCSVAEIEEALQAGLAPLGEYRLLGRMFRRDENRKVALVGLTAETS
HALVPKEIPGKGGIWRVIFKPPDPDNTFLSRLNEFLAGEGMTVGELSRALGHENGSLDPEQGMIPEMWAPMLA
QALEALQPALQCLKYKKLRVFSGRESPEPGEEEFGRWMFHTTQMIKAWQVPDVEKRRRLLESLRGPALDVIRVL
KINNPLITVDECLQALEEVFGVTDNPRELQVKYLTTYHKDEEKLSAYVLRLEPLLQKLVQRGAIERDAVNQARLDQ
VIAGAVHKTIRRELNLPEDGPAPGFLQLLVLIKDYEAAEEEEALLQAILEGNFT

SEQ ID NO: 28
GTERRRDELSEEINNLREKVMKQSEENNNLQSQVQKLTEENTTLREQVEPTPEDEDDDIELRGAAAAAAPPPPIE
EECPEDLPEKFDGNPDMLAPFMAQCQIFMEKSTRDFSVDRVRVCFVTSMMTGRAARWASAKLERSHYLMHN
YPAFMMEMKHVFEDPQRREVAKRKIRRLRQGMGSVIDYSNAFQMIAQDLDWNEPALIDQYHEGLSDHIQEEL
SHLEVAKSLSALIGQCIHIERRLARAAAARKPRSPPRALVLPHIASHHQVDPTEPVGGARMRLTQEEKERRRKLNL
CLYCGTGGHYADNCPAKASKSSPAGKLPGPAVEGPSATGPEIIRSPQDDASSPHLQVMLQIHLPGRHTLFVRAM
IDSGASGNFIDHEYVAQNGIPLRIKDWPILVEAIDGRPIASGPVVHETHDLIVDLGDHREVLSFDVTQSPFFPVVL
GVRWLSTHDPNITWSTRSIVFDSEYCRYHCRMYSPIPPSLPPPAPQPPLYYPVDGYRVYQPVRYYYVQNVYTPV
DEHVYPDHRLVDPHIEMIPGAHSIPSGHVYSLSEPEMAALRDFVARNVKDGLITPTIAPNGAQVLQVKRGWKL
QVSYDCRAPNNFTIQNQYPRLSIPNLEDQAHLATYTEFVPQIPGYQTYPTYAAYPTYPVGFAWYPVGRDGQGRS
LYVPVMITWNPHWYRQPPVPQYPPPQPPPPPPPPPPPSYSTL

SEQ ID NO: 29
GGGGAGCTGGACCACCGGACCAGCGGCGGGCTCCACGCCTACCCCGGGCCGCGGGGCGGGCAGGTGGCC
AAGCCCAACGTGATCCTGCAGATCGGGAAGTGCCGGGCCGAGATGCTGGAGCACGTGCGGCGGACGCAC
CGGCACCTGCTGGCCGAGGTGTCCAAGCAGGTGGAGCGCGAGCTGAAGGGGCTGCACCGGTCGGTCGGG
AAGCTGGAGAGCAACCTGGACGGCTACGTGCCCACGAGCGACTCGCAGCGCTGGAAGAAGTCCATCAAG
GCCTGCCTGTGCCGCTGCCAGGAGACCATCGCCAACCTGGAGCGCTGGGTCAAGCGCAGATGCACGTGT
GGCGCGAGGTGTTCTACCGCCTGGAGCGCTGGGCCGACCGCCTGGATCCACGGGCGGCAAGTACCCGGT
GGGCAGCGAGTCAGCCCGCCACACCGTTTCCGTGGGCGTGGGGGGTCCCGAGAGCTACTGCCACGAGGC
AGACGGCTACGACTACACCGTCAGCCCCTACGCCATCACCCCGCCCCCAGCCGCTGGCGAGCTGCCCGGGC
AGGAGCCCGCCGAGGCCCAGCAGTACCAGCCGTGGGTCCCCGGCGAGGACGGGCAGCCCAGCCCCGCG
TGGACACGCAGATCTTCGAGGACCCTCGAGAGTTCCTGAGCCACCTAGAGGAGTACTTGCGGCAGGTGGG
CGGCTCTGAGGAGTACTGGCTGTCCCAGATCCAGAATACATGAACGGGCCGGCCAAGAAGTGGTGGGA
GTTCAAGCAGGGCTCCGTGAAGAACTGGGTGGAGTTCAAGAAGGAGTTCCTGCAGTACAGCGAGGGCAC
GCTGTCCCGAGAGGCCATCCAGCGCGAGCTGGACCTGCCGCAGAAGCAGGGCGAGCCGCTGGACCAGTTC
CTGTGGCGCAAGCGGGACCTGTACCAGACGCTCTACGTGGACGCGGACGAGGAGGAGATCATCCAGTAC

TABLE 3-continued

Arc and endo-Gag amino acid and nucleotide sequences

GTGGTGGGCACCCTGCAGCCCAAGCTCAAGCGTTTCCTGCGCCACCCCCTGCCCAAGACCCTGGAGCAGCT
CATCCAGAGGGGCATGGAGGTGCAGGATGACCTGGAGCAGGCGGCCGAGCCGGCCGGCCCCCACCTCCC
GGTGGAGGATGAGGCGGAGACCCTCACGCCCGCCCCCAACAGCGAGTCCGTGGCCAGTGACCGGACCCA
GCCCGAG

SEQ ID NO: 30
GGGGAATTGGATCAACGTACTACCGGTGGCCTTCACGCATACCCTGCACCACGCGGGGGCCCTGTCGCGA
AGCCAAATGTCATCCTGCAGATTGGGAAGTGCCGGGCTGAGATGCTGGAGCACGTCCGTCGGACGCATCG
TCATCTTCTTACTGAGGTGTCAAAACAGGTGGAGCGTGAACTCAAAGGCTTGCACCGCAGCGTTGGGAAAC
TTGAAAGCAACTTAGATGGCTATGTGCCGACTGGCGACAGCCAGCGTTGGCGTAAGTCCATCAAAGCATGT
TTGTGTCGTTGCCAGGAAACGATTGCAAACCTGGAGCGTTGGGTCAAACGGGAGATGCATGTCTGGCGTG
AAGTATTTTATCGTTTAGAGCGTTGGGCCGATCGTTTAGAGAGCATGGGTGGTAAGTACCCTGTGGGGAGC
AACCCTTCTCGGCATACGACGTCAGTCGGTGTTGGCGGGCCGGAGTCCTACGGTCATGAAGCGGACACCTA
CGACTATACCGTAAGCCCTTATGCTATTACCCCACCCACCTGCGGCCGGCGAATTACCTGGCCAGGAAGCCG
TTGAGGCTCAACAATACCCTCCTTGGGGGCTGGGCGAGGATGGTCAACCTAGCCCAGGGGTAGACACGCA
AATCTTTGAGGACCCACGGGAGTTTCTTTCCCACCTGGAAGAATACCTGCGTCAGGTTGGTGGGAGCGAAG
AATACTGGCTGTCACAAATTCAAAACCATATGAATGGTCCTGCAAAAAATGGTGGGAATATAAACAGGGT
TCCGTGAAAAACTGGGTTGAGTTTAAAAAGGAGTTTCTTCAATATTCCGAGGGCGCCCTCAGTCGGGAGGC
GGTCCAACGCGAGTTGGACTTGCCACAGAAACAGGGGGAACCACTCGATCAATTCCTTTGGCGGAAACGT
GACCTTTACCAGACATTGTACGTGGATGCAGATGAGGAAGAAATTATCCAATATGTTGTGGGGACCCTGCA
GCCGAAACTGAAACGTTTCCTTCGCCCGCCGCTGCCTAAAACGTTGGAACAACTTATTCAGAAAGGTATGG
AGGTCGAGGATGGCTTAGAACAAGTCGCAGAGCCGGCCTCGCCACACTTGCCTACAGAGGAGGAATCGGA
GGCGCTGACCCCAGCACTTACATCAGAGTCAGTGGCATCAGACCGGACACAACCAGAG

SEQ ID NO: 31
GGGGAGTTAGATCACCGTACAACGGGGGGGTTGCACGCATACCCTGCTCCACGTGGCGGGCCGGCAGCTA
AGCCAAACGTAATCCTGCAGATTGGGAAGTGCCGGGCAGAGATGTTGGAGCACGTCCGGCGGACCCACCG
GCACCTCCTGGCTGAAGTGTCTAAACAAGTAGAACGGGAACTCAAAGGTCTTCATCGTAGCGTCGGGAAAT
TGGAATCGAATTTGGACGGGTATGTTCCTACAGGCGACTCACAGCGGTGGAAAAAGAGCATCAAGGCCTG
CCTGAGTCGCTGCCAGGAGACGATTGCTAACCTCGAACGCTGGGTTAAGCGGGAGATGCACGTTTGGCGC
GAAGTCTTCTACCGGCTGGAGCGTTGGGCTGATCGGCTCGAATCTGGTGGGGGTAAGTATCCAGTTGGGT
CCGACCCTGCTCGCCACACAGTCTCAGTTGGCGTAGGTGGGCCGGAGTCGTATTGCCAAGATGCGGACAA
CTATGATTATACAGTTTCCCCATACGCGATCACACCACCGCCGGCAGCAGGGCAGCTGCCAGGTCAGGAAG
AGGTTGAGGCCCAGCAGTATCCACCATGGGCCCCAGGGGAAGACGGCCAGCTTTCTCCTGGGGTGGACAC
TCAAGTTTTTGAAGATCCGCGTGAATTTCTGCGGCATTTAGAAGATTATCTCCGCCAGGTCGGGGGGTCTG
AAGAGTATTGGTTAAGCCAAATTCAAAACCATATGAACGGCCCGGCCAAGAAGTGGTGGGAGTACAAGCA
AGGGTCTGTGAAAAATTGGGTGGAGTTTAAGAAAGAATTCTTGCAATATTCTGAGGGCACTCTTTCGCGTG
AAGCCATCCAACGCGAACTCGACTTACCGCAGAAACAAGGGGAACCTCTCGACCAATTTCTGTGGCGCAAA
CGCGACCTGTACCAGACTCTTTACGTCGATGCTGAGGAGGAAGAAATTATTCAATACGTAGTTGGCACACT
GCAGCCTAAGCTTAAACGGTTTTTTACGTCCACCATTGCCGAAGACGCTTGAACAACTCATCCAGAAGGGTA
TGGAGGTTCAAGATGGTCTGGAACAGGCAGCGGAACCAGCGGCGGAGGAGGCAGAAGCCCTGACACCTG
CGTTAACTAACGAGTCTGTCGCGAGCGACCGCACCCAGCCGGAA

SEQ ID NO: 32
GGGGAATTAGACCGCCTGAACCCAAGCTCAGGCCTGCATCCATCCTCTGGTTTGCATCCATACCCAGGTCTC
CGGGGCGGGGCAACCGCGAAGCCTAATGTCATTTTGCAAATTGGCAAATGCCGTGCGGAAATGCTTGAAC
ACGTCCGCAAAACTCACCGTCATCTCCTCACAGAAGTATCGCGCCAAGTAGAACGCGAGCTCAAAGGCCTT
CACAAAAGTGTTGGCAAGTTGGAATCAAATCTTGATGGGTACGTACCGTCAAGCGACTTCCCAACGCTGGAA
GAAAAGCATTAAGGCGTGCTTATCCCGTTGCCAAGAGACGATTGCGCATTTAGAACGCTGGGTTAAACGTG
AAATGAATGTATGGCGTGAGGTGTTCTACCGTTTGGAACGTTGGCGGACCGTCTGGAGGCTATGGGCGG
TAAGTATCCTGCCGGTGAGCAGGCCCGGCGTACAGTTTCAGTGGGCGTTGGGGGCCCTGAGACATGTTGT
CCAGGGGATGAAAGTTATGATTGTCCGATTTCTCCGTATGCAGTTCCACCGGCGAGTCTCCGGAA
TCCTTAGACCAAGGGGATCAGCACTATCAGCAGTGGTTTGCCCTCCCGGAGGAGTCCCCTGTTAGCCCTGG
GGTTGATACCCAGATCTTTGAAGATCCTCGCGAGTTTTTACGTCATCTGGAGAAGTACCTGAAACAAGTCG
GCGGGACAGAGGAAGACTGGCTTTCTCAAATCCAGAATCACATGAATGGGCCGGCGAAGAAGTGGTGGG
AGTACAAGCAAGGGAGTGTTAAGAATTGGCTTGAATTTAAGAAGGAATTTTTACAGTATTCGGAGGGCAC
ACTGACGCGGGACGCGTTGAAACGTGAACTGGATCTCCCACAGAAACAAGGCGAACCACTTGATCAATTTT
TATGGCGGAAGCGCGACTTATATCAGACACTCTACGTTGACGCCGATGAAGAGGAAATCATTCAGTACGTC
GTGGGCACTCTTCAGCCGAAATTAAAACGCTTTCTCCATCACCCACTCCCTAAGACGCTTGAGCAGCTTATC
CAACGGGGCCAAGAAGTTCAGAATGGTCTGGAGCCTACCGACGATCTGCAGGCCAACGCACTCAATCGG
AGGACAACGACGAAAGCCTTACCCCCTGCCGTCACCAATGAGAGTACTGCAAGCGAGGGCACCCTGCCAGA
G

SEQ ID NO: 33
GGGCAGCTTGATAACGTTACAAACGCGGGCATCCACTCCTTCCAGGGGCATCGTGGCGTAGCGAATAAGC
CAAATGTCATTCTGCAAATTGGTAAATGTCGTGCGGAAATGCTGGAGCACGTTCGCCGCACCCACCGCCAT
TTATTATCTGAAGTATCTAAGCAGGTAGAACGTGAGCTGAAAGGGCTGCAAAAGTCCGTGGGCAAGCTCG
AGAATAACTTGGAGGATCATGTCCCTACAGATAACCAACGCTGGAAGAAGTCCATTAAAGCGTGCTTGGCT
CGTTGTCAAGAGACTATCGCGCATTTAGAGCGTTGGGTGAAACGCGAAATGAACGTCTGGAAGGAGGTGT
TTTTCCGGCTGAAAAGTGGGCAGACCGGCTGGAGTCAATGGGTGGCAAGTACTGCCCGGGCGAACACG
GGAAACAAACCGTCAGTGTAGGCGTGGGGGGTCCTGAAATCCGGCCTTCGGAGGGGGAAATTTATGATTA
TGCTCTGGATATGAGCCAGATGTATGCACTCACCCCACCTCCAGGCGAAATGCCATCAATCCCACAAGCCCA
TGACAGCTATCAGTGGGTTAGTGTCTCAGAAGATGCCCCGGCGAGCCCTGTCGAAACCCAGGTATTTGAGG
ACCCTCGGGAATTCCTGTCTCACCTGGAGGAATACCTGAAGCAGGTAGGCGGCACGGAGGAGTATTGGTT
GTCCCAGATCCAGAATCACATGAATGGTCCGGCAAAAAATGGTGGGAATATAAACAGGACTCCGTTAAA
AACTGGGTTGAGTTTAAAAAGGAATTCTTGCAATACTCTGAAGGTACTTTAACTCGGGATGCTATTAAGCGT
GAACTCGACTTGCCGCAAAAGGAAGGTGAACCTCTTGACCAATTCCTTTGGCGGAAGCGGGACCTCTATCA
GACACTTTACGTGGACGCGGATGAGGAGGAGATCATTCAGTATGTGGTCGGTACCCTGCAGCCGAAGCTC

TABLE 3-continued

Arc and endo-Gag amino acid and nucleotide sequences

AAGCGTTTCCTGAGCTATCCTCTCCCAAAGACTTTAGAACAGCTCATCCAGCGCGGTAAAGAAGTGCAGGG
TAACATGGATCACTCCGATGAGCCTTCGCCGCAGCGTACACCTGAAATTCAATCAGGTGACTCCGTAGAAT
CTATGCCACCTTCAACAACGGCATCTCCGGTTCCATCTAATGGTACCCAACCTGAGCCGCCGAGCCCGCCAG
CCACCGTTATC

SEQ ID NO: 34
GGGCAACTTGACAACGTAACAAACGCTGGGATTCACTCCTTTCAGGGCCACCGCGGTGTCGCCAACAAGCC
AAACGTAATCTTGCAAATTGGCAAATGCCGTGCGGAGATGTTGGAACACGTTCGTCGTACACATCGTCACT
TGCTGTCGGAAGTCTCTAAACAAGTAGAACGTGAACTTAAAGGGCTTCAAAAGTCAGTCGGCAAATTGGAA
AACAACCTTGAAGACCATGTACCAACCGACAATCAGCGTTGGAGAAAAGTCTATCAAAGCTTGCCTGGCCG
TTGTCAAGAGACGATTGCTCACCTGGAGCGGTGGGTAAAGCGCGAGATGAATGTGTGGAAAGAGGTCTTC
TTCCGCTTGGAAAAATGGGCCGACCGTTTGGAGTCCATGGGCGGTAAATATTGTCCGGGTGAACATGGTA
AGCAAACAGTCTCTGTGGGCGTTGGTGGGCCGGAGATTCGGCCTTCTGAAGGCGAGATTTACGATTATGC
GCTCGACATGTCCCAGATGTATGCGCTTACACCACCACCGGGCGAGGTACCAAGCATTCCTCAAGCGCATG
ACAGTTATCAGTGGGTTAGCGTATCCGAAGACGCTCCTGCCTCGCCGGTGAAGACCCAGGTTTTTGAAGAT
CCTCGTGAATTTTTAAGCCACTTGGAGGAGTATTTGAAGCAGGTAGGGGGGACAGAGGAATATTGGCTGT
CTCAGATCCAGAACCACATGAATGGCCCGGCTAAAAAGTGGTGGGAATACAAACAAGATTCGGTAAAGAA
TTGGGTAGAATTTAAAAAGGAGTTTTTACAGTACTCAGAGGGGACTCTCACGCGTGATGCGATCAAACGCG
AGTTGGATCTTCCTCAAAAAGAGGGGGAGCCACTCGATCAGTTCCTCTGGCGCAAGCGGGATCTCTACCAA
ACACTCTACGTAGACGCAGACGAAGAAGAGATCATCCAGTACGTGGTGGGTACGCTCCAGCCGAAACTCA
AACGTTTCCTCAGCTACCCACTTCCTAAGACTCTGGAACAACTGATTCAGCGGGCAAAGAGGTCCAGGGT
AACATGGACCATTCAGAGGAACCTAGTCCGCAACGTACACCTGAGATCCAATCTGGGGATTCTGTCGATTC
GGTTCCACCTTCTACAACAGCGTCTCCGGTGCCGTCAAATGGGACCCAACCAGAG

SEQ ID NO: 35
GGGCAGCTTGATAATGTAACCAATGCAGGTATCCACTCTTTCCAGGGTCACCGCGGTGTGGCAAACAAGCC
AAATGTTATTCTGCAAATTGGTAAGTGTCGCGCTGAGATGTTAGAACACGTCCGGCGCACGCATCGGCATC
TCCTGTCAGAGGTTTCAAAGCAGGTAGAGCGTGAATTAAAGGGCCTCCAGAAGTCCGTAGGTAAACTCGA
AAATAATCTTGAAGACCACGTTCCTACCGATAATCAACGGTGGAAAAAGTCAATCAAGGCGTGCTTAGCAC
GGTGTCAGGAAACGATCGCGCACCTCGAACGTTGGGTGAAGCGCGAAATGAATGTCTGGAAAGAAGTGTT
CTTCCGGCTTGAGAAGTGGGCTGATCGGCTCGAATCCATGGGTGGCAAATATTGTCCAGGTGATCATGGCA
AGCAAACGGTCTCCGTCGGTGTTGGTGGTCCGGAAATCCGGCCGAGCGAGGGTGAAATCTATGACTACGC
TCTTGATATGTCCCAGATGTATGCACTCACTCCTCCGCGGGTGAGGTCCCGTCGATCCCGCAGGCGCATGA
CTCATACCAATGGGTGTCGACTAGCGAAGACGCACCAGCCTCCCCTGTTGAAACTCAAGTATTCGAGGACC
CGCGTGAGTTCCTGAGCCATTTAGAGGAGTACCTTAAGCAGGTTGGTGGTACCGAGGAATACTGGTTGAG
CCAGATTCAGAATCACATGAACGGGCCGGCTAAGAAATGGTGGGAATACAAGCAGGATTCAGTCAAGAAT
TGGGTCGAATTTAAGAAGGAGTTTTTGCAGTACAGTGAGGGGACGCTCACACGCGACGCTATCAAACGGG
AGCTGGACCTGCCACAAAAGGAGGGTGAACCGCTTGATCAGTTTCTTTGGCGCAAGCGTGATCTGTATCAA
ACCCTGTATGTGGACGCTGACGAAGAAGAGATCATTCAGTACGTGGTTGGGACTCTGCAACCAAAGCTGA
AGCGTTTTCTTTCTTATCCTCTCCCTAAGACACTGGAACAGTTAATCAACGTGGCAAGGAGGTCCAGGGTA
ATATGGACCACTCTGAGGAACCGAGCCCGCAACGTACTCCTGAAATTCAGAGCGGGGATAGTGTCGACTC
AGTTCCTCCAAGTACGACCGCATCCCCGGTCCCAAGTAACGGTACCCAACCAGAG

SEQ ID NO: 36
GGGTCTTGGGGCTTGCAACGTCACGTGGCTGATGAACGTCGTGGCCTCGCTACGCCTACCTACGGCGCGGT
TTGTTCCATTCGGGAGAAAAAGCCTCCCAACTGAGCGGCCAGAGCTGTTTGGAGAAAGAGTTGCTTGGTT
GGAAATGTACGGAGGCAATCGTGGAAATGATGCAAGTCGATAACTTTAACCACGGTAACTTACATAGCTGC
CAAGGCCATCGGGGGATGGCAAATCACAAACCGAACGTAATCCTTCAAATCGGGAAATGTCGCAGAAA
TGTTAGACCACGTGCGTCGCACCCACCGCCATCTCTTGACGGAGGTTTCGAAGCAGGTAGAACGCGAATTG
AAGTCTCTCCAAAAGTCGGTTGGCAAGCTCGAGAATAATCTGGAAGACCACGTGCCATCGGCAGCGGAGA
ACCAACGTTGGAAGAAATCAATTAAAGCCTGCCTGGCCCGGTGCCAAGAAACAATTGCTCACCTCGAACGC
TGGGTTAAACGCGAAATCAACGTCTGGAAAGAAGTATTCTTTCGTCTGGAGAAGTGGGCGGACCGCCTTG
AGTCGGGTGGGGCAAGTATGGGCCTGGTGACCAAAGTCGTCAAACTGTAAGTGTCGGTGTTGGGGCCCC
AGAAATCCAACCGCGGAAAGAAGAAATCTATGACTACGCTCTCGACATGTCGCAGATGTATGCCTTAACAC
CACCGCCGATGGGTGAAGACCCAAACGTACCTCAATCCCACGATAGCTACCAGTGGATTACCATCTCAGAC
GATTCACCTCCGTCGCCAGTGGAAACTCAAATTTTCGAGGATCCAGCCGAATTCCTTACCCATCTCGAGGAT
TATCTTAAGCAAGTGGGCGGGACTGAAGAATATTGGTTGAGTCAGATTCAAAATCATATGAACGGTCCGGC
CAAGAAATGGTGGGAGTACAAACAAGATTCCGTGAAAAACTGGTTGGAATTCAAGAAGGAATTCCTTCAA
TACTCTGAGGGTACTTTGACACGTGACGCAATTAAACAAGAACTTGACTTACCGCAGAAGGACGGCGAGCC
ATTGGATCAATTTCTTTGGCGAAGCGGGACCTGTATCAGACGCTCTATATTGATGCAGAGGAGGAAGAA
GTAATCAATACGTTGTTGGCACACTCCAACCGAAATTAAAACGTTTCCTTTCCCACCCGTATCGAAAACTT
TGGAACAGTTAATCCAACGTGGGAAAGAGGTGGAAGGCAACCTCGATAACTCTGAGGAGCCTAGCCCGCA
ACGGAGTCCAAAGCACCAATTGGGTGGTAGCGTCGAGAGCCTCCCACCTTCGTCGACCGCAAGTCCTGTTG
CGTCAGACGAGACTCACCCAGACGTGAGCGCACCTCCGGTAACGGTGATT

SEQ ID NO: 37
GGGGACGGCGAGACTCAAGCTGAGAATCCATCTACCAGCTTGAACAACACTGACGAAGATATCTTGGAAC
AGCTCAAGAAAATTGTCATGGATCAACAACACCTGTATCAGAAAGAATTAAAGGCATCTTTTGAACAACTC
AGTCGCAAATGTTTTCCCAGATGAACAAATGAATAGCAAGCAAACGGATCTGCTTTTAGAACATCAAAA
ACAGACTGTCAAACATGTAGACAAGCGCGTGGAGTATTTGCGGGCGCAATTCGATGCATCGTTAGGCTGG
CGGTTGAAAGAGCAACACGCGGATATTACGACCAAAATCATTCCTGAGATCATCCAAACGGTGAAGGAAG
ATATTAGCCTGTGTCTTTCTACGCTCTGCAGTATCGCTGAAGATATCCAGACATCACGGGCTACCACTGTCA
CAGGGCATGCTGCCGTACAAACCCATCCTGTGGATCTTTTGGGTGAACACCATTTAGGGACCCACGGGCAC
CCACGCTTACAGTCGACCCGTGTAGGGAAACCAGACGACGTACCTGAGTCGCCGGTAAGCTCGTTTATGCA
AGGTGAGGCGCGTTCCCGGATCGTTGGCAAGAGTCCGATTAAACTGCAATTTCCGACGTTCGGCAAAGCA
AACGATTCTTCCGACCCACTCCAATATCTGGAGCGGTGTGAGGACTTTCTTGCTCTTAACCCTTTAACTGATG
AGGAACTTATGGCTACTTTGCGGAATGTGTTACATGGCACCTCTCGGGATTGTGGGATGTCGCACGTCAT
AAAATCCAAACTTGGCGTGAGTTTAATAAACACTTCCGGGCGGCTTTCCTCAGCGAGGATTATGAAGATGA

TABLE 3-continued

Arc and endo-Gag amino acid and nucleotide sequences

GTTGGCTGAGCGCGTCCGTAACCGCATCCAAAAAGAAGATGAGTCTATCCGCGATTTCGCTTATATGTATC
AGTCCTTGTGCAAGCGGTGGAACCCTGCTATCTGCGAAGGTGATGTAGTAAAGCTCATCCTGAAGAACATC
AATCCACAACTGCCGTCTCAGTTACGCTCCCGGGTCACGACCGTGGATGAGCTTGTTCGCTTGGGCCAGCA
GCTTGAAAAAGATCGTCAGAATCAGCTCCAATATGAGCTTCGGAAGAGTTCCGGCAAAATTATCCAAAAAT
CTAGTTCGTGCGAAACTTCAGCGCTCCCGAACACGAAGAGTACACCTAATCAACAAAACCCTGCTACCAGT
AACCGTCCTCCACAGGTGTATTGCTGGCGGTGTAAGGGTCACCATGCCCCTGCCTCTTGTCCGCAATGGAA
AGCTGATAAGCACCGTGCGCAACCTTCGCGGAGTTCTGGGCCACAAACTCTGACTAATCTCCAAGCTCAAG
ACATC

SEQ ID NO: 38
GGGGAATTGGATCAACGTGCGGCAGGGGGCTTGCGCGCGTACCCGGCGCCGCGTGGTGGTCCAGTTGCC
AAACCGAGCGTAATTCTTCAGATTGGTAAGTGCCGCGCTGAGATGCTGGAACACGTCCGCCGCACGCATCG
CCATCTTCTGACGGAGGTAAGTAAACAAGTGGAGCGCGAACTCAAGGGGTTACATCGGTCTGTCGGTAAG
TTGGAGGGCAATTTAGACGGCTATGTGCCTACCGGTGATTCCCAACGCTGGAAAAAAAGTATCAAGGCGT
GTCTCTGCCGGTGTCAGGAAACAATTGCAAATCTCGAGCGTTGGGTGAAACGTGAGATGCATGTTTGGCGT
GAGGGTATTCTATCGTTTGGAACGGTGGGCAGACCGTTTGGAGTCTATGGGGGGCAAGTATCCGGTGGGCA
CTAACCCGTCGCGGCACACAGTAAGTGTCGGGGTAGGGGCCCGGAAGGCTATTCTCATGAAGCGGATAC
TTATGACTACACGGTGTCTCCGTATGCTATCACGCCACCGCCTGCCGCGGGTGAGTTGCCTGGTCAAGAGG
CTGTCGAGGCACAACAGTACCCTCCATGGGGTCTGGGGGAGGACGGGCAACCAGGTCCGGGCGTGGACA
CGCAGATTTTTGAGGACCCTCGCGAATTTTTGAGCCACTTAGAGGAGTACCTGCGGCAAGTAGGGGGGAG
TGAAGAGTACTGGTTATCGCAATTCAAAATCATATGAATGGCCCTGCGAAGAAATGGTGGGAGTTCAAAC
AGGGGTCAGTCAAGAATTGGGTCGAGTTTAAGAAAGAATTTTTGCAATACAGTGAGGGTACGTTGAGTCG
CGAGGCCATCCAACGTGAACTGGACCTCCCTCAGAAGCAGGGGGAGCCGTTAGATCAATTTTTATGCGG
AAACGTGACTTATACCAAACCCTCTACGTTGACGCTGAGGAAGAAGAAATTATTCAATATGTTGTCGGTAC
GCTGCAGCCAAAGCTGAAGCGGTTCCTCCGTCCTCCACTCCCTAAAACCTTAGAACAATTAATCCAAAAAGG
CATGGAAGTTCAGGACGGGTTAGAACAAGCGGCCGAACCGGCCTCTCCGCGTCTGCCGCCGGAAGAGGA
GAGTGAGGCTCTTACGCCTGCGCTCACGAGCGAATCAGTAGCCTCCGATCGGACACAGCCAGAG

SEQ ID NO: 39
GGGCAGCTTGACAATGTGACGAACGCGGGGATTCACAGCTTTCAAGGGCACCGCGGCGTCGCCAACAAAC
CGAATGTCATTCTGCAAATCGGTAAATGTCGTGCTGAAATGCTTGAGCACGTTCGTCGTACCCATCGTCACT
TGCTTTCTGAAGTATCAAAACAAGTGGAGCGGGAACTCAAAGGCCTGCAAAAGTCAGTGGGTAAATTGGA
GAATAACCTCGAAGACCATGTACCTACAGACAACCAGCGGTGGAAAAAATCTATCAAGGCATGCCTCGCTC
GTTGCCAGGAGACTATTGCCCATCTTGAGCGGTGGGTGAAACGTGAAATGAACGTATGGAAGGAAGTATT
TTTTCGCTTAGAGAAGTGGGCTGATCGTCTTGAATCGATGGGCGGCAAGTACTGTCCTGGGGAACACGGC
AAACAAACTGTATCTGTCGGCGTGGGGGGCCCGGAGATCCGGCCATCGGAAGGGGAAATTTATGATTATG
CTCTCGACATGTCCCAAATGTATGCTCTCACACCAGGGCCAGGGGAAGTACCGTCAATTCCGCAAGCACAC
GACAGCTACCAATGGGTATCTGTGAGCGAGGACGCGCCTGCCTCTCCGGTTGAGACGCAAATCTTTGAGG
ACCCACATGAATTTTTGTCTCATCTTGAAGAATATCTCAAACAGGTTGGCGGCACAGAAGAATACTGGTTAT
CTCAGATCAGAATCACATGAACGGCCCGCTAAAAAGTGGTGGGAGTATAAGCAAGATTCCGTAAAGAA
CTGGGTCGAATTCAAGAAAGAGTTTCTTCAATACTCTGAGGGTACTCTGACGCGCGATGCAATTAAGCGGG
AGTTAGACCTTCCACAAAAAGAGGGGGAGCCTCTTGACCAGTTCCTGTGGCGTAAGCGCGACCTCTATCAG
ACACTTTACGTCGACGCTGATGAAGAAGAGATTATTCAATATGTTGTGGGTACCCTGCAGCCAAAGCTTAA
GCGTTTCCTTAGCTACCCACTTCCGAAAACTCTGGAGTCAGCTCATTCAACGCGGTAAGGAAGTGCAGGGCA
ACATGGACCACTCTGAAGAGCCTAGCCCGCAGCGCACTCCTGAAATCCAATCAGGTGACAGTGTGGAGTCA
ATGCCGCCGTCAACCACCGCTTCTCCGGTACCTAGCAACGGGACGCAACCAGAGCCTCCAAGCCCACCGGC
TACAGTCATC

SEQ ID NO: 40
GGGCAACTTGAGAATATTAACCAAGGTTCCCTGCACGCGTTTCAGGGTCATCGCGGCGTGGTCCATAACAA
CAAGCCTAACGTTATTCTCCAGATCGGGAAGTGCCGCGCCGAAATGCTGGAGCATGTGCGGCGCACCCATC
GCCATTTGCTCACTGAAGTATCAAAACAGGTGGAGCGTGAGTTGAAGGGGTTGCAGAAAAGTGTAGGCAA
ACTTGAAAATAATTTAGAAGACCACGTACCAAGTGCGGCTGAGAACCAACGCTGGAAGAAGTCGATTAAA
GCCTGCTTAGCGCGTTGTCAGGAGACCATTGCGAACTTGGAACGCTGGGTTAAACGTGAGATGAATGTTTG
GAAGGAGGTCTTTTTCCGCTTAGAGCGCTGGGCAGATCGCCTCGAATCCGGGGGTGGCAAGTACTGCCAT
GCAGACCAGGGTCGCCAAACTGTCAGCGTAGGTGTTGGTGGTCCTGAAGTGCGTCCGTCTGAAGGTGAAA
TTTACGATTACGCGTTGGATATGAGCCAAATGTACGCCTTGACTCCGCCGCCTATGGGTGATGTTCCAGTAA
TTCCTCAGCCGCATGACAGTTATCAGTGGGTGACAGATCCGGAAGAAGCGCCACCAAGTCCGGTTGAGAC
ACAAATTTTCGAGGACCCTCGGGAGTTTCTGACCCATCTTGAGGATTATTTAAAACAAGTCGGCGGGACAG
AGGAATATTGGCTCTCACAGATCCAAATCATATGAATGGGCCAGCGAAAAAGTGGTGGGAATATAAACA
GGATAGTGTGAAGAACTGGCTTGAGTTCAAAAAAGAATTCTTGCAGACTTCTCAGAAGGCACGTTAACGCGG
GACGCTATTAAACAGGAACTTGACCTTCCACAAAAAGAAGGGGAACCGCTGGATCAATTCCTCTGGCGCAA
ACGCGATTTGTACCAAACTCTCTACGTCGAGGCAGAAGAAGAGGAGGTCATCCAATATGTAGTTGGCACAC
TGCAACCAAAACTGAAGCGGTTTCTTTCTCATCCGTACCCTAAAACCCTGGAGCAACTCATCCAGCGCGGGA
AGGAAGTTGAGGGGAATTTGGACAATAGTGAAGAACCGTCTCCACACGCGACCCCAGAACATCAGCTGGG
GGACAGTGTGGAATCTTTGCCGCTAGTACTACGGCTTCGCCTGCCGGTTCGGATAAAACGCAACCTGAGA
TTAGCTTACCTCCAACTACAGTCATT

SEQ ID NO: 41
GGGCAATTAGATTCGGTAACCAATGCGGGCGTCCACACCTACCAGGGCCATCGGAGCGTCGCCAATAAAC
CTAACGTCATTCTTCAAATCGGGAAATGTCGGACTGAGATGCTGGAGCATGTCCGTCGGACTCATCGCCAC
CTGCTCACAGAAGTGTCAAAGCAAGTGGAACGTGAACTCAAGGGCTTACAGAAGAGCGTGGGCAAACTGG
AAAACAATCTTGAAGACCATGTCCCAACTGACAATCAGCGGTGGAAGAAGTCAATCAAGGCATGTCTCGCG
CGTTGCCAAGAGACCATTGCTCACCTTGAGCGGTGGGTGAAACGTGAAATGAACGTGTGGAAGGAGGTGT
TCTTTCCGGTTAGAACGCTGGGCCGACCGCCTTGAATCAATGGGTGGTAAATACTGCCCGACGGACTCTGCA
CGTCAGACAGTTAGCGTTGGGGTGGGGGGCCCGGAAATTCGGCCTAGTGAAGGCGAAATCTATGACTACG
CGCTCGATATGAGCCAAATGTACGCTCTTACGCCGTCACCGGGCGAATTGCCGTCCGTCCCTCAACCGCATG
ATTCATACCAGTGGGTCACTAGTCCGGAAGACGCTCCGGCCGTCACCAGTTGAAACGCAGGTATTCGAGGAT

TABLE 3-continued

Arc and endo-Gag amino acid and nucleotide sequences

CCTCGGGAGTTCTTGTGTCATTTGGAAGAGTACCTGAAGCAGGTTGGCGGTACAGAGGAATATTGGCTGA
GCCAGATTCAGAATCATATGAATGGTCCTGCAAAAAAGTGGTGGGAATATAAACAAGACACGGTTAAGAA
TTGGGTGGAATTCAAGAAGGAGTTCTTACAATACAGTGAGGGTACACTTACCCGTGATGCGATTAAGCGG
GAATTAGACCTCCCGCAAAAGGACGGTGAGCCTCTGGATCAATTTTTATGGCGTAAGCGTGACCTCTATCA
GACATTATACATTGATGCCGATGAAGAACAGATCATTCAGTACGTCGTGGGGACATTGCAACCTAAACTCA
AGCGGTTCTTGTCCTATCCACTTCCAAAAACTCTTGAACAATTAATCCAGAAAGGGAAGGAGGTGCAGGGT
TCACTTGACCACAGCGAGGAGCCGAGTCCTCAACGTGCGAGCGAGGCTCGGACGGGCGATAGTGTGGAA
ACCTTGCCGCCTTCTACCACTACATCACCAAATACGTCATCTGGTACACAGCCAGAGGCACCATCGCCTCCA
GCGACGGTAATC

SEQ ID NO: 42
GGGCAGTTAGACAGTGTGACTAACGCCGGGGTGCATACGTACCAGGGGCACCGCGGGGTCGCCAATAAG
CCAAATGTAATTCTCCAGATTGGGAAGTGTCGTACAGAGATGTTGGAACATGTCCGTCGCACTCATCGCCA
CTTGCTCACCGAGGTCTCCAAACAAGTAGAACGCGAACTCAAGGGGCTCCAGAAGAGTGTTGGGAAGTTG
GAGAATAACCTCGAAGACCACGTTCCGACAGATAACCAACGGTGGAAAAAGTCTATTAAAGCCTGTCTCGC
CCGTTGTCAAGAGACAATCGCACACTTGGAACGCTGGGTCAAACGGGAGATGAATGTGTGGAAGGAAGTC
TTCTTCCGTCTCGAGCGGTGGGCGGATCGTTTAGAAAGTATGGGCGGTAAATATTGCCCAACTGACTCGGC
TCGTCAAACGGTGTCGGTTGGCGTAGGCGGCCCGGAAATTCGCCCTAGCGAGGGTGAGATCTATGACTAT
GCACTTGACATGAGTCAGATGTATGCGTTAACTCCGTCGCCAGGGGAGCTTCCAAGTATTCCACAGCCTCA
CGATAGTTATCAATGGGTAACTTCTCCTGAAGACGCCCCAGCATCCCCAGTTGAGACACAAGTATTCGAGG
ACCCTCGTGAGTTTCTCTGTCACCTCGAGGAGTACCTTAAACAGGTAGGCGGGACCGAAGAGTACTGGTTA
TCGCAAATCCAAAACCATATGAATGGTCCTGCCAAAAAGTGGTGGGAGTATAAACAAGATACTGTGAAGA
ATTGGGTAGAGTTCAAGAAGAGTTCTTACAGTACTCTGAGGGACGTTAACTCGTGATGCGATCAAGCGC
GAATTGGATTTACCTCAGAAGGACGGCGAGCCACTCGACCAGTTCTTATGGCGCAAGCGTGACTTGTATCA
AACCCTTTATATCGATGCTGACGAGGAACAAATTATCCAGTACGTAGTCGGTACGTTGCAACCAAAACTTAA
ACGCTTTCTGAGCTACCCATTACCTAAAACGTTGGAGCAACTGATCCAGAAAGGTAAAGAGGTGCAAGGG
AGCCTGGATCATAGTGAAGAACCGAGCCCTCAGCGGGCTTCTGAAGCTCGGACCGGTGATAGCGTCGAAT
CTTTACCACCTAGTACCACAACCAGCCCGAATGCGTCATCTGGTACCCAACCTGAAGCGCCTTCCCCACCTG
CTACAGTCATT

SEQ ID NO: 43
GGGCAGCTCGAGAATGTCAACCATGGGAACCTCCATTCTTTTCAAGGTCATCGCGGCGGCGTCGCCAACAA
GCCAAACGTTATCTTGCAGATCGGTAAATGTCGTGCAGAGATGCTGACCACGTCCGGCGGACCCACCGG
CATTTACTGACAGAGGTATCGAAACAGGTTGAACGTGAGTTGAAGGGGTTACAGAAATCAGTAGGGAAAT
TAGAAAATAACTTAGAAGACCATGTCCCTTCAGCCGTTGAAAACCAGCGTTGGAAAAAATCGATCAAGGCC
TGCCTTTCCCGCTGCCAAGAGACCATTGCCCACCTTGAGCGTTGGGTGAAGCGCGAAGATGAACGTATGGAA
AGAGGTTTTCTTCCGCTTAGAGCGGTGGGCAGATCGGTTGGAATCTGGGGGCGGGAAATATTGTCACGGT
GATAATCATCGTCAAACAGTATCAGTCGGTGTTGGCGGCCCTGAGGTACGTCCATCGAAGGCGAAATTTA
CGATTACGCTCTCGACATGTCGCAAATGTACGCTTTAACACCGCCTAGCCCAGGGGATGTGCCTGTAGTTA
GCCAGCCGCACGACAGCTATCAGTGGGTTACGGTTCCGGAGGATACCCCTCCATCCCCGGTGGAGACGCA
AATCTTCGAGGACCCACGGGAGTTCTTGACCCACTTAGAGGATTACTTAAAGCAAGTGGGGGGTACAGAG
GAATATTGGTTATCTCAGATCCAGAATCACATGAACGGGCCAGCCAAGAAGTGGTGGGAGTATAAGCAAG
ACTCAGTAAAAAATTGGCTCGAGTTTAAGAAGGAATTCCTTCAGTATTCCGAGGGGACACTTACGCGCGAC
GCTATCAAGGAAGAACTTGACCTCCCGCAAAAGGACGGGGAACCTCTTGATCAGTTCCTGTGGCGCAAGC
GCGACTTGTACCAGACCCTGTACGTGGAGGCGGATGAGGAGGAGGTGATCCAGTATGTTGTGGGGACTTT
ACAACCTAAATTAAAGCGTTTTCTCTCACACCCCTTACCCGAAAACGTTAGAGCAACTTATCCAACGGGGCAA
AGAGGTGGAAGGGAACCTCGACAATTCAGAGGAACCAACACCTCAGCGTACTCCAGAACACCAACTGTGT
GGTTCTGTAGAATCGCTGCCTCCTTCCTCTACCGTCAGTCCAGTGGCTAGCGATGGTACTCAACCTGAGACT
TCGCCATTGCCAGCGACTGTTATT

SEQ ID NO: 44
GGGCCATTGACGTTGTTACAAGACTGGTGTCGTGGTGAACATTTAAACACCCGCCGGTGCATGTTGATCCT
CGGTATCCCAGAAGATTGCGGCGAGGATGAGTTCGAAGAGACACTTCAGGAGGCGTGTCGCCATTTAGGG
CGGTACCGCGTGATCGGCCGCATGTTCCGTCGTGAGGAAAATGCCCAAGCGATCCTCTTGGAATTGGCGCA
GGATATTGACTATGCCTTACTCCCTCGGGAAATCCCTGGGAAAGGCGGGCCTTGGGAGGTAATTGTGAAG
CCGCGTAATTCCGACGGCGAATTCTTAAATCGGCTTAATCGCTTTCTTGAAGAGGAGCGCCGTACGGTCTCC
GATATGAACCGTGTTTTGGGCTCGGATACTAACTGTTCAGCCTCCGTGTCACCATTAGTCCTGAATTCTGG
ACTTGGGCACAGACGCTGGCGCAGCTGTCCAACCATTGCTCGAACAGATGCTCTACCGGGAGTTACGGG
TCTTCAGTGGCAATACGATTTCCATCCCAGGTGCTCTCGCTTTTGACGCGTGGCTGGAGCATACCACGGAAA
TGCTTCAAATGTGGCAGGTGCCTGAAGGGGAGAAACGGCGGCGCTTGATGGAGTGTTTGCGGGGGCCAG
CCCTGCAAGTCGTTAGTGGGTTACGTGCATCGAATGCCAGTATCACTGTCGAAGAGTGTCTTGCTGCACTG
CAGCAGGTATTCGGTCCAGTGGAAAGTCATAAGATTGCCCAAGTAAAGTTATGCAAAGCTTACCAGGAGG
CTGGGGAAAAGTAAGCAGCTTCGTTTTGCGTTTGGAGCCACTGCTTCAGCGTGCTGTAGAAAACAACGTG
GTCAGTCGCCGCAATGTCAACCAAACACGTCTTAAGCGTGTTCTGTCGGGCGCCACCCTTCCTGACAAGCTG
CGTGATAAATTGAAGTTAATGAAACAGCGCCGTAAACGCCGGGTTTCTTGGCGTTGATGTTAAACTGTTACG
TGAAGAGGAGGAGTGGGAGGCCACCTTAGGGCCAGACCGCGAGTCATTGAGGGGGTTAGAAGTGGCACC
GCGCCCGCCAGCACGGATTACGGGTGTTGGCGCAGTACCTCTTCCGGCATCCGGGAATTCATTTGATGCCC
GTCCTTCGCAAGGGTACCGGCGCCGTCGGGGTCGTGGTCAGCACCGTCGGGGCGGCGTTGCTCGTGCAGG
CTCTCGTGGCTCTCGTAAGCGGAAACGGCACACCTTCGCTATTCCTGTGGTGAGGATGGCCATATTCGTGT
CCAATGCATTAACCCTAGCAATCTCCTGTTGGCTAAGGAGACCAAAGAGATTTTGGAAGGGGGAGAACGT
GAAGCGCAAACGAATTCACGT

SEQ ID NO: 45
GGGGCTCTTACGCTCTTAGAAGACTGGTGTAAGGGTATGGACATGGACCCGCGGAAGGCTCTCCTGATTGT
AGGTATTCCGATGGAATGCAGTGAGGTGGAAATCCAGGATACAGTTAAAGCTGGTCTTCAACCTCTGTGCG
CTTATCGTGTACTCGGCCGTATGTTCCGGCGGGAGGATAATGCGAAGGCTGTTTTCATTGAGCTGGCAGAC
ACCGTGAATTACACCACGTTACCGTCTCACATTCCGGGTAAAGGGGTTCCTGGGAAGTCGTTGTTAAACC
TCGGAACCCTGACGACGAGTTCCTTTCTCGGCTTAACTACTTCTTGAAAGATGAGGGCCGCTCGATGACGG

TABLE 3-continued

Arc and endo-Gag amino acid and nucleotide sequences

ATGTCGCCCGGGCACTGGGGTGCTGTAGCTTACCTGCGGAATCACTGGACGCGGAAGTAATGCCACAGGT
CCGCTCCCCACCATTAGAACCTCCAAAAGAGAGTATGTGGTACCGTAAGTTAAAAGTGTTTAGTGGTACCG
CGTCGCCTTCGCCGGGGGAGGAGACATTTGAGGACTGGTTAGAGCAAGTCACCGAGATCATGCCTATCTG
GCAAGTATCTGAAGTTGAAAAGCGCCGTCGGTTACTGGAGTCACTCCGGGGCCCGGCACTCTCAATTATGC
GCGTGTTACAAGCCAATAACGATAGCATTACCGTTGAACAGTGTTTGGATGCATTAAAGCAGATCTTTGGC
GACAAGGAAGACTTCCGTGCCTCTCAATTTCGTTTTCTTCAAACGTCCCCTAAAATTGGGGAGAAGGTGAGT
ACGTTCCTGCTGCGTTTAGAGCCACTCTTTGCAAAAGGCCGTTCACAAGAGCCCACTTTCGGTACGTAGTACT
GATATGATTCGGTTAAAGCACCTGTTGGCACGCGTAGCCATGACCCCGGCACTGCGTGGTAAACTCGAATT
ACTCGACCAACGCGGGTGCCCACCTAATTTTCTTGAGCTGATGAAGCTGATCCGGGATGAGGAAGAGTGG
GAGAATACTGAAGCTGTGATGAAAAATAAAGAGAAACCTTCAGGTCGTGGCCGCGGTGCATCAGGCCGTC
AAGCTCGCGCCGAGGCCAGTGTAAGTGCTCCGCAAGCAACAGTCCAAGCACGTAGCTTCTCGATTCTAGC
CCGCAGACGATTCAGGGGGGCTTACCACCTCTTGTCAAGCGTCGGCGCCTTTTGGGTTCGGAGAGCACACG
TGGGGAAGACCACGGGCAAGCTACTTATCCGAAAGCAGAGAATCAGACTCCAGGGCGTGAGGGCCCGCA
GGCGGCTGGGGAGGAACTTGGTAATGAGGCCGGGGCCGGCGCGATGTCCCACCCGAAACCGTGGGAAAC
C

SEQ ID NO: 46
GGGGCTGTGACAATGCTCCAGGACTGGTGCCGTTGGATGGGCGTGAACGCTCGGCGGGGGCTGTTAATCT
TAGGTATCCCTGAAGACTGTGACGATGCAGAGTTCCAAGAGTCGTTAGAAGCTGCACTCCGTCCTATGGGT
CACTTTACTGTACTCGGTAAGGCCTTCCGCGAGGAAGACAACGCTACCGCTGCGCTGGTGGAATTAGATCG
CGAGGTTAATTACGCACTTGTTCCACGCGAAATTCCGGGCACCGGCGGGCCTTGGAACGTCGTGTTCGTTC
CTCGGTGCTCCGGCGAGGAATTCCTGGGGTTAGGCCGCGTGTTCCACTTTCCTGAACAGGAGGGCCAAATG
GTAGAATCGGTTGCGGGGGCACTGGGGGTAGGTCTGCGCCGCGTGTGTTGGTTACGCTCGATCGGGCAA
GCTGTACAACCATGGGTAGAAGCTGTTCGCTGCCAAAGCTTAGGGGTATTTAGTGGTCGTGATCAACCTGC
ACCTGGTGAAGAAAGCTTCGAGGTCTGGTTGGATCATACGACCGAGATGTTGCATGTGTGGCAAGGCGTG
TCGGAACGGGAACGGCGCCGTCGTCTGCTGGAAGGGCTGCGTGGCACAGCCTTACAACTTGTACATGCCTT
ACTGGCAGAAAATCCGGCACGGACAGCACAAGATTGCTTGGCTGCATTAGCCCAAGTTTTTGGTGATAACG
AAAGCCAGGCAACGATTCGTGTTAAATGTTTGACAGCCCAACAGCAGAGTGGCGAACGCCTCTCTGCGTTC
GTTCTCCGCTTAGAAGTACTTCTGCAAAAGGCTATGGAGAAGGAAGCATTGGCGCGCGTCAGCGGATC
GGGTGCGTCTTCGTCAGATGCTGACACGCGCACATCTCACAGAGCCGTTGGATGAAGCCTTACGGAAATTG
CGTATGCAGGGCGTTCTCCGTCTTTTTTGGAAATGCTCGGCTTAGTACGCGAGTCAGAGGCCTGGGAGGC
AAGTCTGGCTCGGTCCGTCCGGGCGCAAACCCAGGAGGGTGCAGGGGCCCGGCGGGGGCCCAAGCAGT
TGCGCGTGCCAGCACTAAGGTTGAAGCTGTACCTGGTGGCCCTGGCCGGGAGCCAGAAGGTCTCCTCCAA
GCCGGGGGCCAAGAAGCGGAAGAACTTCTCCAAGAGGGCTTAAAGCCGGTTTTAGAGGAATGTGACAAT

SEQ ID NO: 47
GGGGCGGTCACCATGTTGCAAGACTGGTGTCGGTGGATGGGCGTGAATGCTCGGCGGGGTTTATTGATCT
TGGGTATCCCAGAAGACTGTGACGACGCCGAGTTCAGGAGTCGCTCGAGGCCGCCCTTCGTCCAATGGG
GCATTTTACGGTTCTGGGCAAGGTGTTCCGTGAAGAGGATAACGCTACAGCAGCTCTTGTGGAGCTTGACC
GTGAGGTGAATTATGCGTTAGTACCTCGCGAGATTCCAGGTACCGGTGGGCCCATGGAACGTAGTCTTCGTC
CCACGTTGCTCGGGGGAGGAATTTCTGGGGCTTGGGCGCGTATTCCACTTTCCAGAACAGGAAGGGCAGA
TGGTCGAAAGCGTAGCAGGCGCTCTTGGCGTTGGTCTCCGGCGCGTGTGCTGGTTACGCTCCATCGGCCAA
GCAGTCCAACCATGGGTTGAAGCCGTACGCTATCAATCTTTAGGTGTCTTCTCAGGCCGTGACCAGCCGGC
GCCTGGTGAGGAATCCTTCGAAGTCTGGCTCGATCATACAACTGGATGCTGCATGTATGGCAAGGTGTCT
CAGAGCGGGAACGCGGCGGCGGTTATTAGAGGGGCTCCGTGGGACTGCGCTCCAATTAGTACATGCGCT
TTTGGCCGAAAATCCAGCCCGTACTGCCCAAGATTGTCTGGCAGCACTCGCCCAAGTATTCGGCGACAACG
AATCGCAGGCAACAATCCGCGTAAAGTGTCTTACAGCACAGCAGCAGTCAGGGGAACGTCTTAGTGCGTTC
GTTCTGCGGCTGGAAGTGTTACTCCAGAAAGCCATGGAAAAGGAGGCATTGGCTCGCGCGAGCGCTGACC
GTGTACGCTGCGCAAATGCTTACTCGCGCACATCTCACCGAGCCTCTCGATGAAGCACTGCGGAAACTG
CGCATGGCAGGCCGCAGCCCGTCTTTCCTGGAAATGTTAGGCTTAGTCCGGGAGTCCGAAGCCTGGGAGG
CCAGTCTGGCACGGTCAGTGCGGGCACAAACGCAAGAGGGTGCAGGGGCACGGGCGGGTGCACAAGCA
GTTGCACGTGCCTCCACTAAAGTTGAGGCAGTGCCGGGTGGGCCAGGCCGTGAACCGGAGGGTTTGCGCC
AAGCCGGCGGGCAGGAAGCCGAAGAATTACTCCAAGAAGGTTTAAAACCGGTTTTGGAGGAATGCGATAA
C

SEQ ID NO: 48
GGGGTGGAAGATTTGGCGGCATCTTACATCGTATTAAAGCTTGAGAACGAAATCCGGCAGGCGCAGGTCC
AATGGTTAATGGAGGAAAACGCCGCCCTGCAGGCCCAGATCCCTGAACTTCAAAAGTCGCAAGCCGCGAA
GGAGTATGATCTTCTGCGTAAATCTTCGGAGGCGAAGGAGCCGCAAAAACTGCCAGAACATATGAATCCAC
CGGCCGCTTGGGAAGCACAAAAGACTCCAGAGTTTAAGGAACACAGAAACCTCCTGAACCACAGGATTT
GCTTCCTTGGGAGCCGCCTGCTGCCTGGGAGTTGCAAGAAGCACCGGCTGCCCCTGAGTCACTGGCTCCGC
CTGCAACCCGTGAGTCTCAGAAACCACCTATGGCGCATGAAATCCCTACTGTATTGGAGGGGCAAGGGCCT
GCCAACACACAAGACGCTACGATTGCTCAAGAACCAAAGAATAGCGAGCCGCAAGACCCTCCAAATATCG
AGAAACCTCAGGAAGCTCCGGAATATCAAGAAACAGCGGCACAGTTGGAGTTTTTAGAACTTCCTCCACCT
CAGGAGCCACTCGAACCGAGCAATGCCAAGAATTTCTCGAGTTGTCGGCTGCCCAGGAGTCCTTAGAAG
GCCTCATTGTAGTTGAAACGTCCGCGGCTTCGGAGTTCCCACAGGCTCCTATCGGGCTTGAAGCCACCGAC
TTTCCGCTGCAGTACACGCTTACCTTCTCTGGCGACAGCCAGAAGTTGCCAGAATTTTTGGTCCAACTCTAC
AGTTATATGCGGGTACGTGGGCACTTATACCCTACCGAGGCGGCGTTAGTGTCGTTTGTAGGCAATTGTTT
CTCAGGGCGCGCGGGCTGGTGGTTTCAGTTGCTTTTGGATATCCAGTCGCCTCTGTTAGAACAGTGTGAAA
GTTTTATCCCGGTTCTCCAAGACACATTTGACAATCCGGAAAACATGAAGGACGCAAACCAATGCATCCACC
AGCTTTGTCAGGGCGAGGGTCATGTGGCCACACACTTCCACCTCATTGCACAAGAGCTTAATTGGGATGAA
AGCACGCTGTGGATCCAGTTCCAGGAAGGCCTGGCCTCATCCATCCAGGATGAACTTTCCCATACATCGCCT
GCTACCAACCTGAGTGATCTGATTACTCAATGCATCTCATTACGGGAGAAGCCTGACCCAAACCCGTTAGG
GAAGTCCTCCTCGGCGAGGGGGATGGCCCGGAAAGTCCGCCAGCAGAAAACCAACCTATGCAAGCTGCGG
ATCAATTGTCCTCACATTTCCGAAGCAGAGTGGGTTCGTTGGCACAAAGGCCGGCTTTGTCTCTATTGCGGC
TATCCGGGTCACTTCGCACGTGATTGCCCAGTGAAGCCACACCAGGCGTTACAGGCAGGGAACATTCAGGC
TTGCCAA

TABLE 3-continued

Arc and endo-Gag amino acid and nucleotide sequences

SEQ ID NO: 49
GGGGTGCAGCCGCAGACTAGCAAAGCTGAATCGCCGGCTCTCGCTGCCTCACCGAACGCACAAATGGATG
ACGTTATTGATACATTAACCTCCCTGCGTCTGACGAATTCGGCTCTGCGGCGGGAGGCTAGCACTCTTCGG
GCCGAGAAAGCAAATTTAACTAATATGCTCGAGTCAGTGATGGCCGAGTTAACGCTGTTACGGACCCGTGC
GCGGATTCCGGGGGCCCTGCAGATTACGCCACCAATTTCGTCTATTACTAGCAACGGTACTCGCCCGATGA
CGACTCCTCCAACTAGTTTACCTGAACCGTTTTCTGGCGATCCTGGCCGGTTAGCTGGTTTCCTTATGCAGAT
GGACCGTTTTATGATCTTTCAAGCTAGCCGGTTTCCAGGGGAGGCAGAGCGTGTTGCGTTCCTGGTGTCGC
GCTTAACTGGCGAAGCAGAAAAATGGGCCATTCCTCACATGCAACCAGACTCTCCTTTGCGTAACAACTATC
AAGGCTTCTTAGCAGAGTTACGGCGGACCTATAAGAGCCCGTTGCGTCACGCCCGGCGGGCGCAAATCCG
GAAGACATCGGCCTCGAACCGGGCAGTCCGTGAACGCCAAATGCTTTGCCGGCAACTTGCATCAGCAGGT
ACAGGCCCATGCCCGGTACACCCTGCTAGTAACGGGACTTCCCCGGCACCGGCATTACCAGCACGGGCGC
GTAACTTA

SEQ ID NO: 50
GGGGACGGTCGGGTACAGTTGATGAAGGCTTTATTGGCTGGCCCTTTACGTCCGGCGGCACGCCGTTGGC
GGAATCCTATTCCATTTCCAGAGACTTTTGATGGGGATACTGATCGCCTCCCGGAGTTTATCGTCCAAACTT
CGTCCTACATGTTCGTTGACGAAAATACTTTCTCTAACGACGCTCTGAAAGTGACATTTCTCATTACCCGGCT
GACAGGTCCAGCCTTGCAATGGGTCATTCCGTACATTCGTAAAGAAAGCCCGCTTCTTAACGACTATCGGG
GTTTCCTGGCCGAGATGAAGCGGGTTTTTGGGTGGGAAGAGGACGAGGACTTT

SEQ ID NO: 51
GGGGAAGGTCGGGTGCAACTTATGAAAGCGTTGCTTGCCCGCCCGCTTCGTCCAGCAGCACGTCGCTGGC
GGAATCCAATTCCTTTCCCGGAGACTTTTGACGGGGACACCGATCGGCTCCCAGAGTTCATTGTGCAGACG
TCAAGCTATATGTTCGTGGATGAGAACACGTTCTCTAACGACGTTGAAAGTGACTTTCTTAATTACGCGT
TTGACTGGCCCGGCTTTACAATGGGTGATTCCATACATTAAGAAAGAGTCACCGCTTCTCAGTGATTATCGC
GGTTTTTTAGCCGAGATGAAGCGGGTCTTCGGGTGGGAAGAAGACGAAGACTTT

SEQ ID NO: 52
GGGCCGCGTGGGCGTTGCCGTCAACAAGGTCCTCGGATTCCGATTTGGGCAGCGGCCAACTATGCCAACG
CCCACCCGTGGCAACAAATGGATAAGGCTTCGCCAGGCGTTGCTTACACACCTTTGGTTGATCCTTGGATTG
AGCGGCCTTGTTGCGGTGACACGGTTTGTGTGCGCACCACAATGGAACAGAAGAGCACAGCGTCAGGCAC
TTGTGGTGGTAAGCCTGCTGAGCGTGGTCCTCTCGCGGGGCATATGCCGAGCTCACGCCCACATCGGGTTG
ATTTCTGTTGGGTTCCTGGTAGCGACCCAGGCACATTCGACGGCAGTCCATGGCTCTTAGATCGCTTTTTGG
CGCAACTTGGTGATTACATGAGTTTTCACTTTGAACACTACCAGGACAATATCAGCCGTGTCTGCGAGATTC
TTCGTCGGTTAACGGGCCGCGCTCAGGCATGGGCTGCTCCTTACCTGGACGGGGACCTTCCACTGCCAGAC
GACTACGAATTGTTTTGTCAAGACCTTAAGGAGGTAGTACAGGACCCTAACAGTTTCGCCGAGTATCACGC
CGTGGTGACTTGTCCACTCCCTCTTGCTTCGTCCCAACTTCCTGTAGCTCCTCAGCTTCCGGTGGTACGCCAA
TACCTTGCGCGCTTCTTGGAGGGCCTTGCTTTGGATATGGGTACGGCGCCTCGGTCACTCCCGGCCGCTAT
GGCCACACCGGCAGTCTCCGGCTCGAACTCCGTTTCTCGTTCTGCCTTATTTGAACAACAACTCACAAAGGA
ATCCACTCCAGGCCCGAAAGAGCCACCTGTTCTCCCTAGCTCGACTTGCTCTAGCAAACGGGTCCTGTCGA
ACCAGCCAGTTCACAACCTGAAGAGGCTGCTCCTACCCCGGTGCCGCGTTTGTCAGAGTCGGCTAACCCAC
CGGCTCAGCGTCCAGACCCTGCTCACCCTGGTGGTCCTAAACCACAAAAAACCGAAGAGGAAGTTTTAGAA
ACTGAGGGGGACCAGGAAGTTAGCCTGGGGACGCCGCAGGAGGTCGTAGAAGCGCCGGAAACACCAGG
TGAACCACCGCTCAGCCCTGGGTTC

SEQ ID NO: 53
GGGGTTGATGAATTGGTGCTCTTGTTGCACGCGCTGTTAATGCGCCATCGGGCGCTTTCCATTGAAAATTCT
CAGTTGATGGAGCAACTTCGCTTGTTGGTCTGCGAACGGGCGAGCCTTCTTCGTCAGGTACGTCCGCCGAG
CTGTCCAGTGCCATTTCCTGAGACTTTTAACGGGGAGTCATCACGGTTACCTGAGTTCATCGTCCAAACCGC
AAGCTATATGTTAGTTAATGAAAATCGCTTTTGCAATGACGCAATGAAAGTCGCTTTTTTGATTAGCCTTCTT
ACTGGTGAAGCAGAAGAATGGGTCGTCCCATACATTGAGATGGATTCACCAATTCTTGGGGACTACCGTGC
GTTCTTGGATGAGATGAAGCAGTGTTTTGGGTGGGACGATGATGAAGATGACGACGATGAGGAAGAGGA
GGATGACTAT

SEQ ID NO: 54
GGGCCTGTGGATTTAGGTCAGGCTTTGGGGTTGTTGCCATCCCTCGCTAAGGCCGAAGATTCCCAATTTAG
CGAAAGCGATGCAGCTTTACAGGAGGAATTGTCTTCTCCGGAAACCGCACGGCAACTTTTTCGTCAATTTCG
CTATCAAGTCATGTCGGGGCCTCATGAAACACTGAAACAGTTACGGAAGTTATGTTTTCAGTGGCTGCAAC
CTGAAGTCCATACAAAGGAACAAATCCTCGAAATTCTGATGCTGGAACAGTTCTTGACCATTCTGCCTGGTG
AAATTCAGATGTGGGTCCGCAAGCAGTGCCCTGGTAGTGGGGAGGAGGCGGTTACGTTAGTAGAATCCCT
GAAAGGTGATCCACAACGGCTCTGGCAATGGATCTCCATCAAGTCCTGGGTCAGGATATCGTCTCGAGA
AAATGGAGTCACCTTCTTGCCAGGTGGGCGAAGTGGAGCCACACCTGGAAGTTGTACCTCAGGAACTGGG
GTTAGAGAATTCATCTTCAGGGCCGGGGAACTTCTTTCGCACATCGTGAAAGAGGAGTCTGACACTGAAG
CAGAGTTGGCGTTAGCGGCATCCCAGCCAGCTCGTTTGGAAGAACGGCTGATTCGGGATCAGGACCTTGG
GGCGTCCCTCCTCCCGGCAGCACCGCAGGAGCAATGGCGTCAATTAGACAGCACTCAAAAAGAACAATATT
GGGACCTGATGCTGGAGACCTACGCAAAATGGTATCCGGCGGGTATCTCACACCCGAAGTCCGATTT
AACGAACTCAATTGAGTTCGGTGAAGAGTTGGCAGGTATTTATTTACATGTAAACGAAAAGATTCCGCGGC
CTACCTGCATTGGTGACCGCCAAGAAAACGACAAAGAAAACCTTAATTTGGAAAACCATCGTGACCAGGAA
TTATTACATGCCAGCTGCCAGGCCTCGGGCGAAGTGCCATCCCAGGCATCGTTACGTGGCTTCTTTACCGAG
GACGAACCTGGTTGCTTCGGCAAGGGGAGAACCTTCCTGAGGCACTTCAGAATATCCAGGATGAGGGGA
CTGGCGAACAGCTGAGCCCGCAAGAACGCATTAGTGAAAAACAGTTGGGTCAACATTTGCCAAATCCGCAC
TCGGGGGAGATGTCGACGATGTGGCTTGAAGAAAAACGGGAGACCAGCCAGAAAGGCCAACCACGTGCA
CCAATGGCGCAGAAATTGCCAACGTGCCGCGAATGTGGCAAAACGTTTTATCGCAATAGTCAACTTATCTTT
CACCAACGCACACACACCGGTGAGACATATTTTCAATGCACCATCTGCAAAAAGGCGTTTCTCCGGTCATCT
GATTTCGTGAAACATCAGCGGACTCATACTGGCGAAAAACCTTGAAATGTGACTATTGTGGCAAGGGCTT
TAGTGATTTTAGCGGGCTTCGGCATCACGAGAAGATCCATACCGGCGAGAAGCCATACAAGTGTCCAATCT
GTGAGAAATCTTTCATCCAGCGCAGTAATTTTAACCGCCACCAACGGGTTCACACCGGTGAAAAGCCTTATA

TABLE 3-continued

Arc and endo-Gag amino acid and nucleotide sequences

AATGCTCGCATTGTGGCAAGAGCTTCAGCTGGAGCTCCTCGCTCGATAAGCATCAACGTTCACATCTGGGG
AAGAAGCCGTTCCAA

SEQ ID NO: 55
GGGACTCTCCGCTTACTTGAGGATTGGTGTCGGGGGATGGACATGAACCCACGTAAGGCCCTTCTTATCGC
CGGGATTTCCCAGTCATGTTCAGTCGCCGAGATTGAAGAGGCGCTCCAAGCCGGGCTTGCTCCTTTAGGCG
AGTATCGTCTCCTTGGGCGGATGTTTCGCCGCGATGAAAATCGCAAAGTAGCGTTGGTTGGTCTCACAGCT
GAAACTAGCCATGCGCTTGTACCTAAAGAAATTCCTGGTAAAGGCGGGATCTGGCGGGTTATTTTTAAACC
ACCGGACCCGGACAATACGTTTCTTTCTCGTTTGAATGAGTTCCTCGCGGGCGAGGGGATGACGGTGGGG
GAACTTAGTCGTGCTCTTGGTCACGAAAATGGGTCATTAGACCCTGAACAGGGTATGATTCGGAAATGTG
GGCGCCGATGCTGGCACAGGCTCTGGAGGCTCTCCAACCGGCTTTACGTGCCTTAAGTACAAGAAGCTGC
GCGTTTTTTCAGGGCGCGAGTCTCCAGAGCCGGGTGAGGAGGAATTCGGCCGTTGGATGTTCCATACCACC
CAGATGATCAAAGCGTGGCAGGTGCCGGATGTCGAGAAACGCCGCCGGCTGTTGGAATCACTCCGCGGGC
CGGCACTTGACGTTATTCGGGTTCTGAAAATTAACAACCCGTTAATTACGGTAGATGAATGTTTGCAAGCAC
TTGAAGAGGTCTTTGGGGTGACTGACAATCCTCGGGAATTGCAAGTAAAATACTTAACGACCTACCATAAG
GACGAGGAGAAATTATCAGCCTACGTACTGCGGCTGGAACCGCTGCTGCAGAAGCTCGTCCAGCGGGGGG
CTATTGAACGGGACGCTGTTAATCAGGCTCGCCTGGATCAGGTAATCGCTGGGGCGGTACATAAAACTATC
CGCCGTGAGCTGAACCTGCCTGAAGACGGGCCGGCGCCAGGCTTTCTTCAACTCCTCGTTTTGATTAAGGA
TTACGAGGCAGCTGAAGAGGAGGAAGCATTACTTCAGGCCATTCTTGAAGGGAACTTTACT

SEQ ID NO: 56
GGGACAGAACGGCGTCGCGACGAATTAAGTGAAGAAATTAATAATCTTCGTGAAAAGGTTATGAAACAGA
GTGAGGAAAACAACAATCTTCAATCCCAAGTCCAGAAACTCACTGAGGAGAATACTACACTCCGTGAGCAA
GTTGAACCTACACCTGAAGATGAAGATGACGACATTGAGTTGCGGGGCGCAGCAGCCGCAGCCGCGCCTC
CGCCGCCGATCGAGGAGGAATGCCCGGAGGATTTACCGGAAAAATTTGATGGTAATCCGGACATGTTAGC
GCCATTCATGGCCCAGTGCCAAATTTTTATGGAAAAGTCTACGCGCGATTTTAGTGTAGATCGCGTACGTGT
ATGTTTTGTGACGAGCATGATGACTGGTCGCGCAGCCCGTTGGGCGTCAGCGAAATTGGAGCGGTCGCAC
TACCTGATGCATAATTACCCGGCGTTCATGATGGAGATGAAACACGTGTTTGAAGACCCGCAGCGGCGGG
AGGTGGCCAAACGCAAGATCCGGCGGTTGCGGCAGGGCATGGGCAGCGTAATTGATTATAGTAATGCGU
TCAAATGATTGCGCAGGATCTGGATTGGAATGAACCTGCTCTCATTGATCAATATCATGAAGGGCTTAGTG
ACCATATTCAAGAGGAACTCTCTCACCTGGAAGTGGCTAAATCTTCTCCCGCCCTTATTGCCAATGCATTC
ATATTGAGCGCCGTCTTGCACGTGCTGCTGCCGCTCGGAAACCGCGTAGTCCACCACGGGCTTTAGTGCTC
CCACATATCGCGTCACACCATCAAGTAGATCCTACTGAGCCAGTGGGGGGTGCACGCATGCGCTTAACCCA
AGAAGAAAAGGAACGTCGTCGTAAGCTGAATTTATGCCTGTACTGCGGCACTGGTGGCCATTATGCCGATA
ACTGTCCTGCCAAAGCCAGTAAGTCAAGCCCGGCTGGGAAACTTCCAGGTCCTGCCGTCGAGGGCCCTTCT
GCTACCGGCCCAGAGATTATCGCTCCCCGCCAAGACGATGCGTCGTCGTCCATCTCCAGGTAATGCTCCAA
ATCCACCTTCCCTGGCCGGCACACACTCTTTGTCCGGGCGATGATTGACTCTGGGGCGTCTGGTAATTTTATT
GATCACGAGTATGTTGCTCAAAATGGTATCCCTCTCCGGATCAAAGACTGGCCTATTCTGGTTGAAGCCATC
GATGGCCGTCCGATCGCGAGCGGTCCTGTGGTTCATGAAACGCATGACCTCATCGTTGATCGGGTGACCA
CCGTGAAGTATTATCCTTTGATGTGACTCAGTCACCGTTTTTTCCAGTTGTTTTGGGCGTCCGTTGGCTTTCG
ACTCACGATCCTAACATCACGTGGTCGACACGGTCGATTGTCTTCGATTCGGAATATTGTCGTTATCATTGC
CGCATGTATTCACCAATTCCGCCGTCTCTCCCGCCGCCTGCCGCCGCAACCTCCTCTGTATTACCCGGTGGAC
GGTTACCGTGTTTACCAGCCAGTTCGCTACTACTACGTACAAAACGTGTACACGCCGTTGATGAACACGTG
TACCCAGATCACCGCCTGGTCGACCCTCATATTGAGATGATCCCGGGTGCGCACTCGATCCCATCGGGCCAT
GTTTATTCCTTGTCTGAGCCAGAAATGGCCGCCTTACGGGATTTTGTGGCCCGGAATGTCAAAGACGGCCT
GATTACCCCGACAATTGCACCAAACGGTGCTCAGGTGTTGCAGGTGAAGCGGGGCTGGAAGTTGCAAGTC
AGCTATGATTGTCGTGCGCCAAACAACTTCACTATTCAGAACCAATATCCACGTCTCAGCATCCCTAATCTCG
AGGACCAGGCACATCTTGCAACATATACTGAATTTGTACCTCAGATTCCTGGCTATCAGACTTATCCTACGT
ATGCTGCCTACCCAACATACCCGGTAGGTTTCGCATGGTACCCAGTAGGCCGGGACGGGCAGGGCCGCTCT
TTATATGTTCCTGTCATGATTACATGGAACCCGCATTGGTACCGCCAGCCTCCGGTCCCACAGTACCCACCTC
CTCAACCTCCACCACCTCCGCCGCCTCCTCCACCGCCACCTTCTTACTCGACATTA

What is claimed is:

1. A capsid comprising a recombinant endogenous Gag polypeptide and a heterologous cargo that is not native to the endogenous Gag polypeptide, wherein the endogenous Gag polypeptide is not an Arc polypeptide.

2. The capsid of claim 1, wherein the endogenous Gag polypeptide is a Paraneoplastic Ma antigen family polypeptide.

3. The capsid of claim 2, wherein the Paraneoplastic Ma antigen family polypeptide comprises:
   a) an amino acid sequence that is SEQ ID NO: 16 or an amino acid sequence that is at least 90% identical to the SEQ ID NO: 16;
   b) an amino acid sequence that is SEQ ID NO: 17 or an amino acid sequence that is at least 90% identical to the SEQ ID NO: 17;
   c) an amino acid sequence that is SEQ ID NO: 18 or an amino acid sequence that is at least 90% identical to the SEQ ID NO: 18;
   d) an amino acid sequence that is SEQ ID NO: 19 or an amino acid sequence that is at least 90% identical to the SEQ ID NO: 19; or
   e) an amino acid sequence that is SEQ ID NO: 27 or an amino acid sequence that is at least 90% identical to the SEQ ID NO: 27.

4. The capsid of claim 2, wherein the heterologous cargo is a nucleic acid.

5. The capsid of claim 4, wherein the heterologous cargo is an RNA.

6. The capsid of claim 2, wherein the heterologous cargo is a therapeutic agent.

7. The capsid of claim 2, wherein the heterologous cargo is a polypeptide.

8. The capsid of claim 2, wherein the heterologous cargo is a gene editing system.

9. The capsid of claim 2, further comprising a second polypeptide.

10. The capsid of claim 9, wherein the second polypeptide is an antibody or binding fragment thereof.

11. The capsid of claim 9, wherein the second polypeptide binds to a target site.

12. The capsid of claim 2, further comprising a delivery component that comprises a microvesicle, a microparticle, a liposome, or a micelle.

13. The capsid of claim 2, further comprising a delivery component that comprises an extracellular vesicle.

14. The capsid of claim 1, wherein the endogenous Gag polypeptide is a retrotransposon Gag-like family polypeptide.

15. The capsid of claim 14, wherein the retrotransposon Gag-like family polypeptide comprises:
 a) an amino acid sequence that is SEQ ID NO: 20 or an amino acid sequence that is at least 90% identical to the SEQ ID NO: 20;
 b) an amino acid sequence that is SEQ ID NO: 21 or an amino acid sequence that is at least 90% identical to the SEQ ID NO: 21;
 c) an amino acid sequence that is SEQ ID NO: 22 or an amino acid sequence that is at least 90% identical to the SEQ ID NO: 22;
 d) an amino acid sequence that is SEQ ID NO: 23 or an amino acid sequence that is at least 90% identical to the SEQ ID NO: 23;
 e) an amino acid sequence that is SEQ ID NO: 24 or an amino acid sequence that is at least 90% identical to the SEQ ID NO: 24; or
 f) an amino acid sequence that is SEQ ID NO: 28 or an amino acid sequence that is at least 90% identical to the SEQ ID NO: 28.

16. The capsid of claim 14, wherein the heterologous cargo is a nucleic acid.

17. The capsid of claim 16, wherein the heterologous cargo is an RNA.

18. The capsid of claim 14, wherein the heterologous cargo is a therapeutic agent.

19. The capsid of claim 14, wherein the heterologous cargo is a polypeptide.

20. The capsid of claim 14, wherein the heterologous cargo is a gene editing system.

21. The capsid of claim 14, further comprising a second polypeptide.

22. The capsid of claim 21, wherein the second polypeptide is an antibody or binding fragment thereof.

23. The capsid of claim 21, wherein the second polypeptide binds to a target site.

24. The capsid of claim 14, further comprising a delivery component that comprises a microvesicle, a microparticle, a liposome, or a micelle.

25. The capsid of claim 14, further comprising a delivery component that comprises an extracellular vesicle.

* * * * *